United States Patent
Franchino et al.

(10) Patent No.: US 8,841,510 B2
(45) Date of Patent: Sep. 23, 2014

(54) MAJOR QTLS CONFERRING RESISTANCE OF CORN TO FIJIVIRUS

(71) Applicants: E I du Pont de Nemours and Company, Wilmington, DE (US); Pioneer Hi-Bred International, Inc., Johnston, IA (US)

(72) Inventors: Jose Alejandro Franchino, Pergamino (AR); Enrique Domingo Kreff, Pergamino (AR); Stanley Luck, Wilmington, DE (US); Teresita Martin, Pergamino (AR); Ana Maria Procopiuk, Pergamino (AR); Guoping Shu, Shenzhen (CN); Adriana Tomas, Newark, DE (US)

(73) Assignees: E I du Pont de Nemours and Company, Wilmington, DE (US); Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 14/035,009

(22) Filed: Sep. 24, 2013

(65) Prior Publication Data
US 2014/0199694 A1 Jul. 17, 2014

Related U.S. Application Data

(63) Continuation-in-part of application No. 12/740,140, filed as application No. PCT/US2008/012327 on Oct. 31, 2008, now abandoned.

(60) Provisional application No. 61/001,455, filed on Nov. 1, 2007.

(51) Int. Cl.
*A01H 1/04* (2006.01)
*C12N 15/10* (2006.01)
*C12Q 1/68* (2006.01)
*C12N 15/29* (2006.01)

(52) U.S. Cl.
CPC .................................. *C12Q 1/6895* (2013.01)
USPC .......................... 800/267; 800/265; 800/320.1

(58) Field of Classification Search
None
See application file for complete search history.

(56) References Cited

U.S. PATENT DOCUMENTS

| 6,872,874 | B1 | 3/2005 | Colbert et al. |
| 2005/0250938 | A1 | 11/2005 | Kriz et al. |
| 2006/0041954 | A1 | 2/2006 | Lu et al. |
| 2007/0192909 | A1 | 8/2007 | Salmeron et al. |

FOREIGN PATENT DOCUMENTS

AR    P20030100125    1/2005

OTHER PUBLICATIONS

Mohan et al., Molecular Breeding, 1997, vol. 3, pp. 87-103.
Marzachi et all, (Seminars in Virology), 1995, vol. 6, pp. 103-108.
Alvarez, M., et al., "Marcadores moleculares y tolerancia a Mal de Rio IV (MRCV) en maiz (*Zea mays* L.) analisis preliminar", VII Congreso Nacional de Maiz, Nov. 7-9, (2001).
Citron, B.A., et al., "Sequences of the *Saccharomyces* Gal region and its transcription in vivo", J. Bacteriol., vol. 158, pp. 269-278 (1984).
Di Renzo, M.A., et al., "Microsatellite markers linked to QTL for resistance to Mal de Rio Cuarto disease in *Zea mays* L", J. Agri. Science, vol. 142, pp. 289-295 (2004).
Distephano, et al., "Sequence analysis of genome segments S4 and S8 of Mal de Rio Cuarto virus (MRCV) . . . ", Arch. Virol. vol. 147, pp. 1699-1709 (2002).
Kreff, E.D., "Genetica de la tolerancia al Mal de Rio Cuarto en maiz . . . ", Tesis para optar al grado de Magister Scientiae, Universidad Nacional de Rosario-INTA, p. 84 (2004).
Mayor, P.J., "Identificacion de marcadores microsatellites ligados . . . ", Tesis para optar al grado de Magister Scientiae, Universidad Nacional de Rosario-INTA, p. 87 (2004).
Remington, D.L., et al., "Structure of linkage disequillibrium and phenotypic associations in the maize genome", Proc. Natl. Acad. Sci., vol. 98, pp. 11479-11484 (2001).
Rodriguez, P.E., et al., "Wheat: A new natural host for the Mal de Rio Cuarto virus in the endemic disease area, Rio Cuarto . . . ", Plant Dis., vol. 82, pp. 149-152 (1998).
Sala, C., et al., "Combinacion de alelos de tres loci de rasgos cuantitativos . . . ", Boletin de patentes No. 238, p. 23, http://www.inpi.gov.ar/pdf/patentes/p120105.pdf (2005).
International Search Report and Written Opinion in international application No. PCT/US08/12327, mailed Feb. 3, 2009.

*Primary Examiner* — Brent T Page
*Assistant Examiner* — Jared Shapiro

(57) ABSTRACT

The invention relates to methods and compositions for identifying maize plants that have newly conferred resistance or enhanced resistance to, or are susceptible to, a Fijivirus, particularly Mal de Río Cuarto Virus (MRCV) and/or Maize Rough Dwarf Virus (MRDV). The methods use molecular genetic markers to identify, select and/or construct resistant plants or identify and counter-select susceptible plants. Maize plants that display newly conferred resistance or enhanced resistance to a Fijivirus that are generated by the methods of the invention are also a feature of the invention.

5 Claims, 17 Drawing Sheets

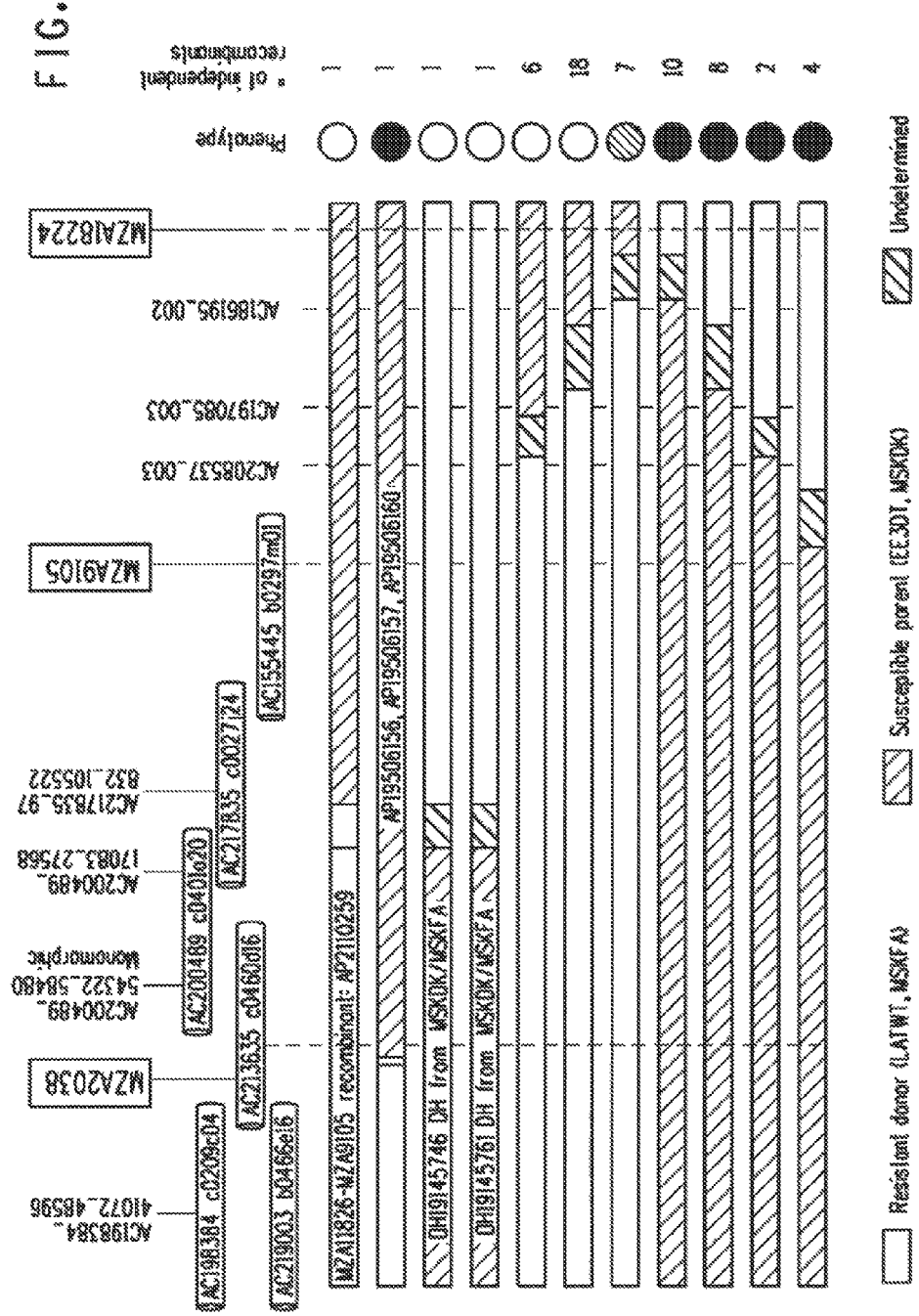

FIG. 13A

```
SEQ ID NO:211        CATCGCCGTTCCTTCCTGGGGATCGGCCGCTCCCTAGCTATCCGGTGGCCAAAGACACGGC  60
SEQ ID NO:212        CATCGTCGTTCCTTCCTGGCCGATCGCGCTTCCTAGCTATCCGGTGGCCAAAGACACGGC  60
                     ***** **********   *******  *******************************

SEQ ID NO:211        TAGTGGTAGGCTCGAGCCGAGACGAGCTCTTGGTGAAGAGAATGAATGTAACGTTACCG  120
SEQ ID NO:212        TAGTGGTAGGCTCGAGTGAGTGAGCTCTTGCTGAAGAGAATGAATGAATGTAACGTTACCG  120
                     ****************    *********** **************************

SEQ ID NO:211        CCTCCTCGGTCGTAGG------------------------------------GGTGT    140
SEQ ID NO:212        CCTCCTCGGTCGTAGTGTAATAAGTTGTAACGCGAGCGTGTTAGCAAGCACAGGGGTTT    180
                     ***************                                     ***  *

SEQ ID NO:211        GTGTATGTGAGGACAAGAGAGGAGCCGAGAGGAGCCGAGAGCGCCAGAGCGTGGCGGGGAAGGAG  200
SEQ ID NO:212        GTGTATGTGAGGACAAGAGAGGAGGAGCCGAGAGGAGCCGAGAGCGTGGCGGGGAAGGAG  240
                     ***********************************************************

SEQ ID NO:211        GGCGTCATGTGTGCCGAGGAATCTAGGACGACTTGTTGGCA---------CCTGGGCCGGGGT  253
SEQ ID NO:212        GGCCTCATGTGTGCCGAGGAATCTAGGACGACTTGTTGGCACTTGGCAGCTCTGGGCCGGGGT  300
                     *** *************************************         ***********

SEQ ID NO:211        GCGTGGCGAGATGCAATGCAAGAACAAGCGGACGGGCCATCTCCGCTCCGGCCACGCTTCCAA  313
SEQ ID NO:212        GCGTGGCCAGATGCAATGCAAGAACAAGCGGACGGGCAT-------CACGCCTCCAG  350
                     *******  ****************************** *       *  * ******
```

FIG. 13B

```
SEQ ID NO:211    GTCCATCCGGGGGCGCCACTCGGCCGCGCCGCTCATTGAGGCCCAGGGCCAAGACGGCGG  373
SEQ ID NO:212    GTCCAACCGGGGGCGCCACTCGGCCGCGCCGCTCATTGAGGCCCAGGGCCAAGACGGCGG  410
                 **** ** ****************************************************

SEQ ID NO:211    CTCCACCCCACGTCACAATTGGCAACAAGAAGCCACACGGCTGGGGACGCGGTCGAAT    433
SEQ ID NO:212    CTCCACCCCACATCACAATTGGCAACAAGAAGCCACACGGCTGGGGTTGGGACGCCTCGAAT    470
                 *********** *******************************    ** ***** ****

SEQ ID NO:211    TTTTCACCAGAAAATACCGTCTGATCCTGGCGTTTCGT------------GAACG     476
SEQ ID NO:212    TTTTCACCAGAAAATACCGTCTCTGATCCCGTTTCGTCAGATGCTATGCTACGTGAACG    530
                 ********************** *****  ******                *****

SEQ ID NO:211    GCAAAACCTAGCAGCAGCAGCAGCAGCATTC------------------------     504
SEQ ID NO:212    GCAAAACCTAGCAGCAGCAGCAGCAGCACTCAGACTGGACAAGAGGAGGAAATCTTTGGGTG  590
                 ***********************  **

SEQ ID NO:211    ------------CACGGGTTCGGATGAC-----ATATCATATCCTCGTCGGAGCGGACT   546
SEQ ID NO:212    GGAACCAAACTGAACGGCGAATCCACGAGTCGGATGACATCGACATATCCTCGTCCGGAGCGGACT   650
                             **   ** ***** ** **

SEQ ID NO:211    CTACGGGCGGAGTCCAGCTGTGGCTGCCGGAAGCGCGGGAATATTCCGGGGAAGCGCGGGAGAGCGACGG  606
SEQ ID NO:212    CGACCGGCGAGTCCAGCTGTGGCTGCCGGAAGCGCGGGAATATTCCGGGGAAGCGCGGGAGAACGACGG  710
                 *  *  *********************************************************
```

FIG. 13C

```
SEQ ID NO:211    CGGCCTCCGGTGGGACCCGGGGCCGAGCGGGAGATGCGGCGAAGATGTTCGGCGCTGATGT   666
SEQ ID NO:212    CGGCCCTCCGGTGGGACCCGGGGCCGAGCGGGAGATGCGGCGAAGATGTTCGGCGCTGATGT  770
                 ******************************************************** **

SEQ ID NO:211    CGCTGGAATATTCGCGCCAGCTGTGTGGCGTCCGGTCCGCTGCCGACCAGACGACCAATG   726
SEQ ID NO:212    CGCTGGAATATTCGCGCCAGCTGTGTGGCGTCCGGTCCGCTGCCGACCAGACGACCAGTG   830
                 ***********************************************************

SEQ ID NO:211    GCAGTGGCCACGGCCTCTCCCTCTTGCTGTTGGAGTTGGATCCACGGACCACTCTCCATC   786
SEQ ID NO:212    GCAGTGGCCACGGCCTCTCCCTCTTGCTGTTGG---------------CCACCCTCTCC   850
                 *********************************                * *** ***

SEQ ID NO:211    CAACATCCATCACAGAGATTCGCGGACGAGACTAATCGCTATTCTCAACACTTT   846
SEQ ID NO:212    ------ATCACAGAGATTCGCGGACGAGACTAATCGCTATTCTCAACACTTTT   902
                       ********************************************* *

SEQ ID NO:211    TAAAACCGTACGTGCGTGCAAAAATGCTAAGGGGCCGTT    880
SEQ ID NO:212    TAAAACCGTGCGTGCCAGAATGCTAAGGGCCGCGTT       936
                 ********* ***** * *********** **  ***
```

MAJOR QTLS CONFERRING RESISTANCE
OF CORN TO FIJIVIRUS

CROSS-REFERENCE TO RELATED
APPLICATION

This application is a continuation-in-part application of U.S. application Ser. No. 12/740,140, now allowed, which claims the benefit of U.S. Provisional Application No. 61/001,455, filed Nov. 1, 2007, which is incorporated by reference in its entirety.

FIELD OF THE INVENTION

The present disclosure relates to compositions and methods useful in creating or enhancing Fijivirus, particularly Mal de Río Cuarto Virus and/or Maize Rough Dwarf Virus, resistance in plants. Additionally, the invention relates to plants that have been genetically transformed with the compositions of the invention.

BACKGROUND OF THE INVENTION

The disease caused by Mal de Río Cuarto Virus (MRCV) is a major corn disease in Argentina, accounting for yield losses of greater than 70% in years of severe outbreak (Rodriguez P E et al. (1998) *Plant Dis.* 82:149-52). The disease is a member of Serogroup 2 of Fijivirus, which includes other viruses such as maize rough dwarf virus, rice black streaked dwarf virus, and pangola stunt virus (Uyeda I & Milne R G (1995) *Semin. Virol.* 6:85-88). The main vector for MRCV is *Delphacodes kuscheli*, but other *Delphacodes* species, such as *D. haywardi* and *D. tigrinus*, and *Toya propinqua* have been shown to carry the virus. The virus does not appear to be transmitted to progeny via seeds. Distéfano et al., Arch. Virol. 147:1699-1709 (2002), analyzed the MRCV sequence and proposed that it is a new Fijivirus species related to MRDV (Maize Rough Dwarf Virus). MRDV is found in several European countries (e.g., the Czech Republic, France, Italy, Norway, Spain, Sweden) and in China, while MRCV has been also detected in Uruguay (Ornaghi J. A., Beviacqua J. E., Aguirrezabala D. A., March G. J. and Lenardón S. L. 1999. Detection of Mal de Río Cuarto virus in Uruguay. Fitopatologia Brasileira 24: 471).

MRCV infection causes abnormal maize development and significantly reduces crop yields. The susceptible phenotype includes stunting, shortening of internodes, multiple ears with scattered grain, deformed tassel with no anthers, presence of small enations in the back of the leaves, reduced roots, cut and reduced leaves. Plants symptoms depend on phenological stage of the plant, plant genotype, and environment (Lenardón et al., “Virus del Mal de Río Cuarto en maíz”, in Proyecto de Investigaciones en Fitovirologia (Lenardón ed.), 2:10 (1999). Most severe symptoms occur when infected at the coleoptile—first leaf stage.

In the severe MRCV outbreak of 1996-1997, over 300,000 hectares of maize in Argentina were affected, resulting in losses totaling approximately $120 million. Increased populations of *Delphacodes kuscheli* in 2006 apparently led to a reoccurrence of the viral disease in Argentinean corn plants, which significantly affected the 2007 harvesting. Susceptible genotypes were strongly affected by MRCV at the endemic region (Córdoba Province) and moderately affected at other maize regions.

The development of molecular genetic markers has facilitated mapping and selection of agriculturally important traits in maize. Markers tightly linked to disease resistant genes are an asset in the rapid identification of resistant maize lines on the basis of genotype by the use of marker assisted selection (MAS). Introgressing disease resistance genes into a desired cultivar would also be facilitated by using suitable DNA markers.

SUMMARY OF THE INVENTION

Compositions and methods for identifying maize plants or germplasm with newly conferred or enhanced resistance to fijivirus are provided. Methods of making maize plants or germplasm that are resistant to fijivirus, e.g., through introgression of desired resistance marker alleles and/or by transgenic production methods, as well as plants and germplasm made by these methods, are also provided. Systems and kits for selecting resistant plants and germplasm are also a feature of the invention.

In some aspects, the invention provides methods for identifying a first maize plant or germplasm (e.g., a line or variety) that has newly conferred resistance, enhanced resistance, or susceptibility to MRCV. In the methods, at least one allele of one or more marker locus (e.g., a plurality of marker loci) that is associated with the newly conferred resistance, enhanced resistance, or susceptibility are detected in the first maize plant or germplasm. The marker loci can be selected from the loci provided in Tables 1 and 2, including MZA625, MZA16656, MZA15451, MZA15490, MZA2038, MZA11826, and MZA9105, as well as any other marker that is linked to these QTL markers (e.g., within about 10 cM of these loci). Tables 1 and 2 show maize markers demonstrating linkage disequilibrium with the MRCV resistance phenotype as determined by association mapping analysis and QTL interval mapping (including single marker regression analysis) methods. The table indicates the genomic-SSR or EST-SSR marker type (all simple sequence repeats) or SNP or MZA markers, the chromosome on which the marker is located and its approximate genetic map position relative to other known markers, given in cM, with position zero being the first (most distal) marker on the chromosome. Also shown are the maize populations used in the analysis and the statistical probability of random segregation of the marker and the resistance/susceptibility phenotype given as an adjusted probability taking into account the variability and false positives of multiple tests. Probability values from single marker regression are also shown.

The invention also provides chromosomal QTL intervals that correlate with MRCV. These intervals are located on linkage group 2. Any marker located within these intervals also finds use as a marker for MRCV resistance and is also a feature of the invention. These intervals include:

(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a.

A plurality of marker loci can be selected in the same plant. Which QTL markers are selected in combination is not particularly limited. The QTL markers used in combinations can be any of the markers listed in Tables 1 and 2, any other marker that is linked to the markers in Tables 1 and 2 (e.g., the linked markers determined from the MaizeGDB resource), or any marker within the QTL intervals described herein.

TABLE 1

| | | | | Adjusted Probability | | | | |
|---|---|---|---|---|---|---|---|---|
| | | | | Structured association | | | Not structured association | |
| Marker | Relative Map Position (cM). PHD v1.4 | Method of Identification | Gene Pool Analyzed/ Mapping Population | Association analysis Myriad Argentine inbreds | Association analysis I Myriad SS inbreds | Association analysis II Myriad SS inbreds | Association analyisis set 1 (SS) inbreds | Association analysis SNPs at MRCV1. Argentine inbreds |
| MZA7588 | 63.17 | Association analysis, identity by descent | Broad Pioneer germplasm | 0.12 | 0.341 | 0.742 | 0.000676917 | |
| MZA8381 | 63.47 | Association analysis, identity by descent | Broad Pioneer germplasm | 0.002 | 0.0037 | 0.0044 | 0.000198191 | less than 0.001 |
| MZA3105 | 63.55 | Association analysis, identity by descent | Broad Pioneer germplasm | 0.0412 | | | | 0.064 |
| MZA482 | 63.64 | Association analysis, identity by descent | Broad Pioneer germplasm | 0.551 | 0.0958 | 0.197 | 0.002172499 | |
| MZA16531 | 63.83 | Association analysis, identity by descent | Broad Pioneer germplasm | | 0.174 | 0.0282 | 0.055088894 | |
| MZA14553 | 64.1 | Association analysis, identity by descent | Broad Pioneer germplasm | | | | | |
| MZA4305 | 64.1 | Association analysis, identity by descent | Broad Pioneer germplasm | 0.644 | 0.0394 | 0.066 | 0.331615457 | |
| MZA625 | 64.1 | Association analysis, identity by descent, QTL mapping | Broad Pioneer germplasm | 0.0476 | 0.685 | 0.74 | 0.000136376 | |
| MZA625-30-A | 64.1 | Identity by descent, QTL mapping | Broad Pioneer germplasm | | | | | less than 0.001 |
| MZA625-29-A | 64.1 | Identity by descent, QTL mapping | Broad Pioneer germplasm | | | | | less than 0.001 |
| MZA15451 | 65.3 | Association analysis, identity by descent | Broad Pioneer germplasm | 0.0105 | 0.0438 | 0.0612 | 0.51165696 | |
| MZA9105 | 65.4 | Association analysis, identity by descent | Broad Pioneer germplasm | 0.0226 | 0.436 | 0.453 | 0.003621576 | |
| MZA9105-8-A | 65.4 | Identity by descent, QTL mapping | Broad Pioneer germplasm | | | | | less than 0.001 |
| MZA9105-6-A | 65.4 | Identity by descent, QTL mapping | Broad Pioneer germplasm | | | | | 0.066 |
| MZA11826 | 66.0 | Association analysis, identity by descent, QTL mapping | Broad Pioneer germplasm | 0.0201 | 0.16 | 0.486 | 1.79182E−06 | |
| MZA11826-803-A | 66.0 | Identity by descent, QTL mapping | Broad Pioneer germplasm | | | | | 0.014 |
| MZA11826-801-A | 66.0 | Identity by descent, QTL mapping | Broad Pioneer germplasm | | | | | 0.034 |
| MZA11826-27-A | 66.0 | Identity by descent, QTL mapping | Broad Pioneer germplasm | | | | | 0.04 |
| MZA15490 | 66.0 | Association analysis, identity by descent | Broad Pioneer germplasm | 0.0079 | 0.186 | 0.523 | 0.4067326 | |
| MZA15490-801-A | 66.0 | Identity by descent, QTL mapping | Broad Pioneer germplasm | | | | | less than 0.001 |
| MZA15490-138-A | 66.0 | Identity by descent, QTL mapping | Broad Pioneer germplasm | | | | | less than 0.001 |
| MZA15490-137-A | 66.0 | Identity by descent, QTL mapping | Broad Pioneer germplasm | | | | | less than 0.001 |

TABLE 1-continued

| | | | | Adjusted Probability | | | | |
|---|---|---|---|---|---|---|---|---|
| | | | | Structured association | | | Not structured association | |
| Marker | Relative Map Position (cM). PHD v1.4 | Method of Identification | Gene Pool Analyzed/ Mapping Population | Association analysis Myriad Argentine inbreds | Association analysis I Myriad SS inbreds | Association analysis II Myriad SS inbreds | Association analyisis set 1 (SS) inbreds | Association analysis SNPs at MRCV1. Argentine inbreds |
| MZA16656 | 66.0 | Association analysis, identity by descent, QTL mapping | Broad Pioneer germplasm | 0.000194 | 0.452 | 0.474 | 0.011514162 | |
| MZA16656-8-A | 66.0 | Identity by descent, QTL mapping | Broad Pioneer germplasm | | | | | less than 0.001 |
| MZA16656-19-A | 66.0 | Identity by descent, QTL mapping | Broad Pioneer germplasm | | | | | less than 0.001 |
| MZA2038 | 66.0 | Association analysis, identity by descent | Broad Pioneer germplasm | 0.0035 | 0.104 | 0.391 | 2.66345E−06 | |
| MZA2038-76-A | 66.0 | Identity by descent, QTL mapping | Broad Pioneer germplasm | | | | | 0.161 |
| MZA2038-71-A | 66.0 | Identity by descent, QTL mapping | Broad Pioneer germplasm | | | | | 0.298 |
| MZA2803 | 66.0 | Association analysis, identity by descent | Broad Pioneer germplasm | 0.404 | 0.0728 | 0.0916 | 0.116318398 | |
| MZA18224 | 68.8 | Association analysis, identity by descent, QTL mapping | Broad Pioneer germplasm | 0.000066 | 0.039 | 0.041 | 0.003921924 | |
| MZA18224-801-A | 68.8 | Identity by descent, QTL mapping | Broad Pioneer germplasm | | | | | 0.052 |
| MZA2349 | 68.8 | Association analysis, identity by descent | Broad Pioneer germplasm | 0.0498 | 0.238 | 0.185 | 0.001262359 | 0.277 |
| MZA564 | 68.8 | Association analysis, identity by descent | Broad Pioneer germplasm | 0.756 | 0.167 | 0.0524 | 0.000254878 | |
| MZA11066 | 70.7 | Association analysis, identity by descent | Broad Pioneer germplasm | 0.617 | 0.819 | 0.786 | 0.330400979 | |
| MZA18180 | 71.3 | Association analysis, identity by descent | Broad Pioneer germplasm | 0.0272 | 0.0201 | 0.0204 | 0.091180064 | 0.005 |
| MZA8442 | 71.4 | Association analysis, identity by descent | Broad Pioneer germplasm | 0.000234 | 0.0358 | 0.0402 | 0.000598737 | |
| MZA15563 | 71.5 | Association analysis, identity by descent | Broad Pioneer germplasm | 0.0754 | 0.0079 | 0.0079 | 0.114427854 | 0.524 |
| MZA18036 | 71.8 | Association analysis, identity by descent | Broad Pioneer germplasm | 0.000138 | 0.112 | 0.0474 | 0.008370189 | 0.007 |
| MZA15264 | 71.9 | Association analysis, identity by descent | Broad Pioneer germplasm | 0.794 | 0.608 | 0.664 | 0.207135606 | |
| MZA10384 | 72.2 | Association analysis, identity by descent | Broad Pioneer germplasm | 0.706 | 0.133 | 0.0442 | 0.001530899 | |
| MZA12874 | 72.3 | Association analysis, identity by descent | Broad Pioneer germplasm | 0.829 | 0.141 | 0.215 | 0.009463312 | 0.059 |
| MZA12454 | 72.4 | Association analysis, identity by descent | Broad Pioneer germplasm | 0.000064 | 0.126 | 0.088 | 5.75703E−05 | |
| MZA8926 | 72.9 | Association analysis, identity by descent | Broad Pioneer germplasm | 0.0089 | | | 0.641842316 | |
| MZA5057 | 73.0 | Association analysis, identity by descent | Broad Pioneer germplasm | 4.5231E−05 | 0.0246 | 0.0098 | 0.050959299 | less than 0.001 |

TABLE 1-continued

| Marker | Relative Map Position (cM). PHD v1.4 | Method of Identification | Gene Pool Analyzed/ Mapping Population | Adjusted Probability | | | | |
|---|---|---|---|---|---|---|---|---|
| | | | | Structured association | | | Not structured association | |
| | | | | Association analysis Myriad Argentine inbreds | Association analysis I Myriad SS inbreds | Association analysis II Myriad SS inbreds | Association analyisis set 1 (SS) inbreds | Association analysis SNPs at MRCV1. Argentine inbreds |
| BNLG1327 | 66.9 | Link between Pioneer and public maps | Extrapolation by map position | | | | | |
| BNLG1458B | | Link between Pioneer and public maps | Extrapolation by map position | | | | | |
| UMC1261 | 70.0 | Link between Pioneer and public maps | Extrapolation by map position | | | | | |
| UMC1262 | 70.2 | Link between Pioneer and public maps | Extrapolation by map position | | | | | |

TABLE 2

| | QTL mapping | | | | |
|---|---|---|---|---|---|
| Marker | PH7WT × PH3DT mapping pop | PH9TJ × PH890 mapping pop | PH7WT × PH3DT BC3F3 by MAS | MEPS populations (adjusted probability) | Notes |
| MZA625 | QTL position extrapolated from LOD score peak. LOD score peak: >6 Position 65.8; flanking markers umc1756- umc1518 | QTL position extrapolated from LOD score peak. LOD score peak: >20; Position 65.99-68.8; flanking markers MZA625- MZA18224 | QTL position corresponding to the highest associated markers. LOD score peak: >10 | less than 0.05 | QTL position by using the information across different association analysis, QTL mapping studies and Identity by descent information. Markers to extrapolate the QTL position to public maps |
| MZA15451 | | | | | |
| MZA9105 | | | | | |
| MZA11826 | | | | | |
| MZA15490 | | | | | |
| MZA16656 | | | | | |
| MZA2038 | | | | | |
| MZA2803 | | | | | |
| BNLG1327 | | | | | |
| BNLG1458B | | | | | |
| UMC1261 | | | | | |
| UMC1262 | | | | | |

The markers that are linked to the QTL markers of Tables 1 and 2 can be closely linked, for example, within about 10 cM from the Tables 1 and 2 QTL markers. In some embodiments, the linked locus displays a genetic recombination distance of 9 centiMorgans, 8, 7, 6, 5, 4, 3, 2, 1, 0.75, 0.5 or 0.25, or less from the QTL marker.

In some embodiments, preferred QTL markers are selected from MZA625, MZA16656, MZA15451, MZA15490, MZA2038, MZA11826, and MZA9105. Most preferred are QTL markers selected from MZA15490 and MZA2038.

In some embodiments, the germplasm is a maize line or variety. In some aspects, the newly conferred resistance, enhanced resistance, or susceptibility of a maize plant to MRCV can be quantitated using any suitable means, for example 1 to 9 scale (MRCV score), where 1, represents a highly susceptible genotype and 9, a completely resistant genotype; 4 represents a genotype with the minimum level of resistance to generate a commercial hybrid.

A second way of evaluating MRCV resistance is by evaluating the percentage of highly susceptible plants on a specific genotype. For example, a field experiment where the genotypes are arranged on a randomly completely block design and each experimental unit is represented by a field row of 4 meters and approximately 20 plants are planted on each row. The MRCV enhanced resistance is evaluated by observing each experimental unit and assigning a field score (1 to 9 scale). At the same time, the percentage of highly susceptible plants on each experimental unit is assayed.

Any of a variety of techniques can be used to identify a marker allele. It is not intended that the method of allele detection be limited in any way. Methods for allele detection typically include molecular identification methods such as amplification and detection of the marker amplicon. For example, an allelic form of a polymorphic simple sequence repeat (SSR) or of a single nucleotide polymorphism (SNP) can be detected, e.g., by an amplification based technology. In these and other amplification based detection methods, the marker locus or a portion of the marker locus is amplified (e.g., via PCR, LCR or transcription using a nucleic acid isolated from a maize plant of interest as a template), and the resulting amplified marker amplicon is detected. In one example of such an approach, an amplification primer or amplification primer pair is admixed with genomic nucleic acid isolated from the first maize plant or germplasm, wherein the primer or primer pair is complementary or partially complementary to at least a portion of the marker locus, and is capable of initiating DNA polymerization by a DNA polymerase using the maize genomic nucleic acid as a template. The primer or primer pair (e.g., a primer pair provided in Table 3) is extended in a DNA polymerization reaction having a DNA polymerase and a template genomic nucleic acid to generate at least one amplicon.

TABLE 3

| Marker Name | Left Primer Sequence | Right Primer Sequence | Repeat | Also Known As (AKA) |
|---|---|---|---|---|
| BNLG1327 | SEQ ID NO: 49 | SEQ ID NO: 50 | CT(25) | bmc1327, A4615G09, p-bnlg1327, A4615G10, bnlg1327, LGI456705 |
| BNLG1458B | SEQ ID NO: 51 | SEQ ID NO: 52 | — | bnlg1458, p-bnlg1458, A4651C06, bmc1458, A4651C05 |
| UMC1261 | SEQ ID NO: 53 | SEQ ID NO: 54 | (TG)8 | Al987278 |
| UMC1262 | SEQ ID NO: 55 | SEQ ID NO: 56 | (GTC)4 | Al987278 |

Table 3 lists genomic and SSR markers, including those markers that demonstrated linkage disequilibrium with the MRCV resistance phenotype (directly or by extrapolation from the genetic map). Table 3 provides the sequences of the left and right PCR primers used in the SSR marker locus genotyping analysis. Also shown is the pigtail sequence used on the 5' end of the right primer, and the number of nucleotides in the tandem repeating element in the SSR.

In any case, data representing the detected allele(s) can be transmitted (e.g., electronically or via infrared, wireless or optical transmission) to a computer or computer readable medium for analysis or storage. In some embodiments, plant RNA is the template for the amplification reaction. In other embodiments, plant genomic DNA is the template for the amplification reaction. In some embodiments, the QTL marker is a SNP type marker, and the detected allele is a SNP allele (see, e.g., Table 4 (showing SNP markers at QTL position and the specific PH7WT (=630=PH14J) and PH9TJ haplotypes)), and the method of detection is allele specific hybridization (ASH).

TABLE 4

| QTL | MRCV1 | | | | | | | |
|---|---|---|---|---|---|---|---|---|
| STARS | PASS | PASS | PASS | PASS | PASS | PASS | PASS | PASS |
| Ctg Pos | 745 | 745 | 897 | 897 | | | | 897 |
| Ctg | 203 | 203 | 203 | 203 | | | | 203 |
| PHD | 64.1 | 64.1 | 66.0 | 66.0 | 66.0 | 66.0 | 66.0 | 66.0 |
| Chromosome | 2 | 2 | 2 | 2 | 2 | 2 | 2 | 2 |
| Sample Name | MZA-625-29-A | MZA625-30-A | MZA16656-8-A | MZA16656-19-A | MZA15490-137-A | MZA15490-138-A | MZA15490-801-A | MZA2038-71-A |
| PH7WT | C | T | C | G | C | G | G | A |
| PH9TJ | C | T | T | A | A | C | C | T |

| QTL | MRCV1 | | | | | | |
|---|---|---|---|---|---|---|---|
| STARS | PASS | PASS | PASS | PASS | PASS | PASS | PASS |
| Ctg Pos | 930 | 930 | 930 | 930 | 930 | 1018 | 1018 |
| Ctg | 203 | 203 | 203 | 203 | 203 | 203 | 203 |
| PHD | 66.0 | 66.0 | 66.0 | 66.0 | 66.0 | 65.4 | 65.4 |
| Chromosome | 2 | 2 | 2 | 2 | 2 | 2 | 2 |
| Sample Name | MZA2038-76-A | C00081-01-A | MZA11826-27-A | MZA11826-801-A | MZA11826-803-A | MZA9105-6-A | MZA9105-8-A |
| PH7WT | T | P | C | A | C | G | A |
| PH9TJ | C | X | T | G | T | G | A |

In some embodiments, the allele that is detected is a favorable allele that positively correlates with newly conferred resistance or enhanced resistance. Alternatively, the allele that is detected can be an allele that correlates with disease susceptibility or reduced disease resistance, and that allele is counter-selected. For example, alleles that can be selected for (favorable alleles, e.g., PH7WT and PH9TJ (see Table 5)) or against (unfavorable alleles, e.g., PH3DT, PH890, and PH6 KW (see Table 5)).

Similarly, in other embodiments, if an allele is correlated with newly conferred resistance or enhanced resistance to MRCV, the method can include introgressing the allele into a second maize plant or germplasm to produce an introgressed maize plant or germplasm. In some embodiments, the second maize plant or germplasm will typically display reduced resistance to MRCV as compared to the first maize plant or germplasm, while the introgressed maize plant or germplasm will display an increased resistance to MRCV as compared to the second maize plant or germplasm. An introgressed maize

TABLE 5

| QTL | | MRCV1 | | | | | | | |
|---|---|---|---|---|---|---|---|---|---|
| STARS | | PASS | PASS | PASS | PASS | PASS | PASS | PASS | PASS |
| Ctg Pos | | 745 | 745 | 897 | 897 | | | | 897 |
| Ctg | | 203 | 203 | 203 | 203 | | | | 203 |
| PHD | | 64.1 | 64.1 | 66.0 | 66.0 | 66.0 | 66.0 | 66.0 | 66.0 |
| Chromosome | | 2 | 2 | 2 | 2 | 2 | 2 | 2 | 2 |
| Sample Name | MRCV1 | MZA-625-29-A | MZA625-30-A | MZA16656-8-A | MZA16656-19-A | MZA15490-137-A | MZA15490-138-A | MZA15490-801-A | MZA2038-71-A |
| PH7WT | Positive Effect | C | T | C | G | C | G | G | A |
| PH9TJ | Positive Effect | C | T | T | A | A | C | C | T |
| PH3DT | Negative Effect | T | C | T | A | A | C | C | T |
| PH890 | Negative Effect | T | C | C | A | A | C | C | T |
| PH6KW | Negative Effect | T | C | T | A | A | C | C | A |

| QTL | | MRCV1 | | | | | | |
|---|---|---|---|---|---|---|---|---|
| STARS | | PASS | PASS | PASS | PASS | PASS | PASS | PASS |
| Ctg Pos | | 930 | 930 | 930 | 930 | 930 | 1018 | 1018 |
| Ctg | | 203 | 203 | 203 | 203 | 203 | 203 | 203 |
| PHD | | 66.0 | 66.0 | 66.0 | 66.0 | 66.0 | 65.4 | 65.4 |
| Chromosome | | 2 | 2 | 2 | 2 | 2 | 2 | 2 |
| Sample Name | MRCV1 | MZA2038-76-A | C00081-01-A | MZA11826-27-A | MZA11826-801-A | MZA11826-803-A | MZA9105-6-A | MZA9105-8-A |
| PH7WT | Positive Effect | T | P | C | A | C | G | A |
| PH9TJ | Positive Effect | C | X | T | G | T | G | A |
| PH3DT | Negative Effect | C | X | T | G | T | A | G |
| PH890 | Negative Effect | C | X | T | G | T | A | G |
| PH6KW | Negative Effect | T | P | C | A | C | G | A |

In the case where more than one marker is selected, an allele is selected for each of the markers; thus, two or more alleles are selected. In some embodiments, it can be the case that a marker locus will have more than one advantageous allele, and in that case, either allele can be selected.

It will be appreciated that the ability to identify QTL marker loci that correlate with newly conferred resistance, enhanced resistance, or susceptibility to MRCV provides a method for selecting plants that have favorable marker loci as well. That is, any plant that is identified as comprising a desired marker locus (e.g., a marker allele that positively correlates with resistance) can be selected for, while plants that lack the locus, or that have a locus that negatively correlates with resistance, can be selected against. Thus, in one method, subsequent to identification of a marker locus, the methods include selecting (e.g., isolating) the first maize plant or germplasm, or selecting a progeny of the first plant or germplasm. In some embodiments, the resulting selected first maize plant or germplasm can be crossed with a second maize plant or germplasm (e.g., an elite or exotic maize, depending on characteristics that are desired in the progeny).

plant or germplasm produced by these methods is also a feature of the invention. (In some embodiments, the favorable introgressed allele is PH7WT/PH9TJ, see Table 5).

In other aspects, various mapping populations are used to determine the linked markers of the invention. In one embodiment, the mapping population used is the population derived from the cross PH7WT×PH3DT or PH9TJ×PH890. In other embodiments, other populations can be used. In other aspects, various software is used in determining linked marker loci. For example, TASSEL, MapManager-QTX, and GeneFlow all find use with the invention. In some embodiments, such as when software is used in the linkage analysis, the detected allele information (i.e., the data) is electronically transmitted or electronically stored, for example, in a computer readable medium.

In other aspects, various mapping populations are used to determine the linked markers that find use in constructing the transgenic plant. In one embodiment, the mapping population used is the population derived from the cross PH7WT× PH3DT or PH9TJ×PH890. In other embodiments, other populations can be used. In other aspects, various software is used in determining linked marker loci used to construct the transgenic plant. For example, TASSEL, MapManager-QTX, and GeneFlow all find use with the invention.

Systems for identifying a maize plant predicted to have newly conferred resistance or enhanced resistance to MRCV are also a feature of the invention. Typically, the systems include a set of marker primers and/or probes configured to detect at least one favorable allele of one or more marker locus associated with newly conferred resistance or enhanced resistance to MRCV, wherein the marker locus or loci are selected from: MZA7588, MZA8381, MZA3105, MZA482, MZA16531, MZA14553, MZA4305, MZA625, MZA15451, MZA9105, MZA11826, MZA15490, MZA16656, MZA2038, MZA2803, MZA18224, MZA2349, MZA564, MZA11066, MZA18180, MZA8442, MZA15563, MZA18036, MZA15264, MZA10384, MZA12874, MZA12454, MZA8926, and MZA5057, as well as any other marker that is linked (or in some embodiments, closely linked, e.g., demonstrating not more than 10% recombination frequency) to these QTL markers; and furthermore, any marker locus that is located within the chromosomal QTL intervals including:

(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a.

In some embodiments, preferred QTL markers used are selected from MZA625, MZA16656, MZA15451, MZA15490, MZA2038, MZA11826, and MZA9105.

Where a system that performs marker detection or correlation is desired, the system can also include a detector that is configured to detect one or more signal outputs from the set of marker probes or primers, or amplicon thereof, thereby identifying the presence or absence of the allele and/or system instructions that correlate the presence or absence of the favorable allele with the predicted resistance. The precise configuration of the detector will depend on the type of label used to detect the marker allele. Typical embodiments include light detectors, radioactivity detectors, and the like. Detection of the light emission or other probe label is indicative of the presence or absence of a marker allele. Similarly, the precise form of the instructions can vary depending on the components of the system, e.g., they can be present as system software in one or more integrated unit of the system, or can be present in one or more computers or computer readable media operably coupled to the detector. In one typical embodiment, the system instructions include at least one look-up table that includes a correlation between the presence or absence of the favorable allele and predicted newly conferred resistance, enhanced resistance, or susceptibility.

In some embodiments, the system can be comprised of separate elements or can be integrated into a single unit for convenient detection of markers alleles and for performing marker-resistance trait correlations. In some embodiments, the system can also include a sample, for example, genomic DNA, amplified genomic DNA, cDNA, amplified cDNA, RNA, or amplified RNA from maize or from a selected maize plant tissue.

Kits are also a feature of the invention. For example, a kit can include appropriate primers or probes for detecting resistance-associated marker loci and instructions in using the primers or probes for detecting the marker loci and correlating the loci with predicted MRCV resistance. The kits can further include packaging materials for packaging the probes, primers or instructions, controls such as control amplification reactions that include probes, primers or template nucleic acids for amplifications, molecular size markers, or the like.

DEFINITIONS

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term "maize plant" includes whole maize plants, maize plant cells, maize plant protoplast, maize plant cell or maize tissue culture from which maize plants can be regenerated, maize plant calli, maize plant clumps and maize plant cells that are intact in maize plants or parts of maize plants, such as maize seeds, maize cobs, maize flowers, maize cotyledons, maize leaves, maize stems, maize buds, maize roots, maize root tips and the like.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

The term "allele" refers to one of two or more different nucleotide sequences that occur at a specific locus. For example, a first allele can occur on one chromosome, while a second allele occurs on a second homologous chromosome, e.g., as occurs for different chromosomes of a heterozygous individual, or between different homozygous or heterozygous individuals in a population. A "favorable allele" is the allele at a particular locus that confers, or contributes to, an agronomically desirable phenotype, e.g., resistance to MRCV, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease-prone plants. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele "positively" correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal region where a polymorphic nucleic acid, trait determinant, gene or marker is located. Thus, for example, a "gene locus" is a specific chromosome location in the genome of a species where a specific gene can be found.

The term "quantitative trait locus" or "QTL" refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

The terms "marker", "molecular marker", "marker nucleic acid", and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele", alternatively an "allele of a marker locus", is one of a plurality of polymorphic nucleotide sequences found at a marker locus in a population that is polymorphic for the marker locus. In some aspects, the present invention provides marker loci correlating with resistance to MRCV in maize. Each of the identified markers is expected to be in close physical and genetic proximity (resulting in physical and/or genetic linkage) to a genetic element, e.g., a QTL, that contributes to resistance.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes.

Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

As used herein, the term "linkage" is used to describe the degree with which one marker locus is "associated with" another marker locus or some other locus (for example, a resistance locus).

As used herein, "linkage equilibrium" describes a situation where two markers independently segregate, i.e., sort among progeny randomly. Markers that show linkage equilibrium are considered unlinked (whether or not they lie on the same chromosome).

As used herein, "linkage disequilibrium" describes a situation where two markers segregate in a non-random manner, i.e., have a recombination frequency of less than 50% (and by definition, are separated by less than 50 cM on the same linkage group). Markers that show linkage disequilibrium are considered linked. Linkage occurs when the marker locus and a linked locus are found together in progeny plants more frequently than not together in the progeny plants. As used herein, linkage can be between two markers, or alternatively between a marker and a phenotype. A marker locus can be associated with (linked to) a trait, e.g., a marker locus can be associated with newly conferred resistance or enhanced resistance to a plant pathogen when the marker locus is in linkage disequilibrium with the resistance trait. The degree of linkage of a molecular marker to a phenotypic trait is measured, e.g., as a statistical probability of co-segregation of that molecular marker with the phenotype.

As used herein, the linkage relationship between a molecular marker and a phenotype is given as a "probability" or "adjusted probability". The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p=0.5). For example, a significant probability can be less than 0.25, less than 0.20, less than 0.15, or less than 0.1.

The term "physically linked" is sometimes used to indicate that two loci, e.g., two marker loci, are physically present on the same chromosome.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic resistance). For example, in some aspects, these markers can be termed linked QTL markers. In other aspects, especially useful molecular markers are those markers that are linked or closely linked.

In some aspects, linkage can be expressed as any desired limit or range. For example, in some embodiments, two linked loci are two loci that are separated by less than 50 cM map units. In other embodiments, linked loci are two loci that are separated by less than 40 cM. In other embodiments, two linked loci are two loci that are separated by less than 30 cM. In other embodiments, two linked loci are two loci that are separated by less than 25 cM. In other embodiments, two linked loci are two loci that are separated by less than 20 cM. In other embodiments, two linked loci are two loci that are separated by less than 15 cM. In some aspects, it is advantageous to define a bracketed range of linkage, for example, between 10 and 20 cM, or between 10 and 30 cM, or between 10 and 40 cM.

The more closely a marker is linked to a second locus, the better an indicator for the second locus that marker becomes. Thus, in one embodiment, closely linked loci such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited.

In some aspects, for example in the context of the present invention, generally the genetic elements located within a single chromosome interval are also genetically linked, typically within a genetic recombination distance of, for example, less than or equal to 20 cM, or alternatively, less than or equal to 10 cM. That is, two genetic elements within a single chromosome interval undergo recombination at a frequency of less than or equal to 20% or 10%.

In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The phrase "disease caused by Mal de Río Cuarto Virus" or "disease caused by MRCV" refers to the plant disease caused by an infection of the plant with MRCV.

"Newly conferred resistance" or "enhanced resistance" in a maize plant to MRCV is an indication that the maize plant is less affected with respect to yield and/or survivability or other relevant agronomic measures, upon introduction of the causative agents of that disease. Resistance is a relative term, indicating that the infected plant produces better yield of maize than another, similarly treated, more susceptible plant. That is, the conditions cause a reduced decrease in maize survival and/or yield in a resistant maize plant, as compared to a susceptible maize plant.

One of skill will appreciate that maize plant resistance to MRCV varies widely, can represent a spectrum of more resistant or less resistant phenotypes, and can vary depending on the severity of the infection. However, by simple observation, one of skill can determine the relative resistance or susceptibility of different plants, plant lines or plant families to MRCV, and furthermore, will also recognize the phenotypic gradations of "resistant" (an exemplary scoring system is presented in Example 7 below). As used in the art, "resistance" is sometimes referred to as "general resistance", "rate-reducing resistance", or "partial resistance".

The term "crossed" or "cross" in the context of this invention means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and it's parents, grand parents, great-grand parents, etc.

An "elite line" or "elite strain" is an agronomically superior line that has resulted from many cycles of breeding and selection for superior agronomic performance. Numerous elite lines are available and known to those of skill in the art of maize breeding. An "elite population" is an assortment of elite individuals or lines that can be used to represent the state of the art in terms of agronomically superior genotypes of a given crop species, such as maize. Similarly, an "elite germplasm" or elite strain of germplasm is an agronomically superior germplasm, typically derived from and/or capable of giving rise to a plant with superior agronomic performance, such as an existing or newly developed elite line of maize.

In contrast, an "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, or enhancer regions) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

An "exogenous nucleic acid" is a nucleic acid that is not native to a specified system (e.g., a germplasm, plant, or variety), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" in reference to a nucleic acid or polypeptide indicates that the material (e.g., a recombinant nucleic acid, gene, polynucleotide, or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from its natural context and cloned into any type of artificial nucleic acid vector. Protocols and reagents to produce recombinant molecules, especially recombinant nucleic acids, are common and routine in the art. In one embodiment, an artificial chromosome can be created and inserted into maize plants by any method known in the art (e.g., direct transfer processes, such as, e.g., PEG-induced DNA uptake, protoplast fusion, microinjection, electroporation, and microprojectile bombardment). An artificial chromosome is a piece of DNA that can stably replicate and segregate alongside endogenous chromosomes. It has the capacity to accommodate and express heterologous genes inserted therein. Integration of heterologous DNA into the megareplicator region (primary replication initiation site of centromeres) or in close proximity thereto, initiates a large-scale amplification of megabase-size chromosomal segments, which leads to de novo chromosome formation. See, e.g., U.S. Pat. No. 6,077,697, incorporated herein by reference.

The term recombinant can also refer to an organism that harbors recombinant material, e.g., a plant that comprises a recombinant nucleic acid is considered a recombinant plant. In some embodiments, a recombinant organism is a transgenic organism.

The term "introduced" when referring to translocating a heterologous or exogenous nucleic acid into a cell refers to the incorporation of the nucleic acid into the cell using any methodology. The term encompasses such nucleic acid introduction methods as "transfection", "transformation", and "transduction".

As used herein, the term "vector" is used in reference to polynucleotide or other molecules that transfer nucleic acid segment(s) into a cell. The term "vehicle" is sometimes used interchangeably with "vector". A vector optionally comprises parts which mediate vector maintenance and enable its intended use (e.g., sequences necessary for replication, genes imparting drug or antibiotic resistance, a multiple cloning site, or operably linked promoter/enhancer elements which enable the expression of a cloned gene). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Positional cloning" is a cloning procedure in which a target nucleic acid is identified and isolated by its genomic proximity to marker nucleic acid. For example, a genomic nucleic acid clone can include part or all of two more chromosomal regions that are proximal to one another. If a marker can be used to identify the genomic nucleic acid clone from a genomic library, standard methods such as subcloning or sequencing can be used to identify and/or isolate subsequences of the clone that are located near the marker.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

The term "genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome segment.

The terms "phenotype", or "phenotypic trait" or "trait" refers to one or more trait of an organism. The phenotype can be observable to the naked eye, or by any other means of evaluation known in the art, e.g., microscopy, biochemical analysis, genomic analysis, or an assay for a particular disease resistance. In some cases, a phenotype is directly controlled by a single gene or genetic locus, i.e., a "single gene trait". In other cases, a phenotype is the result of several genes.

A "molecular phenotype" is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

A "set" of markers or probes refers to a collection or group of markers or probes, or the data derived therefrom, used for a common purpose, e.g., identifying maize plants with a desired trait (e.g., resistance to MRCV). Frequently, data corresponding to the markers or probes, or data derived from their use, is stored in an electronic medium. While each of the members of a set possess utility with respect to the specified purpose, individual markers selected from the set as well as subsets including some, but not all, of the markers are also effective in achieving the specified purpose.

A "look up table" is a table that correlates one form of data to another, or one or more forms of data with a predicted outcome that the data is relevant to. For example, a look up table can include a correlation between allele data and a predicted trait that a plant comprising a given allele is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM, RAM, or flash memory), optical storage media (e.g., CD-ROM), magnetic storage media (computer hard drives, floppy disks, etc.), punch cards, and many others that are commercially available. Information can be transmitted between a system of interest and the computer, or to or from the computer and the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

BRIEF DESCRIPTION OF THE DRAWINGS AND SEQUENCES

FIG. 1A shows a structured association analysis of an Argentinean group. Note: significant region (p-value: less than 0.00005) from position 65.99 to 85.84. X axis: Distance expressed on cM from the extreme of Chr 2. Y axis: probability value. FIG. 1B shows a structured association analysis for an SS group. Note: main significant marker at MRCV1, MZA1525 at position 54.62 and MZA11826 at position 65.99. X axis: Distance expressed on cM from the extreme of chromosome 2. Y axis: probability value. FIG. 1C shows a structured association analysis for another SS group. Note: The highest associated marker on the short arm of chromosome 2 was MZA12899 at position 53.83 (p=0.000298). X axis: Distance expressed on cM from the extreme of chromosome 2. Y axis: probability value.

FIG. 2 shows an interval mapping for the PH3DT×PH7WT cross. Chromosome 2, LOD score peak: position 65.89, 46% of phenotypic variation.

FIG. 3A shows a graphic of genotypes at the QTL region and averaged phenotypes (MRCVSC) for a group of recombinants of the high resolution mapping BC5F3 population from the cross PH3DT×PH7WT. The piece of the resistant parent into the susceptible background and the region of recombination is shown. The region includes the recombinants located between MZA1525-98-A and MZA10094-9-A. FIG. 3B shows a graphic of genotypes at the QTL region and averaged phenotypes (MRCVSC) for a group of recombinants of the high resolution mapping BC5F3 population from the cross PH3DT×PH7WT. The piece of the resistant parent into the susceptible background and the region of recombination is shown. The region includes the recombinants located between MZA15490 and MZA18224. It also includes three recombinants in the interval MZA11826 to MZA9105 genetically characterized. Phenotype is indicated by the circles at the right of the graphic (black circles: susceptible; white circles: resistant; diagonal lined circle: mix of resistant and susceptible; gray circles: unknown).

FIG. 4 shows an interval mapping for the PH3DT×PH7WT cross. Chromosome 2, LOD score peak: position 65.99 (MZA2038). MZA11826 and MZA9105 were not included in the analysis because there were not recombinants respects to MZA2038 in this specific population. Note: the genetic map was adapted to permit interval mapping at 65.99 position; markers MZA16656, MZA15490 and MZA2038 are highly linked on distances below 0.5 cM, but they were artificially positioned at distances of 0.5 cM for this specific analysis.

FIG. 5 shows an interval mapping analysis for the PH9TJ× PH890 cross on specific QTL regions on Chr 2 and Chr 5. Chromosome 2, LOD score peak: position 65.99-68.8. There were no recombinants between the preferred markers and markers at position 68.8; thus, only MZA9105 was included as representative of preferred markers for this analysis.

Figure 8:
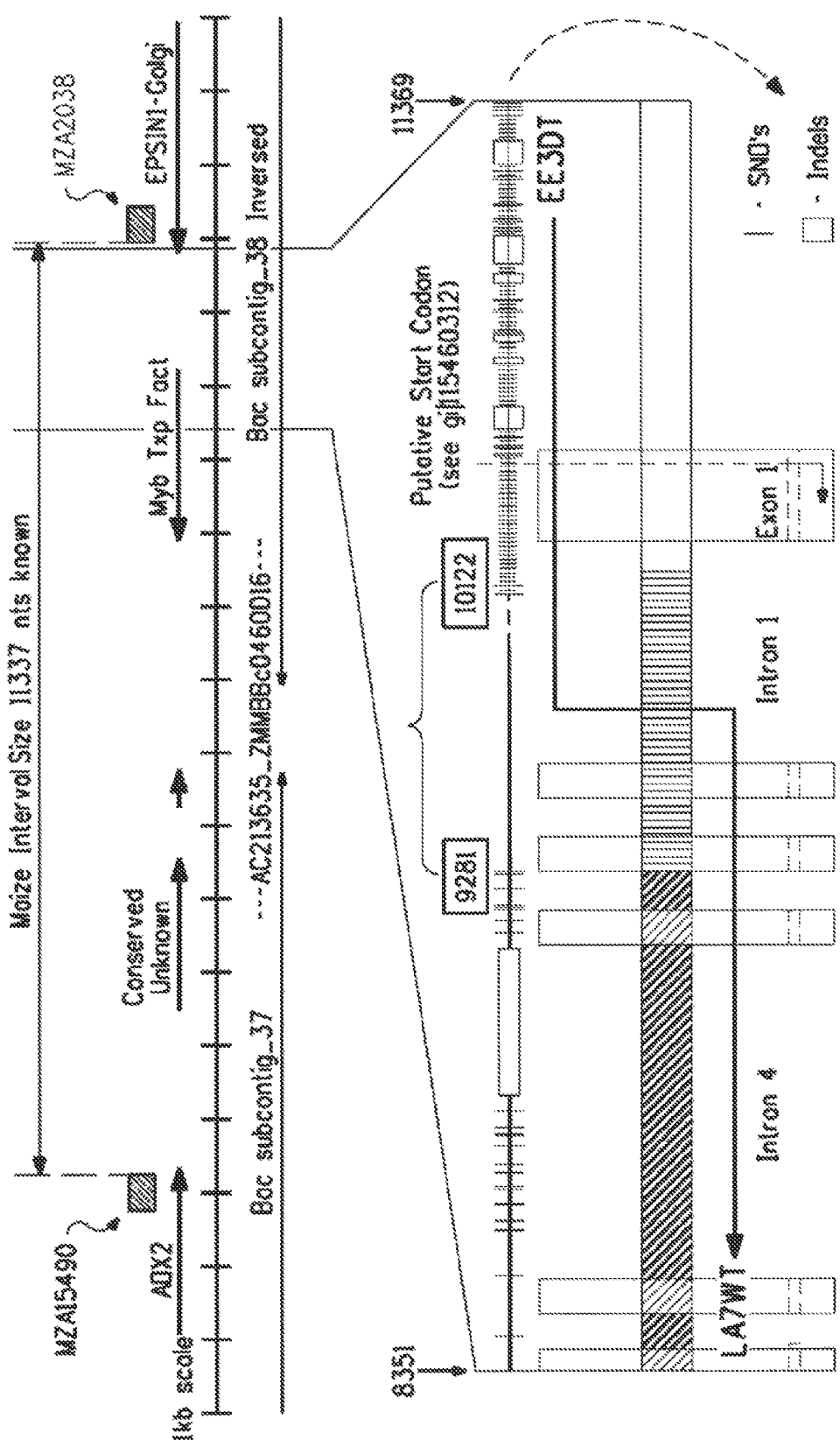

FIG. 8 shows a graphic description of a recombinant at the MZA15490 to MZA2038 interval. The point of recombination was located inside PCO644442, generating a quimeric gene from resistant (PH7WT) and susceptible (PH3DT) parents. The position of SNPs and indels is indicated in the sequenced region.

Figure 9:
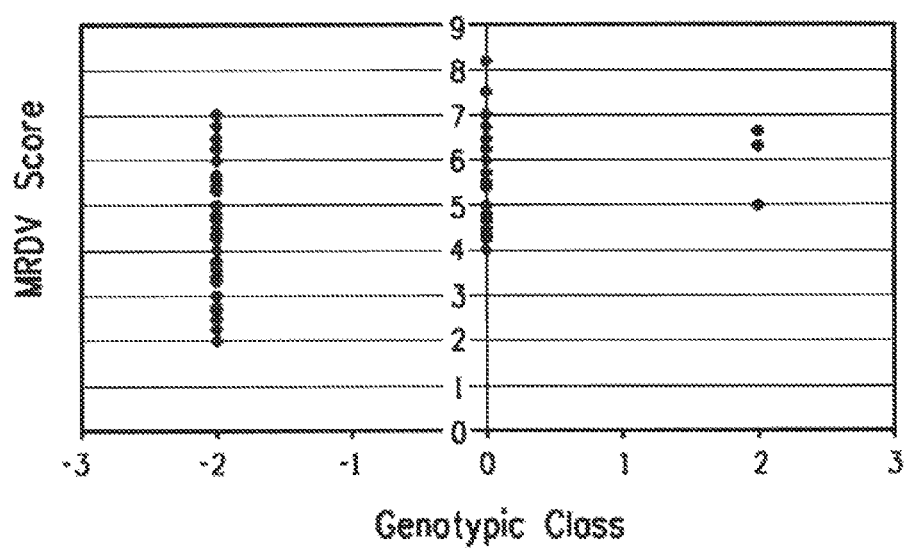

FIG. 9 shows the performance (MRDV score) of maize hybrids under MRDV infection across genotypic classes for the region of preferred markers. "−2", "0" and "2" in the X coordinate (genotypic class) represent the genotypic classes of susceptible haplotype, heterozygous haplotype and homozygous resistant haplotype, respectively.

Figure 10:
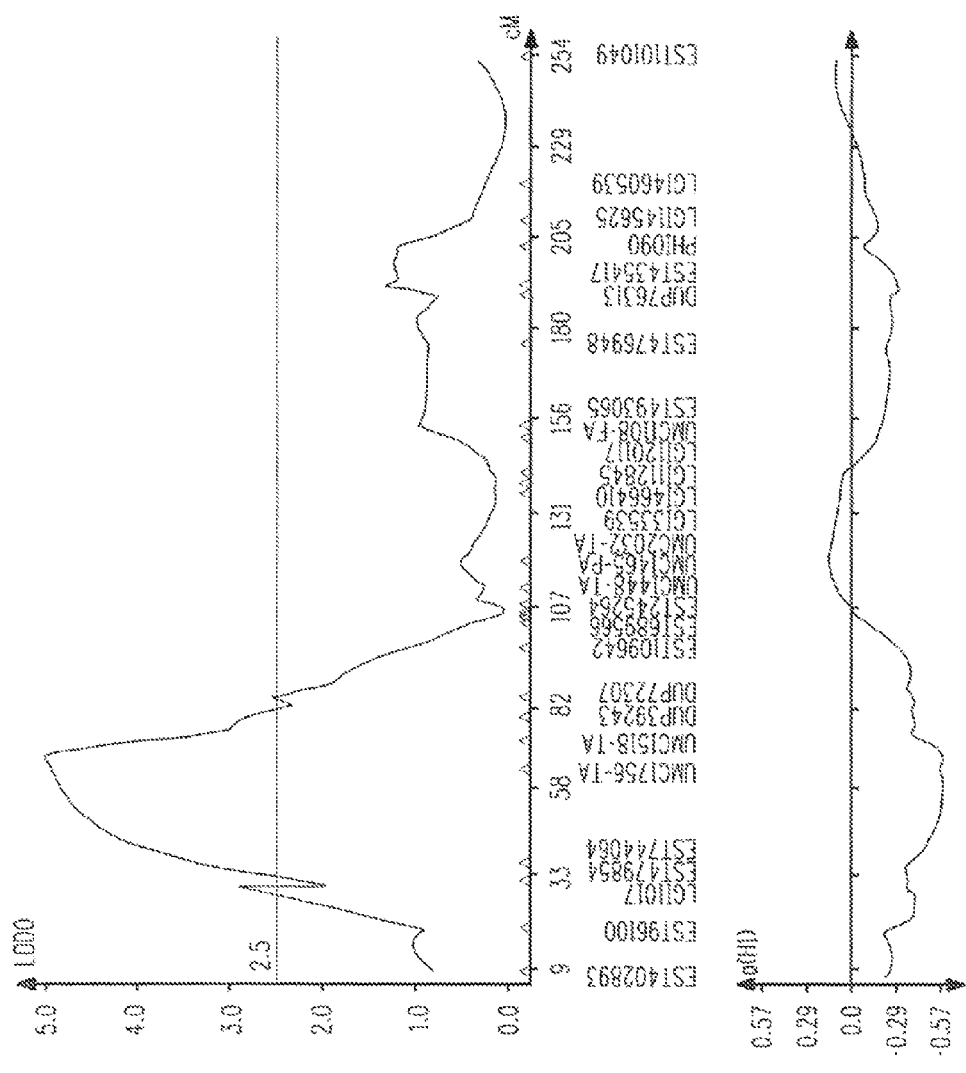

FIG. 10 is an interval map of mean phenotypic scores across three crop seasons for the PH7WT×PH3DT mapping population. Note that the LOD score peak is close to umc1756.

Figure 11:
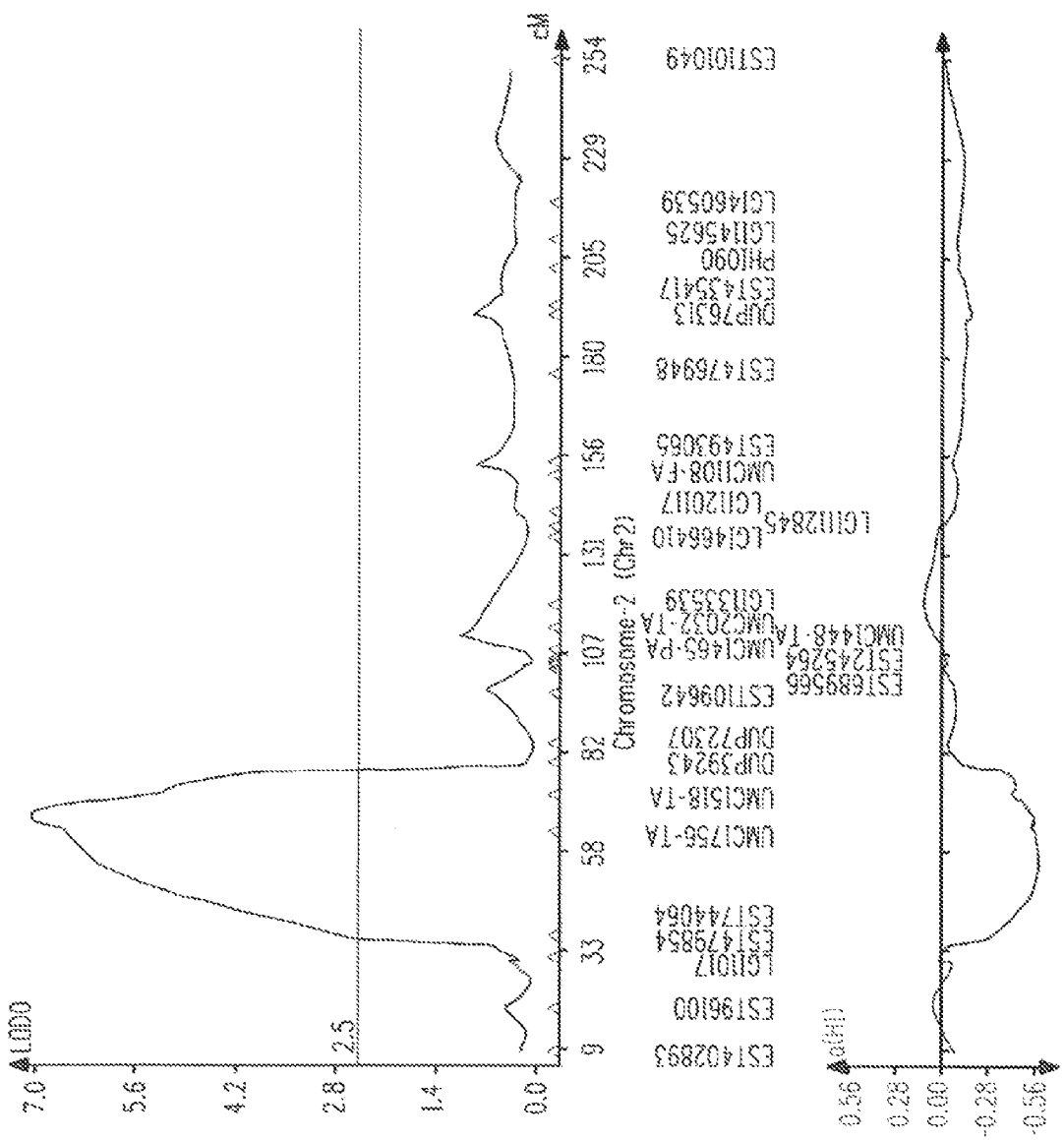

FIG. 11 is a composite interval map of mean phenotypic scores across three crop seasons for the PH7WT×PH3DT mapping population. Note that the LOD score peak is close to the umc1756-umc1518 interval.

Figure 12:
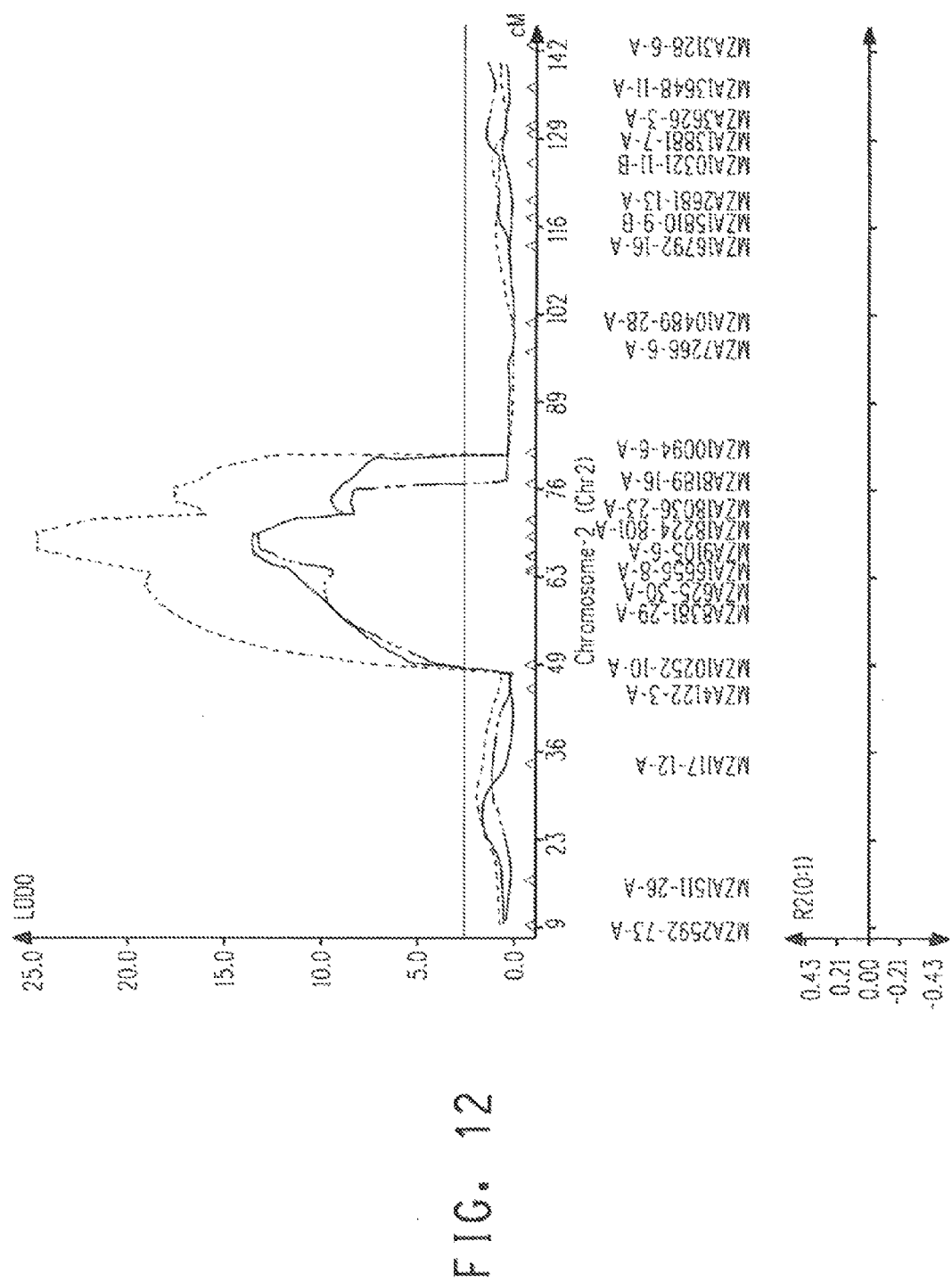

FIG. 12 is a composite interval map of the PH9TJ×PH890 mapping population. The LOD score peak for the MRCV1 QTL was located at position 65.99-68.8.

FIGS. 13A-C show a ClustalW sequence alignment between SEQ ID NO:211 (pco644442 promoter from PH7WT) and SEQ ID NO:212 (pco644442 promoter from PH3DT).

The following sequence descriptions summarize the Sequence Listing attached hereto. The Sequence Listing contains one letter codes for nucleotide sequence characters and the single and three letter codes for amino acids as defined in the IUPAC-IUB standards described in Nucleic Acids Research 13:3021-3030 (1985) and in the Biochemical Journal 219(2):345-373 (1984).

SEQ ID NOs: 1-5, 8-11, 14, 15, 18, 21, 25, 29, 30, 32, 34-37, 39, and 42-48 are consensus sequences for the MZA markers found in Table 6.

SEQ ID NOs: 6, 7, 12, 13, 16, 17, 19, 20, 22-24, 26-28, 31, 33, 38, 40, and 41 are SNP consensus sequences for the SNP markers found in Table 7.

SEQ ID NOs: 49-56 are left and right primer sequences for the public markers found in Table 3.

SEQ ID NOs: 57-172 are forward external, forward internal, reverse internal, and reverse external primers for the MZA markers found in Table 6.

SEQ ID NOs: 173-210 are forward and reverse primers for the SNP markers found in Table 7.

SEQ ID NO:211 is the PCO644442 promoter region of maize inbred line PH7WT.

SEQ ID NO:212 is the PCO644442 promoter region of maize inbred line PH3DT.

SEQ ID NO:213 is the sequence region including MRQV_08351 and MRQV_10673 for maize inbred line PH3DT.

SEQ ID NO:214 is the sequence region including MRQV_08351 and MRQV_10673 for maize inbred line AP19506160.

SEQ ID NO:215 is the sequence region including MRQV_08351 and MRQV_10673 for maize inbred line AP19506157.

SEQ ID NO:216 is the sequence region including MRQV_08351 and MRQV_10673 for maize inbred line AP19506156.

SEQ ID NO:217 is the sequence region including MRQV_08351 and MRQV_10673 for maize inbred line PH7WT.

SEQ ID NO:218 is the sequence region including MRQV_08351 and MRQV_10673 for maize inbred line 630.

SEQ ID NO:219 is the sequence region including MRQV_08351 and MRQV_10673 for maize inbred line PHG63.

SEQ ID NO:220 is the sequence region including MRQV_08351 and MRQV_10673 for maize inbred line PHK09.

SEQ ID NO:221 is the sequence region including MRQV_08351 and MRQV_10673 for maize inbred line PHR33.

SEQ ID NO:222 is the sequence region including MRQV_08351 and MRQV_10673 for maize inbred line 501.

SEQ ID NO:223 is the sequence region including MRQV_08351 and MRQV_10673 for maize inbred line 157.

SEQ ID NO:224 is the sequence region including MRQV_08351 and MRQV_10673 for maize inbred line PHK56.

SEQ ID NO:225 is the sequence region including MRQV_08351 and MRQV_10673 for maize inbred line 661.

SEQ ID NO:226 is the sequence region including MRQV_08351 and MRQV_10673 for maize inbred line PHR03.

SEQ ID NO:227 is the sequence region including MRQV_08351 and MRQV_10673 for maize inbred line 1047.

SEQ ID NO:228 is the sequence region including MRQV_08351 and MRQV_10673 for maize inbred line PHJ40.

SEQ ID NO:229 is the sequence region including MRQV_08351 and MRQV_10673 for maize inbred line 274.

SEQ ID NO:230 is the sequence region including MRQV_08351 and MRQV_10673 for maize inbred line 165.

SEQ ID NO:231 is the sequence region including MRQV_08351 and MRQV_10673 for maize inbred line B73.

SEQ ID NO:232 is the sequence region including MRQV_08351 and MRQV_10673 for maize inbred line PHN47.

SEQ ID NO:233 is the sequence region including MRQV_08351 and MRQV_10673 for maize inbred line PH26N.

SEQ ID NO:234 is the sequence region including MRQV_08351 and MRQV_10673 for maize inbred line PHDG9.

SEQ ID NO:235 is the sequence region including MRQV_08351 and MRQV_10673 for maize inbred line ST10H60.

SEQ ID NO:236 is the sequence region including MRQV_08351 and MRQV_10673 for maize inbred line PHKP5.

SEQ ID NO:237 represents an allelic variation of SEQ ID NO:26.

DETAILED DESCRIPTION OF THE INVENTION

The identification and selection of maize plants that show resistance to MRCV using MAS can provide an effective and environmentally friendly approach to overcoming losses caused by this disease. The present invention provides maize marker loci that demonstrate statistically significant co-segregation with MRCV resistance. Detection of these loci or additional linked loci can be used in marker assisted maize breeding programs to produce resistant plants, or plants with improved resistance to MRCV or a related fijivirus. The linked SSR and SNP markers identified herein are provided in Tables 1 and 2. These markers include MZA625, MZA16656, MZA15451, MZA15490, MZA2038, MZA11826, and MZA9105.

Each of the SSR-type markers display a plurality of alleles that can be visualized as different sized PCR amplicons. The PCR primers that are used to generate the SSR-marker amplicons are provided in Table 3. The alleles of SNP-type markersare determined using an allele-specific hybridization protocol, as known in the art. The PCR primers used to amplify the SNP domain, and the allele-specific probes used to genotype the locus, are provided in Tables 6 and 7.

TABLE 6

MZA primers

| MZA Marker | Forward/external | Forward/internal | Reverse/internal | Reverse/external | MZA consensus |
|---|---|---|---|---|---|
| MZA7588 | SEQ ID NO: 57 | SEQ ID NO: 58 | SEQ ID NO: 59 | SEQ ID NO: 60 | SEQ ID NO: 1 |
| MZA8381 | SEQ ID NO: 61 | SEQ ID NO: 62 | SEQ ID NO: 63 | SEQ ID NO: 64 | SEQ ID NO: 2 |
| MZA3105 | SEQ ID NO: 65 | SEQ ID NO: 66 | SEQ ID NO: 67 | SEQ ID NO: 68 | SEQ ID NO: 3 |
| MZA482 | SEQ ID NO: 69 | SEQ ID NO: 70 | SEQ ID NO: 71 | SEQ ID NO: 72 | SEQ ID NO: 4 |
| MZA16531 | SEQ ID NO: 73 | SEQ ID NO: 74 | SEQ ID NO: 75 | SEQ ID NO: 76 | SEQ ID NO: 5 |
| MZA625 | SEQ ID NO: 77 | SEQ ID NO: 78 | SEQ ID NO: 79 | SEQ ID NO: 80 | SEQ ID NO: 8 |
| MZA4305 | SEQ ID NO: 81 | SEQ ID NO: 82 | SEQ ID NO: 83 | SEQ ID NO: 84 | SEQ ID NO: 9 |
| MZA14553 | SEQ ID NO: 85 | SEQ ID NO: 86 | SEQ ID NO: 87 | SEQ ID NO: 88 | SEQ ID NO: 10 |
| MZA15451 | SEQ ID NO: 89 | SEQ ID NO: 90 | SEQ ID NO: 91 | SEQ ID NO: 92 | SEQ ID NO: 11 |
| MZA9105 | SEQ ID NO: 93 | SEQ ID NO: 94 | SEQ ID NO: 95 | SEQ ID NO: 96 | SEQ ID NO: 14 |
| MZA2803 | SEQ ID NO: 97 | SEQ ID NO: 98 | SEQ ID NO: 99 | SEQ ID NO: 100 | SEQ ID NO: 15 |
| MZA2038 | SEQ ID NO: 101 | SEQ ID NO: 102 | SEQ ID NO: 103 | SEQ ID NO: 104 | SEQ ID NO: 18 |
| MZA16656 | SEQ ID NO: 105 | SEQ ID NO: 106 | SEQ ID NO: 107 | SEQ ID NO: 108 | SEQ ID NO: 21 |
| MZA15490 | SEQ ID NO: 109 | SEQ ID NO: 110 | SEQ ID NO: 111 | SEQ ID NO: 112 | SEQ ID NO: 25 |
| MZA11826 | SEQ ID NO: 113 | SEQ ID NO: 114 | SEQ ID NO: 115 | SEQ ID NO: 116 | SEQ ID NO: 29 |
| MZA564 | SEQ ID NO: 117 | SEQ ID NO: 118 | SEQ ID NO: 119 | SEQ ID NO: 120 | SEQ ID NO: 30 |
| MZA2349 | SEQ ID NO: 121 | SEQ ID NO: 122 | SEQ ID NO: 123 | SEQ ID NO: 124 | SEQ ID NO: 32 |
| MZA18224 | SEQ ID NO: 125 | SEQ ID NO: 126 | SEQ ID NO: 127 | SEQ ID NO: 128 | SEQ ID NO: 34 |
| MZA11066 | SEQ ID NO: 129 | SEQ ID NO: 130 | SEQ ID NO: 131 | SEQ ID NO: 132 | SEQ ID NO: 35 |
| MZA18180 | SEQ ID NO: 133 | SEQ ID NO: 134 | SEQ ID NO: 135 | SEQ ID NO: 136 | SEQ ID NO: 36 |
| MZA8442 | SEQ ID NO: 137 | SEQ ID NO: 138 | SEQ ID NO: 139 | SEQ ID NO: 140 | SEQ ID NO: 37 |
| MZA15563 | SEQ ID NO: 141 | SEQ ID NO: 142 | SEQ ID NO: 143 | SEQ ID NO: 144 | SEQ ID NO: 39 |
| MZA18036 | SEQ ID NO: 145 | SEQ ID NO: 146 | SEQ ID NO: 147 | SEQ ID NO: 148 | SEQ ID NO: 42 |
| MZA15264 | SEQ ID NO: 149 | SEQ ID NO: 150 | SEQ ID NO: 151 | SEQ ID NO: 152 | SEQ ID NO: 43 |
| MZA10384 | SEQ ID NO: 153 | SEQ ID NO: 154 | SEQ ID NO: 155 | SEQ ID NO: 156 | SEQ ID NO: 44 |
| MZA12874 | SEQ ID NO: 157 | SEQ ID NO: 158 | SEQ ID NO: 159 | SEQ ID NO: 160 | SEQ ID NO: 45 |
| MZA12454 | SEQ ID NO: 161 | SEQ ID NO: 162 | SEQ ID NO: 163 | SEQ ID NO: 164 | SEQ ID NO: 46 |
| MZA8926 | SEQ ID NO: 165 | SEQ ID NO: 166 | SEQ ID NO: 167 | SEQ ID NO: 168 | SEQ ID NO: 47 |
| MZA5057 | SEQ ID NO: 169 | SEQ ID NO: 170 | SEQ ID NO: 171 | SEQ ID NO: 172 | SEQ ID NO: 48 |

TABLE 7

| | SNP primers | | SNP alleles | |
|---|---|---|---|---|
| SNP Marker | Forward | Reverse | SNP | SNP consensus |
| MZA625-30-A | SEQ ID NO: 173 | SEQ ID NO: 174 | T/C | SEQ ID NO: 7 (SNP at position 186) |
| MZA625-29-A | SEQ ID NO: 175 | SEQ ID NO: 176 | T/C | SEQ ID NO: 7 (SNP at position 165) |
| MZA9105-8-A | SEQ ID NO: 177 | SEQ ID NO: 178 | G/A | SEQ ID NO: 12 (SNP at position 123) |
| MZA9105-6-A | SEQ ID NO: 179 | SEQ ID NO: 180 | G/A | SEQ ID NO: 13 (SNP at position 98) |
| MZA2038-76-A | SEQ ID NO: 181 | SEQ ID NO: 182 | T/C | SEQ ID NO: 16 (SNP at position 277) |
| MZA2038-71-A | SEQ ID NO: 183 | SEQ ID NO: 184 | T/A | SEQ ID NO: 17 (SNP at position 258) |
| MZA16656-8-A | SEQ ID NO: 185 | SEQ ID NO: 186 | T/C | SEQ ID NO: 19 (SNP at position 85) |
| MZA16656-19-A | SEQ ID NO: 187 | SEQ ID NO: 188 | G/A | SEQ ID NO: 20 (SNP at position 218) |
| MZA15490-801-A | SEQ ID NO: 189 | SEQ ID NO: 190 | G/C | SEQ ID NO: 22 (SNP at position 96) |
| MZA15490-138-A | SEQ ID NO: 191 | SEQ ID NO: 192 | G/C | SEQ ID NO: 23 (SNP at position 96) |
| MZA15490-137-A | SEQ ID NO: 193 | SEQ ID NO: 194 | C/A | SEQ ID NO: 24 (SNP at position 84) |
| MZA11826-803-A | SEQ ID NO: 195 | SEQ ID NO: 196 | C/T | SEQ ID NO: 27 (SNP at position 714) |
| MZA11826-801-A | SEQ ID NO: 197 | SEQ ID NO: 198 | A/G | SEQ ID NO: 26 (SNP at position 89) |
| MZA11826-27-A | SEQ ID NO: 199 | SEQ ID NO: 200 | T/C | SEQ ID NO: 28 (SNP at position 222) |
| MZA2349-71-A | SEQ ID NO: 201 | SEQ ID NO: 202 | T/C | SEQ ID NO: 31 (SNP at position 133) |
| MZA18224-801-A | SEQ ID NO: 203 | SEQ ID NO: 204 | A/G | SEQ ID NO: 33 (SNP at position 188) |
| MZA15563-12-A | SEQ ID NO: 205 | SEQ ID NO: 206 | T/A | SEQ ID NO: 38 (SNP at position 601) |
| MZA18036-9-A | SEQ ID NO: 207 | SEQ ID NO: 208 | A/G | SEQ ID NO: 40 (SNP at position 90) |
| MZA18036-23-A | SEQ ID NO: 209 | SEQ ID NO: 210 | A/G | SEQ ID NO: 41 (SNP at position 285) |

Tables 6 and 7 list the SNP markers that demonstrated linkage disequilibrium with the MRCV resistance phenotype. These tables provide the sequences of the PCR primers used to generate a SNP-containing amplicon, and the allele-specific probes that were used to identify the SNP allele in an allele-specific hybridization assay (ASH assay).

As recognized in the art, any other marker that is linked to a QTL marker (e.g., a disease resistance marker) also finds use for that same purpose. Examples of additional markers that are linked to the disease resistance markers recited herein are provided. For example, a linked marker can be determined from the closely linked markers provided in Table 8.

TABLE 8

| Linked Markers |
|---|
| pco061820a, pco116928a, sog0930a, pco102443, sog5467ac, cl7211_1l, k4-14p, pco135612a, pco101521, si687005h09c, si707023g07c, cl15901_1a, pco134907, si660032f12i, cl7048_1b, cl2578_1, cl5312_1a, pco094715, sog5829a, cl30_1e, pco125905, sog0690, cl36282_1b, pco118508, gpm636, pco066747a, pco083425q, sog5844av, bnlg1458b, si606065e12a, cl22018_1, pco091058, si946053g10, sog1265, sog0743c, cl9862_1, pco114887, bnlg1327, sog5587a, cl1488_-4a, pco085208a, sog1295c, sog5609b, sog0912a, tel7sc1ah, si66060d11b, cl10933_1d, cl37019_1a, sog1856ae, pco117007l, cl40761_1a, siaf099388e, pco137067a, sog2274m, |

TABLE 8-continued Linked Markers cl31185_3a, pco098939a, pco151039r, cl11825_1a, pco122145b, cl24291_1a, si618065b03a, si707029g03a, sog1495a, IDP4006, umc1262a, umc1261a, sog5758o It is not intended, however, that linked markers finding use with the invention be limited to those recited in Table 8.

The invention also provides chromosomal QTL intervals that correlate with MRCV resistance. These intervals are located on linkage group 2. Any marker located within these intervals finds use as a marker for MRCV resistance. These intervals include:

(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a.

Methods for identifying maize plants or germplasm that carry preferred alleles of resistance marker loci are a feature of the invention. In these methods, any of a variety of marker detection protocols are used to identify marker loci, depending on the type of marker loci. Typical methods for marker detection include amplification and detection of the resulting amplified markers, e.g., by PCR, LCR, transcription based amplification methods, or the like. These include ASH, SSR detection, RFLP analysis and many others.

Although particular marker alleles can show co-segregation with a disease resistance or susceptibility phenotype, it is important to note that the marker locus is not necessarily part of the QTL locus responsible for the resistance or susceptibility. For example, it is not a requirement that the marker polynucleotide sequence be part of a gene that imparts disease resistance (for example, be part of the gene open reading frame). The association between a specific marker allele with the resistance or susceptibility phenotype is due to the original "coupling" linkage phase between the marker allele and the QTL resistance or susceptibility allele in the ancestral maize line from which the resistance or susceptibility allele originated. Eventually, with repeated recombination, crossing over events between the marker and QTL locus can change this orientation. For this reason, the favorable marker allele may change depending on the linkage phase that exists within the resistant parent used to create segregating populations. This does not change the fact that the genetic marker can be used to monitor segregation of the phenotype. It only changes which marker allele is considered favorable in a given segregating population.

Identification of maize plants or germplasm that include a marker locus or marker loci linked to a resistance trait or traits provides a basis for performing marker assisted selection of maize. Maize plants that comprise favorable markers or favorable alleles are selected for, while maize plants that comprise markers or alleles that are negatively correlated with resistance can be selected against. Desired markers and/or alleles can be introgressed into maize having a desired (e.g., elite or exotic) genetic background to produce an introgressed resistant maize plant or germplasm. In some aspects, it is contemplated that a plurality of resistance markers are sequentially or simultaneous selected and/or introgressed. The combinations of resistance markers that are selected for in a single plant is not limited, and can include any combination of markers recited in Tables 1 and 2, any markers linked to the markers recited in Tables 1 and 2, or any markers located within the QTL intervals defined herein.

As an alternative to standard breeding methods of introducing traits of interest into maize (e.g., introgression), transgenic approaches can also be used. In these methods, exogenous nucleic acids that encode traits linked to markers are introduced into target plants or germplasm. For example, a nucleic acid that codes for a resistance trait is cloned, e.g., via positional cloning and introduced into a target plant or germplasm.

Verification of resistance can be performed by available resistance protocols (see, e.g., Example 10). Resistance assays are useful to verify that the resistance trait still segregates with the marker in any particular plant or population, and, of course, to measure the degree of resistance improvement achieved by introgressing or recombinantly introducing the trait into a desired background.

Systems, including automated systems for selecting plants that comprise a marker of interest and/or for correlating presence of the marker with resistance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Kits are also a feature of the invention. For example, a kit can include appropriate primers or probes for detecting resistance-associated marker loci and instructions in using the primers or probes for detecting the marker loci and correlating the loci with predicted MRCV resistance. The kits can further include packaging materials for packaging the probes, primers or instructions, controls such as control amplification reactions that include probes, primers or template nucleic acids for amplifications, molecular size markers, or the like.

Resistance Markers and Favorable Alleles

In traditional linkage analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked". The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside on the same chromosome. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in two genes segregating separately into progeny.

A common measure of linkage is the frequency with which traits cosegregate. This can be expressed as a percentage of cosegregation (recombination frequency) or, also commonly, in centiMorgans (cM). The cM is named after the pioneering geneticist Thomas Hunt Morgan and is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in maize, 1 cM correlates, on average, to about 2,140,000 base pairs (2.14 Mbp).

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation. The markers herein, as described in Tables 1 and 2, e.g., MZA625, MZA16656, MZA15451, MZA15490, MZA2038, MZA11826, and MZA9105, as well as any of the chromosome intervals
- (i) MZA8381 and MZA18180;
- (ii) MZA4305 and MZA2803;
- (iii) MZA15490 and MZA2038;
- (iv) bnlg1458b and umc1261a;
- (v) bnlg1458b and umc1262a;
- (vi) bnlg1327 and umc1261a; and
- (viii) bnlg1327 and umc1262a;

have been found to correlate with newly conferred resistance, enhanced resistance, or susceptibility to MRCV in maize. This means that the markers are sufficiently proximal to a resistance trait that they can be used as a predictor for the resistance trait. This is extremely useful in the context of marker assisted selection (MAS), discussed in more detail herein. In brief, maize plants or germplasm can be selected for markers or marker alleles that positively correlate with resistance, without actually raising maize and measuring for newly conferred resistance or enhanced resistance (or, contrarily, maize plants can be selected against if they possess markers that negatively correlate with newly conferred resistance or enhanced resistance). MAS is a powerful shortcut to selecting for desired phenotypes and for introgressing desired traits into cultivars of maize (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the most preferred QTL markers are a subset of the markers provided in Tables 1 and 2. For example, the most preferred markers are MZA15490 and MZA2038.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

A favorable allele of a marker is that allele of the marker that co-segregates with a desired phenotype (e.g., disease resistance). As used herein, a QTL marker has a minimum of one favorable allele, although it is possible that the marker might have two or more favorable alleles found in the population. Any favorable allele of that marker can be used advantageously for the identification and construction of resistant maize lines. Optionally, one, two, three or more favorable allele(s) of different markers are identified in, or introgressed into a plant, and can be selected for or against during MAS. Desirably, plants or germplasm are identified that have at least one such favorable allele that positively correlates with newly conferred or enhanced resistance.

Alternatively, a marker allele that co-segregates with disease susceptibility also finds use with the invention, since that allele can be used to identify and counter select disease-susceptible plants. Such an allele can be used for exclusionary purposes during breeding to identify alleles that negatively correlate with resistance, to eliminate susceptible plants or germplasm from subsequent rounds of breeding.

In some embodiments of the invention, a plurality of marker alleles are simultaneously selected for in a single plant or a population of plants. In these methods, plants are selected that contain favorable alleles from more than one resistance marker, or alternatively, favorable alleles from more than one resistance marker are introgressed into a desired maize germplasm. One of skill in the art recognizes that the simultaneous selection of favorable alleles from more than one disease resistance marker in the same plant is likely to result in an additive (or even synergistic) protective effect for the plant.

One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are routine and well known in the art, and furthermore, that the identification and use of such favorable alleles is well within the scope of the invention. Furthermore still, identification of favorable marker alleles in maize populations other than the populations used or described herein is well within the scope of the invention.

Amplification primers for amplifying SSR-type marker loci are a feature of the invention. Another feature of the invention is primers specific for the amplification of SNP domains (SNP markers), and the probes that are used to genotype the SNP sequences. Tables 6 and 7 provide specific primers for marker locus amplification and probes for detecting amplified marker loci. However, one of skill will immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the invention is not limited to the primers and probes specifically recited herein.

In some aspects, methods of the invention utilize an amplification step to detect/genotype a marker locus. However, it will be appreciated that amplification is not a requirement for marker detection—for example, one can directly detect unamplified genomic DNA simply by performing a Southern blot on a sample of genomic DNA. Procedures for performing Southern blotting, amplification (PCR, LCR, or the like) and many other nucleic acid detection methods are well established and are taught, e.g., in Sambrook et al., *Molecular Cloning—A Laboratory Manual* ($3^{rd}$ Ed.), Vol. 1-3, Cold Spring Harbor Laboratory, Cold Spring Harbor, N.Y., 2000

("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2002) ("Ausubel") and *PCR Protocols A Guide to Methods and Applications* (Innis et al. eds) Academic Press Inc. San Diego, Calif. (1990) ("Innis"). Additional details regarding detection of nucleic acids in plants can also be found, e.g., in *Plant Molecular Biology* (1993) Croy (ed.) BIOS Scientific Publishers, Inc. ("Croy").

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. While the exemplary markers provided in the figures and tables herein are either SSR or SNP (ASH) markers, any of the aforementioned marker types can be employed in the context of the invention to identify chromosome segments encompassing genetic element that contribute to superior agronomic performance (e.g., newly conferred resistance or enhanced resistance).

QTL Chromosome Intervals

In some aspects, the invention provides QTL chromosome intervals, where a QTL (or multiple QTL) that segregate with MRCV resistance are contained in those intervals. A variety of methods well known in the art are available for identifying chromosome intervals (also as described in detail in Examples 1 and 2). The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for disease resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

The present invention provides maize chromosome intervals, where the markers within that interval demonstrate co-segregation with resistance to MRCV. Thus, each of these intervals comprises at least one MRCV resistance QTL as shown in Table 9.

TABLE 9

| Flanking Markers | Method(s) of Identification |
|---|---|
| MZA8381 and MZA1810 | Association analysis, identity by descent |
| MZA4305 and MZA2803 | Association analysis, identity by descent |
| MZA15490 and MZA2038 | Association analysis, identity by descent |
| bnlg1458b and umc1261a | Linkage to a preferred marker |
| bnlg1458b and umc1262a | Linkage to a preferred marker |
| bnlg1327 and umc1261a | Linkage to a preferred marker |
| bnlg1327 and umc1262a | Linkage to a preferred marker |

Each of the intervals described above shows a clustering of markers that co-segregate with MRCV resistance. This clustering of markers occurs in relatively small domains on the linkage groups, indicating the presence of one or more QTL in those chromosome regions. QTL intervals were drawn to encompass the markers that co-segregate with resistance. The intervals are defined by the markers on their termini, where the interval encompasses all the markers that map within the interval as well as the markers that define the termini.

In some cases, an interval can be drawn where the interval is defined by linkage to a preferred marker. For example, an interval on chromosome 2 is defined where any marker that is linked to the marker MZA16656 is a member of that interval. For example, as used here, linkage is defined as any marker that is within 25 cM from MZA16656. This interval on chromosome 2 is further illustrated in Table 8. The markers that are linked to MZA16656 (e.g., within 5 cM of MZA16656) as determined by any suitable genetic linkage map (for example, the IBM2 2005 Neighbors Frame 2 map found on the MaizeGDB website). These markers are shown in genetic order. Each of the markers listed, including the terminal markers pco061820a and sog5758o, are members of the interval. The pco061820a and sog5758o markers are known in the art.

As described above, an interval (e.g., a chromosome interval or a QTL interval) need not depend on an absolute measure of interval size such as a centimorgans value. An interval can be described by the terminal markers that define the endpoints of the interval, and typically the interval will include the terminal markers that define the extent of the interval. An interval can include any marker localizing within that chromosome domain, whether those markers are currently known or unknown. The invention provides a variety of means for defining a chromosome interval, for example, in the lists of linked markers of Table 8, and in references cited herein.

Linked Markers

From the present disclosure and widely recognized in the art, it is clear that any genetic marker that has a significant probability of co-segregation with a phenotypic trait of interest (e.g., in the present case, a newly conferred resistance or enhanced resistance trait) can be used as a marker for that trait. A list of useful QTL markers provided by the present invention is provided in Tables 1 and 2.

In addition to the QTL markers noted in Tables 1 and 2, additional markers linked to (showing linkage disequilibrium with) the QTL markers can also be used to predict the newly conferred resistance or enhanced resistance trait in a maize plant. In other words, any other marker showing less than 50% recombination frequency (separated by a genetic distance less than 50 cM) with a QTL marker of the invention (e.g., the markers provided in Tables 1 and 2) is also a feature of the invention. Any marker that is linked to a QTL marker can also be used advantageously in marker-assisted selection for the particular trait.

Genetic markers that are linked to QTL markers (e.g., QTL markers provided in Tables 1 and 2) are particularly useful when they are sufficiently proximal (e.g., closely linked) to a given QTL marker so that the genetic marker and the QTL marker display a low recombination frequency. In the present invention, such closely linked markers are a feature of the invention. As defined herein, closely linked markers display a recombination frequency of about 10% or less (the given marker is within 10 cM of the QTL). Put another way, these closely linked loci co-segregate at least 90% of the time. Indeed, the closer a marker is to a QTL marker, the more effective and advantageous that marker becomes as an indicator for the desired trait.

Thus, in other embodiments, closely linked loci such as a QTL marker locus and a second locus display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

In some aspects, linked markers (including closely linked markers) of the invention are determined by review of a genetic map, for example, the integrated genetic maps found on the MaizeGDB website. For example, it is shown herein that the linkage group 2 markers MZA625, MZA16656, MZA15451, MZA15490, MZA2038, MZA11826, and MZA9105 correlate with at least one MRCV resistance QTL. Markers that are linked to MZA625, MZA16656, MZA15451, MZA15490, MZA2038, MZA11826, and MZA9105 can be determined from the list provided in Table 8 (see also Table 11, which shows Rice Locus and Working Maize Gene ID of genetic markers between MZA625 and MZA9105).

TABLE 11

| PHD Chr | PHD Map Pos | UC7 PCO Vs. Myriad Amplicons | Locus Order | Rice Locus | Working Maize Gene ID | Annotation Summary |
|---|---|---|---|---|---|---|
| 2 | 64.05 | MZA625 | Loc_029 | LOC_Os04g51320 | AC191302_5part | Transcription Factor |
| | | | Loc_028 | LOC_Os04g51310 | AC191302_3 | Putrescine-binding protein; Hypothetical protein |
| | | | Loc_027 | LOC_Os04g51300 | pco600856 | Putative L-ascorbate peroxidase |
| | | | Loc_025 | LOC_Os04g51280 | pco530474 | Plastid development protein; DAG |
| | | | Loc_024 | LOC_Os04g51270 | pco593067 | Hypothetical protein; Vacuolar ATP synthase subunit? |
| | | | Loc_023 | LOC_Os04g51260 | AC191302_6 | Hypothetical protein |
| | | | Loc_022 | LOC_Os04g51250 | Inferred by rice and sorghum | Hypothetical protein |
| | | | Loc_021 | LOC_Os04g51240 | pco641713 | Hypothetical protein |
| | | | Loc_016 | LOC_Os04g51190 | pco591841 | Growth regulating factor |
| | | | Loc_015 | LOC_Os04g51180 | Genomic_PCO622600_PCO666161 | G protein-coupled receptor 89C (Homo sapiens) |
| 2 | 65.99 | MZA166656 | Loc_014 | LOC_Os04g51172 | pco638426 | Major intrinsic protein; NIP; BREVIS RADIX like 1 |
| | | | Loc_013 | LOC_Os04g51166 | pco514627 | Hypothetical protein |
| 2 | 65.30 | MZA15451 | Loc_012 | LOC_Os04g51160 LOC_Os04g51150 | pco588936 | Alternative oxidase AOX3 |
| | | | Loc_010 | LOC_Os04g51140 | Inferred by rice and sorghum | Hypothetical protein |
| | | | Loc_009 | LOC_Os04g51130 | pco644442 | Myb-like; 2-component response regulator |
| 2 | 65.99 | MZA2038 | Loc_008 | LOC_Os04g51120 | pco641455 | Clathrin interactor; Epsin; Hypothetical protein |
| | | | Loc_007 | LOC_Os04g51110 | pco640541 | CDC20 WD-repeat protein |
| | | | Loc_006 | LOC_Os04g51100 | pco651091 | Cobalamin synthesis protein |
| | | | Loc_005 | LOC_Os04g51090 | pco571541 | Hypothetical protein |
| | | | Loc_004 | LOC_Os04g51080 | pco525409 | Scramblase |
| | | | Loc_003 | LOC_Os04g51070 | pco553755 | Hypothetical protein |
| | | | Loc_002 | LOC_Os04g51060 | pco644099 | Hypothetical protein |
| 2 | 65.44 | MZA9105 | Loc_001 | LOC_Os04g51050 | pco588179 | Receptor protein kinase |

For example, markers on linkage group 2 that are linked to MZA625, MZA16656, MZA15451, MZA15490, MZA2038, MZA11826, and MZA9105 include those listed in Table 12.

TABLE 12

| Marker | Map Position |
| --- | --- |
| pco061820a | 148.07 |
| pco116928a | 148.07 |
| sog0930a | 148.07 |
| pco102443 | 148.07 |
| pco133385a | 148.07 |
| sog5467ac | 148.07 |
| cl7211_1l | 148.08 |
| K4-14p | 148.08 |
| pco135612a | 148.08 |
| si687005h09c | 148.08 |
| si707023g07c | 148.08 |
| cl15901_1a | 148.08 |
| pco134907 | 148.08 |
| si660032f12i | 148.08 |
| cl7048_1b | 148.08 |
| cl2578_1 | 148.09 |
| cl5312_1a | 148.09 |
| pco094715 | 148.09 |
| sog5829a | 148.09 |
| cl30_1e | 148.09 |
| pco125905 | 148.09 |
| sog0690 | 148.09 |
| cl36282_1b | 148.09 |
| pco118508 | 148.09 |
| gpm636 | 148.09 |
| pco066747a | 148.09 |
| pco083425q | 148.09 |
| sog5844av | 148.09 |
| bnlg1458b | 148.09 |
| si606065e12a | 148.09 |
| cl22018_1 | 148.09 |
| pco091058 | 148.09 |
| si946053g10 | 148.10 |
| sog1265 | 148.10 |
| sog0743c | 148.10 |
| cl9862_1 | 148.10 |
| pco114887 | 148.10 |
| bnlg1327 | 148.10 |
| sog5587a | 148.10 |
| cl1488_-4a | 148.11 |
| pco085208a | 148.11 |
| sog1295c | 148.11 |
| sog5609b | 148.11 |
| sog0912a | 148.11 |
| tel7sc1ah | 148.11 |
| si660060d11b | 148.11 |
| cl10933_1d | 148.11 |
| cl37019_1a | 148.11 |
| sog1856ae | 148.11 |
| pco117007l | 148.11 |
| cl40761_1a | 148.11 |
| siaf099388e | 148.11 |
| pco137067a | 148.11 |
| sog2274m | 148.11 |
| cl31185_3a | 148.11 |
| pco098939a | 148.11 |
| pco150139r | 148.11 |
| cl11825_1a | 148.11 |
| pco122145b | 148.11 |
| cl24291_1a | 148.11 |
| si618065g03a | 148.11 |
| si707029g03a | 148.11 |
| sog1495a | 148.75 |
| umc1262a | 153.10 |
| umc1261a | 154.60 |
| sog5758o | 154.71 |

Similarly, linked markers (including closely linked markers) of the invention can be determined by review of any suitable maize genetic map. For example, integrated genetic maps can be found on the MaizeGDB website resource.

It is not intended that the determination of linked or closely linked markers be limited to the use of any particular maize genetic map. Indeed, a large number of maize genetic maps is available and are well known to one of skill in the art. Alternatively, the determination of linked and closely linked markers can be made by the generation of an experimental dataset and linkage analysis.

It is also not intended that the identification of markers that are linked (e.g., within about 50 cM or within about 10 cM) to the MRCV resistance QTL markers identified herein be limited to any particular map or methodology. The integrated genetic maps provided on the MaizeGDB website serve only as example for identifying linked markers. Indeed, linked markers as defined herein can be determined from any genetic map known in the art (an experimental map or an integrated map), or alternatively, can be determined from any new mapping dataset.

It is noted that lists of linked and closely linked markers may vary between maps and methodologies due to various factors. First, the markers that are placed on any two maps may not be identical, and furthermore, some maps may have a greater marker density than another map. Also, the mapping populations, methodologies and algorithms used to construct genetic maps can differ. One of skill in the art recognizes that one genetic map is not necessarily more or less accurate than another, and furthermore, recognizes that any maize genetic map can be used to determine markers that are linked and closely linked to the QTL markers of the present invention.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype, to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly maize plants, that have newly conferred resistance or enhanced resistance to, or are susceptible to, MRCV by identifying plants having a specified allele at one of those loci, e.g., MZA625, MZA16656, MZA15451, MZA15490, MZA2038, MZA11826, or MZA9105. In one embodiment, identified resistant plants have the haplotype: C at MRQV_08351-173, A at MRQV_08351-262, G at MRQV_08351-280, G at MRQV_08351-323, C at MRQV_08351-369, C at MRQV_08351-372.

Similarly, by identifying plants lacking the desired marker locus, susceptible or less resistant plants can be identified and, e.g., eliminated from subsequent crosses. Similarly, these marker loci can be introgressed into any desired genomic background, germplasm, plant, line, variety, etc., as part of an overall MAS breeding program designed to enhance maize yield. In one embodiment, identified susceptible plants have the haplotype: T at MRQV_08351-173, T at MRQV_08351-262, A at MRQV_08351-280, C at MRQV_08351-323, T at MRQV_08351-369, T at MRQV_08351-372.

The invention also provides chromosome QTL intervals that find equal use in MAS to select plants that demonstrate newly conferred or enhanced MRCV resistance. Similarly, the QTL intervals can also be used to counter-select plants that are susceptible or have reduced resistance MRCV. Any marker that maps within the QTL interval (including the termini of the intervals) finds use with the invention. These intervals are defined by the following pairs of markers:
(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a.

In general, MAS uses polymorphic markers that have been identified as having a significant likelihood of co-segregation with a resistance trait. Such markers are presumed to map near a gene or genes that give the plant its resistance phenotype, and are considered indicators for the desired trait, and are termed QTL markers. Plants are tested for the presence of a desired allele in the QTL marker. The most preferred markers (or marker alleles) are those that have the strongest association with the resistance trait.

Linkage analysis is used to determine which polymorphic marker allele demonstrates a statistical likelihood of co-segregation with the resistance phenotype (thus, a "resistance marker allele"). Following identification of a marker allele for co-segregation with the resistance phenotype, it is possible to use this marker for rapid, accurate screening of plant lines for the resistance allele without the need to grow the plants through their life cycle and await phenotypic evaluations, and furthermore, permits genetic selection for the particular resistance allele even when the molecular identity of the actual resistance QTL is unknown. Tissue samples can be taken, for example, from the first leaf of the plant and screened with the appropriate molecular marker, and it is rapidly determined which progeny will advance. Linked markers also remove the impact of environmental factors that can often influence phenotypic expression.

A polymorphic QTL marker locus can be used to select plants that contain the marker allele (or alleles) that correlate with the desired resistance phenotype, typically called marker-assisted selection (MAS). In brief, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein, e.g., in the section entitled "TECHNIQUES FOR MARKER DETECTION". After the presence (or absence) of a particular marker allele in the biological sample is verified, the plant is selected (e.g., used to make progeny plants by selective breeding).

Maize plant breeders desire combinations of resistance loci with genes for high yield and other desirable traits to develop improved maize varieties. Screening large numbers of samples by non-molecular methods (e.g., trait evaluation in maize plants) can be expensive, time consuming, and unreliable. Use of the polymorphic markers described herein, when genetically-linked to resistance loci, provide an effective method for selecting resistant varieties in breeding programs. For example, one advantage of marker-assisted selection over field evaluations for resistance is that MAS can be done at any time of year, regardless of the growing season. Moreover, environmental effects are largely irrelevant to marker-assisted selection.

When a population is segregating for multiple loci affecting one or multiple traits, e.g., multiple loci involved in resistance, or multiple loci each involved in resistance to different diseases, the efficiency of MAS compared to phenotypic screening becomes even greater, because all the loci can be evaluated in the lab together from a single sample of DNA. In the present instance, the MZA625, MZA16656, MZA15451, MZA15490, MZA2038, MZA11826, and MZA9105 markers, as well as any of the chromosome intervals
(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a;
can be assayed simultaneously or sequentially from a single sample or a population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable resistance marker loci) into an otherwise desirable genetic background from the recurrent parent (e.g., an otherwise high yielding maize line). The more cycles of backcrossing that are done, the greater the genetic contribution of the recurrent parent to the resulting introgressed variety. This is often necessary, because resistant plants may be otherwise undesirable, e.g., due to low yield, low fecundity, or the like. In contrast, strains which are the result of intensive breeding programs may have excellent yield, fecundity or the like, merely being deficient in one desired trait such as resistance to MRCV.

The presence and/or absence of a particular genetic marker or allele, e.g., MZA625, MZA16656, MZA15451, MZA15490, MZA2038, MZA11826, and MZA9105 markers, as well as any of the chromosome intervals
(i) MZA8381 and MZA18180;
(ii) MZA4305 and MZA2803;
(iii) MZA15490 and MZA2038;
(iv) bnlg1458b and umc1261a;
(v) bnlg1458b and umc1262a;
(vi) bnlg1327 and umc1261a; and
(viii) bnlg1327 and umc1262a;
in the genome of a plant is made by any method noted herein. If the nucleic acids from the plant are positive for a desired genetic marker allele, the plant can be self fertilized to create a true breeding line with the same genotype, or it can be crossed with a plant with the same marker or with other desired characteristics to create a sexually crossed hybrid generation.

Introgression of Favorable Alleles—Efficient Backcrossing of Resistance Markers into Elite Lines One application of MAS, in the context of the present invention is to use the newly conferred resistance or enhanced resistance markers to increase the efficiency of an introgression or backcrossing effort aimed at introducing a resistance QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

Thus, the markers and methods of the present invention can be utilized to guide marker assisted selection or breeding of maize varieties with the desired complement (set) of allelic forms of chromosome segments associated with superior agronomic performance (resistance, along with any other available markers for yield, etc.). Any of the disclosed marker alleles can be introduced into a maize line via introgression, by traditional breeding (or introduced via transformation, or both), to yield a maize plant with superior agronomic performance. The number of alleles associated with resistance that can be introduced or be present in a maize plant of the present invention ranges from 1 to the number of alleles disclosed herein, each integer of which is incorporated herein as if explicitly recited.

The present invention also extends to a method of making a progeny maize plant and these progeny maize plants, per se. The method comprises crossing a first parent maize plant with a second maize plant and growing the female maize plant under plant growth conditions to yield maize plant progeny. Methods of crossing and growing maize plants are well within the ability of those of ordinary skill in the art. Such maize plant progeny can be assayed for alleles associated with resistance and, thereby, the desired progeny selected. Such progeny plants or seed can be sold commercially for maize production, used for food, processed to obtain a desired constituent of the maize, or further utilized in subsequent rounds of breeding. At least one of the first or second maize plants is a maize plant of the present invention in that it comprises at least one of the allelic forms of the markers of the present invention, such that the progeny are capable of inheriting the allele.

A method of the present invention can be applied to at least one related maize plant such as from progenitor or descendant lines in the subject maize plant's pedigree such that inheritance of the desired resistance allele can be traced. The number of generations separating the maize plants being subject to the methods of the present invention will generally be from 1 to 20, commonly 1 to 5, and typically 1, 2, or 3 generations of separation, and quite often a direct descendant or parent of the maize plant will be subject to the method (i.e., one generation of separation).

Introgression of Favorable Alleles—Incorporation of "Exotic" Germplasm while Maintaining Breeding Progress Genetic diversity is important for long term genetic gain in any breeding program. With limited diversity, genetic gain will eventually plateau when all the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite×exotic maize lines by subjecting the segregating progeny to MAS to maintain major yield alleles, along with the resistance marker alleles herein.

Positional Cloning

The molecular marker loci and alleles of the present invention, e.g., MZA625, MZA16656, MZA15451, MZA15490, MZA2038, MZA11826, and MZA9105 markers, as well as any of the chromosome intervals
  (i) MZA8381 and MZA18180;
  (ii) MZA4305 and MZA2803;
  (iii) MZA15490 and MZA2038;
  (iv) bnlg1458b and umc1261a;
  (v) bnlg1458b and umc1262a;
  (vi) bnlg1327 and umc1261a; and
  (viii) bnlg1327 and umc1262a;
can be used, as indicated previously, to identify a resistance QTL, which can be cloned by well established procedures, e.g., as described in detail in Ausubel, Berger and Sambrook, herein.

These resistance clones are first identified by their genetic linkage to markers of the present invention. Isolation of a nucleic acid of interest is achieved by any number of methods as discussed in detail in such references as Ausubel, Berger and Sambrook, herein, and Clark, Ed. (1997) *Plant Molecular Biology: A Laboratory Manual* Springer-Verlag, Berlin.

For example, "positional gene cloning" uses the proximity of a resistance marker to physically define an isolated chromosomal fragment containing a resistance QTL gene. The isolated chromosomal fragment can be produced by such well known methods as digesting chromosomal DNA with one or more restriction enzymes, or by amplifying a chromosomal region in a polymerase chain reaction (PCR), or any suitable alternative amplification reaction. The digested or amplified fragment is typically ligated into a vector suitable for replication and, e.g., expression, of the inserted fragment. Markers that are adjacent to an open reading frame (ORF) associated with a phenotypic trait can hybridize to a DNA clone (e.g., a clone from a genomic DNA library), thereby identifying a clone on which an ORF (or a fragment of an ORF) is located. If the marker is more distant, a fragment containing the ORF is identified by successive rounds of screening and isolation of clones which together comprise a contiguous sequence of DNA, a process termed "chromosome walking", resulting in a "contig" or "contig map". Protocols sufficient to guide one of skill through the isolation of clones associated with linked markers are found in, e.g., Berger, Sambrook and Ausubel, all herein.

Generation of Transgenic Cells and Plants

The present invention also relates to host cells and organisms which are transformed with nucleic acids corresponding to resistance QTL identified according to the invention. For example, such nucleic acids include chromosome intervals (e.g., genomic fragments), ORFs and/or cDNAs that encode a newly conferred resistance or enhanced resistance trait. Additionally, the invention provides for the production of polypeptides that provide newly conferred resistance or enhanced resistance by recombinant techniques.

General texts which describe molecular biological techniques for the cloning and manipulation of nucleic acids and production of encoded polypeptides include Berger, Sambrook, and Ausubel supra. These texts describe mutagenesis, the use of vectors, promoters and many other relevant topics related to, e.g., the generation of clones that comprise nucleic acids of interest, e.g., marker loci, marker probes, QTL that segregate with marker loci, etc.

Methods for MRCV Resistant Maize Plants

Experienced plant breeders can recognize resistant maize plants in the field and can select the resistant individuals or populations for breeding purposes or for propagation. In this context, the plant breeder recognizes "resistant" and "non-resistant", or "susceptible", maize plants.

Such plant breeding practitioners will appreciate that plant resistance is a phenotypic spectrum consisting of extremes in resistance, susceptibility and a continuum of intermediate resistance phenotypes. Resistance also varies due to environmental effects and the severity of pathogen infection. Evaluation of phenotypes using reproducible assays and resistance scoring methods are of value to scientists who seek to identify genetic loci that impart resistance, conduct marker assisted selection for resistant populations, and for introgression techniques to breed a resistance trait into an elite maize line, for example.

In contrast to fortuitous field observations that classify plants as either "resistant" or "susceptible", various systems are known for scoring the degree of plant resistance or susceptibility. These techniques can be applied to different fields at different times, and provide approximate resistance scores that can be used to characterize a given strain regardless of growth conditions or location.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

The present study was completed by two different association analysis approaches: 1) Population-based Structured association analysis and 2) Pedigree-based association analysis. By identifying such genetic markers, marker assisted selection (MAS) can be used to improve the efficiency of breeding for improved resistance of maize to MRCV infection. Association mapping is known in the art, and is described in various sources, e.g., Jorde (2000) Genome Res. 10:1435-1444; Remington et al. (2001) "Structure of linkage disequilibrium and phenotype associations in the maize genome," Proc Natl Acad Sci USA 98:11479-11484; Weiss and Clark (2002) Trends Genet. 18:19-24; and Shu et al. (2003) "Detection Power of Random, Case-Control, and Case-Parent Control Designs for Association Tests and Genetic Mapping of Complex Traits," Proceedings of 15th Annual KSU Conference on Applied Statistics in Agriculture 15:191-204.

Example 1

Association Mapping Analysis

An association mapping strategy was undertaken to identify maize genetic markers associated with resistance to MRCV infection, which is the causative agent of "Mal de Río Cuarto".

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," Nat Genet 7:180-184; Hastbacka et al. (1992) "Linkage disequilibrium mapping in isolated founder populations: diastrophic dysplasia in Finland," Nat Genet 2:204-211; Kerem et al. (1989) "Identification of the cystic fibrosis gene: genetic analysis," Science 245:1073-1080) and maize (Remington et al., (2001) "Structure of linkage disequilibrium and phenotype associations in the maize genome," Proc Natl Acad Sci USA 98:11479-11484; Thornsberry et al. (2001) "Dwarf8 polymorphisms associate with variation in flowering time," Nat Genet 28:286-289; reviewed by Flint-Garcia et al. (2003) "Structure of linkage disequilibrium in plants," Annu Rev Plant Biol. 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," Nat Rev Genet 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants," Annu Rev Plant Biol. 54:357-374).

Elite breeding lines provide a valuable starting point for association analyses. Association analyses use quantitative phenotypic scores (e.g., disease tolerance rated from one to nine for each maize line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable maize map (for example, a composite map) can optionally be used to help observe distribution of the identified QTL markers and/or QTL marker clustering using previously determined map locations of the markers.

Maize Lines and Phenotypic Scoring

Maize lines were phenotypically scored based on their degree of resistance to MRCV infection (in contrast to simple categorization of "tolerant" or "susceptible"). The plant varieties used in the analysis were from diverse sources, including elite germplasm, commercially released cultivars and other public varieties. The collections comprised 475 maize lines. The lines used in the study had a broad maturity range varying from CRM (comparative relative maturity) 90 to CRM 140, representing the main inbreds of Pioneer germplasm.

The degree of plant resistance to MRCV infection varied widely, as measured using a scale from one (highly susceptible) to nine (highly resistant). Generally, a score of two (2) indicated the most susceptible strains, a score of four (4) was assigned as the threshold to consider a plant susceptible or resistant (less than 4, susceptible; 4 or higher is resistant) and a score of seven (5-7) was assigned to the most resistant lines. Resistance scores of eight (8) and nine (9) were reserved for resistance levels that are very rare and generally not observed in existing germplasm. If no disease was present in a field, no resistance scoring was done. However, if a disease did occur in a specific field location, all of the lines in that location were scored. Scores for test strains accumulated over multiple locations and multiple years, and an averaged (e.g., consensus) score was ultimately assigned to each line.

Resistance scores for the 475 inbred collection were collected over several growing seasons (394 inbreds were evaluated at the same time in the growing season). Data collection was typically done in one scoring after flowering time.

In assessing the linkage of markers to tolerance, a quantitative approach was used, where a resistance score for each maize line was assessed and incorporated into the association mapping statistical analysis.

Maize Genotyping

A collection of 475 maize lines was analyzed by DNA sequencing at 4000-10000 genes (genetic loci). SNP variation was used to generate specific haplotypes across inbreds at each loci. This data was used for identifying associations between alleles and MRCV resistance at genome level.

Statistical Methods

A structure-based association analysis is conducted using standard association mapping methods where the population structure is controlled by using marker data. The model-based cluster analysis software, Structure, developed by Pritchard et al. was used with haplotype data for 880 elite maize inbreds at two hundred markers to estimate admixture coefficients and assign the inbreds to seven subpopulations (J. K. Pritchard, M. Stephens and P. J. Donnelly (2000) "Inference of population structure using multilocus genotype data," Genetics 155: 945-959). This reduces the occurrence of false positives that can arise due to the effect of population structure on association mapping statistics. Kuiper's statistic for testing whether two distributions are the same is used to test a given marker for association between haplotype and phenotype in a given subpopulation (W. H. Press, S. A. Teukolsky, W. T. Vetterling, B. P. Flannery, 2002; Numerical Recipes in C, second edition, Cambridge University Press, NY).

The Pedigree-based association mapping is conducted using GPA Procedure (General Pedigree-Based Association Analysis), developed by Shu et al. (Guoping Shu, Beiyan Zeng, and Oscar Smith, 2003; Detection Power of Random, Case-Control, and Case-Parent Control Designs for Association Tests and Genetic Mapping of Complex Traits. Proceedings of 15th Annual KSU Conference on Applied Statistics in Agriculture. 15: 191-204). The GPA Procedure is a conditional likelihood-based association mapping software implemented in SAS Computer Language Version 9.0 (2001, SAS Institute, Cary, N.C.).

Results

Tables 1 and 2 provide tables listing the maize markers that demonstrated linkage disequilibrium with the MRCV phenotype using the Association Mapping method, and they were validated on segregating populations. Also indicated in Tables 1 and 2 are the chromosomes on which the markers are located and their approximate map position relative to other known markers, given in cM, with position zero being the first (most distal from centromere) marker known at the beginning of the chromosome. These map positions are not absolute, and represent an estimate of map position. Tables 6 and 7 provide the primer and probe sequences used to type the SNP markers.

The statistical probabilities that the marker allele and disease tolerance phenotype are segregating independently are reflected in the association mapping adjusted probability values in Tables 1 and 2, which is a probability (P) derived from analysis of association between genotype and phenotype. The lower the probability value, the more significant is the association between the marker genotype at that locus and the MRCV infection tolerance phenotype.

Non-structured association analysis for the named SS group revealed the presence of two peaks of probability on chromosome 2, at position 65.99 represented by markers MZA2038 (p=0.00000266) and MZA11826 (p=0.00000179) and at position 127.18-131.13 represented by markers MZA11806 (p=0.000002) and MZA14212 (p=0.00000327). The non-structured analysis also revealed several other associations across the genome. The only consistent association that it was validated by independent approaches corresponded to the position 65.99 on chromosome 2. The non-structured analysis increases the power to evaluate the whole allele variability for a target region but at the same time increase the number of false positive associations because population structure is not corrected by this analysis.

Figure 1A:
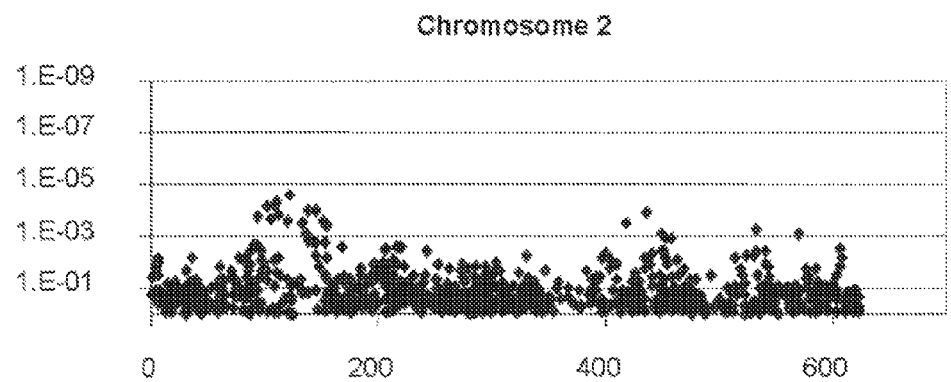
Figure 1B:
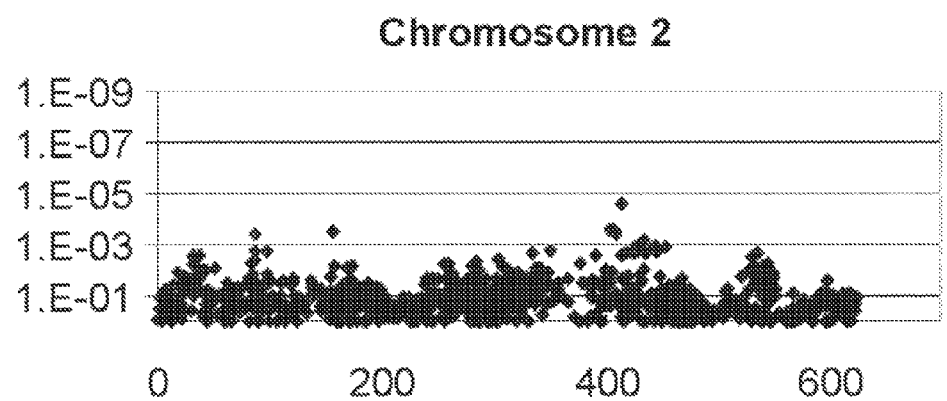

FIG. 1A shows a structured association analysis of a group of argentinian inbreds (or inbreds target for the argentine breeding program) where several markers were significant at 0.0005 p-level at the region from position 65.99 to 85.84, including MZA16656 (P=0.000194), MZA18224 (p=0.000066) and MZA5057 (p=0.000045). FIG. 1B shows a structured association analysis for an SS group where on the short arm of chromosome 2, the most associated markers were MZA1525 at position 54.62 (p=0.00043) and MZA11826 at position 65.99 (p=0.00168). Two additional associations were observed at position 91.19 represented by marker MZA13812 (p=0.000299) and position 154.06 represented by marker MZA10682 (p=0.000024).

Figure 1C:
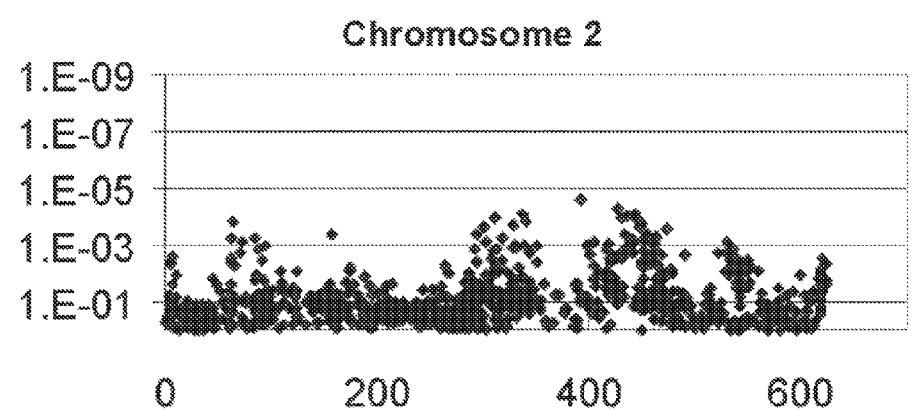

FIG. 1C shows a structured association analysis for the SS group with a different set of phenotypic data. The highest associated marker on the short arm of chromosome 2 was MZA12899 at position 53.83 (p=0.000298). There were other associated markers in the long arm of chromosome 2 where the highest associated markers were MZA1067 (Map position: 141.9; p=0.000094) and MZA10832 (Map position: 159.8; p=0.000086).

Example 2

QTL Interval Mapping and Single Marker Regression Analysis

A QTL interval mapping and a single marker regression analysis was undertaken to identify maize chromosome intervals and genetic markers (respectively) that are associated with resistance and allow the plant resistance of maize to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

Two main mapping populations for MRCV resistance were created from the crosses of inbreds PH7WT (resistant genotype) and PH3DT (highly susceptible genotype), and PH9TJ (resistant genotype) and PH890 (susceptible genotype). The PH7WT×PH3DT population consisted of 120 F5/F7 families and the PH9TJ×PH890 consisted of 212 BC2F4/BC2F5 families.

Phenotypic Scoring

Phenotypic scoring of each of the lines was based on sets of phenotypic data collected from the field on two (PH890× PH9TJ cross) or three different crop seasons (PH7WT× PH3DT).

Maize Genotyping

Maize F5 progeny of PH7WT×PH3DT were genotyped using a total of 246 polymorphic and good quality markers and the BC2F4 progeny of PH890×PH9TJ were genotyped with 167 polymorphic and good quality markers. First round of genotyping included SSR markers. A second round of genotyping with a set of 101 polymorphic and good quality markers was performed on F7 PH7WT×PH3DT progeny. A second round of genotyping was performed on PH890× PH9TJ population by using a set of makers at specific genomic regions.

Windows QTL Cartographer (the most up-to-date version of this software was used according the date of QTL mapping) was used for both the marker regression analysis and QTL interval mapping. LOD scores (logarithm of the odds ratio) were estimated across the genome according the standard QTL mapping procedures. The term "likelihood of odds" is used to describe the relative probability of two or more explanations of the sources of variation in a trait. The probability of these two different explanations (models) can be computed, and the most likely model chosen. If model A is 1000 times more probable than model B, then the ratio of the odds are 1000:1 and the logarithm of the odds ratio is 3.

Both the raw data for individual replications and years, and mean scores, were used in QTL interval mapping. The LOD threshold was 2.5. A confidence interval was estimated for each QTL. The positions obtained are then plotted as a histogram overlaying the interval mapping figure.

Results

QTL Interval Mapping

The present study identified various chromosome intervals that correlate with QTLs that associate with resistance/susceptibility to MRCV infection. The QTLs were identified using the field data. One major, significant QTL was located on linkage group 2 on both mapping crosses (see FIGS. 12-14; see also Table 13, which shows a QTL marker regression analysis for the PH890×PH9TJ cross).

TABLE 13

| Marker | Chrom. | Position | b1 | $F_{(1, n-2)}$ | pr(F) | Rep 1 | b1 |
|---|---|---|---|---|---|---|---|
| MZA117-12-A | 2 | 34.53 | −0.245 | 4.691 | 0.032 | * | −0.117 |
| MZA4122-3-A | 2 | 45.60 | −0.354 | 11.881 | 0.001 | *** | −0.383 |
| MZA10252-10-A | 2 | 48.85 | −0.389 | 13.624 | 0 | *** | −0.444 |
| MZA8381-29-A | 2 | 63.47 | −0.640 | 45.160 | 0 | **** | −0.716 |
| MZA625-30-A | 2 | 64.05 | −0.638 | 50.504 | 0 | **** | −0.686 |
| MZA16656-8-A | 2 | 65.99 | −0.719 | 66.790 | 0 | **** | −0.727 |
| MZA9105-6-A | 2 | 65.44 | −0.719 | 66.790 | 0 | **** | −0.727 |
| MZA9510-8-A | 2 | 65.44 | −0.702 | 64.097 | 0 | **** | −0.720 |
| MZA18224-801-A | 2 | 68.80 | −0.739 | 69.538 | 0 | **** | −0.730 |
| MZA2349-71-A | 2 | 68.80 | −0.694 | 60.777 | 0 | **** | −0.625 |
| MZA18036-23-A | 2 | 71.75 | −0.576 | 41.165 | 0 | **** | −0.531 |
| MZA8189-16-A | 2 | 76.80 | −0.542 | 37.689 | 0 | **** | −0.538 |
| MZA10094-6-A | 2 | 80.90 | −0.501 | 30.686 | 0 | **** | −0.475 |
| MZA7266-6-A | 2 | 96.43 | −0.267 | 5.081 | 0.025 | * | −0.169 |
| MZA15573-12-A | 5 | 144.73 | −0.153 | 1.371 | 0.243 |  | −0.332 |
| MZA7908-20-A | 5 | 152.87 | −0.284 | 7.206 | 0.008 | ** | −0.421 |
| MZA8726-9-A | 5 | 154.05 | −0.326 | 10.429 | 0.001 | ** | −0.459 |
| MZA4599-24-A | 5 | 167.44 | −0.237 | 5.649 | 0.019 | * | −0.235 |
| MZA8048-8-A | 5 | 168.07 | −0.231 | 5.339 | 0.022 | * | −0.234 |
| MZA3899-10-A | 5 | 175.23 | −0.123 | 1.292 | 0.257 |  | −0.225 |

|  | $F_{(1, n-2)}$ | pr(F) | Rep 2 | b1 | $F_{(1, n-2)}$ | pr(F) | Mean Score |
|---|---|---|---|---|---|---|---|
| MZA117-12-A | 1.026 | 0.313 |  | −0.242 | 7.452 | 0.007 | ** |
| MZA4122-3-A | 13.637 | 0 | *** | −0.383 | 23.661 | 0 | **** |
| MZA10252-10-A | 17.587 | 0 | **** | −0.380 | 21.621 | 0 | **** |
| MZA8381-29-A | 58.110 | 0 | **** | −0.640 | 85.828 | 0 | **** |
| MZA625-30-A | 58.803 | 0 | **** | −0.622 | 90.530 | 0 | **** |
| MZA16656-8-A | 66.005 | 0 | **** | −0.685 | 117.393 | 0 | **** |
| MZA9105-6-A | 66.005 | 0 | **** | −0.685 | 117.393 | 0 | **** |
| MZA9510-8-A | 65.830 | 0 | **** | −0.673 | 114.098 | 0 | **** |
| MZA18224-801-A | 64.530 | 0 | **** | −0.698 | 119.381 | 0 | **** |
| MZA2349-71-A | 44.607 | 0 | **** | −0.651 | 100.026 | 0 | **** |
| MZA18036-23-A | 32.632 | 0 | **** | −0.543 | 65.053 | 0 | **** |
| MZA8189-16-A | 35.626 | 0 | **** | −0.529 | 64.896 | 0 | **** |
| MZA10094-6-A | 26.107 | 0 | **** | −0.477 | 48.187 | 0 | **** |
| MZA7266-6-A | 1.955 | 0.164 |  | −0.223 | 5.677 | 0.018 | * |
| MZA15573-12-A | 6.482 | 0.012 | * | −0.234 | 5.252 | 0.023 | * |

TABLE 13-continued

| | | | | | | | |
|---|---|---|---|---|---|---|---|
| MZA7908-20-A | 16.156 | 0 | **** | −0.336 | 17.077 | 0 | **** |
| MZA8726-9-A | 21.357 | 0 | **** | −0.375 | 23.713 | 0 | **** |
| MZA4599-24-A | 5.380 | 0.022 | * | −0.293 | 14.552 | 0 | *** |
| MZA8048-8-A | 5.305 | 0.022 | * | −0.291 | 14.201 | 0 | *** |
| MZA3899-10-A | 4.264 | 0.040 | * | −0.211 | 6.270 | 0.013 | * |

A second QTL was identified on linkage group 5 at position 150-160 (PH890×PH9TJ pop) and another at position 200-220 on linkage group 5 (PH7WT×PH3DT pop). A third QTL was mapped on PH7WT×PH3DT at position 165-185 on chromosome 2.

Single Marker Regression

Using single marker regression, there are a number of markers showing association with the resistant phenotype at a confidence level of P=0.05 or better, as shown in Tables 1 and 2. Some of the markers identified in the marker regression analysis show a concordance of observations with the association mapping, where the different approaches identify the same markers. For example, there are markers at the region from 55 to 70 cM on Chr 2 identified by both marker regression and association mapping.

Discussion/Conclusions

This present study has identified chromosome intervals and individual markers that correlate with MRCV resistance. Markers that lie within these intervals are useful for use in MAS, as well as other purposes.

Example 3

QTL Validation by Marker Assisted Selection

A QTL interval mapping and a single marker regression analysis was undertaken to identify maize chromosome intervals and genetic markers (respectively) that are associated with resistance and allow the resistance to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

One main population for validation and mapping of MRCV resistance was created from the cross of inbreds PH7WT and PH3DT. Other populations were generated to validate the effect of this QTL across backgrounds. The PH7WT×PH3DT population consisted of 82 BC3F3 families generated by introgress by markers the QTL mapped on chromosome 2 into PH3DT. There were 4 additional BC1F3 populations generated by marker assisted selection that consisted of 24 BC1F3 from the cross PH6 KW×PH7WT, 12 BC1F3 from the cross PH6B8×PH7WT, 3 BC1F3 from the cross PHP3P1×PH7WT and 6 BC1F3 from the cross PH6GF×PH7WT. These populations were generated by selfing specific BC3 or BC1 plants and deriving BC3F3 or BC1F3 families with allelic variation at the QTL region.

Phenotypic Scoring

Phenotypic scoring of each of the BC1F3, BC3F3 and parents was based on sets of phenotypic data collected from the field on one crop season.

Maize Genotyping

Maize BC1F2 progeny from the different crosses and BC3F3 from the cross PH7WT×PH3DT were genotyped by using polymorphic SNPs at the QTL region. BC3F3 were subjected to background clean at BC3 stage, especially at chromosome 5 QTL. Markers included SNP markers.

Windows QTL Cartographer (up-to-date version according the date of QTL mapping) was used for both the marker regression analysis and QTL interval mapping. LOD scores (logarithm of the odds ratio) were estimated across the genome according the standard QTL mapping procedures.

Both the raw data for individual replications and mean scores were used in QTL interval mapping. The LOD threshold was 2.5. A confidence interval was estimated for each QTL. The positions obtained are then plotted as a histogram overlaying the interval mapping figure.

As these population were generated by marker assisted selection (not random events of recombination), marker regression analysis was considered as powerful as interval mapping analysis.

Results

QTL Interval Mapping

The present study identified a single chromosome interval that correlated with QTLs associated with resistance/susceptibility to MRCV infection. The QTL were identified using the field data. One major significant QTL was located on linkage group 2 on the main validation BC3F3 population. The main markers at this QTL in the main validation population when checked on the other BC1F3 progenies confirmed the effect of this QTL on resistance/susceptibility to MRCV infection.

Single Marker Regression

Figure 2:
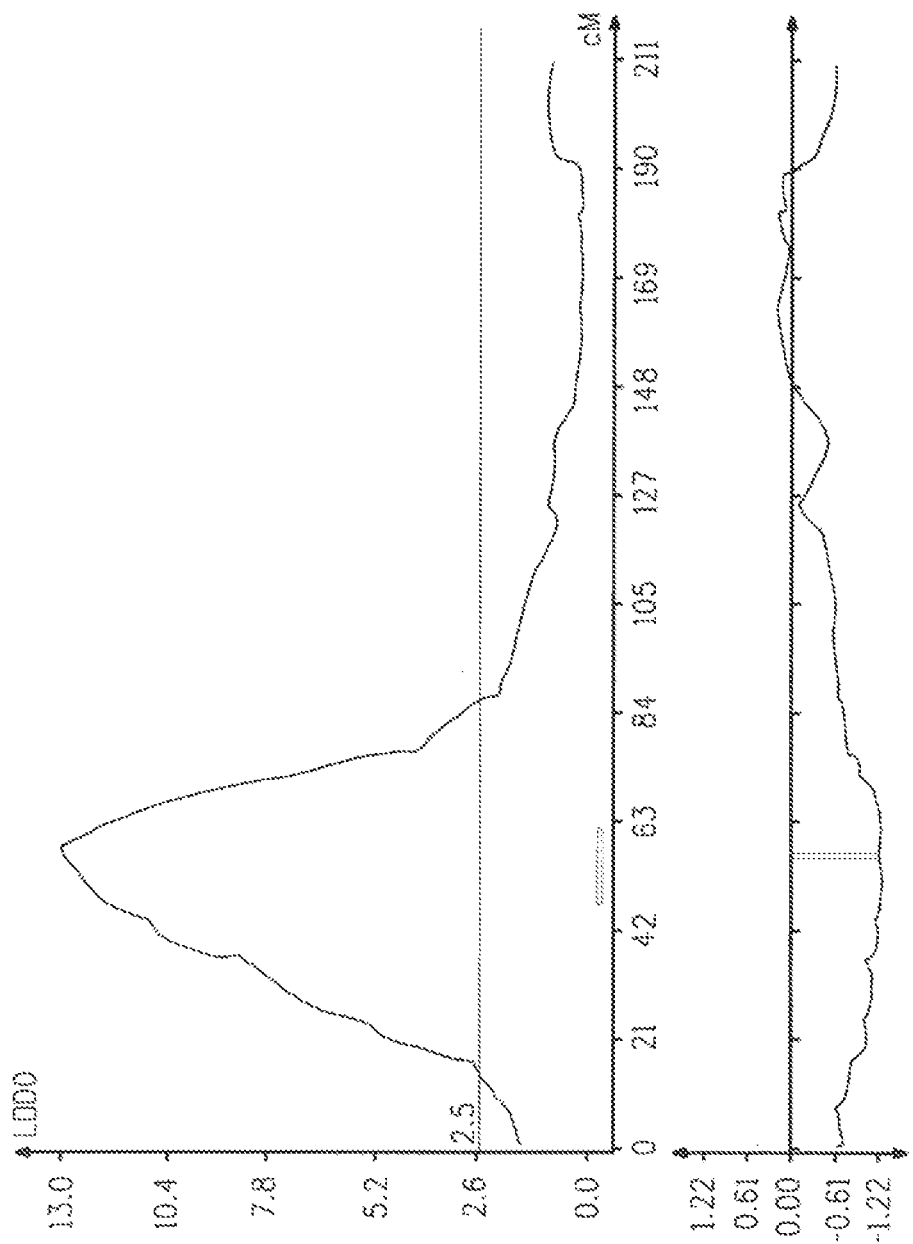
Figure 3A:
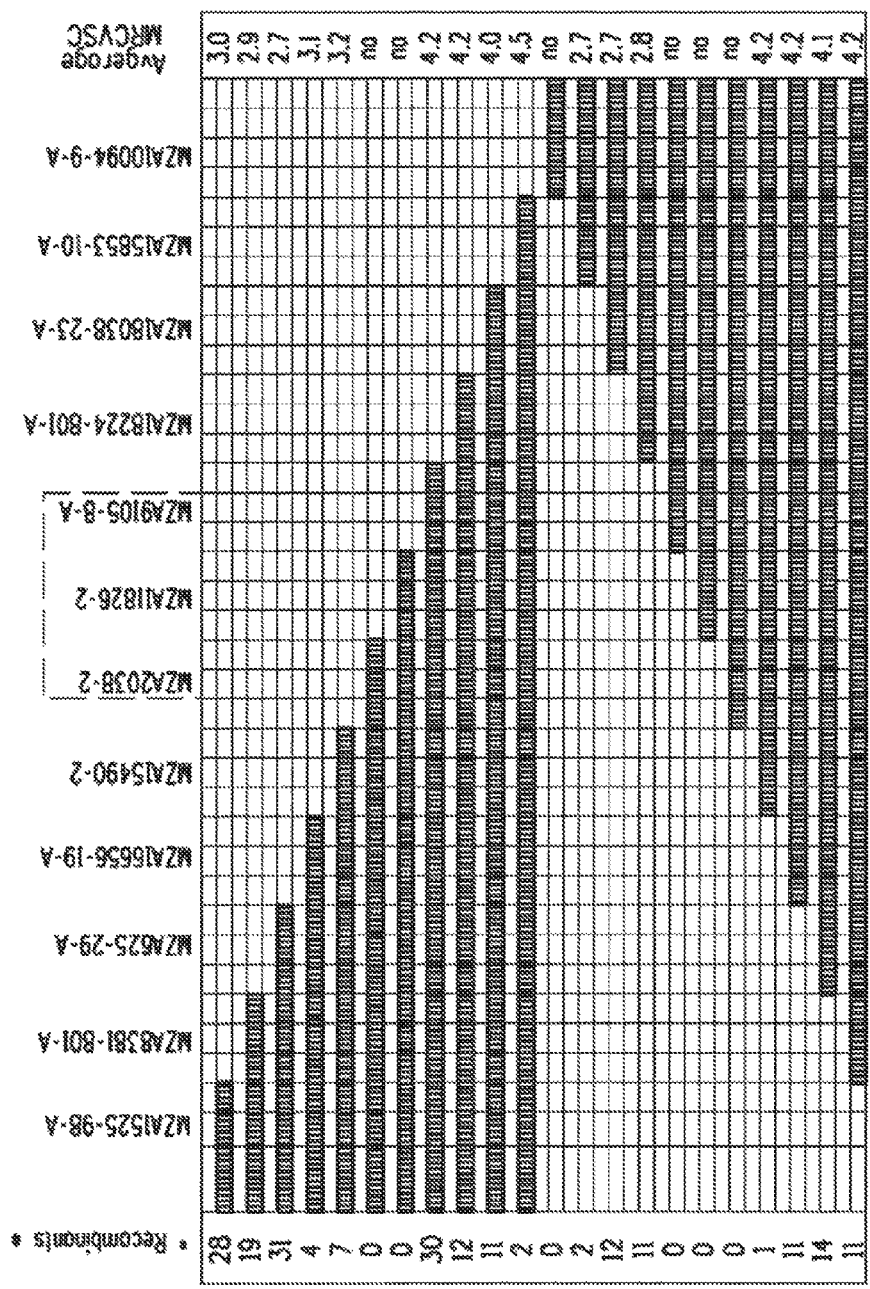
Figure 4:
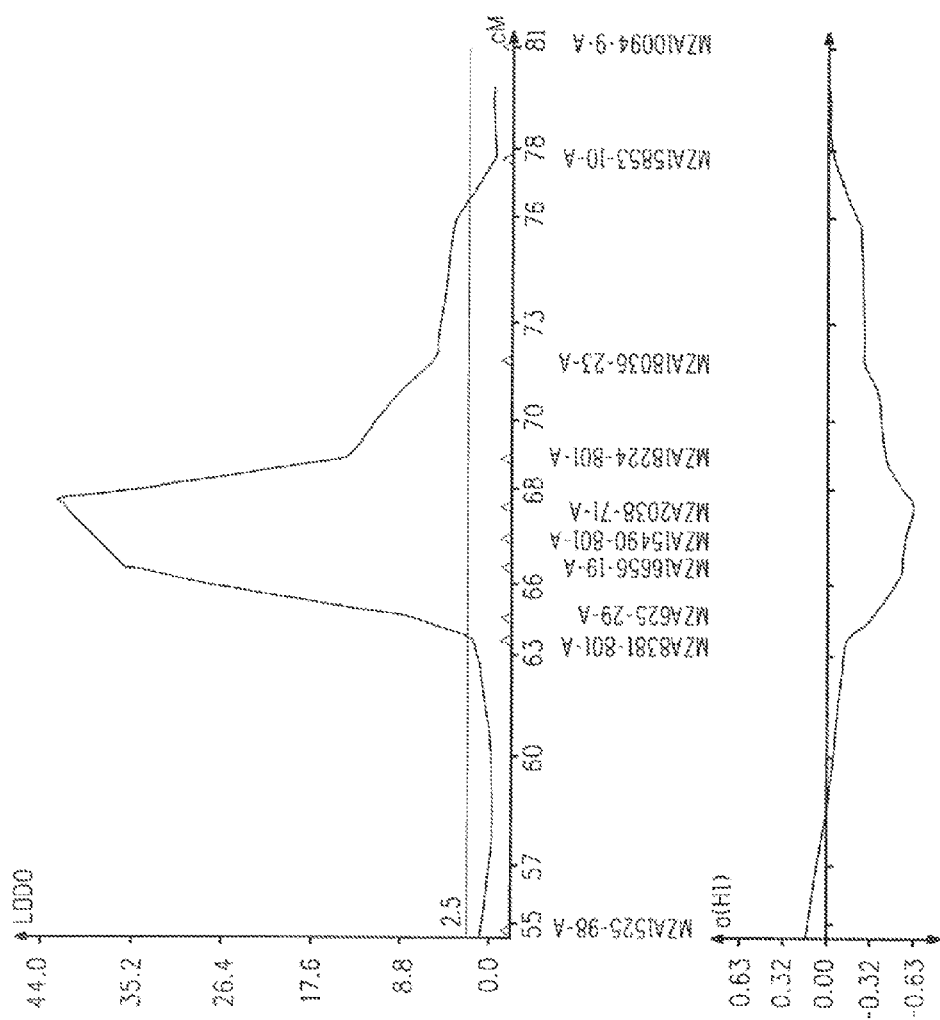
Figure 5:
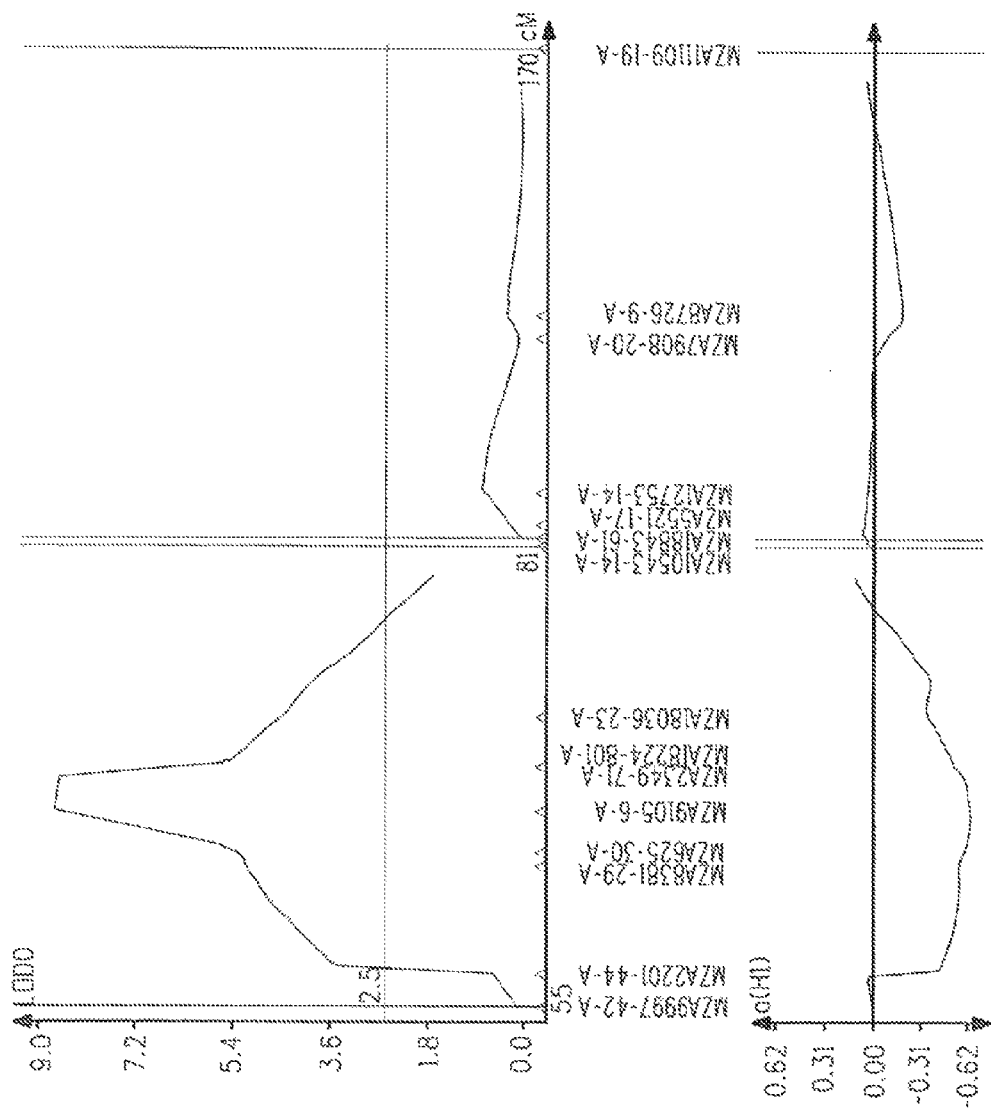

Using single marker regression, there are a number of markers showing association with the resistant phenotype at a confidence level of P=0.05 or better, as shown in Tables 1 and 2. Some of the markers identified in the marker regression analysis show a concordance of observations with the association mapping, where the different approaches identify the same markers. For example, there are markers at the region from 55 to 70 cM on chromosome 2 identified by both marker regression and association mapping. See FIG. 2 for interval mapping and Table 14 for marker regression analysis for the PH3DT×PH7WT cross. Note that replication #3 was affected by herbicide stress. MRCVSC=MRCV phenotypic score. Inc. Sev. Symp.=frequency of plants with severe symptoms on each experimental unit.

TABLE 14

| Marker | Chrom. | Position | Inc sev symptoms F(1, n-2) pr(F) | Rep 1 | Inc sev symptoms F(1, n-2) pr(F) | Rep 2 | Inc sev symptoms F(1, n-2) pr(F) | Rep 3 | Inc sev symptoms F(1,n-2) pr(F) | Mean Score |
|---|---|---|---|---|---|---|---|---|---|---|
| MZA2592-73-A | 2 | 9.29 | 3.49 0.07 |  | 4.22 0.04 |  | 1.19 0.28 |  | 6.29 0.01 | * |
| MZA225-50-A | 2 | 25.51 | 5.57 0.02 | * | 3.10 0.08 |  | 1.38 0.24 |  | 6.35 0.01 | * |
| MZA3334-4-A | 2 | 33.38 | 9.98 0 | ** | 2.15 0.015 |  | 5.60 0.02 | * | 10.58 0 | ** |
| MZA4122-3-A | 2 | 45.60 | 26.19 0 | **** | 9.49 0 | ** | 10.21 0 | ** | 31.82 0 | **** |
| MZA8067-27-A | 2 | 52.77 | 28.10 0 | **** | 9.21 0 | ** | 9.57 0 | ** | 31.56 0 | **** |
| MZA5822-15-A | 2 | 53.53 | 30.53 0 | **** | 10.77 0 | ** | 10.26 0 | ** | 35.66 0 | **** |
| MZA1525-98-A | 2 | 54.62 | 32.66 0 | **** | 12.89 0 | *** | 10.85 0 | ** | 40.37 0 | **** |
| MZA8381-801-A | 2 | 63.47 | 34.31 0 | **** | 14.25 0 | *** | 11.56 0 | ** | 43.52 0 | **** |
| MZA625-29-A | 2 | 64.05 | 34.27 0 | **** | 13.94 0 | *** | 11.91 0 | *** | 44.63 0 | **** |
| MZA625-30-A | 2 | 65.99 | 34.88 0 | **** | 14.21 0 | *** | 11.78 0 | *** | 44.21 0 | **** |
| MZA16656-19-A | 2 | 65.99 | 32.03 0 | **** | 13.17 0 | *** | 11.08 0 | ** | 40.36 0 | **** |
| MZA15490-801-A | 2 | 65.99 | 34.31 0 | **** | 14.66 0 | *** | 11.46 0 | ** | 44.16 0 | **** |
| MZA2038-71-A | 2 | 65.99 | 34.31 0 | **** | 14.66 0 | *** | 11.46 0 | ** | 44.16 0 | **** |
| MZA11826-803-A | 2 | 65.99 | 34.31 0 | **** | 14.66 0 | *** | 11.46 0 | ** | 44.16 0 | **** |
| MZA11826-801-A | 2 | 65.99 | 34.31 0 | **** | 14.66 0 | *** | 11.46 0 | ** | 44.16 0 | **** |
| MZA9105-8-A | 2 | 65.44 | 34.30 0 | **** | 14.67 0 | *** | 11.46 0 | ** | 44.16 0 | **** |
| MZA18224-801-A | 2 | 68.80 | 34.19 0 | **** | 14.76 0 | *** | 11.39 0 | ** | 44.14 0 | **** |
| MZA18036-23-A | 2 | 71.75 | 29.40 0 | * | 11.65 0 | ** | 9.41 0 | ** | 35.80 0 | **** |
| MZA15853-10-A | 2 | 77.72 | 23.81 0 | **** | 5.97 0.02 | * | 6.02 0.02 | * | 22.76 0 | **** |
| MZA10094-6-A | 2 | 80.90 | 23.24 0 | **** | 5.82 0.02 | * | 7.91 0.01 | ** | 24.05 0 | **** |
| MZA15844-19-A | 2 | 82.87 | 19.48 0 | **** | 3.67 0.06 |  | 8.16 0.01 | ** | 19.32 0 | **** |
| MZA4425-25-A | 2 | 85.68 | 12.42 0 | *** | 1.94 0.17 |  | 6.37 0.01 | * | 12.15 0 | *** |
| MZA7964-33-A | 2 | 94.40 | 6.24 0.02 | * | 2.08 0.15 |  | 6.23 0.02 | * | 7.90 0.01 | ** |
| MZA1962-33-A | 2 | 96.01 | 5.32 0.02 | * | 2.01 0.16 |  | 6.93 0.01 | * | 7.36 0.01 | ** |
| MZA5581-13-A | 2 | 105.99 | 4.91 0.03 | * | 1.47 0.23 |  | 7.99 0.01 | ** | 7.70 0.01 | ** |
| MZA3439-8-A | 2 | 128.57 | 4.27 0.04 | * | 0.90 0.35 |  | 7.34 0.01 | ** | 6.51 0.01 | * |
| MZA4564-49-A | 2 | 142.10 | 5.85 0.02 | * | 0.66 0.42 |  | 8.59 0 | ** | 7.49 0.01 | ** |
| MZA10883-17-A | 2 | 158.98 | 0.20 0.66 |  | 0.02 0.89 |  | 2.26 0.14 |  | 0.24 0.63 |  |
| MZA12915-19-A | 2 | 170.53 | 0.00 0.98 |  | 0.01 0.91 |  | 0.57 0.45 |  | 0.04 0.84 |  |
| MZA10488-21-A | 2 | 177.67 | 0.19 0.66 |  | 0.01 0.91 |  | 0.11 0.74 |  | 0.03 0.87 |  |
| MZA3152-16-A | 2 | 191.27 | 0.15 0.70 |  | 0.11 0.74 |  | 0.74 0.39 |  | 0.00 1.00 |  |
| MZA505-250-A | 2 | 201.35 | 1.20 0.28 |  | 2.22 0.14 |  | 1.53 0.22 |  | 3.55 0.06 |  |

| Marker | Chrom. | Position | MRCVSC F(1, n-2) pr(F) | Rep 1 | MRCVSC F(1, n-2) pr(F) | Rep 2 | MRCVSC F(1, n-2) pr(F) | Rep 3 | MRCVSC F(1, n-2) pr(F) | Mean Score |
|---|---|---|---|---|---|---|---|---|---|---|
| MZA2592-73-A | 2 | 9.29 | 2.87 0.09 |  | 0.86 0.36 |  | 0.02 0.90 |  | 1.37 0.25 |  |
| MZA225-50-A | 2 | 25.51 | 8.89 0 | ** | 3.31 0.07 |  | 1.15 0.29 |  | 5.63 0.02 | * |
| MZA3334-4-A | 2 | 33.38 | 21.58 0 | **** | 4.03 0.05 | * | 2.48 0.12 |  | 11.67 0 | ** |
| MZA4122-3-A | 2 | 45.60 | 35.56 0 | **** | 6.06 0.02 | * | 4.90 0.03 | * | 20.90 0 | **** |
| MZA8067-27-A | 2 | 52.77 | 48.72 0 | **** | 9.52 0 | ** | 8.85 0 | ** | 32.41 0 | **** |
| MZA5822-15-A | 2 | 53.53 | 53.73 0 | **** | 9.93 0 | ** | 9.06 0 | ** | 34.53 0 | **** |
| MZA1525-98-A | 2 | 54.62 | 58.15 0 | **** | 10.12 0 | ** | 8.96 0 | ** | 35.86 0 | **** |
| MZA8381-801-A | 2 | 63.47 | 58.64 0 | **** | 12.09 0 | *** | 9.52 0 | ** | 39.57 0 | **** |
| MZA625-29-A | 2 | 64.05 | 63.88 0 | **** | 13.29 0 | *** | 10.82 0 | ** | 40.92 0 | **** |
| MZA625-30-A | 2 | 65.99 | 60.02 0 | **** | 12.44 0 | *** | 9.81 0 | ** | 40.33 0 | **** |
| MZA16656-19-A | 2 | 65.99 | 59.49 0 | **** | 11.23 0 | ** | 10.13 0 | ** | 38.87 0 | **** |
| MZA15490-801-A | 2 | 65.99 | 62.05 0 | **** | 13.09 0 | *** | 10.51 0 | ** | 41.62 0 | **** |
| MZA2038-71-A | 2 | 65.99 | 62.05 0 | **** | 13.09 0 | *** | 10.51 0 | ** | 41.62 0 | **** |
| MZA11826-803-A | 2 | 65.99 | 62.05 0 | **** | 13.09 0 | *** | 10.51 0 | ** | 41.62 0 | **** |
| MZA11826-801-A | 2 | 65.99 | 62.05 0 | **** | 13.09 0 | *** | 10.51 0 | ** | 41.62 0 | **** |
| MZA9105-8-A | 2 | 65.44 | 62.03 0 | **** | 13.09 0 | *** | 10.50 0 | ** | 41.61 0 | **** |
| MZA18224-801-A | 2 | 68.80 | 61.77 0 | **** | 13.10 0 | *** | 10.43 0 | ** | 41.50 0 | **** |
| MZA18036-23-A | 2 | 71.75 | 47.25 0 | **** | 11.83 0 | *** | 7.58 0.01 | ** | 40.17 0 | **** |
| MZA15853-10-A | 2 | 77.72 | 43.32 0 | **** | 8.75 0 | ** | 6.44 0.01 | * | 31.80 0 | **** |
| MZA10094-6-A | 2 | 80.90 | 37.87 0 | **** | 7.62 0.01 | ** | 9.31 0 | ** | 31.20 0 | **** |
| MZA15844-19-A | 2 | 82.87 | 33.89 0 | **** | 4.90 0.03 | * | 8.38 0.01 | ** | 26.58 0 | **** |
| MZA4425-25-A | 2 | 85.68 | 19.92 0 | **** | 1.44 0.23 |  | 5.28 0.02 | * | 15.62 0 | *** |
| MZA7964-33-A | 2 | 94.40 | 12.94 0 | *** | 2.44 0.12 |  | 7.06 0.01 | ** | 13.89 0 | *** |
| MZA1962-33-A | 2 | 96.01 | 11.02 0 | ** | 2.34 0.13 |  | 7.63 0.01 | ** | 13.26 0 | *** |
| MZA5581-13-A | 2 | 105.99 | 8.12 0.01 | ** | 1.93 0.17 |  | 6.48 0.01 | * | 14.69 0 | *** |
| MZA3439-8-A | 2 | 128.57 | 2.93 0.09 |  | 1.47 0.23 |  | 2.82 0.10 |  | 7.13 0.01 | ** |
| MZA4564-49-A | 2 | 142.10 | 2.90 0.09 |  | 1.47 0.23 |  | 2.98 0.09 |  | 6.78 0.01 | * |
| MZA10883-17-A | 2 | 158.98 | 0.00 0.96 |  | 0.86 0.36 |  | 0.28 0.60 |  | 1.83 0.18 |  |
| MZA12915-19-A | 2 | 170.53 | 0.67 0.42 |  | 0.43 0.51 |  | 0.16 0.69 |  | 0.57 0.45 |  |
| MZA10488-21-A | 2 | 177.67 | 0.21 0.65 |  | 0.01 0.95 |  | 0.04 0.85 |  | 0.01 0.91 |  |
| MZA3152-16-A | 2 | 191.27 | 0.62 0.43 |  | 0.32 0.57 |  | 0.00 1.00 |  | 0.31 0.58 |  |
| MZA505-250-A | 2 | 201.35 | 0.66 0.42 |  | 0.23 0.63 |  | 0.07 0.80 |  | 0.80 0.37 |  |

The effect of MRCV1 allelic variation on several backgrounds was evaluated by the phenotypic data of BC1F3s progeny with allelic variation at MRCV1 region. MRCV1 resistant allele showed a positive effect across another 4 genetic backgrounds (PH6GF, PHP3P1, PH6B8 and PH6KW inbreds). Table 15 below shows the mean phenotypic score for BC1F3 progeny with allelic variation at MRCV1 region.

TABLE 15

| Marker position 65.99 | Inbreds | | | |
|---|---|---|---|---|
| | PH6GF | PHP3P1 | PH6B8 | PH6KW |
| Inbred score | 3.8 | 2.5 | 3 | 3 |
| BC1F3 susceptible allele (AA) | 5.00 | 4.10 | 4.50 | 4.19 |
| BC1F3 heterozygous allele (AB) | — | 3.53 | 5.17 | 4.26 |
| BC1F3 resistant allele (BB) | 6.11 | 6.17 | 5.47 | 5.00 |
| QTL effect | 1.11 | 2.07 | 0.97 | 0.81 |

Discussion/Conclusions

This present study has identified chromosome intervals and individual markers that correlate with MRCV resistance. Markers that lie within these intervals are useful for use in MAS, as well as other purposes.

Example 4

QTL Validation on DH Breeding Populations

A QTL marker regression analysis was undertaken to identify maize chromosome intervals and genetic markers (respectively) that are associated with resistance and allow the resistance to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

Marker enhanced pedigree selection (MEPS) populations means the scheme of breeding population populations for MRCV resistance were created from different crosses of inbreds. The crosses included: a) Crosses with MRCV1 fixed: PHKEF×PHBNA, PHKEF×PHS2G, PHKFD×PHS3J, PHKFA×PHBNA, PHKFA×PHKEF, PHS2Y×PHKEF, and b) Crosses with MRCV1 segregating: PH3DT×PHKEF, PHKEF×PH9PR, PHKEF×PH9PR, PHKEF×PHKDK, PHKDN×PHKFD, PHKDN×PHS3J, PHKFD×PHCOG, PHKDK×PHKFA, PHKDN×PH9PH.

TABLE 16

| Population | # Ind | MRCV1 |
|---|---|---|
| PHKEF/PHBNA | 9 | Fixed |
| PHKEF/PHS2G | 13 | Fixed |
| PHKFD/PHS3J | 12 | Fixed |
| PHKFA/PHBNA | 12 | Fixed |
| PHKFA/PHKEF | 34 | Fixed |
| PHS2Y/PHKEF | 12 | Fixed |
| PH3DT/PHKEF | 11 | Segregating |
| PHKEF/PH9PR | 12 | Segregating |
| PHKEF/PHKDK | 18 | Segregating |
| PHKDN/PHKFD | 30 | Segregating |
| PHKDN/PHS3J | 11 | Segregating |
| PHKFD/PHC0G | 9 | Segregating |
| PHKDK/PHKFA | 15 | Segregating |
| PHKDN/PH9PH | 8 | Segregating |

These populations were generated by the doubled haploids process. The number of individuals characterized for MRCV resistance were included in Table 16. Fingerprint data at the main QTL region and identity by descent information was used to define QTL segregating and QTL fixed populations.

Phenotypic Scoring

Phenotypic scoring of each of the DH MEPS population was based on sets of phenotypic data collected from the field in one crop season.

Maize Genotyping

Maize DH progeny from the different crosses were genotyped by using a set of 756 SNPs distributed in the maize genome. The positions obtained are then plotted as a histogram overlaying the interval mapping figure.

Results

QTL Marker Analysis

The present study identified a single major chromosome interval that correlated with QTL associated with resistance/susceptibility to MRCV infection when populations from SS crosses Resistant×Susceptible and segregating for MRCV major QTL on chromosome 2 were selected "a priori" 2. The QTL were identified using the field data. One major, significant QTL was located on linkage group 2. Genetic crosses between inbreds harboring the positive allele of the major QTL on chromosome 2 (QTL fixed by parents) showed most of the progenies with a field MRCV score of 4 or higher.

Single Marker Regression

Using single marker regression, there are a number of markers showing association with the resistant phenotype at a confidence level of P=0.05 or better, as shown in Tables 1 and 2. Some of the markers identified in the marker regression analysis show a concordance of observations with the association mapping, where the different approaches identify the same markers. For example, there are markers at the region from 55 to 70 cM on chromosome 2 identified by both marker regression and association mapping. On a group of SS inbreds, main association was located at the MZA10538 marker (position 54.5). On a group of NSS inbreds, a major association was located at position 72 cM.

Discussion/Conclusions

This present study has identified chromosome intervals and individual markers that correlate with MRCV resistance. Markers that lie within these intervals are useful for use in MAS, as well as other purposes.

Example 5

Main Inbreds Characterization

A set of key argentine genetic materials were phenotypically and genetically characterized to confirm maize genetic marker loci associated with resistance to MRCV. By identifying such genetic markers, marker assisted selection (MAS) can be used to improve the efficiency of breeding for improved resistance of maize to MRCV.

Maize Lines and Resistance Scoring

The plant varieties used in the analysis were from diverse sources, including elite germplasm, commercially released cultivars and other public lines representing a broad range of germplasm related to the argentine breeding program and including main sources of MRCV resistance.

The groups of maize lines were assembled for the analysis based on their phenotypic responses against MRCV infection, where the plants were sorted into either highly susceptible or highly resistant varieties. The classifications of resistance and susceptible were based solely on observations of fortuitous, naturally occurring disease incidence in field tests over several years. The degree of plant resistance to MRCV infection varied widely, as measured using a scale from one (highly susceptible) to nine (highly tolerant). Generally, a score of two (2) indicated the most susceptible strains, a score of four (4) was assigned as the threshold to consider a plant susceptible or resistant (less than 4, susceptible; 4 or higher is resistant) and a score of seven (5-7) was assigned to the most resistant lines. Resistance scores of eight (8) and nine (9) were reserved for resistance levels that are very rare and generally not observed in existing germplasm. If no disease was present in a field, no resistance scoring was done. However, if a disease did occur in a specific field location, all of the lines in that location were scored. Scores for test strains accumulated over multiple locations and multiple years, and an averaged (e.g., consensus) score was ultimately assigned to each line.

Data collection was typically done in one scoring time. Scoring time is placed after flowering time.

In assessing association of markers to resistance, a comparison by simple regression approach was used. Allele origin was checked by the identity by descent approach. Using this approach, those maize lines that were considered to be representative of either the resistant or susceptible classes were used for assessing association. A list of resistant lines was constructed, where inbreds having a resistance score of 4 or greater were considered "Resistant". Similarly, maize lines with scores of three or less were collectively considered susceptible. Only lines that could be reliably placed into the two groups were used. Once a line is included in the "Resistant" or "susceptible" group, it was treated as an equal in that group. The actual quantitative ratings were also used for association test. In addition to this test, the identity by descent information was used to confirm the resistant allele origin at the highest associated markers.

In the study, 85 maize lines were identified that were considered resistant in the phenotypic spectrum; these plants formed the "RESISTANT" group. Also, 35 maize lines were identified that were judged to be susceptible to MRCV; these strains formed the "SUSCEPTIBLE" group.

Maize Genotyping

Each of the tolerant and susceptible lines was genotyped with a set of 63 SNP markers that span the QTL region at Chromosome 2 using techniques well known in the art. The genotyping protocol consisted of collecting young leaf tissue and isolating genomic DNA from pooled tissue of each inbred. The maize genomic DNA was extracted by the CTAB method, as described in Maroof et al. (1984) Proc. Natl. Acad. Sci. (USA) 81:8014-8018.

The isolated genomic DNA was then used in PCR reactions using amplification primers specific for a large number of markers that covered the QTL region. SNP-type markers were genotyped using an ASH protocol.

The underlying logic is that markers with significantly different allele distributions between the resistant and susceptible groups (i.e., non-random distributions) might be associated with the trait and can be used to separate them for purposes of marker assisted selection of maize lines with previously uncharacterized or characterized resistance or susceptibility to MRCV. The present analysis examined one marker locus at a time and determined if the allele distribution within the resistant group is significantly different from the allele distribution within the susceptible group. This analysis compares the plants' phenotypic score with the genotypes at the target loci.

Results

Tables 1 and 2 list maize markers that demonstrated linkage disequilibrium with the MRCV resistant/susceptibility phenotype. Also indicated in those tables is where the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the adjusted probability values.

Tables 6 and 7 provide the PCR primer sequences that were used to genotype these marker loci.

The non-random distribution of alleles between the resistant and susceptible plant groups at the various marker loci in Tables 1 and 2 is good evidence that a QTL influencing MRCV resistance is linked to these marker loci. Considering that most of the inbreds of this set correspond to a specific breeding program (argentine breeding program), it is expected that Applicants have found linkage disequilibrium with other markers on flanking regions of the gene. The highest associated markers corresponded to the previously considered preferred markers.

As well known in the art, the level of association of target markers to a trait of interest will be determined by the level of linkage disequilibrium at the target region on that specific set of genetic materials. Table 17 below shows the level of association across the target region between the genotypic data of SNPs markers and the response to MRCV.

TABLE 17

| Chr | Pos | Marker | b0 | b1 | $F(1, n-2)$ | pr(F) | MRCV Trait |
|---|---|---|---|---|---|---|---|
| 2 | 64.05 | MZA625-29-A | 1.612 | −0.322 | 95.712 | 0 | **** |
| 2 | 64.05 | MZA625-30-A | 1.602 | −0.326 | 92.373 | 0 | **** |
| 2 | 65.99 | MZA16656-8-A | 1.613 | −0.255 | 44.107 | 0 | **** |
| 2 | 65.99 | MZA16656-19-A | 1.571 | −0.344 | 105.781 | 0 | **** |
| 2 | 65.99 | MZA15490-137-A | 1.724 | −0.189 | 23.834 | 0 | **** |
| 2 | 65.99 | MZA15490-138-A | 1.731 | −0.179 | 20.667 | 0 | **** |
| 2 | 65.99 | MZA15490-801-A | 1.727 | −0.172 | 19.222 | 0 | **** |
| 2 | 65.99 | MZA2038-71-A | 1.702 | −0.045 | 1.095 | 0.298 | |
| 2 | 65.99 | MZA2038-76-A | 1.691 | −0.063 | 1.987 | 0.161 | |
| 2 | 65.99 | MZA11826-801-A | 1.673 | −0.098 | 4.614 | 0.034 | * |
| 2 | 65.99 | MZA11826-27-A | 1.681 | −0.092 | 4.315 | 0.04 | * |
| 2 | 65.99 | MZA11826-803-A | 1.673 | −0.113 | 6.286 | 0.014 | * |
| 2 | 65.44 | MZA9105-8-A | 1.576 | −0.226 | 22.461 | 0 | **** |
| 2 | 65.44 | MZA9105-6-A | 1.681 | −0.081 | 3.452 | 0.066 | |

In order to evaluate the effect of the allelic variation at this QTL at the hybrid level, a set of 371 hybrids (heterogenous genetic backgrounds) was characterized according to the presence of one (heterozygous for the QTL) or two resistant alleles (homozygous for the QTL) from the parent lines. A positive and additive effect of the resistant allele at the major QTL was observed on the hybrid combinations; no maternal effects were observed. Table 18 below shows the field performance of hybrids with different genotypes at the major QTL.

TABLE 18

| Hybrid genotype at major QTL | Number of hybrids | MRCVSC | Category |
|---|---|---|---|
| AA, homozygous susceptible allele | 65 | 3.8 | Susceptible |
| BA, heterozygous, female resistant allele | 121 | 4.41 | Resistant |
| AB, heterozygous, male resistant allele | 96 | 4.46 | Resistant |
| BB, homozygous resistant allele | 89 | 4.76 | Resistant |

Discussion

There are a number of ways to use the information provided in this analysis for the development of improved maize varieties. One application is to use the associated markers (or more based on a higher probability cutoff value) as candidates for mapping QTL in specific populations that are segregating for plants having tolerance to MRCV infection. In this application, one proceeds with conventional QTL mapping in a segregating population, but focusing on the markers that are associated with MRCV infection tolerance, instead of using markers that span the entire genome. This makes mapping efforts more cost-effective by dramatically reducing lab resources committed to the project. For example, instead of screening segregating populations with a large set of markers that spans the entire genome, one would screen with only those few markers that met some statistical cutoff in the allele association study. This will not only reduce the cost of mapping but will also eliminate false leads that will undoubtedly occur with a large set of markers. In any given cross, it is likely that only a small subset of the associated markers will actually be correlated with tolerance to MRCV infection. Once the few relevant markers are identified in any tolerant parent, future marker assisted selection (MAS) efforts can focus on only those markers that are important for that source of tolerance. By pre-selecting lines that have the allele associated with tolerance via MAS, one can eliminate the undesirable susceptible lines and concentrate the expensive field testing resources on lines that have a higher probability of being resistant to MRCV infection.

Example 6

QTL Evaluation on F3 Breeding Populations

Marker associations are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

Old scheme of breeding was based on the traditional pedigree based method of making F1 crosses and deriving several self generations (F2, F3, F4, etc.). With the goal of checking the importance of the positive and negative alleles at the major QTL for MRCV resistance in a specific set of argentine breeding materials, these steps were followed: a) Selection of resistant parents whose resistance is expected to be based on the major MRCV1; b) Selecting a total of 2372 F3 families originated from multiple breeding crosses; c) Making two groups of F3 families, a first group, based on crosses between parents without the positive alleles of the major QTL and a second group with both parents harboring the positive allele at the major QTL. Fingerprint data at the main QTL region and identity by descent information was used to define QTL segregating and QTL fixed populations (positive/negative). MZA16656 and/or flanking markers were the key markers to define the presence of MRCV1 positive allele.

The total number of individuals located on these groups was 2372. Fingerprint data at main QTL region and identity by descent information was used to define QTL segregating and QTL fixed populations.

Phenotypic Scoring

Phenotypic scoring of each of the F3 populations was based on sets of phenotypic data collected from the field on one crop season.

Maize Genotyping

Individual F3 families were not genotyped. Genotype at major QTL on each individual F3 was estimated according to the specific alleles on both parents. If both parents in a specific F3 population harbor the positive allele at MRCV1, all the progenies from that cross were considered as having the positive allele. If both parents in a specific F3 population harbor the negative allele at MRCV1, all the progenies from that cross were considered as having the negative allele. Standard software was used to the marker ANOVA analysis.

Results

QTL Marker Analysis

The present study supported the conclusion that a major chromosome interval correlated with QTL associated with resistance/susceptibility to MRCV infection when populations from crosses fixed at MRCV major QTL on chromosome 2 were selected “a priori”.

Single Marker ANOVA

Using marker ANOVA, there are a number of markers showing association with the tolerance phenotype at a confidence level of P=0.05 or better, as shown in Tables 1 and 2. Some of the markers identified in the marker ANOVA analysis show a concordance of observations with the association mapping, where the different approaches identify the same markers. For example, there are markers at the region from 55 to 70 cM on chromosome 2 identified by both marker regression and association mapping.

Discussion/Conclusions

This present study has identified chromosome intervals and individual markers that correlate with MRCV resistance. Markers that lie within these intervals are useful for use in MAS, as well as other purposes. In this example, Applicants evaluated the effect on MRCV resistance of the allelic variation at MRCV1, and there was a clear the association between this allelic variation and the expected phenotype on a high number of F3 progenies.

Table 19 below shows the F-test of the model where the Source is QTL and two levels of the source were considered: Level AA: F3 populations with fixed susceptible alleles at target region (position 65.99 or inferred by flanking markers) and Level BB: F3 populations with fixed resistant alleles at target region (position 65.99 or inferred by flanking markers).

TABLE 19

| One-Way ANOVA: MRCVSC score versus QTL | | | | | |
|---|---|---|---|---|---|
| Source | DF | SS | MS | F | P |
| QTL | 1 | 1656.41 | 1656.41 | 1383.90 | 0.000 |
| Error | 2370 | 2836.69 | 1.20 | | |
| Total | 2371 | 4493.10 | | | |

S = 1.094; R-Sq = 6.87%; R-Sq(adj) = 36.84%
References:
DF. Degree of freedom.
SS. Square Sum.
MS. Mean square.
F. F value.
P. Probability value.

References

DF. Degree of freedom. SS. Square Sum. MS. Mean square. F. F value. P. Probability value.

Table 20 below shows a mean test where level AA and level BB represents the allelic variation at target QTL and according to the model included in Table 19. Phenotypic mean for level AA was 3.42 (MRCV susceptible category) and phenotypic mean for level BB was 5.138 (MRCV resistant category).

TABLE 20

| Level | N | Mean | StDev |
|---|---|---|---|
| AA | 1462 | 3.420 | 1.048 |
| BB | 910 | 5.138 | 1.164 |

```
Individual 95% Confidence Interval For
Mean Based on Pooled StDev
-----+-----------+-----------+-----------+------
 (*-)
                                    (*-)
-----+-----------+-----------+-----------+------
   3.50        4.00        4.50        5.00
```

Pooled StDev = 1.094
References:
N: Number of F3 families.
Mean: Phenotypic mean of each level.
StDev: Standard deviation.

References

N: Number of F3 families. Mean: Phenotypic mean of each level. StDev: Standard deviation.

Example 7

High-Resolution Gene Mapping and Near-Isogenic Lines

High-resolution gene mapping by progeny testing of homozygous recombinant plants was undertaken for high resolution positioning of the MRCV resistance genes. QTL interval mapping and a single marker regression analysis were performed to identify maize chromosome intervals and genetic markers (respectively) that are associated with resistance and enhance resistance to MRCV infection. QTL mapping and marker regression are widely used methods to identify genetic loci that co-segregate with a desired phenotype. By identifying such genetic loci, marker assisted selection (MAS) can be used to improve the efficiency of breeding for improved maize inbreds and hybrids.

Maize Lines

One main population for high-resolution gene mapping of MRCV resistance was created from the cross of inbreds PH7WT and PH3DT. Another population for fine mapping in an independent source was created from the cross of inbreds PH9TJ and PH890. The PH7WT×PH3DT population consisted of 256 BC5F3 families generated by selfing and fixing selected recombinant BC5 plants from a total of 3000 BC5 plants harboring a heterozygous fragment at the region from 50 to 80 cM on chromosome 2. This strategy permitted coverage with recombinants of the whole QTL region (Tables 7 and 8, and FIG. 3A and FIG. 3B). The PH9TJ×PH890 population consisted of 245 BC3F3 families generated by: a) Crossing selected BC2F4 plants homozygous for the major QTL on chromosomes 2 and 5 with PH890 (susceptible parent); b) Making two self generations to advance to fixed BC3F3 families.

Table 21 shows the number of BC5F3s recombinants generated from the cross PH3DT×PH7WT. An expected Kb size for each marker interval is also included. Table 22 shows the number of BC5F3s recombinants generated from the cross PH3DT×PH7WT. A comparison with the first estimation of gene content is included.

TABLE 21

| Marker | Pioneer Genetic Map* | Fingerprint bands** | Estimated size of each interval (sequence data) | Total Recombinants | BC5F3s |
|---|---|---|---|---|---|
| MZA625 | 64.05 | | | | |
| MZA16656 | 65.99 | 152 | Higher than 100 Kb | 76 | 59 |
| MZA15451 | 65.99 | — | 10 Kb | — | — |
| MZA15490 | 65.99 | — | Less than 100 Kb | 3 | 2 |
| MZA2038 | 65.99 | 0 | Less than 20 Kb | 1 | 1 |
| MZA11826 | 65.99 | 33 | Higher than 20 Kb | 0 | 0 |
| MZA9150-8-A | 65.44 | 88 | Higher than 50 Kb | 0 | 0 |
| MZA18224-801-A | 68.80 | 400 | Higher than 165 Kb | 51 | 44 |

*Marker ordered according to sequencing, physical, and recombination. Pioneer genetic map is included only as reference.

**Number of fingerprint bands between pairs of markers.

TABLE 22

| PHD Chr | PHD Map Pos | UC7 PCO Vs. Myriad Amplicons | Locus Order | Working Maize Gene ID | Annotation Summary | Recombinants |
|---|---|---|---|---|---|---|
| 2 | 64.05 | MZA625 | Loc_029 | AC191302_5part | Transcription Factor | 59 |
| | | | Loc_028 | AC191302_3 | Putrescine-binding protein; Hypothetical protein | |
| | | | Loc_027 | pco600856 | Putative L-ascorbate peroxidase | |
| | | | Loc_025 | pco530474 | Plastid development protein; DAG | |
| | | | Loc_024 | pco593067 | Hypothetical protein; Vacuolar ATP synthase subunit? | |
| | | | Loc_023 | AC191302_6 | Hypothetical protein | |
| | | | Loc_022 | Inferred by rice and sorghum | Hypothetical protein | |
| | | | Loc_021 | pco641713 | Hypothetical protein | |
| | | | Loc_016 | pco591841 | Growth regulating factor | |
| | | | Loc_015 | Genomic_PC0622600 PC0666161 | G protein-coupled receptor 89C (Homo sapiens) | |
| 2 | 65.99 | MZA166656 | Loc_014 | pco638426 | Major intrinsic protein; NIP; BREVIS RADIX like 1 | |
| | | | Loc_013 | pco514627 | Hypothetical protein | 2 |
| 2 | 65.30 | MZA15451 | Loc_012 | pco588936 | Alternative oxidase AOX3 | |
| | 65.99 | MZA15490 | | pco642154 | Alternative oxidase AOX2 | |
| | | | Loc_010 | Inferred by rice and sorghum | Hypothetical protein | 1 |
| | | | Loc_009 | pco64444 | Myb-like; 2-component response regulator | |
| 2 | 65.99 | MZA2038 | Loc_008 | pco641455 | Clathrin interactor; Epsin; Hypothetical protein | |
| | | | Loc_007 | pco640541 | CDC20 WD-repeat protein | 0 |
| | | | Loc_006 | pco651091 | Cobalamin synthesis protein | |
| | | MZA11826 | | | | |
| | | | Loc_005 | pco571541 | Hypothetical protein | |
| | | | Loc_004 | pco525409 | Scramblase | |
| | | | Loc_003 | pco553755 | Hypothetical protein | |
| | | | Loc_002 | pco644099 | Hypothetical protein | |
| 2 | 65.44 | MZA9105 | Loc_001 | pco588179 | Receptor protein kinase | |
| | | AC208537(CAP) | | | | 13 |
| | | AC197085(CAP) | | | | 2 |
| | | MZA18224 | | | | 23 |

BC5F3 near-isogenic lines (NIL) harboring allelic variation at the region of the preferred markers (MZA16656, MZA15451, MZA15490, MZA2038, MZA11826 and MZA9105) were generated by marker assisted selection from the PH7WT×PH3DT cross. The NILs were generated by introgressing the QTL region from PH7WT into PH3DT, cleaning the genetic background, and selecting specific recombinants at the region of the preferred markers. By selfing individual BC5F2 plants harboring a heterozygous fragment at the region of the preferred markers, negative and positive near-isogenic lines were derived, and the QTL was treated as a single Mendelian factor.

Phenotypic Scoring

Phenotypic scoring of each of the BC5F3 families from PH7WT×PH3DT cross and the 245 BC3F3 families from PH9TJ×PH890 cross and parents was based on sets of phenotypic data collected from the field (field experiments under natural infection, Córdoba Province, Argentina) on one crop season.

In addition to the phenotyping scoring, the specific isolines at the region of preferred markers were characterized by ELISA test for virus in the Buenos Aires Province, Argentina.

Maize Genotyping

Maize BC5F3 progeny from PH7WT×PH3DT cross and BC3F3 from the PH9TJ×PH890 cross were genotyped by using polymorphic SNPs at the QTL region on chromosome 2 (see Example 2). In addition, two CAPS markers were designed and used to genotype the BC5F3 progenies; these two CAPS markers were positioned to the interval MZA9105 to MZA18224. In the case of the PH9TJ×PH890 cross, additional markers were positioned on the chromosome 5 QTL. The BC5F3s from PH7WT×PH3DT cross were subjected to background cleaning at BC3 stage, especially at chromosome 5 QTL. The BC3F3s from PH9TJ×PH890 cross were subjected to background cleaning at BC2 stage.

Windows QTL Cartographer (up-to-date version according the date of QTL mapping) was used for both the marker regression analysis and QTL interval mapping. LOD scores (logarithm of the odds ratio) were estimated across the target regions according the standard QTL mapping procedures.

Mean scores were used in QTL interval mapping. The LOD threshold was 2.5. A confidence interval was estimated for each QTL. The positions obtained are then plotted as a histogram overlaying the interval mapping figure.

As these population were generated by marker assisted selection (not random events of recombination), marker regression analysis was considered as powerful as interval mapping analysis.

Results

QTL Interval Mapping

The present study identified a single chromosome interval that correlated with QTLs associated with resistance/susceptibility to MRCV infection. The QTL were identified using the field data. One major, significant QTL was located on linkage group 2 at the position of "preferred markers" on the high resolution mapping pops from PH7WT×PH3DT and PH9TJ×PH890 crosses. The additional QTL on chromosome 5 from PH9TJ×PH890 cross was not significant in this analysis.

Single Marker Regression

Using single marker regression, there are a number of markers showing association with the resistant phenotype at a confidence level of P=0.05 or better, as shown in Tables 23 and 24. The markers identified in the marker regression analysis show a high resolution gene position for the target QTL, coincident with the position of the preferred markers. See Table 23 for marker regression analysis (MRCVSC=MRCV phenotypic score) and FIG. 4 for interval mapping for the PH7WT×PH3DT cross. See Table 24 for a QTL marker regression analysis for the PH9TJ×PH890 cross on specific QTL at chromosomes 2 and 5 (MRCVSC=MRCV phenotypic score) and FIG. 5 for interval mapping for the PH7WT×PH3DT cross.

TABLE 23

| Marker | Position | b0 | b1 | F(1, n-2) | pr(F) | MRCVSC |
|---|---|---|---|---|---|---|
| MZA1525-98-A | 54.62 | 3.423 | −0.330 | 9.144 | 0.003 | ** |
| MZA8381-801-A | 63.47 | 3.337 | −0.429 | 15.852 | 0 | *** |
| MZA625-29-A | 64.05 | 3.362 | −0.422 | 16.218 | 0 | *** |
| MZA16656-19-A | 65.99 | 3.300 | −0.589 | 38.934 | 0 | **** |
| MZA15490-137-A | 65.99 | 3.331 | −0.597 | 42.193 | 0 | **** |
| MZA2038-71-A | 65.99 | 3.377 | −0.628 | 51.838 | 0 | **** |
| MZA11826-801-A | 65.99 | 3.377 | −0.628 | 51.838 | 0 | **** |
| MZA9105-8-A | 65.44 | 3.377 | −0.628 | 51.838 | 0 | **** |
| AC208537_003 | | 3.448 | −0.257 | 5.276 | 0.025 | * |
| AC197085_003 | | 3.472 | −0.135 | 1.331 | 0.253 | |
| MZA18224-801-A | 68.80 | 3.403 | 0.095 | 0.595 | 0.443 | |

TABLE 24

| Marker | Chr | Pos | b0 | b1 | −2 ln(L0/L1) | F(1, n-2) | pr(F) | MRCVSC |
|---|---|---|---|---|---|---|---|---|
| MZA9997-42-A | 2 | 54.56 | 3.891 | −0.460 | 37.209 | 39.855 | 0 | **** |
| MZA2201-44-A | 2 | 56.95 | 3.828 | −0.334 | 24.549 | 25.610 | 0 | **** |
| MZA8381-29-A | 2 | 63.47 | 3.939 | −0.465 | 33.536 | 35.647 | 0 | **** |
| MZA625-30-A | 2 | 64.05 | 3.907 | −0.485 | 38.029 | 40.803 | 0 | **** |
| MZA9105-6-A | 2 | 66.00 | 3.887 | −0.547 | 51.358 | 56.671 | 0 | **** |
| MZA2349-71-A | 2 | 68.80 | 3.907 | −0.534 | 49.417 | 54.307 | 0 | **** |
| MZA18224-801-A | 2 | 68.80 | 3.902 | −0.531 | 48.959 | 53.751 | 0 | **** |
| MZA18036-23-A | 2 | 71.75 | 3.906 | −0.505 | 43.106 | 46.746 | 0 | **** |
| MZA10543-14-A | 2 | 81.45 | 3.934 | −0.054 | 0.332 | 0.320 | 0.572 | |
| MZA18843-61-A | 5 | 141.08 | 3.897 | 0.004 | 0.003 | 0.003 | 0.958 | |
| MZA5521-17-A | 5 | 141.62 | 3.895 | 0.009 | 0.014 | 0.014 | 0.906 | |
| MZA12753-14-A | 5 | 143.95 | 3.886 | 0.044 | 0.333 | 0.331 | 0.566 | |
| MZA7908-20-A | 5 | 152.87 | 3.903 | −0.046 | 0.311 | 0.309 | 0.579 | |
| MZA8726-9-A | 5 | 154.05 | 3.901 | −0.050 | 0.385 | 0.382 | 0.537 | |
| MZA11109-19-A | 5 | 169.77 | 3.895 | 0.036 | 0.156 | 0.155 | 0.694 | |

Near Isogenic Lines

The near isogenic lines harboring allelic variation at the region of preferred markers showed a significant difference in their response to the disease in Córdoba Province. Table 25 shows the genotype of SNPs at the region of preferred markers for the near isogenic lines (negative isoline=susceptible haplotype; positive isoline=resistant haplotype); the introgressed fragment is represented by the SNP polymorphics at markers from MZA16656-19-A to MZA9105-8-A while flanking monomorphics markers MZA625-30-A and MZA18224-801-A represent the susceptible haplotype on both near isogenic lines. The ELISA test for virus (samples from Buenos Aires Province) showed 0% of plants positive for virus in the isolines harboring the resistant allele, while 38% of plants were positive for virus in the isolines harboring the susceptibility allele.

Note: ELISA test was not performed on materials planted in Córdoba Province (the disease pressure was higher than in Buenos Aires Province). However, the presence of enations (a specific symptom of Fijivirus) on both resistant and susceptible materials in Córdoba Province indicates the presence of the virus in the plants.

TABLE 25

| Isoline | MZA625-30-A | MZA16656-19-A | MZA15490-801-A | MZA15490-137-A | MZA2038-71-A | MZA2038-76-A | MZA11826-801-A | MZA11826-803-A | MZA9105-8-A | MZA18224-801-A |
|---|---|---|---|---|---|---|---|---|---|---|
| | 64.05 | 65.99 | 65.99 | 65.99 | 65.99 | 65.99 | 65.99 | 65.99 | 65.44 | 68.8 |
| Negative | C | A | C | A | T | C | G | T | G | A |
| Positive | C | G | G | C | A | T | A | C | A | A |

Discussion/Conclusions

This present study has identified chromosome intervals and individual markers that correlate with MRCV resistance. Markers that lie within these intervals are useful for use in MAS, as well as other purposes. The high resolution gene position facilitates the cloning of the target QTL.

Example 8

Gene Positioning, Sequencing and Candidate Genes

Sequencing, genetic and physical information for the region of the preferred markers was integrated to characterize the target region. Information from independent approaches (recombination data, association analysis and conservative fragments) was used to identify a specific interval for the generation of additional sequencing data.

Maize Lines and Phenotypic Scoring

Maize lines were phenotypically scored based on their degree of resistance to MRCV infection (in contrast to simple categorization of "tolerant" or "susceptible"). The plant varieties used in the analysis were from diverse sources, including elite germplasm, commercially released cultivars and other public varieties. The collections comprised 883 maize lines. The lines used in the study had a broad maturity range varying from CRM (comparative relative maturity) 90 to CRM 140, representing the main inbreds of Pioneer germplasm.

The degree of plant resistance to MRCV infection varied widely, as measured using a scale from one (highly susceptible) to nine (highly resistant). Generally, a score of two (2) indicated the most susceptible strains, a score of four (4) was assigned as the threshold to consider a plant susceptible or resistant (less than 4, susceptible; 4 or higher is resistant) and a score of seven (5-7) was assigned to the most resistant lines. Resistance scores of eight (8) and nine (9) were reserved for resistance levels that are very rare and generally not observed in existing germplasm. If no disease was present in a field, no resistance scoring was done. However, if a disease did occur in a specific field location, all of the lines in that location were scored. Scores for test strains were accumulated over multiple locations and multiple years, and an averaged (e.g., consensus) score was ultimately assigned to each line.

Resistance scores for part of the 883 inbred collections were collected over several growing seasons (394 inbreds were evaluated at the same time in the growing season). Data collection was typically done in one scoring after flowering time.

Maize Genotyping

A collection of 883 maize lines was analyzed by DNA sequencing at 4000-10000 genes (genetic loci). SNP variation was used to generate specific haplotypes across inbreds at each locus. This data was used for identifying associations between alleles and MRCV resistance at genome level.

Maize Pedigree—Resistance Sources

A Pioneer pedigree database was used to understand the relationship between inbreds and haplotypes. This database contains the pedigree relationship between Pioneer inbreds since 1919. In the case of public inbreds, public information about pedigree and origins was incorporated to understand inbred and haplotype relationship. A list of key founders representing sources of resistance and susceptibility to MRCV in Pioneer germplasm (including public lines) was created by using pedigree, phenotypic and genotypic data. Most of the susceptible inbreds trace back to a specific set of haplotypes from U.S. germplasm (Public lines as B37, B73, B14, OH07, C103 and Pioneer inbreds 165 and 938); an exception is PH26N coming from tropical germplasm.

Gene Positioning

The interval between markers MZA15490 and MZA2038 (FIG. 6) was considered as a candidate region for studying the allelic diversity at the resistance gene region. This region was selected by using information from:

a) Recombinants. The positioning by recombinants was showed in Example 7. The phenotypic data for two recombinants at MZA16656 to MZA15490 interval and one recombinant at MZA15490 to MZA2038 interval was used to delimitate the left side of the gene position. From recombination population, there were no available recombinants at the region MZA2038-MZA11826-MZA9105.

b) Genotypic and phenotypic information across inbreds from Pioneer germplasm was used to detect a conservative fragment across resistant/susceptible inbreds. The detection of a conservative fragment was performed inside specific pedigrees and across multiple independent founders when enough conservative SNPs were available across independent founders.

Natural Allelic Diversity and Founder Relationship

The interval MZA15490 to MZA2038 was selected for allelic diversity analysis because of the high probability of harboring a candidate gene or the high linkage disequilibrium with a candidate gene. As the full sequence at MZA15490 to MZA2038 interval is available for B73 (B73=274) line, a group of 13 small sequence fragments were targeted for sequencing in a set of tester's lines. The tester's lines (Table 26) included: a) some of the key resistant and susceptible inbreds and haplotypes; b) the resistant and susceptible parents from the mapping populations PH7WT×PH3DT and PH9TJ×PH890; c) key recombinants from the inbred set and recombination population (PHG63 and a recombinant at MZA15490 to MZA2038 interval).

Table 26 shows a list of tester's lines including sources of resistance and susceptibility to MRCV in Pioneer germplasm and a recombinant at MZA15490-MZA2038 interval.

TABLE 26

| Inbred | Phenotype | Expected haplotype | n |
|---|---|---|---|
| PH9TJ | Resistant | PH9TJ | 1 |
| PHJ40 | Resistant | PHJ40 | 5 |
| PHGD3 | — | PHGD3 | 2 |
| 383 | Resistant | — | 1 |
| PHG63 | Resistant | 630 | 14 |
| 630 | Resistant | 630 | 14 |
| PH7WT | Resistant | 630 | 14 |
| PHR33 | Resistant | PHR33 | 1 |
| 501 | — | 501 | — |
| PH467 | Resistant | PH467 | 1 |
| PHDG9 | Resistant | PHDG9 | 1 |
| PHK09 | Resistant | PHK09 | 1 |
| 274 | Susceptible | 274 | 47 |
| 1047 | Susceptible | 1047 | 23 |

TABLE 26-continued

| Inbred | Phenotype | Expected haplotype | n |
|---|---|---|---|
| PH26N | Susceptible | PH26N | 1 |
| PH3DT | Susceptible | 274 | 47 |
| PH890 | Susceptible | 1047 | 23 |
| 165 | Susceptible | 165 | 33 |
| 661 | Susceptible | PHAN0 | 93 |
| PHR03 | Susceptible | PHAN0 | 93 |
| PHK56 | Susceptible | PHAN0 | 93 |
| PHN47 | Susceptible | PHN47 | 1 |
| PHNV8 | Susceptible | PHNV8 | 1 |
| ap19506156 | Susceptible | Recombinant | 1 |
| ap19506157 | Susceptible | Recombinant | 1 |
| ap19506160 | Susceptible | Recombinant | 1 |
| 157 | Susceptible | 625 | 7 |

TABLE 26-continued

| Inbred | Phenotype | Expected haplotype | n |
|---|---|---|---|
| 625 | Susceptible | 625 | 7 |
| PHKP5 | — | PHKP5 | 1 |

Figure 7:
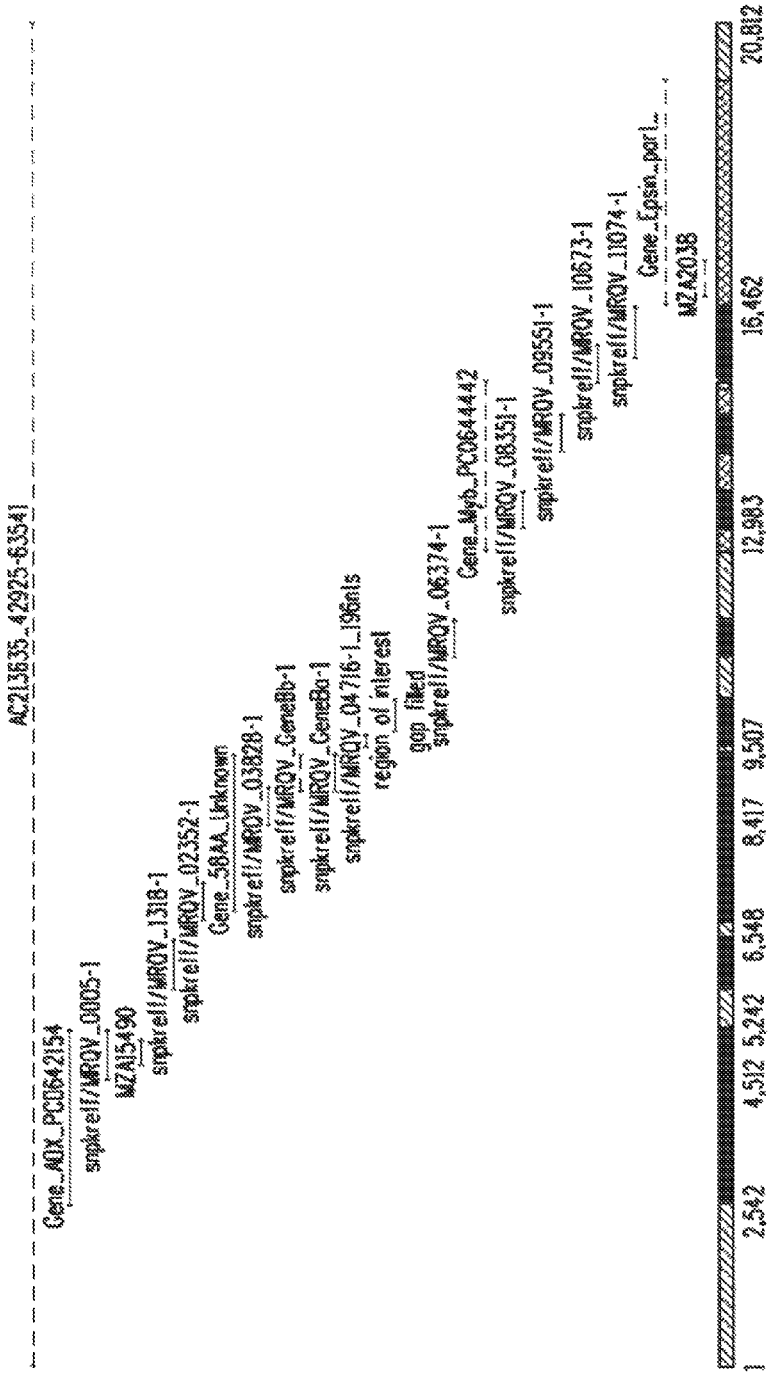
FIG. 7 shows a graphic of the region at the MZA15490 to MZA2038 interval where the position of specific sequenced fragments in a group of representative susceptible and resistant inbreds is indicated.

FIG. 7 shows the position of the targeted fragments in the MZA15490 to MZA2038 interval and the position of candidate genes. Sequencing results were obtained for sequences named: MRQV_00005-1; MRQV_1318-1; MRQV_02352-1; MRQV_03828-1; MRQV_06374-1; MRQV_08351-1; MRQV_09551-1-1; MRQV_10673-1 and MRQV_11074-1. The sequences across the group of tester inbreds for the segments MRQV_08351-1 and MRQV_10673-1 are provided herein, including polymorphic SNPs to characterize haplotypes (see Table 27). The sequence position in the MZA15490 to MZA2038 interval was included in the FIG. 7.

TABLE 27

```
SEQ_ID_NO_213  TCGCATCTGCAGCTTCTTTTGCACCTGATTACAGACATAAGCACTTGTAGCGTTTATGGA  60

SEQ_ID_NO_222  TCGCATCTGCAGCTTCTTTTGCACCTGATTACAGACATAAGCACTTGTAGCGTTTATGGA  60

SEQ_ID_NO_220  TCGCATCTGCAGCTTCTTTTGCACCTGATTACAGACATAAGCACTTGTAGCGTTTATGGA  60

SEQ_ID_NO_235  TCGCATCTGCAGCTTCTTTTGCACCTGATTACAGACATAAGCACTTGTAGCGTTTATGGA  60

SEQ_ID_NO_225  TCGCATCTGCAGCTTCTTTTGCACCTGATTACAGACATAAGCACTTGTAGCGTTTATGGA  60

SEQ_ID_NO_226  TCGCATCTGCAGCTTCTTTTGCACCTGATTACAGACATAAGCACTTGTAGCGTTTATGGA  60

SEQ_ID_NO_228  TCGCATCTGCAGCTTCTTTTGCACCTGATTACAGACATAAGCACTTGTAGCGTTTATGGA  60

SEQ_ID_NO_227  TCGCATCTGCAGCTTCTTTTGCACCTGATTACAGACATAAGCACTTGTAGCGTTTATGGA  60

SEQ_ID_NO_223  TCGCATCTGCAGCTTCTTTTGCACCTGATTACAGACATAAGCACTTGTAGCGTTTATGGA  60

SEQ_ID_NO_215  TCGCATCTGCAGCTTCTTTTGCACCTGATTACAGACATAAGCACTTGTAGCGTTTATGGA  60

SEQ_ID_NO_216  TCGCATCTGCAGCTTCTTTTGCACCTGATTACAGACATAAGCACTTGTAGCGTTTATGGA  60

SEQ_ID_NO_214  TCGCATCTGCAGCTTCTTTTGCACCTGATTACAGACATAAGCACTTGTAGCGTTTATGGA  60

SEQ_ID_NO_233  TCGCATCTGCAGCTTCTTTTGCACCTGATTACAGACATAAGCACTTGTAGCGTTTATGGA  60

SEQ_ID_NO_236  TCGCATCTGCAGCTTCTTTTGCACCTGATTACAGACATAAGCACTTGTAGCGTTTATGGA  60

SEQ_ID_NO_231  TCGCATCTGCAGCTTCTTTTGCACCTGATTACAGACATAAGCACTTGTAGCGTTTATGGA  60

SEQ_ID_NO_229  TCGCATCTGCAGCTTCTTTTGCACCTGATTACAGACATAAGCACTTGTAGCGTTTATGGA  60

SEQ_ID_NO_230  TCGCATCTGCAGCTTCTTTTGCACCTGATTACAGACATAAGCACTTGTAGCGTTTATGGA  60

SEQ_ID_NO_232  TCGCATCTGCAGCTTCTTTTGCACCTGATTACAGACATAAGCACTTGTAGCGTTTATGGA  60

SEQ_ID_NO_234  TCGCATCTGCAGCTTCTTTTGCACCTGATTACAGACATAAGCACTTGTAGCGTTTATGGA  60

SEQ_ID_NO_218  TCGCATCTGCAGCTTCTTTTGCACCTGATTACAGACATAAGCACTTGTAGCGTTTATGGA  60

SEQ_ID_NO_219  TCGCATCTGCAGCTTCTTTTGCACCTGATTACAGACATAAGCACTTGTAGCGTTTATGGA  60

SEQ_ID_NO_217  TCGCATCTGCAGCTTCTTTTGCACCTGATTACAGACATAAGCACTTGTAGCGTTTATGGA  60

SEQ_ID_NO_221  TCGCATCTGCAGCTTCTTTTGCACCTGATTACAGACATAAGCACTTGTAGCGTTTATGGA  60

SEQ_ID_NO_224  TCGCATCTGCAGCTTCTTTTGCACCTGATTACAGACATAAGCACTTGTAGCGTTTATGGA  60
               ************************************************************

SEQ_ID_NO_213  AGAAAGTTTTGGAGTGCAGATCTCATGACAATGATGTAAATCTATCTTGCCTCAGTTTGT  120

SEQ_ID_NO_222  AGAAAGGTTTGGAGTGCAGATCTCATGACAATGATGTAAATCTATCTTGCCTCAGTTTGT  120

SEQ_ID_NO_220  AGAAAGTTTTGGAGTGCAGATCTCATGACAATGATGTAAATCTATCTTGCCTCAGTTTGT  120

SEQ_ID_NO_235  AGAAAGTTTTGGAGTGCAGATCTCATGACAATGATGTAAATCTATCTTGCCTCAGTTTGT  120
```

TABLE 27-continued

| | | |
|---|---|---|
| SEQ_ID_NO_225 | AGAAAGTTTTGGAGTGCAGATCTCATGACAATGATGTAAATCTATCTTGCCTCAGTTTGT | 120 |
| SEQ_ID_NO_226 | AGAAAGTTTTGGAGTGCAGATCTCATGACAATGATGTAAATCTATCTTGCCTCAGTTTGT | 120 |
| SEQ_ID_NO_228 | AGAAAGTTTTGGAGTGCAGATCTCATGACAATGATGTAAATCTATCTTGCCTCAGTTTGT | 120 |
| SEQ_ID_NO_227 | AGAAAGTTTTGGAGTGCAGATCTCATGACAATGATGTAAATCTATCTTGCCTCAGTTTGT | 120 |
| SEQ_ID_NO_223 | AGAAAGTTTTGGAGTGCAAATCTCATGACAATGATGTAAATCTGTCTTGCCTCAGTTTGT | 120 |
| SEQ_ID_NO_215 | AGAAAGTTTTGGAGTGCAAATCTCATGACAATGATGTAAATCTATCTTGCCTCAGTTTGT | 120 |
| SEQ_ID_NO_216 | AGAAAGTTTTGGAGTGCAAATCTCATGACAATGATGTAAATCTATCTTGCCTCAGTTTGT | 120 |
| SEQ_ID_NO_214 | AGAAAGTTTTGGAGTGCAAATCTCATGACAATGATGTAAATCTATCTTGCCTCAGTTTGT | 120 |
| SEQ_ID_NO_233 | AGAAAGTTTTGGAGTGCAGATCTCATGACAATGATGTAAATCTATCTTGCCTCAGTTTGT | 120 |
| SEQ_ID_NO_236 | AGAAAGTTTTGGAGTGCAGATCTCATGACAATGATGTAAATCTATCTTGCCTCAGTTTGT | 120 |
| SEQ_ID_NO_231 | AGAAAGTTTTGGAGTGCAGATCTCATGACAATGATGTAAATCTATCTTGCCTCAGTTTGT | 120 |
| SEQ_ID_NO_229 | AGAAAGTTTTGGAGTGCAGATCTCATGACAATGATGTAAATCTATCTTGCCTCAGTTTGT | 120 |
| SEQ_ID_NO_230 | AGAAAGTTTTGGAGTGCAGATCTCATGACAATGATGTAAATCTATCTTGCCTCAGTTTGT | 120 |
| SEQ_ID_NO_232 | AGAAAGTTTTGGAGTGCAGATCTCATGACAATGATGTAAATCTATCTTGCCTCAGTTTGT | 120 |
| SEQ_ID_NO_234 | AGAAAGTTTTGGAGTGCAGATCTCATGACAATGATGTAAATCTATCTTGCCTCAGTTTGT | 120 |
| SEQ_ID_NO_218 | AGAAAGTTTTGGAGTGCAAATCTCATGACAATGATGTAAATCTATCTTGCCTCAGTTTGT | 120 |
| SEQ_ID_NO_219 | AGAAAGTTTTGGAGTGCAAATCTCATGACAATGATGTAAATCTATCTTGCCTCAGTTTGT | 120 |
| SEQ_ID_NO_217 | AGAAAGTTTTGGAGTGCAAATCTCATGACAATGATGTAAATCTATCTTGCCTCAGTTTGT | 120 |
| SEQ_ID_NO_221 | AGAAAGGTTTGGAGTGCAGATCTCATGACAATGATGTAAATCTATCTTGCCTCAGTTTGT | 120 |
| SEQ_ID_NO_224 | AGAAAGTTTTGGAGTGCAGATCTCATGACAATGATGTAAATCTATCTTGCCTCAGTTTGT | 120 |
| | ****** ********** ************************* **************** | |
| SEQ_ID_NO_213 | TCTTGTAGTTTCCTTTGGACTTGAATTTGATACCTTAGTGCATCGCTAAGTGCTATTTCT | 180 |
| SEQ_ID_NO_222 | TCTTGTAGTTTCCTTTGGACTTGAATTTGATACCTTAGTGCATCGCTAAGTGCTATTTCT | 180 |
| SEQ_ID_NO_220 | TCTTGTAGTTTCCTTTGGACTTGAATTTGATACCTTAGTGCATCGCTAAGTGCTATTTCT | 180 |
| SEQ_ID_NO_235 | TCTTGTAGTTTCCTTTGGACTTGAATTTGATACCTTAGTGCATCGCTAAGTGCTATTTCT | 180 |
| SEQ_ID_NO_225 | TCTTGTAGTTTCCTTTGGACTTGAATTTGATACCTTAGTGCATCGCTAAGTGCTATTTCT | 180 |
| SEQ_ID_NO_226 | TCTTGTAGTTTCCTTTGGACTTGAATTTGATACCTTAGTGCATCGCTAAGTGCTATTTCT | 180 |
| SEQ_ID_NO_228 | TCTTGTAGTTTCCTTTGGACTTGAATTTGATACCTTAGTGCATCGCTAAGTGCTATTTCT | 180 |
| SEQ_ID_NO_227 | TCTTGTAGTTTCCTTTGGACTTGAATTTGATACCTTAGTGCATCGCTAAGTGCTATTTCT | 180 |
| SEQ_ID_NO_223 | TCTTGTAGTTTCCTTTGGACTTGAATTTGATACCTTAGTGCATCGCTAAGTGCTATTTCT | 180 |
| SEQ_ID_NO_215 | TCTTGTAGTTTCCTTTGGACTTGAATTTGATACCTTAGTGCATCGCTAAGTGCTATTTCT | 180 |
| SEQ_ID_NO_216 | TCTTGTAGTTTCCTTTGGACTTGAATTTGATACCTTAGTGCATCGCTAAGTGCTATTTCT | 180 |
| SEQ_ID_NO_214 | TCTTGTAGTTTCCTTTGGACTTGAATTTGATACCTTAGTGCATCGCTAAGTGCTATTTCT | 180 |
| SEQ_ID_NO_233 | TCTTGTAGTTTCCTTTGGACTTGAATTTGATACCTTAGTGCATCGCTAAGTGCTATTTCT | 180 |
| SEQ_ID_NO_236 | TCTTGTAGTTTCCTTTGGACTTGAATTTGATACCTTAATGCATCGCTAAGTGCTATTTCT | 180 |
| SEQ_ID_NO_231 | TCTTGTAGTTTCCTTTGGACTTGAATTTGATACCTTAGTGCATCGCTAAGTGCTATTTCT | 180 |
| SEQ_ID_NO_229 | TCTTGTAGTTTCCTTTGGACTTGAATTTGATACCTTAGTGCATCGCTAAGTGCTATTTCT | 180 |
| SEQ_ID_NO_230 | TCTTGTAGTTTCCTTTGGACTTGAATTTGATACCTTAGTGCATCGCTAAGTGCTATTTCT | 180 |
| SEQ_ID_NO_232 | TCTTGTAGTTTCCTTTGGACTTGAATTTGATACCTTAGTGCATCGCTAAGTGCTATTTCT | 180 |
| SEQ_ID_NO_234 | TCTTGTAGTTTCCTTTGGACTTGAATTTGATACCTTAATGCATCGCTAAGTGCTATTTCT | 180 |

TABLE 27-continued

| | | |
|---|---|---|
| SEQ_ID_NO_218 | TCTTGTAGTTTCCTTTGGACTTGAATTTGATACCTTAGTGCATCGCTAAGTGCTATTTCT | 180 |
| SEQ_ID_NO_219 | TCTTGTAGTTTCCTTTGGACTTGAATTTGATACCTTAGTGCATCGCTAAGTGCTATTTCT | 180 |
| SEQ_ID_NO_217 | TCTTGTAGTTTCCTTTGGACTTGAATTTGATACCTTAGTGCATCGCTAAGTGCTATTTCT | 180 |
| SEQ_ID_NO_221 | TCTTGTAGTTTCCTTTGGACTTGAATTTGATACCTTAGTGCATCGCTAAGTGCTATTTCT | 180 |
| SEQ_ID_NO_224 | TCTTGTAGTTTCCTTTGGACTTGAATTTGATACCTTAGTGCATCGCTAAGTGCTGGTTCT | 180 |
| | **************************************** **************** **** | |
| SEQ_ID_NO_213 | CTGATTCACATAAGAAATGTGATACAAATGGTTAGTTCAATCAATGCAGAAAAGTTCAAT | 240 |
| SEQ_ID_NO_222 | CTGATTCACATAAGAAATGTGATACAAATGGTTAGCTCAATCAATGCAGAAAAGTTCAAC | 240 |
| SEQ_ID_NO_220 | CTGATTCACATAAGAAATGCGATACAAATGGTTAGTTCAGTCAATGCAGAAAAGTTCAAC | 240 |
| SEQ_ID_NO_235 | CTGATTCACATAAGAAATGTGATACAAATGGTTAGCTCAATCAATGCAGAAAAGTTCAAC | 240 |
| SEQ_ID_NO_225 | CTGATTCACATAAGAAATGTGATACAAATGGTTAGTTCAATCAATGCAGAAAAGTTCAAT | 240 |
| SEQ_ID_NO_226 | CTGATTCACATAAGAAATGTGATACAAATGGTTAGTTCAATCAATGCAGAAAAGTTCAAT | 240 |
| SEQ_ID_NO_228 | CTGATTCACATAAGAAATGTGATACAAATGGTTAGTTCAATCAATGCAGAAAAGTTCAAT | 240 |
| SEQ_ID_NO_227 | CTGATTCACATAAGAAATGTGATACAAATGGTTAGTTCAATCAATGCAGAAAAGTTCAAT | 240 |
| SEQ_ID_NO_223 | CTGATTCGCATAAGAAATGCGATACAAATGGTTAGTTCAATCAATGCAGAAAAGTTCAAC | 240 |
| SEQ_ID_NO_215 | CTGATTCACATAAGAAATGTGATACAAATGGTTAGTTCAATCAATGCAGAAAAGTTCAAC | 240 |
| SEQ_ID_NO_216 | CTGATTCACATAAGAAATGTGATACAAATGGTTAGTTCAATCAATGCAGAAAAGTTCAAC | 240 |
| SEQ_ID_NO_214 | CTGATTCACATAAGAAATGTGATACAAATGGTTAGTTCAATCAATGCAGAAAAGTTCAAC | 240 |
| SEQ_ID_NO_233 | CTGATTCACATAAGAAATGTGATACAAATGGTTAGTTCAATCAATGCAGAAAAGTTCAAT | 240 |
| SEQ_ID_NO_236 | CTGATTCACATAAGAAATGCGATACAAATGGTTAGTTCAATCAATGCAGAAAAGTTCAAC | 240 |
| SEQ_ID_NO_231 | CTGATTCACATAAGAAATGTGATACAAATGGTTAGTTCAATCAATGCAGAAAAGTTCAAT | 240 |
| SEQ_ID_NO_229 | CTGATTCACATAAGAAATGTGATACAAATGGTTAGTTCAATCAATGCAGAAAAGTTCAAT | 240 |
| SEQ_ID_NO_230 | CTGATTCACATAAGAAATGTGATACAAATGGTTAGTTCAATCAATGCAGAAAAGTTCAAT | 240 |
| SEQ_ID_NO_232 | CTGATTCACATAAGAAATGTGATACAAATGGTTAGTTCAATCAATGCAGAAAAGTTCAAT | 240 |
| SEQ_ID_NO_234 | CTGATTCACATAAGAAATGCGATACAAATGGTTAGTTCAATCAATGCAGAAAAGTTCAAC | 240 |
| SEQ_ID_NO_218 | CTGATTCACATAAGAAATGTGATACAAATGGTTAGTTCAATCAATGCAGAAAAGTTCAAC | 240 |
| SEQ_ID_NO_219 | CTGATTCACATAAGAAATGTGATACAAATGGTTAGTTCAATCAATGCAGAAAAGTTCAAC | 240 |
| SEQ_ID_NO_217 | CTGATTCACATAAGAAATGTGATACAAATGGTTAGTTCAATCAATGCAGAAAAGTTCAAC | 240 |
| SEQ_ID_NO_221 | CTGATTCACATAAGAAATGTGATACAAATGGTTAGCTCAATCAATGCAGAAAAGTTCAAC | 240 |
| SEQ_ID_NO_224 | CTGATTCACATAAGAAATGTGATACAAATGGTTAGTTCAATCAATGCAGAAAAGTTCAAT | 240 |
| | ****** *********** *************** *** ****************** | |
| SEQ_ID_NO_213 | CAAATAAAATGGGCCCACTGCAGTCAATTAACAGGCATTCAATAGGATTCACATTCCTGG | 300 |
| SEQ_ID_NO_222 | CAAATAAAATGGGCCCACTGCAGTCAATTAACAGGCATTCAATAGGATTCACATTCCTGG | 300 |
| SEQ_ID_NO_220 | AAAATAAAATGGGCCCACTGCAGTCAATTAACAGGCATTCAACAGCATTCACATTCCTGG | 300 |
| SEQ_ID_NO_235 | CAAATAAAATGGGCCCACTGCAGTCAATTAACAGGCATTCAATAGGATTCACATTCCTGG | 300 |
| SEQ_ID_NO_225 | CAAATAAAATGGGCCCACTGCAGTCAATTAACAGGCATTCAATAGGATTCACATTCCTGG | 300 |
| SEQ_ID_NO_226 | CAAATAAAATGGGCCCACTGCAGTCAATTAACAGGCATTCAATAGGATTCACATTCCTGG | 300 |
| SEQ_ID_NO_228 | CAAATAAAATGGGCCCACTGCAGTCAATTAACAGGCATTCAATAGGATTCACATTCCTGG | 300 |
| SEQ_ID_NO_227 | CAAATAAAATGGGCCCACTGCAGTCAATTAACAGGCATTCAATAGGATTCACATTCCTGG | 300 |
| SEQ_ID_NO_223 | AAAATAAAATGGGCCCACTGCAGTCAATTAACAGGCATTCAACAGCATTCACATTCCTGG | 300 |
| SEQ_ID_NO_215 | CAAATAAAATGGGCCCACTGCAGTCAATTAACAGGCATTCAATAGGATTCACATTCCTGG | 300 |

TABLE 27-continued

| | | |
|---|---|---|
| SEQ_ID_NO_216 | CAAATAAAATGGGCCCACTGCAGTCAATTAACAGGCATTCAATAGGATTCACATTCCTGG | 300 |
| SEQ_ID_NO_214 | CAAATAAAATGGGCCCACTGCAGTCAATTAACAGGCATTCAATAGGATTCACATTCCTGG | 300 |
| SEQ_ID_NO_233 | CAAATAAAATGGGCCCACTGCAGTCAATTAACAGGCATTCAATAGGATTCACATTCCTGG | 300 |
| SEQ_ID_NO_236 | CAAATAAAATGGGCCCACTGCAGTCAATTAACAGGCATTCAATAGGATTCACATTCCTGG | 300 |
| SEQ_ID_NO_231 | CAAATAAAATGGGCCCACTGCAGTCAATTAACAGGCATTCAATAGGATTCACATTCCTGG | 300 |
| SEQ_ID_NO_229 | CAAATAAAATGGGCCCACTGCAGTCAATTAACAGGCATTCAATAGGATTCACATTCCTGG | 300 |
| SEQ_ID_NO_230 | CAAATAAAATGGGCCCACTGCAGTCAATTAACAGGCATTCAATAGGATTCACATTCCTGG | 300 |
| SEQ_ID_NO_232 | CAAATAAAATGGGCCCACTGCAGTCAATTAACAGGCATTCAATAGGATTCACATTCCTGG | 300 |
| SEQ_ID_NO_234 | CAAATAAAATGGGCCCACTGCAGTCAATTAACAGGCATTCAATAGGATTCACATTCCTGG | 300 |
| SEQ_ID_NO_218 | CAAATAAAATGGGCCCACTGCAGTCAATTAACAGGCATTCAATAGGATTCACATTCCTGG | 300 |
| SEQ_ID_NO_219 | CAAATAAAATGGGCCCACTGCAGTCAATTAACAGGCATTCAATAGGATTCACATTCCTGG | 300 |
| SEQ_ID_NO_217 | CAAATAAAATGGGCCCACTGCAGTCAATTAACAGGCATTCAATAGGATTCACATTCCTGG | 300 |
| SEQ_ID_NO_221 | CAAATAAAATGGGCCCACTGCAGTCAATTAACAGGCATTCAATAGGATTCACATTCCTGG | 300 |
| SEQ_ID_NO_224 | CAAATAAAATGGGCCCACTGCAGTCAATTAACAGGCATTCAATAGGATTCACATTCCTGG | 300 |
| | ****************************************** ** ************* | |
| SEQ_ID_NO_213 | GCTTCTATATATGGAAGTTTGCATACAATGTTTTGGAAATAAAATGAAATATAAATTGCT | 360 |
| SEQ_ID_NO_222 | GCTTCTATATATGGAAGTTTGCATACAAAGTTTTGGAAATAAAATGGAATATAAATTGCT | 360 |
| SEQ_ID_NO_220 | GCCTCTATATATGGAAGTTTGCATACAAAGTTTTGGAAATAAAATGGAATAGAAATTGCT | 360 |
| SEQ_ID_NO_235 | GCTTCTATATATGGAAGTTTGCATACAAAGTTTTGGAAATAAAATGGAATAGAAATTGCT | 360 |
| SEQ_ID_NO_225 | GCTTCTATATATGGAAGTTTGCATACAATGTTTTGGAAATAAAATGAAATATAAATTGCT | 360 |
| SEQ_ID_NO_226 | GCTTCTATATATGGAAGTTTGCATACAATGTTTTGGAAATAAAATGAAATATAAATTGCT | 360 |
| SEQ_ID_NO_228 | GCTTCTATATATGGAAGTTTGCATACAATGTTTTGGAAATAAAATGAAATATAAATTGCT | 360 |
| SEQ_ID_NO_227 | GCTTCTATATATGGAAGTTTGCATACAATGTTTTGGAAATAAAATGAAATATAAATTGCT | 360 |
| SEQ_ID_NO_223 | GCCTCTATATATGGAAGTTTGCATACAAAGTTTTGGAAATAAAATGGAATAGAAATTGCT | 360 |
| SEQ_ID_NO_215 | GCTTCTATATATGGAAGTTTGCATACAAAGTTTTTGAAATAAAATGGAATAGAAATTGCT | 360 |
| SEQ_ID_NO_216 | GCTTCTATATATGGAAGTTTGCATACAAAGTTTTTGAAATAAAATGGAATAGAAATTGCT | 360 |
| SEQ_ID_NO_214 | GCTTCTATATATGGAAGTTTGCATACAAAGTTTTTGAAATAAAATGGAATAGAAATTGCT | 360 |
| SEQ_ID_NO_233 | GCTTCTATATATGGAAGTTTGCATACAATGTTTTGGAAATAAAATGAAATATAAATTGCT | 360 |
| SEQ_ID_NO_236 | GCTTCTATATATGGAAGTTTGCATACAAAGTTTTGGAAATAAAATGGAATAGAAATTGCT | 360 |
| SEQ_ID_NO_231 | GCTTCTATATATGGAAGTTTGCATACAATGTTTTGGAAATAAAATGAAATATAAATTGCT | 360 |
| SEQ_ID_NO_229 | GCTTCTATATATGGAAGTTTGCATACAATGTTTTGGAAATAAAATGAAATATAAATTGCT | 360 |
| SEQ_ID_NO_230 | GCTTCTATATATGGAAGTTTGCATACAATGTTTTGGAAATAAAATGAAATATAAATTGCT | 360 |
| SEQ_ID_NO_232 | GCTTCTATATATGGAAGTTTGCATACAATGTTTTGGAAATAAAATGAAATATAAATTGCT | 360 |
| SEQ_ID_NO_234 | GCTTCTATATATGGAAGTTTGCATACAAAGTTTTGGAAATAAAATGGAATAGAAATTGCT | 360 |
| SEQ_ID_NO_218 | GCTTCTATATATGGAAGTTTGCATACAAAGTTTTTGAAATAAAATGGAATAGAAATTGCT | 360 |
| SEQ_ID_NO_219 | GCTTCTATATATGGAAGTTTGCATACAAAGTTTTTGAAATAAAATGGAATAGAAATTGCT | 360 |
| SEQ_ID_NO_217 | GCTTCTATATATGGAAGTTTGCATACAAAGTTTTTGAAATAAAATGGAATAGAAATTGCT | 360 |
| SEQ_ID_NO_221 | GCTTCTATATATGGAAGTTTGCATACAAAGTTTTGGAAATAAAATGGAATATAAATTGCT | 360 |
| SEQ_ID_NO_224 | GCTTCTATATATGGAAGTTTGCATACAATGTTTTGGAAATAAAATGAAATATAAATTGCT | 360 |
| | ** ********************** ***** ********** **** ******* | |
| SEQ_ID_NO_213 | TGCATTTAGTGTAAGTTAATACTCGCTCCCTTCTCGAATATTTGTCGTCCGCTAGTTCAT | 420 |

TABLE 27-continued

| SEQ_ID_NO_222 | TGCATTTAGTGTAAGTTAATACCCGCTCTGTTCTCGAATATTTGTCACCCGCTAGTTCAT | 420 |
| --- | --- | --- |
| SEQ_ID_NO_220 | TGCATTTAGTGTAAGTTAATACCCGCTCCGTTCTCGAATATTTGTCGCCTGCTAGTTCAT | 420 |
| SEQ_ID_NO_235 | TGCATTTAGTGTAAGTTAATACCCGCT-------------------------AGTTCAT | 394 |
| SEQ_ID_NO_225 | TGCATTTAGTGTAAGTTAATACTCGCTCCCTTCTCGAATATTTGTCGTCCGCTAGTTCAT | 420 |
| SEQ_ID_NO_226 | TGCATTTAGTGTAAGTTAATACTCGCTCCCTTCTCGAATATTTGTCGTCCGCTAGTTCAT | 420 |
| SEQ_ID_NO_228 | TGCATTTAGTGTAAGTTAATACTCGCTCCCTTCTCGAATATTTGTCGTCCGCTAGTTCAT | 420 |
| SEQ_ID_NO_227 | TGCATTTAGTGTAAGTTAATACTCGCTCCCTTCTCGAATATTTGTCGTCCGCTAGTTCAT | 420 |
| SEQ_ID_NO_223 | TGCATTTAGTGTAAGTTAATACTCCATCCGTTCTTAAATATTTGTCGGCCGCTAGTTTAT | 420 |
| SEQ_ID_NO_215 | TGCATTTAGTGTAAGTTAATACTAGCTCCGTTCTCGAATATTTGTCGTCCGCTAGTTCAT | 420 |
| SEQ_ID_NO_216 | TGCATTTAGTGTAAGTTAATACTAGCTCCGTTCTCGAATATTTGTCGTCCGCTAGTTCAT | 420 |
| SEQ_ID_NO_214 | TGCATTTAGTGTAAGTTAATACTAGCTCCGTTCTCGAATATTTGTCGTCCGCTAGTTCAT | 420 |
| SEQ_ID_NO_233 | TGCATTTAGTGTAAGTTAATACTCGCTCCCTTCTCGAATATTTGTCGTCCGCTAGTTCAT | 420 |
| SEQ_ID_NO_236 | TGCATTTAGTGTAAGTTAATAC-------------------------CCGCTAGTTCAT | 394 |
| SEQ_ID_NO_231 | TGCATTTAGTGTAAGTTAATACTCGCTCCCTTCTCGAATATTTGTCGTCCGCTAGTTCAT | 420 |
| SEQ_ID_NO_229 | TGCATTTAGTGTAAGTTAATACTCGCTCCCTTCTCGAATATTTGTCGTCCGCTAGTTCAT | 420 |
| SEQ_ID_NO_230 | TGCATTTAGTGTAAGTTAATACTCGCTCCCTTCTCGAATATTTGTCGTCCGCTAGTTCAT | 420 |
| SEQ_ID_NO_232 | TGCATTTAGTGTAAGTTAATACTCGCTCCCTTCTCGAATATTTGTCGTCCGCTAGTTCAT | 420 |
| SEQ_ID_NO_234 | TGCATTTAGTGTAAGTTAATAC-------------------------CCGCTAGTTCAT | 394 |
| SEQ_ID_NO_218 | TGCATTTAGTGTAAGTTAATACTAGCTCCGTTCTCGAATATTTGTCGTCCGCTAGTTCAT | 420 |
| SEQ_ID_NO_219 | TGCATTTAGTGTAAGTTAATACTAGCTCCGTTCTCGAATATTTGTCGTCCGCTAGTTCAT | 420 |
| SEQ_ID_NO_219 | TGCATTTAGTGTAAGTTAATACTAGCTCCGTTCTCGAATATTTGTCGTCCGCTAGTTCAT | 420 |
| SEQ_ID_NO_221 | TGCATTTAGTGTAAGTTAATACCCGCTCTGTTCTCGAATATTTGTCACCCGCTAGTTCAT | 420 |
| SEQ_ID_NO_224 | TGCATTTAGTGTAAGTTAATACTCGCTCCCTTCTCGAATATTTGTCGTCCGCTAGTTCAT | 420 |
|  | ********************                                 **** ** |  |
| SEQ_ID_NO_213 | TTTTGAACTAAAACATGATAAATAAAAAAAC-GGAAGGAGTACATGTTTGTAACAGGAGA | 479 |
| SEQ_ID_NO_222 | TTTTGAACTAAAACACGACAAATAAAAAAAC-GGAAGGAGTACATGTTTGTAACAGGAGA | 479 |
| SEQ_ID_NO_220 | TTTTGAACTAAAACACGACAAATAAAAAAACGGAAGGAGTACATGTTTGTAACAGGAGA | 480 |
| SEQ_ID_NO_235 | TTTTTAACTAAAACACGACAAATAAAAAAAT--GGAGGAGTACATCTTTGTAACAGGTGA | 452 |
| SEQ_ID_NO_225 | TTTTGAACTAAAACATGATAAATAAAAAAAC-GGAAGGAGTACATGTTTGTAACAGGAGA | 479 |
| SEQ_ID_NO_226 | TTTTGAACTAAAACATGATAAATAAAAAAAC-GGAAGGAGTACATGTTTGTAACAGGAGA | 479 |
| SEQ_ID_NO_228 | TTTTGAACTAAAACATGATAAATAAAAAAAC-GGAAGGAGTACATGTTTGTAACAGGAGA | 479 |
| SEQ_ID_NO_227 | TTTTGAACTAAAACATGATAAATAAAAAAAC-GGAAGGAGTACATGTTTGTAACAGGAGA | 479 |
| SEQ_ID_NO_223 | TTTTGAACTAAAACACGACAAATAAAAAAACGGAGGGAGTACATGTTTATAACAGGTGA | 480 |
| SEQ_ID_NO_215 | TTTTGAACTAAAACACGACAAATAAAAAAAC-GGAAGGAGTACATGTTTGTAACAGGTGA | 479 |
| SEQ_ID_NO_216 | TTTTGAACTAAAACACGACAAATAAAAAAAC-GGAAGGAGTACATGTTTGTAACAGGTGA | 479 |
| SEQ_ID_NO_214 | TTTTGAACTAAAACACGACAAATAAAAAAAC-GGAAGGAGTACATGTTTGTAACAGGTGA | 479 |
| SEQ_ID_NO_233 | TTTTGAACTAAAACATGATAAATAAAAAAAC-GGAAGGAGTACATGTTTGTAACAGGAGA | 479 |
| SEQ_ID_NO_236 | TTTTTAACTAAAACACGACAAATAAAAAAAT-GGA-GGAGTACATCTTTGTAACAGGTGA | 452 |
| SEQ_ID_NO_231 | TTTTGAACTAAAACATGATAAATAAAAAAAC-GGAAGGAGTACATGTTTGTAACAGGAGA | 479 |
| SEQ_ID_NO_229 | TTTTGAACTAAAACATGATAAATAAAAAAAC-GGAAGGAGTACATGTTTGTAACAGGAGA | 479 |
| SEQ_ID_NO_230 | TTTTGAACTAAAACATGATAAATAAAAAAAC-GGAAGGAGTACATGTTTGTAACAGGAGA | 479 |

TABLE 27-continued

```
SEQ_ID_NO_232   TTTTGAACTAAAACATGATAAATAAAAAAAC-GGAAGGAGTACATGTTTGTAACAGGAGA   479
SEQ_ID_NO_234   TTTTTAACTAAAACACGACAAATAAAAAAAT--GGAGGAGTACATCTTTGTAACAGGTGA   452
SEQ_ID_NO_218   TTTTGAACTAAAACACGACAAATAAAAAAAC-GGAAGGAGTACATGTTTGTAACAGGTGA   479
SEQ_ID_NO_219   TTTTGAACTAAAACACGACAAATAAAAAAAC-GGAAGGAGTACATGTTTGTAACAGGTGA   479
SEQ_ID_NO_217   TTTTGAACTAAAACACGACAAATAAAAAAAC-GGAAGGAGTACATGTTTGTAACAGGTGA   479
SEQ_ID_NO_221   TTTTGAACTAAAACACGACAAATAAAAAAAC-GGAAGGAGTACATGTTTGTAACAGGAGA   479
SEQ_ID_NO_224   TTTTGAACTAAAACATGATAAATAAAAAAAC-GGAAGGAGTACATGTTTGTAACAGGAGA   479
                **** ********** ** **********   * ********* *** ******* **

SEQ_ID_NO_213   GCCCATGAATACTTGCTTGTAACAGGTGGAGCGCTAAGTATGCTTAGGAGAACTTTAGGC   539
SEQ_ID_NO_222   GCCCCTGAATACTTGCTTGTAACAGGTGGAGCGCTAAGTATGCTTAGGAGAACTTTAGGC   539
SEQ_ID_NO_220   GCCCCTGAATACTTGCTTGTAACAGGTGGAGCGCTAAGTATGCTTAGGAGAACTTTAGGC   540
SEQ_ID_NO_235   GCC--TGAATACTTGTTTGTAGCAGGTGGGGCGCTAAGTATGCTTAGGAGAAGTTTAGGC   510
SEQ_ID_NO_225   GCCCATGAATACTTGCTTGTAACAGGTGGAGCGCTAAGTATGCTTAGGAGAACTTTAGGC   539
SEQ_ID_NO_226   GCCCATGAATACTTGCTTGTAACAGGTGGAGCGCTAAGTATGCTTAGGAGAACTTTAGGC   539
SEQ_ID_NO_228   GCCCATGAATACTTGCTTGTAACAGGTGGAGCGCTAAGTATGCTTAGGAGAACTTTAGGC   539
SEQ_ID_NO_227   GCCCATGAATACTTGCTTGTAACAGGTGGAGCGCTAAGTATGCTTAGGAGAACTTTAGGC   539
SEQ_ID_NO_223   GCC---GAATACTTGGTTGTAACAGGTGGGGCGCTAAGTATGCTTAGGAGAACTTTAGGC   537
SEQ_ID_NO_215   GCCCCTGAATACTTGCTTGTAACAGGTGGAGCACTAAGTATGCTTAG---AACTTTAGGC   536
SEQ_ID_NO_216   GCCCCTGAATACTTGCTTGTAACAGGTGGAGCACTAAGTATGCTTAG---AACTTTAGGC   536
SEQ_ID_NO_214   GCCCCTGAATACTTGCTTGTAACAGGTGGAGCACTAAGTATGCTTAG---AACTTTAGGC   536
SEQ_ID_NO_233   GCCCATGAATACTTGCTTGTAACAGGTGGAGCGCTAAGTATGCTTAGGAGAACTTTAGGC   539
SEQ_ID_NO_236   GCC--TGAATACTTGTTTGTAGCAGGTGGGGCGCTAAGTATGCTTAGGAGAAGTTTAGGC   510
SEQ_ID_NO_231   GCCCATGAATACTTGCTTGTAACAGGTGGAGCGCTAAGTATGCTTAGGAGAACTTTAGGC   539
SEQ_ID_NO_229   GCCCATGAATACTTGCTTGTAACAGGTGGAGCGCTAAGTATGCTTAGGAGAACTTTAGGC   539
SEQ_ID_NO_230   GCCCATGAATACTTGCTTGTAACAGGTGGAGCGCTAAGTATGCTTAGGAGAACTTTAGGC   539
SEQ_ID_NO_232   GCCCATGAATACTTGCTTGTAACAGGTGGAGCGCTAAGTATGCTTAGGAGAACTTTAGGC   539
SEQ_ID_NO_234   GCC--TGAATACTTGTTTGTAGCAGGTGGGGCGCTAAGTATGCTTAGGAGAAGTTTAGGC   510
SEQ_ID_NO_218   GCCCCTGAATACTTGCTTGTAACAGGTGGAGCACTAAGTATGCTTAG---AACTTTAGGC   536
SEQ_ID_NO_219   GCCCCTGAATACTTGCTTGTAACAGGTGGAGCACTAAGTATGCTTAG---AACTTTAGGC   536
SEQ_ID_NO_217   GCCCCTGAATACTTGCTTGTAACAGGTGGAGCACTAAGTATGCTTAG---AACTTTAGGC   536
SEQ_ID_NO_221   GCCCCTGAATACTTGCTTGTAACAGGTGGAGCGCTAAGTATGCTTAGGAGAACTTTAGGC   539
SEQ_ID_NO_224   GCCCATGAATACTTGCTTGTAACAGGTGGAGCGCTAAGTATGCTTAGGAGAACTTTAGGC   539
                ***   ********* **** ******* ** **************   ** *******

SEQ_ID_NO_213   AACTTGTATTCTTTAGCACTTCGACGCAGTTTGTATGGTAATATCTACTGATAGACAGAA   599
SEQ_ID_NO_222   AACTTGTATTCTTTAGCACTTCGACGCCGTTTGTATGGTAATATCTACTGATAGACAGAA   599
SEQ_ID_NO_220   AACTTGTATTCTTTAGCACTTCGACGCCGTTTGTATGGTAATATCTACTGATAGACAGAA   600
SEQ_ID_NO_235   AACTTGTATTCTGTAGCATTTCGACGCCGTTTGTATGGTAATATCTACTGATAGGCAGAA   570
SEQ_ID_NO_225   AACTTGTATTCTTTAGCACTTCGACGCAGTTTGTATGGTAATATCTACTGATAGACAGAA   599
SEQ_ID_NO_226   AACTTGTATTCTTTAGCACTTCGACGCAGTTTGTATGGTAATATCTACTGATAGACAGAA   599
SEQ_ID_NO_228   AACTTGTATTCTTTAGCACTTCGACGCAGTTTGTATGGTAATATCTACTGATAGACAGAA   599
SEQ_ID_NO_227   AACTTGTATTCTTTAGCACTTCGACGCAGTTTGTATGGTAATATCTACTGATAGACAGAA   599
```

TABLE 27-continued

| | | |
|---|---|---|
| SEQ_ID_NO_223 | AACTTGTATTCTGTAGCACTTCGACGCCGTTTGTATGGTAATATCTACTGATAGACAGAA | 597 |
| SEQ_ID_NO_215 | AACTTGTATTCTTTAGCACTTCGACGCCGTTTGTATGGTAATATCTACTGATAGACAGAA | 596 |
| SEQ_ID_NO_216 | AACTTGTATTCTTTAGCACTTCGACGCCGTTTGTATGGTAATATCTACTGATAGACAGAA | 596 |
| SEQ_ID_NO_214 | AACTTGTATTCTTTAGCACTTCGACGCCGTTTGTATGGTAATATCTACTGATAGACAGAA | 596 |
| SEQ_ID_NO_233 | AACTTGTATTCTTTAGCACTTCGACGCAGTTTGTATGGTAATATCTACTGATAGACAGAA | 599 |
| SEQ_ID_NO_236 | AACTTGTATTCTGTAGCATTTCGACGCCGTTTGTATGGTAATATCTACTGATAGGCAGAA | 570 |
| SEQ_ID_NO_231 | AACTTGTATTCTTTAGCACTTCGACGCAGTTTGTATGGTAATATCTACTGATAGACAGAA | 599 |
| SEQ_ID_NO_229 | AACTTGTATTCTTTAGCACTTCGACGCAGTTTGTATGGTAATATCTACTGATAGACAGAA | 599 |
| SEQ_ID_NO_230 | AACTTGTATTCTTTAGCACTTCGACGCAGTTTGTATGGTAATATCTACTGATAGACAGAA | 599 |
| SEQ_ID_NO_232 | AACTTGTATTCTTTAGCACTTCGACGCAGTTTGTATGGTAATATCTACTGATAGACAGAA | 599 |
| SEQ_ID_NO_234 | AACTTGTATTCTGTAGCATTTCGACGCCGTTTGTATGGTAATATCTACTGATAGGCAGAA | 570 |
| SEQ_ID_NO_218 | AACTTGTATTCTTTAGCACTTCGACGCCGTTTGTATGGTAATATCTACTGATAGACAGAA | 596 |
| SEQ_ID_NO_219 | AACTTGTATTCTTTAGCACTTCGACGCCGTTTGTATGGTAATATCTACTGATAGACAGAA | 596 |
| SEQ_ID_NO_217 | AACTTGTATTCTTTAGCACTTCGACGCCGTTTGTATGGTAATATCTACTGATAGACAGAA | 596 |
| SEQ_ID_NO_221 | AACTTGTATTCTTTAGCACTTCGACGCCGTTTGTATGGTAATATCTACTGATAGACAGAA | 599 |
| SEQ_ID_NO_224 | AACTTGTATTCTTTAGCACTTCGACGCAGTTTGTATGGTAATATCTACTGATAGACAGAA | 599 |
| | ************ ***** ******** *************************** ***** | |
| SEQ_ID_NO_213 | TCCTGGTTTTGGA----TTTTTAATTTTTCCTGCTTTTGGTTACACCTCTACAGTCCCAT | 655 |
| SEQ_ID_NO_222 | TCCTGGTTTTGGAATTTTTTTTATTTTTCCTGCTTTTGGTTACACCTCTACAGTCCCAT | 659 |
| SEQ_ID_NO_220 | TCCTGGTTTTGGAATTTTTTT--ATTTTTCCTGCTTTTGGTTACACCTCTACAGTCCCAT | 658 |
| SEQ_ID_NO_235 | TCCTGGTT---GGATTTTTTT-------TCCTGCTTTTGTTTACACCTATACAGTCCCAT | 620 |
| SEQ_ID_NO_225 | TCCTGGTTTTGGA--TTTTTA--ATTTTTCCTGCTTTTGGTTACACCTCTACAGTCCCAT | 655 |
| SEQ_ID_NO_226 | TCCTGGTTTTGGA--TTTTTA--ATTTTTCCTGCTTTTGGTTACACCTCTACAGTCCCAT | 655 |
| SEQ_ID_NO_228 | TCCTGGTTTTGGA--TTTTTA--ATTTTTCCTGCTTTTGGTTACACCTCTACAGTCCCAT | 655 |
| SEQ_ID_NO_227 | TCCTGGTTTTGGA--TTTTTA--ATTTTTCCTGCTTTTGGTTACACCTCTACAGTCCCAT | 655 |
| SEQ_ID_NO_223 | TCCTGGTTTTTGG--AAAAAA--AAAATTCCTGCTTTTGGTTACACCTCTACAGTCCCAT | 653 |
| SEQ_ID_NO_215 | TCCTGGTTTTGGATTTTTTTTTATTTTTCCTGTTTTTGGTTACACCTCTACAGTCCCAT | 656 |
| SEQ_ID_NO_216 | TCCTGGTTTTGGATTTTTTTTTATTTTTCCTGTTTTTGGTTACACCTCTACAGTCCCAT | 656 |
| SEQ_ID_NO_214 | TCCTGGTTTTGGATTTTTTTTTATTTTTCCTGTTTTTGGTTACACCTCTACAGTCCCAT | 656 |
| SEQ_ID_NO_233 | TCCTGGTTTTGGATTTTTA----ATTTTTCCTGCTTTTGGTTACACCTCTACAGTCCCAT | 655 |
| SEQ_ID_NO_236 | TCCTGGTT--GGATTTTTT--------TTTCCTGCTTTTGTTTACACCTATACAGTCCCAT | 620 |
| SEQ_ID_NO_231 | TCCTGGTTTTGGATTTTTA----ATTTTTCCTGCTTTTGGTTACACCTCTACAGTCCCAT | 655 |
| SEQ_ID_NO_229 | TCCTGGTTTTGGATTTTTA----ATTTTTCCTGCTTTTGGTTACACCTCTACAGTCCCAT | 655 |
| SEQ_ID_NO_230 | TCCTGGTTTTGGATTTTTA----ATTTTTCCTGCTTTTGGTTACACCTCTACAGTCCCAT | 655 |
| SEQ_ID_NO_232 | TCCTGGTTTTGGATTTTTA----ATTTTTCCTGCTTTTGGTTACACCTCTACAGTCCCAT | 655 |
| SEQ_ID_NO_234 | TCCTGGTT--GGATTTTTT--------TTTCCTGCTTTTGTTTACACCTATACAGTCCCAT | 620 |
| SEQ_ID_NO_218 | TCCTGGTTTTGGATTTTTTTTTATTTTTCCTGTTTTTGGTTACACCTCTACAGTCCCAT | 656 |
| SEQ_ID_NO_219 | TCCTGGTTTTGGATTTTTTTTTATTTTTCCTGTTTTTGGTTACACCTCTACAGTCCCAT | 656 |
| SEQ_ID_NO_217 | TCCTGGTTTTGGATTTTTTTTTATTTTTCCTGTTTTTGGTTACACCTCTACAGTCCCAT | 656 |
| SEQ_ID_NO_221 | TCCTGGTTTTGGAATTTTTTTT-ATTTTCCTGCTTTTGGTTACACCTCTACAGTCCCAT | 658 |

TABLE 27-continued

| | | |
|---|---|---|
| SEQ_ID_NO_224 | TCCTGGTTTTGGA---TTTTTA-ATTTTTCCTGCTTTTGGTTACACCTCTACAGTCCCAT<br>******* * **** ***** ******* *********** | 655 |
| SEQ_ID_NO_213 | ACTCGCAGTCCAATAGTACATGGTCTGATAATAAACCAATTAAGAAGGACTCATGTCTCA | 715 |
| SEQ_ID_NO_222 | ACTCGCAGTCGAATAATACATGGTCTGATAATAAACCAATTA---AGGACTCATGTCTCA | 716 |
| SEQ_ID_NO_220 | ACTCGCAGTCGAATAATACATGGTCTGATAATAAACCAATTAAG---GACTCATGTCTCA | 715 |
| SEQ_ID_NO_235 | ACTCGCAGTCGAATAATACATGGTCTGATGATAAACCAATTAAGAAGGACTCATGTCTCA | 680 |
| SEQ_ID_NO_225 | ACTCGCAGTCCAATAGTACATGGTCTGATAATAAACCAATTAAGAAGGACTCATGTCTCA | 715 |
| SEQ_ID_NO_226 | ACTCGCAGTCCAATAGTACATGGTCTGATAATAAACCAATTAAGAAGGACTCATGTCTCA | 715 |
| SEQ_ID_NO_228 | ACTCGCAGTCCAATAGTACATGGTCTGATAATAAACCAATTAAGAAGGACTCATGTCTCA | 715 |
| SEQ_ID_NO_227 | ACTCGCAGTCCAATAGTACATGGTCTGATAATAAACCAATTAAGAAGGACTCATGTCTCA | 715 |
| SEQ_ID_NO_223 | ACTCGCAGTCGAATAATACATGGTCTGATAATAAACCAATTAAG---GACTCATGTCTCA | 710 |
| SEQ_ID_NO_215 | ACTCGCAGTCCAATAATACATGGTCTGATAATAAACCAATTAAGAAGGACTCATGTCTCA | 716 |
| SEQ_ID_NO_216 | ACTCGCAGTCCAATAATACATGGTCTGATAATAAACCAATTAAGAAGGACTCATGTCTCA | 716 |
| SEQ_ID_NO_214 | ACTCGCAGTCCAATAATACATGGTCTGATAATAAACCAATTAAGAAGGACTCATGTCTCA | 716 |
| SEQ_ID_NO_233 | ACTCGCAGTCCAATAGTACATGGTCTGATAATAAACCAATTAAGAAGGACTCATGTCTCA | 715 |
| SEQ_ID_NO_236 | ACTCGCAGTCGAATAATACATGGTCTGATGATAAACCAATTAAGAAGGACTCATGTCTCA | 680 |
| SEQ_ID_NO_231 | ACTCGCAGTCCAATAGTACATGGTCTGATAATAAACCAATTAAGAAGGACTCATGTCTCA | 715 |
| SEQ_ID_NO_229 | ACTCGCAGTCCAATAGTACATGGTCTGATAATAAACCAATTAAGAAGGACTCATGTCTCA | 715 |
| SEQ_ID_NO_230 | ACTCGCAGTCCAATAGTACATGGTCTGATAATAAACCAATTAAGAAGGACTCATGTCTCA | 715 |
| SEQ_ID_NO_232 | ACTCGCAGTCCAATAGTACATGGTCTGATAATAAACCAATTAAGAAGGACTCATGTCTCA | 715 |
| SEQ_ID_NO_234 | ACTCGCAGTCGAATAATACATGGTCTGATGATAAACCAATTAAGAAGGACTCATGTCTCA | 680 |
| SEQ_ID_NO_218 | ACTCGCAGTCCAATAATACATGGTCTGATAATAAACCAATTAAGAAGGACTCATGTCTCA | 716 |
| SEQ_ID_NO_219 | ACTCGCAGTCCAATAATACATGGTCTGATAATAAACCAATTAAGAAGGACTCATGTCTCA | 716 |
| SEQ_ID_NO_217 | ACTCGCAGTCCAATAATACATGGTCTGATAATAAACCAATTAAGAAGGACTCATGTCTCA | 716 |
| SEQ_ID_NO_221 | ACTCGCAGTCGAATAATACATGGTCTGATAATAAACCAATTAAG---GACTCATGTCTCA | 715 |
| SEQ_ID_NO_224 | ACTCGCAGTCCAATAGTACATGGTCTGATAATAAACCAATTAAGAAGGACTCATGTCTCA<br>********* **** ************* ************    ************ | 715 |
| SEQ_ID_NO_213 | GTCATTA----------------------------------------------------- | 722 |
| SEQ_ID_NO_222 | GTCATTA----------------------------------------------------- | 723 |
| SEQ_ID_NO_220 | GTCATTA----------------------------------------------------- | 722 |
| SEQ_ID_NO_235 | GTCATTA----------------------------------------------------- | 687 |
| SEQ_ID_NO_225 | GTCATTA----------------------------------------------------- | 722 |
| SEQ_ID_NO_226 | GTCATTA----------------------------------------------------- | 722 |
| SEQ_ID_NO_228 | GTCATTA----------------------------------------------------- | 722 |
| SEQ_ID_NO_227 | GTCATTA----------------------------------------------------- | 722 |
| SEQ_ID_NO_223 | GTCATTA----------------------------------------------------- | 717 |
| SEQ_ID_NO_215 | GTCATTAGGCTGTCTCCAACAACGTCCTCTATATTCATCCTCTATATCTGTCCTTTACAG | 776 |
| SEQ_ID_NO_216 | GTCATTAGGCTGTCTCCAACAACGTCCTCTATATTCATCCTCTATATCTGTCCTTTACAG | 776 |
| SEQ_ID_NO_214 | GTCATTAGGCTGTCTCCAACAACGTCCTCTATATTCATCCTCTATATCTGTCCTTTACAG | 776 |
| SEQ_ID_NO_233 | GTCATTA----------------------------------------------------- | 722 |
| SEQ_ID_NO_236 | GTCATTA----------------------------------------------------- | 687 |

TABLE 27-continued

| | | |
|---|---|---|
| SEQ_ID_NO_231 | GTCATTA------------------------------------------------------ | 722 |
| SEQ_ID_NO_229 | GTCATTA------------------------------------------------------ | 722 |
| SEQ_ID_NO_230 | GTCATTA------------------------------------------------------ | 722 |
| SEQ_ID_NO_232 | GTCATTA------------------------------------------------------ | 722 |
| SEQ_ID_NO_234 | GTCATTA------------------------------------------------------ | 687 |
| SEQ_ID_NO_218 | GTCATTAGGCTGTCTCCAACAACGTCCTCTATATTCATCCTCTATATCTGTCCTTTACAG | 776 |
| SEQ_ID_NO_219 | GTCATTAGGCTGTCTCCAACAACGTCCTCTATATTCATCCTCTATATCTGTCCTTTACAG | 776 |
| SEQ_ID_NO_217 | GTCATTAGGCTGTCTCCAACAACGTCCTCTATATTCATCCTCTATATCTGTCCTTTACAG | 776 |
| SEQ_ID_NO_221 | GTCATTA------------------------------------------------------ | 722 |
| SEQ_ID_NO_224 | GTCATTA------------------------------------------------------ | 722 |
| | ******* | |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_215 | TCTCCTCTAAAAAATTTCATCCTATATATCTCATTTCTCTCCAACAACGTCCTCTAAATC | 836 |
| SEQ_ID_NO_216 | TCTCCTCTAAAAAATTTCATCCTATATATCTCATTTCTCTCCAACAACGTCCTCTAAATC | 836 |
| SEQ_ID_NO_214 | TCTCCTCTAAAAAATTTCATCCTATATATCTCATTTCTCTCCAACAACGTCCTCTAAATC | 836 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | TCTCCTCTAAAAAATTTCATCCTATATATCTCATTTCTCTCCAACAACGTCCTCTAAATC | 836 |
| SEQ_ID_NO_219 | TCTCCTCTAAAAAATTTCATCCTATATATCTCATTTCTCTCCAACAACGTCCTCTAAATC | 836 |
| SEQ_ID_NO_217 | TCTCCTCTAAAAAATTTCATCCTATATATCTCATTTCTCTCCAACAACGTCCTCTAAATC | 836 |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |

TABLE 27-continued

| | | |
|---|---|---|
| SEQ_ID_NO_223 | ------------------------------------------------------------ | |
| SEQ_ID_NO_215 | ACGTCCTCTATACTCAAATACTCATATTAAAGACATTTTTTAATTTTATTTTTTATACAT | 896 |
| SEQ_ID_NO_216 | ACGTCCTCTATACTCAAATACTCATATTAAAGACATTTTTTAATTTTATTTTTTATACAT | 896 |
| SEQ_ID_NO_214 | ACGTCCTCTATACTCAAATACTCATATTAAAGACATTTTTTAATTTTATTTTTTATACAT | 896 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | ACGTCCTCTATACTCAAATACTCATATTAAAGACATTTTTTAATTTTATTTTTTATACAT | 896 |
| SEQ_ID_NO_219 | ACGTCCTCTATACTCAAATACTCATATTAAAGACATTTTTTAATTTTATTTTTTATACAT | 896 |
| SEQ_ID_NO_217 | ACGTCCTCTATACTCAAATACTCATATTAAAGACATTTTTTAATTTTATTTTTTATACAT | 896 |
| SEQ_ID_NO_221 | ------------------------------------------------------------ | |
| SEQ_ID_NO_224 | ------------------------------------------------------------ | |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_215 | ACGTAATTATCATACTCTCAAATGTATTGTGCATATTTTAGTTTTGCTAAACCGGTTATT | 956 |
| SEQ_ID_NO_216 | ACGTAATTATCATACTCTCAAATGTATTGTGCATATTTTAGTTTTGCTAAACCGGTTATT | 956 |
| SEQ_ID_NO_214 | ACGTAATTATCATACTCTCAAATGTATTGTGCATATTTTAGTTTTGCTAAACCGGTTATT | 956 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | ACGTAATTATCATACTCTCAAATGTATTGTGCATATTTTAGTTTTGCTAAACCGGTTATT | 956 |
| SEQ_ID_NO_219 | ACGTAATTATCATACTCTCAAATGTATTGTGCATATTTTAGTTTTGCTAAACCGGTTATT | 956 |
| SEQ_ID_NO_217 | ACGTAATTATCATACTCTCAAATGTATTGTGCATATTTTAGTTTTGCTAAACCGGTTATT | 956 |
| SEQ_ID_NO_221 | ------------------------------------------------------------ | |
| SEQ_ID_NO_224 | ------------------------------------------------------------ | |

TABLE 27-continued

| SEQ_ID_NO_213 | ------------------------------------------------------------ | |
| --- | --- | --- |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_216 | TAAAGTAGTCAAATGGATAGAGGACCGTTTAGAGAAACTCTATATATAGAGAATTCAGCA | 1016 |
| SEQ_ID_NO_214 | TAAAGTAGTCAAATGGATAGAGGACCGTTTAGAGAAACTCTATATATAGAGAATTCAGCA | 1016 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | TAAAGTAGTCAAATGGATAGAGGACCGTTTAGAGAAACTCTATATATAGAGAATTCAGCA | 1016 |
| SEQ_ID_NO_219 | TAAAGTAGTCAAATGGATAGAGGACCGTTTAGAGAAACTCTATATATAGAGAATTCAGCA | 1016 |
| SEQ_ID_NO_217 | TAAAGTAGTCAAATGGATAGAGGACCGTTTAGAGAAACTCTATATATAGAGAATTCAGCA | 1016 |
| SEQ_ID_NO_221 | ------------------------------------------------------------ | |
| SEQ_ID_NO_224 | ------------------------------------------------------------ | |
| SEQ_ID_NO_213 | ------------------------------------------------------------ | |
| SEQ_ID_NO_222 | ------------------------------------------------------------ | |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | ------------------------------------------------------------ | |
| SEQ_ID_NO_223 | ------------------------------------------------------------ | |
| SEQ_ID_NO_215 | TAAAGTAGTCAAATGGATAGAGGACCGTTTAGAGAAACTCTATATATAGAGAATTCAGCA | 1016 |
| SEQ_ID_NO_216 | GCGTCCTCTAAATTTAAAGGACCGTTTAGAGGACGTTGCTGGAGAGCGTAGAGGACCGTT | 1076 |
| SEQ_ID_NO_214 | GCGTCCTCTAAATTTAAAGGACCGTTTAGAGGACGTTGCTGGAGAGCGTAGAGGACCGTT | 1076 |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |

TABLE 27-continued

| | | |
|---|---|---|
| SEQ_ID_NO_232 | ---------------------------------------------------------------- | |
| SEQ_ID_NO_234 | ---------------------------------------------------------------- | |
| SEQ_ID_NO_218 | GCGTCCTCTAAATTTAAAGGACCGTTTAGAGGACGTTGCTGGAGAGCGTAGAGGACCGTT | 1076 |
| SEQ_ID_NO_219 | GCGTCCTCTAAATTTAAAGGACCGTTTAGAGGACGTTGCTGGAGAGCGTAGAGGACCGTT | 1076 |
| SEQ_ID_NO_217 | GCGTCCTCTAAATTTAAAGGACCGTTTAGAGGACGTTGCTGGAGAGCGTAGAGGACCGTT | 1076 |
| SEQ_ID_NO_221 | ---------------------------------------------------------------- | |
| SEQ_ID_NO_213 | ----------------------------------------------------------TG | 724 |
| SEQ_ID_NO_222 | ----------------------------------------------------------TG | 725 |
| SEQ_ID_NO_220 | ----------------------------------------------------------TG | 724 |
| SEQ_ID_NO_235 | ----------------------------------------------------------TG | 689 |
| SEQ_ID_NO_225 | ----------------------------------------------------------TG | 724 |
| SEQ_ID_NO_226 | ----------------------------------------------------------TG | 724 |
| SEQ_ID_NO_228 | ----------------------------------------------------------TG | 724 |
| SEQ_ID_NO_227 | ----------------------------------------------------------TG | 724 |
| SEQ_ID_NO_223 | ----------------------------------------------------------TG | 719 |
| SEQ_ID_NO_215 | TGGTCCTCTATATTTAGGGTAGAGAACCCTTTAGGGGCCTTGTTGGAGCCAGCCTTATG | 1136 |
| SEQ_ID_NO_216 | TGGTCCTCTATATTTAGGGTAGAGAACCCTTTAGGGGCCTTGTTGGAGCCAGCCTTATG | 1136 |
| SEQ_ID_NO_214 | TGGTCCTCTATATTTAGGGTAGAGAACCCTTTAGGGGCCTTGTTGGAGCCAGCCTTATG | 1136 |
| SEQ_ID_NO_233 | ----------------------------------------------------------TG | 724 |
| SEQ_ID_NO_236 | ----------------------------------------------------------TG | 689 |
| SEQ_ID_NO_231 | ----------------------------------------------------------TG | 724 |
| SEQ_ID_NO_229 | ----------------------------------------------------------TG | 724 |
| SEQ_ID_NO_230 | ----------------------------------------------------------TG | 724 |
| SEQ_ID_NO_232 | ----------------------------------------------------------TG | 724 |
| SEQ_ID_NO_234 | ----------------------------------------------------------TG | 689 |
| SEQ_ID_NO_218 | TGGTCCTCTATATTTAGGGTAGAGAACCCTTTAGGGGCCTTGTTGGAGCCAGCCTTATG | 1136 |
| SEQ_ID_NO_219 | TGGTCCTCTATATTTAGGGTAGAGAACCCTTTAGGGGCCTTGTTGGAGCCAGCCTTATG | 1136 |
| SEQ_ID_NO_217 | TGGTCCTCTATATTTAGGGTAGAGAACCCTTTAGGGGCCTTGTTGGAGCCAGCCTTATG | 1136 |
| SEQ_ID_NO_221 | ----------------------------------------------------------TG | 724 |
| SEQ_ID_NO_224 | ----------------------------------------------------------TG | 724 |
| | ** | |
| SEQ_ID_NO_213 | ACTTGAGCATAGGAGTTGAGATCAAGAAATATTTGAGTTGCAGCTTAAGGTCCAGA---- | 780 |
| SEQ_ID_NO_222 | ACTTGAGCATAGGAGTTGAGATCAAGAAATATTTGAGTTGCAGCTTAAGGTTCAGA---- | 781 |
| SEQ_ID_NO_220 | ACTTGAGCATAGGAGTTCAGATCGAGAAATATTTGAGTTGCAGCTTAAGGTTCAGA---- | 780 |
| SEQ_ID_NO_235 | ACTTGAGCATAGGAGTTCAGATCGAGAAATATTTGAGTTGCAGCTTAAGGTTCAGA---- | 745 |
| SEQ_ID_NO_225 | ACTTGAGCATAGGAGTTGAGATCAAGAAATATTTGAGTTGCAGCTTAAGGTCCAGA---- | 780 |
| SEQ_ID_NO_226 | ACTTGAGCATAGGAGTTGAGATCAAGAAATATTTGAGTTGCAGCTTAAGGTCCAGA---- | 780 |
| SEQ_ID_NO_228 | ACTTGAGCATAGGAGTTGAGATCAAGAAATATTTGAGTTGCAGCTTAAGGTCCAGA---- | 780 |
| SEQ_ID_NO_227 | ACTTGAGCATAGGAGTTGAGATCAAGAAATATTTGAGTTGCAGCTTAAGGTCCAGA---- | 780 |
| SEQ_ID_NO_223 | ACTTGAGCATAGGAGTTGAGATCGAGAAATATTTGAGTTACAGCTTAAGGTTCAGACTTC | 779 |

TABLE 27-continued

| | | |
|---|---|---|
| SEQ_ID_NO_215 | ACTTGAGCATAGGAGTTGAGATCAAGAAATATGTGAGTTGCAGCTTAAGGTTCAGA---- | 1192 |
| SEQ_ID_NO_216 | ACTTGAGCATAGGAGTTGAGATCAAGAAATATGTGAGTTGCAGCTTAAGGTTCAGA---- | 1192 |
| SEQ_ID_NO_214 | ACTTGAGCATAGGAGTTGAGATCAAGAAATATGTGAGTTGCAGCTTAAGGTTCAGA---- | 1192 |
| SEQ_ID_NO_233 | ACTTGAGCATAGGAGTTGAGATCAAGAAATATTTGAGTTGCAGCTTAAGGTCCAGA---- | 780 |
| SEQ_ID_NO_236 | ACTTGAGCATAGGAGTTCAGATCGAGAAATATTTGAGTTGCAGCTTAAGGTTCAGA---- | 745 |
| SEQ_ID_NO_231 | ACTTGAGCATAGGAGTTGAGATCAAGAAATATTTGAGTTGCAGCTTAAGGTCCAGA---- | 780 |
| SEQ_ID_NO_229 | ACTTGAGCATAGGAGTTGAGATCAAGAAATATTTGAGTTGCAGCTTAAGGTCCAGA---- | 780 |
| SEQ_ID_NO_230 | ACTTGAGCATAGGAGTTGAGATCAAGAAATATTTGAGTTGCAGCTTAAGGTCCAGA---- | 780 |
| SEQ_ID_NO_232 | ACTTGAGCATAGGAGTTGAGATCAAGAAATATTTGAGTTGCAGCTTAAGGTCCAGA---- | 780 |
| SEQ_ID_NO_234 | ACTTGAGCATAGGAGTTGAGATCAAGAAATATTTGAGTTGCAGCTTAAGGTCCAGA---- | 745 |
| SEQ_ID_NO_218 | ACTTGAGCATAGGAGTTGAGATCAAGAAATATGTGAGTTGCAGCTTAAGGTTCAGA---- | 1192 |
| SEQ_ID_NO_219 | ACTTGAGCATAGGAGTTGAGATCAAGAAATATGTGAGTTGCAGCTTAAGGTTCAGA---- | 1192 |
| SEQ_ID_NO_217 | ACTTGAGCATAGGAGTTGAGATCAAGAAATATGTGAGTTGCAGCTTAAGGTTCAGA---- | 1192 |
| SEQ_ID_NO_221 | ACTTGAGCATAGGAGTTGAGATCAAGAAATATTTGAGTTGCAGCTTAAGGTTCAGA---- | 780 |
| SEQ_ID_NO_224 | ACTTGAGCATAGGAGTTGAGATCAAGAAATATTTGAGTTGCAGCTTAAGGTCCAGA---- | 780 |
| | **************** ***** ******* ****** *********** **** | |
| SEQ_ID_NO_213 | ---GAGGAAATCCCCATACACTTGCTTGTAACGGTATGAATGTATGATCATTTTTTTTC | 837 |
| SEQ_ID_NO_222 | ---GAGGAAATCCCCATACACGTGCTTGTAACGGTATGGTCAT-------TTTTTTTTC | 831 |
| SEQ_ID_NO_220 | ---GAGGAAACCCCCATACACTTGCTTGTAACGGT--------ATGATCATTTTTTTT-G | 828 |
| SEQ_ID_NO_235 | ---GAGGAAATCCC-ATACACTTGCTTGTAACGAT--------ATGATCATTTTTTTT-C | 792 |
| SEQ_ID_NO_225 | ---GAGGAAATCCCCATACACTTGCTTGTAACGGTATGAATGTATGATCATTTTTTTTC | 837 |
| SEQ_ID_NO_226 | ---GAGGAAATCCCCATACACTTGCTTGTAACGGTATGAATGTATGATCATTTTTTTTC | 837 |
| SEQ_ID_NO_228 | ---GAGGAAATCCCCATACACTTGCTTGTAACGGTATGAATGTATGATCATTTTTTTTC | 837 |
| SEQ_ID_NO_227 | ---GAGGAAATCCCCATACACTTGCTTGTAACGGTATGAATGTATGATCATTTTTTTTC | 837 |
| SEQ_ID_NO_223 | AGAGAGGAAATCCCCATACACTTGCTTGTAACGGT--------ATGATCATTTTTTTT-C | 830 |
| SEQ_ID_NO_215 | ---GAGGAAATCCCCATACACTTGCTTGTAACGGT--------ATGATCATATCTTTT-C | 1240 |
| SEQ_ID_NO_216 | ---GAGGAAATCCCCATACACTTGCTTGTAACGGT--------ATGATCATATCTTTT-C | 1240 |
| SEQ_ID_NO_214 | ---GAGGAAATCCCCATACACTTGCTTGTAACGGT--------ATGATCATATCTTTT-C | 1240 |
| SEQ_ID_NO_233 | ---GAGGAAATCCCCATACACTTGCTTGTAACGGTATGAATGTATGATCATTTTTTTTC | 837 |
| SEQ_ID_NO_236 | ---GAGGAAATCCC-ATACACTTGCTTGTAACGAT--------ATGATCATTTTTTTT-C | 792 |
| SEQ_ID_NO_231 | ---GAGGAAATCCCCATACACTTGCTTGTAACGGTATGAATGTATGATCATTTTTTTTC | 837 |
| SEQ_ID_NO_229 | ---GAGGAAATCCCCATACACTTGCTTGTAACGGTATGAATGTATGATCATTTTTTTTC | 837 |
| SEQ_ID_NO_230 | ---GAGGAAATCCCCATACACTTGCTTGTAACGGTATGAATGTATGATCATTTTTTTTC | 837 |
| SEQ_ID_NO_232 | ---GAGGAAATCCCCATACACTTGCTTGTAACGGTATGAATGTATGATCATTTTTTTTC | 837 |
| SEQ_ID_NO_234 | ---GAGGAAATCCCCATACACTTGCTTGTAACGGTATGAATGTATGATCATTTTTTTTC | 802 |
| SEQ_ID_NO_218 | ---GAGGAAATCCCCATACACTTGCTTGTAACGGT--------ATGATCATATCTTTT-C | 1240 |
| SEQ_ID_NO_219 | ---GAGGAAATCCCCATACACTTGCTTGTAACGGT--------ATGATCATATCTTTT-C | 1240 |
| SEQ_ID_NO_217 | ---GAGGAAATCCCCATACACTTGCTTGTAACGGT--------ATGATCATATCTTTT-C | 1240 |
| SEQ_ID_NO_221 | ---GAGGAAATCCCCATACACGTGCTTGTAACGGTATGG--------TCATTTTTTTTC | 829 |
| SEQ_ID_NO_224 | ---GAGGAAATCCCCATACACTTGCTTGTAACGGTATGAATGTATGATCATTTTTTTTC | 837 |
| | ******* *** ****** *********** *              * * **** | |

TABLE 27-continued

| SEQ_ID_NO_213 | AAGGTAACATTTTCTAGCATCTTCACCTGTCTACTTGACTGAATGCAGTATATATTAGTT | 897 |
| --- | --- | --- |
| SEQ_ID_NO_222 | AAGGTAACATTTTCTAGCATCTTCAGCTGTCTACTTGACTGAATGCAGTATATATTAGTT | 891 |
| SEQ_ID_NO_220 | AAGGTAACATTTTCTAGCATCTTCAGCTGTCTACTTGACTGAATGCAGTATATATTAGTT | 888 |
| SEQ_ID_NO_235 | AAGGTAACATTTTCTAGCATCTTCAGCTGTCTACTTGACTGAATGCAGTATATATTAGTT | 852 |
| SEQ_ID_NO_225 | AAGGTAACATTTTCTAGCATCTTCACCTGTCTACTTGACTGAATGCAGTATATATTAGTT | 897 |
| SEQ_ID_NO_226 | AAGGTAACATTTTCTAGCATCTTCACCTGTCTACTTGACTGAATGCAGTATATATTAGTT | 897 |
| SEQ_ID_NO_228 | AAGGTAACATTTTCTAGCATCTTCACCTGTCTACTTGACTGAATGCAGTATATATTAGTT | 897 |
| SEQ_ID_NO_227 | AAGGTAACATTTTCTAGCATCTTCACCTGTCTACTTGACTGAATGCAGTATATATTAGTT | 897 |
| SEQ_ID_NO_223 | AAGGTAACATTTTCTAGCATCTTCACCTGTCTACTTGACTGAATGCAGTATATATTAGTT | 890 |
| SEQ_ID_NO_215 | AAGGTAACATTTTCTAGCATCTTCAGCTGTCTACTTGACTGAATGCAGTATATATTAGTT | 1300 |
| SEQ_ID_NO_216 | AAGGTAACATTTTCTAGCATCTTCAGCTGTCTACTTGACTGAATGCAGTATATATTAGTT | 1300 |
| SEQ_ID_NO_214 | AAGGTAACATTTTCTAGCATCTTCAGCTGTCTACTTGACTGAATGCAGTATATATTAGTT | 1300 |
| SEQ_ID_NO_233 | AAGGTAACATTTTCTAGCATCTTCACCTGTCTACTTGACTGAATGCAGTATATATTAGTT | 897 |
| SEQ_ID_NO_236 | AAGGTAACATTTTCTAGCATCTTCAGCTGTCTACTTGACTGAATGCAGTATATATTAGTT | 852 |
| SEQ_ID_NO_231 | AAGGTAACATTTTCTAGCATCTTCACCTGTCTACTTGACTGAATGCAGTATATATTAGTT | 897 |
| SEQ_ID_NO_229 | AAGGTAACATTTTCTAGCATCTTCACCTGTCTACTTGACTGAATGCAGTATATATTAGTT | 897 |
| SEQ_ID_NO_230 | AAGGTAACATTTTCTAGCATCTTCACCTGTCTACTTGACTGAATGCAGTATATATTAGTT | 897 |
| SEQ_ID_NO_232 | AAGGTAACATTTTCTAGCATCTTCACCTGTCTACTTGACTGAATGCAGTATATATTAGTT | 897 |
| SEQ_ID_NO_234 | AAGGTAACATTTTCTAGCATCTTCACCTGTCTACTTGACTGAATGCAGTATATATTAGTT | 862 |
| SEQ_ID_NO_218 | AAGGTAACATTTTCTAGCATCTTCAGCTGTCTACTTGACTGAATGCAGTATATATTAGTT | 1300 |
| SEQ_ID_NO_219 | AAGGTAACATTTTCTAGCATCTTCAGCTGTCTACTTGACTGAATGCAGTATATATTAGTT | 1300 |
| SEQ_ID_NO_217 | AAGGTAACATTTTCTAGCATCTTCAGCTGTCTACTTGACTGAATGCAGTATATATTAGTT | 1300 |
| SEQ_ID_NO_221 | AAGGTAACATTTTCTAGCATCTTCAGCTGTCTACTTGACTGAATGCAGTATATATTAGTT | 889 |
| SEQ_ID_NO_224 | AAGGTAACATTTTCTAGCATCTTCACCTGTCTACTTGACTGAATGCAGTATATATTAGTT | 897 |
|  | ********************** ******************************** |  |
| SEQ_ID_NO_213 | GTAATAACTACTGGCCTTCTGCTGTGCACAAAAGGCGGGTATTACCACTTGCAGAAATTT | 957 |
| SEQ_ID_NO_222 | GTAATAAATACTGGCCTTCTGCTGTGCACAAAAGGCGGGTATTACCACTTGCAGAAATTT | 951 |
| SEQ_ID_NO_220 | GTAATAAATACTGCCCTTCTGCTGTGCACAAAAGGCGGGTATTACCACTTGCAGAAATTT | 948 |
| SEQ_ID_NO_235 | GTAATAAATACTGCCCTTCTGCTGTGCACAAAAGGCGGGTATTACCACTTGCAGAAATTT | 912 |
| SEQ_ID_NO_225 | GTAATAACTACTGGCCTTCTGCTGTGCACAAAAGGCGGGTATTACCACTTGCAGAAATTT | 957 |
| SEQ_ID_NO_226 | GTAATAACTACTGGCCTTCTGCTGTGCACAAAAGGCGGGTATTACCACTTGCAGAAATTT | 957 |
| SEQ_ID_NO_228 | GTAATAACTACTGGCCTTCTGCTGTGCACAAAAGGCGGGTATTACCACTTGCAGAAATTT | 957 |
| SEQ_ID_NO_227 | GTAATAACTACTGGCCTTCTGCTGTGCACAAAAGGCGGGTATTACCACTTGCAGAAATTT | 957 |
| SEQ_ID_NO_223 | GTAATAAATACTGCTCTTCTGCTGTGCAGAAAGGCGGGTATTACCACTTGCAGAAATTT | 950 |
| SEQ_ID_NO_215 | GTAATAAATACTGCCCTTCTGCTGTGCACAAAAGGCGGGTATTACCACTTGCAGAAATTT | 1360 |
| SEQ_ID_NO_216 | GTAATAAATACTGCCCTTCTGCTGTGCACAAAAGGCGGGTATTACCACTTGCAGAAATTT | 1360 |
| SEQ_ID_NO_214 | GTAATAAATACTGCCCTTCTGCTGTGCACAAAAGGCGGGTATTACCACTTGCAGAAATTT | 1360 |
| SEQ_ID_NO_233 | GTAATAACTACTGGCCTTCTGCTGTGCACAAAAGGCGGGTATTACCACTTGCAGAAATTT | 957 |
| SEQ_ID_NO_236 | GTAATAAATACTGCCCTTCTGCTGTGCACAAAAGGCGGGTATTACCACTTGCAGAAATTT | 912 |
| SEQ_ID_NO_231 | GTAATAACTACTGGCCTTCTGCTGTGCACAAAAGGCGGGTATTACCACTTGCAGAAATTT | 957 |
| SEQ_ID_NO_229 | GTAATAACTACTGGCCTTCTGCTGTGCACAAAAGGCGGGTATTACCACTTGCAGAAATTT | 957 |

TABLE 27-continued

| | | |
|---|---|---|
| SEQ_ID_NO_230 | GTAATAACTACTGGCCTTCTGCTGTGCACAAAAGGCGGGTATTACCACTTGCAGAAATTT | 957 |
| SEQ_ID_NO_232 | GTAATAACTACTGGCCTTCTGCTGTGCACAAAAGGCGGGTATTACCACTTGCAGAAATTT | 957 |
| SEQ_ID_NO_234 | GTAATAACTACTGGCCTTCTGCTGTGCACAAAAGGCGGGTATTACCACTTGCAGAAATTT | 922 |
| SEQ_ID_NO_218 | GTAATAAATACTGCCCTTCTGCTGTGCACAAAAGGCGGGTATTACCACTTGCAGAAATTT | 1360 |
| SEQ_ID_NO_219 | GTAATAAATACTGCCCTTCTGCTGTGCACAAAAGGCGGGTATTACCACTTGCAGAAATTT | 1360 |
| SEQ_ID_NO_217 | GTAATAAATACTGCCCTTCTGCTGTGCACAAAAGGCGGGTATTACCACTTGCAGAAATTT | 1360 |
| SEQ_ID_NO_221 | GTAATAAATACTGGCCTTCTGCTGTGCACAAAAGGCGGGTATTACCACTTGCAGAAATTT | 949 |
| SEQ_ID_NO_224 | GTAATAACTACTGGCCTTCTGCTGTGCACAAAAGGCGGGTATTACCACTTGCAGAAATTT | 957 |
| | ****** ***** ************* ****************************** | |
| SEQ_ID_NO_213 | GTCGGGTAAAGGTAATTGCCAGTTACCTTGTGTTCTTCCCTTGATCAGGAACACCTGGAG | 1017 |
| SEQ_ID_NO_222 | GTCGGGTCAAGGTAATTGCCAGTTACCTTGTGTTCTTCCCTTCATCAGGAACACCTGGAG | 1011 |
| SEQ_ID_NO_220 | GTCGGGTAAAGGTAATTGCCAGTTACCTTGTGTTCTTCCCTTCATCAGGAACACCTGGAG | 1008 |
| SEQ_ID_NO_235 | GTCGGGTAAAGGTAATTGCCAGTTACCTTGTGTTCTTCCCTTCATCAGGAACACCTGGAG | 972 |
| SEQ_ID_NO_225 | GTCGGGTAAAGGTAATTGCCAGTTACCTTGTGTTCTTCCCTTGATCAGGAACACCTGGAG | 1017 |
| SEQ_ID_NO_226 | GTCGGGTAAAGGTAATTGCCAGTTACCTTGTGTTCTTCCCTTGATCAGGAACACCTGGAG | 1017 |
| SEQ_ID_NO_228 | GTCGGGTAAAGGTAATTGCCAGTTACCTTGTGTTCTTCCCTTGATCAGGAACACCTGGAG | 1017 |
| SEQ_ID_NO_227 | GTCGGGTAAAGGTAATTGCCAGTTACCTTGTGTTCTTCCCTTGATCAGGAACACCTGGAG | 1017 |
| SEQ_ID_NO_223 | GTCGGGTAAAGGTAATTGCCAGTTACCTTGTGTTCTTCCCTTCATCAGGAACACCTGGAG | 1010 |
| SEQ_ID_NO_215 | GTCGGGTAAAGGTAATTGCCAGTTACCTTGTGTTCTTCCCTTGATCAGGAACACCTGGAG | 1420 |
| SEQ_ID_NO_216 | GTCGGGTAAAGGTAATTGCCAGTTACCTTGTGTTCTTCCCTTGATCAGGAACACCTGGAG | 1420 |
| SEQ_ID_NO_214 | GTCGGGTAAAGGTAATTGCCAGTTACCTTGTGTTCTTCCCTTGATCAGGAACACCTGGAG | 1420 |
| SEQ_ID_NO_233 | GTCGGGTAAAGGTAATTGCCAGTTACCTTGTGTTCTTCCCTTGATCAGGAACACCTGGAG | 1017 |
| SEQ_ID_NO_236 | GTCGGGTAAAGGTAATTGCCAGTTACCTTGTGTTCTTCCCTTCATCAGGAACACCTGGAG | 972 |
| SEQ_ID_NO_231 | GTCGGGTAAAGGTAATTGCCAGTTACCTTGTGTTCTTCCCTTGATCAGGAACACCTGGAG | 1017 |
| SEQ_ID_NO_229 | GTCGGGTAAAGGTAATTGCCAGTTACCTTGTGTTCTTCCCTTGATCAGGAACACCTGGAG | 1017 |
| SEQ_ID_NO_230 | GTCGGGTAAAGGTAATTGCCAGTTACCTTGTGTTCTTCCCTTGATCAGGAACACCTGGAG | 1017 |
| SEQ_ID_NO_232 | GTCGGGTAAAGGTAATTGCCAGTTACCTTGTGTTCTTCCCTTGATCAGGAACACCTGGAG | 1017 |
| SEQ_ID_NO_234 | GTCGGGTAAAGGTAATTGCCAGTTACCTTGTGTTCTTCCCTTGATCAGGAACACCTGGAG | 982 |
| SEQ_ID_NO_218 | GTCGGGTAAAGGTAATTGCCAGTTACCTTGTGTTCTTCCCTTGATCAGGAACACCTGGAG | 1420 |
| SEQ_ID_NO_219 | GTCGGGTAAAGGTAATTGCCAGTTACCTTGTGTTCTTCCCTTGATCAGGAACACCTGGAG | 1420 |
| SEQ_ID_NO_217 | GTCGGGTAAAGGTAATTGCCAGTTACCTTGTGTTCTTCCCTTGATCAGGAACACCTGGAG | 1420 |
| SEQ_ID_NO_221 | GTCGGGTCAAGGTAATTGCCAGTTACCTTGTGTTCTTCCCTTGATCAGGAACACCTGGAG | 1009 |
| SEQ_ID_NO_224 | GTCGGGTAAAGGTAATTGCCAGTTACCTTGTGTTCTTCCCTTGATCAGGAACACCTGGAG | 1017 |
| | ****** ***************************** ***************** | |
| SEQ_ID_NO_213 | GAGGATGCGCTGTGGTTGAACCGAAGCC---CTGTGAGCGAAGTACTGATGACAGAAAGA | 1074 |
| SEQ_ID_NO_222 | GAGGATGCGCTGTGGTTGAACTGAAGCCGCCCTGTGAGCGAAGTACTGATGACAGAAAGA | 1071 |
| SEQ_ID_NO_220 | GAGGATGCGCTGTGGTTGAACTGAAGCC---CTGCGAGAGAAGTACTGATGACAGAAAGA | 1065 |
| SEQ_ID_NO_235 | GAGGATGCGCTGTGGTTGAACTGAAGCC---CTGCGAGAGAAGTACTGATGACAGAAAGA | 1029 |
| SEQ_ID_NO_225 | GAGGATGCGCTGTGGTTGAACCGAAGCC---CTGTGAGCGAAGTACTGATGACAGAAAGA | 1074 |
| SEQ_ID_NO_226 | GAGGATGCGCTGTGGTTGAACCGAAGCC---CTGTGAGCGAAGTACTGATGACAGAAAGA | 1074 |
| SEQ_ID_NO_228 | GAGGATGCGCTGTGGTTGAACCGAAGCC---CTGTGAGCGAAGTACTGATGACAGAAAGA | 1074 |

TABLE 27-continued

| | | |
|---|---|---|
| SEQ_ID_NO_227 | GAGGATGCGCTGTGGTTGAACCGAAGCC---CTGTGAGCGAAGTACTGATGACAGAAAGA | 1074 |
| SEQ_ID_NO_223 | GAGGATGCGCTGTGGTTGAACCGAAGCC---CTGTGAGCGAAGTACTGATGACAGAAAGA | 1067 |
| SEQ_ID_NO_215 | GAGGATGCGCTGTGGTTGAACCGAAGCC---CTGTGAGCGAAGTACTGATGACAGAAAGA | 1477 |
| SEQ_ID_NO_216 | GAGGATGCGCTGTGGTTGAACCGAAGCC---CTGTGAGCGAAGTACTGATGACAGAAAGA | 1477 |
| SEQ_ID_NO_214 | GAGGATGCGCTGTGGTTGAACCGAAGCC---CTGTGAGCGAAGTACTGATGACAGAAAGA | 1477 |
| SEQ_ID_NO_233 | GAGGATGCGCTGTGGTTGAACCGAAGCC---CTGTGAGCGAAGTACTGATGACAGAAAGA | 1074 |
| SEQ_ID_NO_236 | GAGGATGCGCTGTGGTTGAACTGAAGCC---CTGCGAGAGAAGTACTGATGACAGAAAGA | 1029 |
| SEQ_ID_NO_231 | GAGGATGCGCTGTGGTTGAACCGAAGCC---CTGTGAGCGAAGTACTGATGACAGAAAGA | 1074 |
| SEQ_ID_NO_229 | GAGGATGCGCTGTGGTTGAACCGAAGCC---CTGTGAGCGAAGTACTGATGACAGAAAGA | 1074 |
| SEQ_ID_NO_230 | GAGGATGCGCTGTGGTTGAACCGAAGCC---CTGTGAGCGAAGTACTGATGACAGAAAGA | 1074 |
| SEQ_ID_NO_232 | GAGGATGCGCTGTGGTTGAACCGAAGCC---CTGTGAGCGAAGTACTGATGACAGAAAGA | 1074 |
| SEQ_ID_NO_234 | GAGGATGCGCTGTGGTTGAACCGAAGCC---CTGTGAGCGAAGTACTGATGACAGAAAGA | 1039 |
| SEQ_ID_NO_218 | GAGGATGCGCTGTGGTTGAACCGAAGCC---CTGTGAGCGAAGTACTGATGACAGAAAGA | 1477 |
| SEQ_ID_NO_219 | GAGGATGCGCTGTGGTTGAACCGAAGCC---CTGTGAGCGAAGTACTGATGACAGAAAGA | 1477 |
| SEQ_ID_NO_217 | GAGGATGCGCTGTGGTTGAACCGAAGCC---CTGTGAGCGAAGTACTGATGACAGAAAGA | 1477 |
| SEQ_ID_NO_221 | GAGGATGCGCTGTGGTTGAACTGAAGCCGCCCTGTGAGCGAAGTACTGATGACAGAAAGA | 1069 |
| SEQ_ID_NO_224 | GAGGATGCGCTGTGGTTGAACCGAAG---CCCTGTGAGCGAAGTACTGATGACAGAAAGA | 1074 |
| | ******************** ****    *** *** ******************** | |
| SEQ_ID_NO_213 | GCGGAAGATAAGATAAGAAAGGAA-CCCTTGCGCGGCAAGGCCTGGTGACATAGAGGTAG | 1133 |
| SEQ_ID_NO_222 | GCGGAAGATAAGATAAGAAAGGAA-CGCTTGCGCGGCAAGGCCTGGTGACATAGAGGTAG | 1130 |
| SEQ_ID_NO_220 | GCGGAAGATAAGATAAGAAAGGAACCCTTGCGCGGCAGGGCCTGGTGACATAGAGGTAG | 1125 |
| SEQ_ID_NO_235 | GCGGAAGATAAGATAAGAAAGGAACCCTTGCGCGGCAAGGCCTGGTGACATAGAGGTAG | 1089 |
| SEQ_ID_NO_225 | GCGGAAGATAAGATAAGAAAGGAA-CCCTTGCGCGGCAAGGCCTGGTGACATAGAGGTAG | 1133 |
| SEQ_ID_NO_226 | GCGGAAGATAAGATAAGAAAGGAA-CCCTTGCGCGGCAAGGCCTGGTGACATAGAGGTAG | 1133 |
| SEQ_ID_NO_228 | GCGGAAGATAAGATAAGAAAGGAA-CCCTTGCGCGGCAAGGCCTGGTGACATAGAGGTAG | 1133 |
| SEQ_ID_NO_227 | GCGGAAGATAAGATAAGAAAGGAA-CCCTTGCGCGGCAAGGCCTGGTGACATAGAGGTAG | 1133 |
| SEQ_ID_NO_223 | GCGGAAGATAAGATAAGAAAGGAA-CCCTTGCGCGGCAAGGCCTGGTGACATAGAGGTAG | 1126 |
| SEQ_ID_NO_215 | GCGGAAGATAAGATAAGAAAGGAA-CCCTTGCGCGGCAAGGCCTGGTGACATAGAGGTAG | 1536 |
| SEQ_ID_NO_216 | GCGGAAGATAAGATAAGAAAGGAA-CCCTTGCGCGGCAAGGCCTGGTGACATAGAGGTAG | 1536 |
| SEQ_ID_NO_214 | GCGGAAGATAAGATAAGAAAGGAA-CCCTTGCGCGGCAAGGCCTGGTGACATAGAGGTAG | 1536 |
| SEQ_ID_NO_233 | GCGGAAGATAAGATAAGAAAGGAA-CCCTTGCGCGGCAAGGCCTGGTGACATAGAGGTAG | 1133 |
| SEQ_ID_NO_236 | GCGGAAGATAAGATAAGAAAGGAACCCTTGCGCGGCAAGGCCTGGTGACATAGAGGTAG | 1089 |
| SEQ_ID_NO_231 | GCGGAAGATAAGATAAGAAAGGAA-CCCTTGCGCGGCAAGGCCTGGTGACATAGAGGTAG | 1133 |
| SEQ_ID_NO_229 | GCGGAAGATAAGATAAGAAAGGAA-CCCTTGCGCGGCAAGGCCTGGTGACATAGAGGTAG | 1133 |
| SEQ_ID_NO_230 | GCGGAAGATAAGATAAGAAAGGAA-CCCTTGCGCGGCAAGGCCTGGTGACATAGAGGTAG | 1133 |
| SEQ_ID_NO_232 | GCGGAAGATAAGATAAGAAAGGAA-CCCTTGCGCGGCAAGGCCTGGTGACATAGAGGTAG | 1133 |
| SEQ_ID_NO_234 | GCGGAAGATAAGATAAGAAAGGAA-CCCTTGCGCGGCAAGGCCTGGTGACATAGAGGTAG | 1098 |
| SEQ_ID_NO_218 | GCGGAAGATAAGATAAGAAAGGAA-CCCTTGCGCGGCAAGGCCTGGTGACATAGAGGTAG | 1536 |
| SEQ_ID_NO_219 | GCGGAAGATAAGATAAGAAAGGAA-CCCTTGCGCGGCAAGGCCTGGTGACATAGAGGTAG | 1536 |
| SEQ_ID_NO_217 | GCGGAAGATAAGATAAGAAAGGAA-CCCTTGCGCGGCAAGGCCTGGTGACATAGAGGTAG | 1536 |

TABLE 27-continued

| SEQ_ID_NO_221 | GCGGAAGATAAGATAAGAAAGGAA-CGCTTGCGCGGCAAGGCCTGGTGACATAGAGGTAG | 1128 |
| --- | --- | --- |
| SEQ_ID_NO_224 | GCGGAAGATAAGATAAGAAAGGAA-CCCTTGCGCGGCAAGGCCTGGTGACATAGAGGTAG | 1133 |
| | ************************ * ********** ******************** | |
| SEQ_ID_NO_213 | TG-CGAGGCTCATACCGCCGCCGCTGGCAGGTTCCAGGCCTGTGCTTTTCTTGCCCTGTA | 1192 |
| SEQ_ID_NO_222 | TG-CGAGGCTCATACCGCCGCCGCTGGCAGGTTCGAGGCCTGTGCTTTTCTTGCCCTGTT | 1189 |
| SEQ_ID_NO_220 | TG-CGAGGCTCATACCGCCGCCGCTGGCAGGTTCCAGGCCTGTGCTTTTCTTGCCCTGTA | 1184 |
| SEQ_ID_NO_235 | TG-CGAGGCTCATACCGCCG---CTGGCAGGTTCCAGGCCTGTGCTTTTCTTGCCCTGTA | 1145 |
| SEQ_ID_NO_225 | TG-CGAGGCTCATACCGCCGCCGCTGGCAGGTTCCAGGCCTGTGCTTTTCTTGCCCTGTA | 1192 |
| SEQ_ID_NO_226 | TG-CGAGGCTCATACCGCCGCCGCTGGCAGGTTCCAGGCCTGTGCTTTTCTTGCCCTGTA | 1192 |
| SEQ_ID_NO_228 | TGGCGAGGCTCATACCGCCGCCGCTGGCAGGTTCCAGGCCTGTGCTTTTCTTGCCCTGTA | 1193 |
| SEQ_ID_NO_227 | TG-CGAGGCTCATACCGCCGCCGCTGGCAGGTTCCAGGCCTGTGCTTTTCTTGCCCTGTA | 1192 |
| SEQ_ID_NO_223 | TG-CGAGGCTCATACCGCCGCCGCTGGCAGGTTCCAGGCCTGTGCTTTTCTTGCCCTGTA | 1185 |
| SEQ_ID_NO_215 | TG-CGAGGCTCATACCGCCGCCGCTGGCAGGTTCCAGGCCTGTGCTTTTCTTGCCCTGTA | 1595 |
| SEQ_ID_NO_216 | TG-CGAGGCTCATACCGCCGCCGCTGGCAGGTTCCAGGCCTGTGCTTTTCTTGCCCTGTA | 1595 |
| SEQ_ID_NO_214 | TG-CGAGGCTCATACCGCCGCCGCTGGCAGGTTCCAGGCCTGTGCTTTTCTTGCCCTGTA | 1595 |
| SEQ_ID_NO_233 | TG-CGAGGCTCATACCGCCGCCGCTGGCAGGTTCSAGGCCTGTGCTTTTCTTGCCCTGTA | 1192 |
| SEQ_ID_NO_236 | TG-CGAGGCTCATACCGCC---GCTGGCAGGTTCCAGGCCTGTGCTTTTCTTGCCCTGTA | 1145 |
| SEQ_ID_NO_231 | TG-CGAGGCTCATACCGCCGCCGCTGGCAGGTTCCAGGCCTGTGCTTTTCTTGCCCTGTA | 1192 |
| SEQ_ID_NO_229 | TG-CGAGGCTCATACCGCCGCCGCTGGCAGGTTCCAGGCCTGTGCTTTTCTTGCCCTGTA | 1192 |
| SEQ_ID_NO_230 | TG-CGAGGCTCATACCGCCGCCGCTGGCAGGTTCCAGGCCTGTGCTTTTCTTGCCCTGTA | 1192 |
| SEQ_ID_NO_232 | TG-CGAGGCTCATACCGCCGCCGCTGGCAGGTTCCAGGCCTGTGCTTTTCTTGCCCTGTA | 1192 |
| SEQ_ID_NO_234 | TG-CGAGGCTCATACCGCCGCCGCTGGCAGGTTCCAGGCCTGTGCTTTTCTTGCCCTGTA | 1157 |
| SEQ_ID_NO_218 | TG-CGAGGCTCATACCGCCGCCGCTGGCAGGTTCCAGGCCTGTGCTTTTCTTGCCCTGTA | 1595 |
| SEQ_ID_NO_219 | TG-CGAGGCTCATACCGCCGCCGCTGGCAGGTTCCAGGCCTGTGCTTTTCTTGCCCTGTA | 1595 |
| SEQ_ID_NO_217 | TG-CGAGGCTCATACCGCCGCCGCTGGCAGGTTCCAGGCCTGTGCTTTTCTTGCCCTGTA | 1595 |
| SEQ_ID_NO_221 | TG-CGAGGCTCATACCGCCGCCGCTGGCAGGTTCGAGGCCTGTGCTTTTCTTGCCCTGTA | 1187 |
| SEQ_ID_NO_224 | TG-CGAGGCTCATACCGCCGCCGCTGGCAGGTTCCAGGCCTGTGCTTTTCTTGCCCTGTA | 1192 |
| | ** ***************    **********  ********************** | |
| SEQ_ID_NO_213 | TCCCCAGTCTATACTTCTGCGCACATCAGACGAGCCTCAGTGTTTCGGCACAGTGGTGCA | 1252 |
| SEQ_ID_NO_222 | TCCCCATTCTATACTTCTGCGCACATCAGACGAGCCTCAGTGTTTCGGCACAGTGGTGCA | 1249 |
| SEQ_ID_NO_220 | TCCCCAGTCTATACTTCTGCGCACATCAGACGAGCGTCAGTGTTTCGGCACAGTGGTGCA | 1244 |
| SEQ_ID_NO_235 | TCCCCAGTCTATACTTCTGCGCACATCAGACGAGCCTCAGTGTTTCGGCACAGTGGTGCA | 1205 |
| SEQ_ID_NO_225 | TCCCCAGTCTATACTTCTGCGCACATCAGACGAGCCTCAGTGTTTCGGCACAGTGGTGCA | 1252 |
| SEQ_ID_NO_226 | TCCCCAGTCTATACTTCTGCGCACATCAGACGAGCCTCAGTGTTTCGGCACAGTGGTGCA | 1252 |
| SEQ_ID_NO_228 | TCCCCAGTCTATACTTCTGCGCACATCAGACGAGCCTCAGTGTTTCGGCACAGTGGTGCA | 1253 |
| SEQ_ID_NO_227 | TCCCCAGTCTATACTTCTGCGCACATCAGACGAGCCTCAGTGTTTCGGCACAGTGGTGCA | 1252 |
| SEQ_ID_NO_223 | TCCCCAGTCTATACTTCTGCGCACATCAGACGAGCCTCAGTGTTTCGGCACAGTGGTGCA | 1245 |
| SEQ_ID_NO_215 | TCCCCAGTCTATACTTCTGCGCACATCAGACGAGCCTCAGTGTTTCGGCACAGTGGTGCA | 1655 |
| SEQ_ID_NO_216 | TCCCCAGTCTATACTTCTGCGCACATCAGACGAGCCTCAGTGTTTCGGCACAGTGGTGCA | 1655 |
| SEQ_ID_NO_214 | TCCCCAGTCTATACTTCTGCGCACATCAGACGAGCCTCAGTGTTTCGGCACAGTGGTGCA | 1655 |
| SEQ_ID_NO_233 | TCCCCAGTCTATACTTCTGCGCACATCAGACGAGCGTCAGTGTTTCGGCACAGTGGTGCA | 1252 |

TABLE 27-continued

| | | |
|---|---|---|
| SEQ_ID_NO_236 | TCCCCAGTCTATACTTCTGCGCACATCAGACGAGCCTCAGTGTTTCGGCACAGTGGTGCA | 1205 |
| SEQ_ID_NO_231 | TCCCCAGTCTATACTTCTGCGCACATCAGACGAGCCTCAGTGTTTCGGCACAGTGGTGCA | 1252 |
| SEQ_ID_NO_229 | TCCCCAGTCTATACTTCTGCGCACATCAGACGAGCCTCAGTGTTTCGGCACAGTGGTGCA | 1252 |
| SEQ_ID_NO_230 | TCCCCAGTCTATACTTCTGCGCACATCAGACGAGCCTCAGTGTTTCGGCACAGTGGTGCA | 1252 |
| SEQ_ID_NO_232 | TCCCCAGTCTATACTTCTGCGCACATCAGACGAGCCTCAGTGTTTCGGCACAGTGGTGCA | 1252 |
| SEQ_ID_NO_234 | TCCCCAGTCTATACTTCTGCGCACATCAGACGAGCCTCAGTGTTTCGGCACAGTGGTGCA | 1217 |
| SEQ_ID_NO_218 | TCCCCAGTCTATACTTCTGCGCACATCAGACGAGCCTCAGTGTTTCGGCACAGTGGTGCA | 1655 |
| SEQ_ID_NO_219 | TCCCCAGTCTATACTTCTGCGCACATCAGACGAGCCTCAGTGTTTCGGCACAGTGGTGCA | 1655 |
| SEQ_ID_NO_217 | TCCCCAGTCTATACTTCTGCGCACATCAGACGAGCCTCAGTGTTTCGGCACAGTGGTGCA | 1655 |
| SEQ_ID_NO_221 | TCCCCAGTCTATACTTCTGCGCACATCAGACGAGCCTCAGTGTTTCGGCACAGTGGTGCA | 1247 |
| SEQ_ID_NO_224 | TCCCCAGTCTATACTTCTGCGCACATCAGACGAGCCTCAGTGTTTCGGCACAGTGGTGCA | 1252 |
| | ****** ************************* ************************ | |
| SEQ_ID_NO_213 | ACAGAAAA-GGAGAGTGCTGG----TAGGTAACGCTGAGGCGGTGAAGAAAGAGAGGTCA | 1307 |
| SEQ_ID_NO_222 | ACAAAAAA-AGAGAGTGCTGG----TAGGTAACCCTNNNNNNNNNNNNNNNNNNNNNNNN | 1304 |
| SEQ_ID_NO_220 | ACAGAAAA-GGAGAGTGCTGG--- TAGGTAACGCTGAGGCGGTGAAGAAAGAGAGGTCA | 1299 |
| SEQ_ID_NO_235 | ACAGAAAA-GGAGAGTGCTGG----TAGGTAACGCTGAGGCGGTGAAGAAAGAGAGGTCA | 1260 |
| SEQ_ID_NO_225 | ACAGAAAA-GGAGAGTGCTGG----TAGGTAACGCTGAGGCGGTGAAGAAAGAGAGGTCA | 1307 |
| SEQ_ID_NO_226 | ACAGAAAA-GGAGAGTGCTGG----TAGGTAACGCTGAGGCGGTGAAGAAAGAGAGGTCA | 1307 |
| SEQ_ID_NO_228 | ACAGAAAA-GGAGAGTGCTGG----TAGGTAACGCTGAGGCGGTGAAGAAAGAGAGGTCA | 1308 |
| SEQ_ID_NO_227 | ACAGAAAA-GGAGAGTGCTGG----TAGGTAACGCTGAGGCGGTGAAGAAAGAGAGGTCA | 1307 |
| SEQ_ID_NO_223 | ACAGAAAA-GGAGAGTGCTGC----TA----ACGCTGAGGCGGTGAAGAAAGAGAGGTCG | 1296 |
| SEQ_ID_NO_215 | ACAGAAAA-GGAGAGTGCTGG----TAGGTAACGCTGAGGCGGTGAAGAAAGAGAGGTCA | 1710 |
| SEQ_ID_NO_216 | ACAGAAAA-GGAGAGTGCTGG----TAGGTAACGCTGAGGCGGTGAAGAAAGAGAGGTCA | 1710 |
| SEQ_ID_NO_214 | ACAGAAAA-GGAGAGTGCTGG----TAGGTAACGCTGAGGCGGTGAAGAAAGAGAGGTCA | 1710 |
| SEQ_ID_NO_233 | ACAGAAAA-GGAGAGTGCTGG----TAGGTAACGCTGAGGCGGTGAAGAAAGAGAGGTCA | 1307 |
| SEQ_ID_NO_236 | ACAGAAAAGGAGAGTGCTGGACTGCTGGTAACGCTGAGGCGGTGAAGAAAGAGAGGTCA | 1265 |
| SEQ_ID_NO_231 | ACAGAAAA-GGAGAGTGCTGG----TAGGTAACGCTGAGGCGGTGAAGAAAGAGAGGTCA | 1307 |
| SEQ_ID_NO_229 | ACAGAAAA-GGAGAGTGCTGG----TAGGTAACGCTGAGGCGGTGAAGAAAGAGAGGTCA | 1307 |
| SEQ_ID_NO_230 | ACAGAAAA-GGAGAGTGCTGG----TAGGTAACGCTGAGGCGGTGAAGAAAGAGAGGTCA | 1307 |
| SEQ_ID_NO_232 | ACAGAAAA-GGAGAGTGCTGG----TAGGTAACGCTGAGGCGGTGAAGAAAGAGAGGTCA | 1307 |
| SEQ_ID_NO_234 | ACAGAAAA-GGAGAGTGCTGG----TAGGTAACGCTGAGGCGGTGAAGAAAGAGAGGTCA | 1272 |
| SEQ_ID_NO_218 | ACAGAAAA-GGAGAGTGCTGG----TAGGTAACGCTGAGGCGGTGAAGAAAGAGAGGTCA | 1710 |
| SEQ_ID_NO_219 | ACAGAAAA-GGAGAGTGCTGG----TAGGTAACGCTGAGGCGGTGAAGAAAGAGAGGTCA | 1710 |
| SEQ_ID_NO_217 | ACAGAAAA-GGAGAGTGCTGG----TAGGTAACGCTGAGGCGGTGAAGAAAGAGAGGTCA | 1710 |
| SEQ_ID_NO_221 | ACAGAAAA-GGAGAGTGCTGG----TAGGTAACGCTGAGGCGGTGAAGAAAGAGAGGTCA | 1302 |
| SEQ_ID_NO_224 | ACAGAAAA-GGAGAGTGCTGG----TAGGTAACGCTGAGGCGGTGAAGAAAGAGAGGTCA | 1307 |
| | *** **** **********             ** ** | |
| SEQ_ID_NO_213 | GACGGACCTGGAGGTGGCTTTTTAACTGGTAAAGAGTGAGGTCTTTCATGCCCATCAATC | 1367 |
| SEQ_ID_NO_222 | NNNNNNNNNNNNNNNNNNNNNNNNNNNNNNNNNNNNNNNNNNNNNNNNNNNNNNNNNNNN | 1364 |
| SEQ_ID_NO_220 | GACGGACCTGGAGGTGGCTTTTTAACTGGTAAAGAGTGAGGTCTTTCATGCCCATCAATC | 1359 |
| SEQ_ID_NO_235 | GACGGACCTGGAGGTGGCTTTTTAACTGGTAAAGAGTGAGGTCTTTCATGCCCATCAATC | 1320 |

TABLE 27-continued

| SEQ_ID_NO_225 | GACGGACCTGGAGGTGGCTTTTTAACTGGTAAAGAGTGAGGTCTTTCATGCCCATCAATC | 1367 |
|---|---|---|
| SEQ_ID_NO_226 | GACGGACCTGGAGGTGGCTTTTTAACTGGTAAAGAGTGAGGTCTTTCATGCCCATCAATC | 1367 |
| SEQ_ID_NO_228 | GACGGACCTGGAGGTGGCTTTTTAACTGGTAAAGAGTGAGGTCTTTCATGCCCATCAATC | 1368 |
| SEQ_ID_NO_227 | GACGGACCTGGAGGTGGCTTTTTAACTGGTAAAGAGTGAGGTCTTTCATGCCCATCAATC | 1367 |
| SEQ_ID_NO_223 | GACGGACCTGGAGGTGGCTTTTTAACTGGTAAAGAGTGAGGTCTTTCATGCCCATCAATC | 1356 |
| SEQ_ID_NO_215 | GACGGACCTGGAGGTGGCTTTTTAACTGGTAAAGAGTGAGGTCTTTCATGCCCATCAATC | 1770 |
| SEQ_ID_NO_216 | GACGGACCTGGAGGTGGCTTTTTAACTGGTAAAGAGTGAGGTCTTTCATGCCCATCAATC | 1770 |
| SEQ_ID_NO_214 | GACGGACCTGGAGGTGGCTTTTTAACTGGTAAAGAGTGAGGTCTTTCATGCCCATCAATC | 1770 |
| SEQ_ID_NO_233 | GACGGACCTGGAGGTGGCTTTTTAACTGGTAAAGAGTGAGGTCTTTCATGCCCATCAATC | 1367 |
| SEQ_ID_NO_236 | GACGGACCTGGAGGTGGCTTTTTAACTGGTAAAGAGTGAGGTCTTTCATGCCCATCAATC | 1325 |
| SEQ_ID_NO_231 | GACGGACCTGGAGGTGGCTTTTTAACTGGTAAAGAGTGAGGTCTTTCATGCCCATCAATC | 1367 |
| SEQ_ID_NO_229 | GACGGACCTGGAGGTGGCTTTTTAACTGGTAAAGAGTGAGGTCTTTCATGCCCATCAATC | 1367 |
| SEQ_ID_NO_230 | GACGGACCTGGAGGTGGCTTTTTAACTGGTAAAGAGTGAGGTCTTTCATGCCCATCAATC | 1367 |
| SEQ_ID_NO_232 | GACGGACCTGGAGGTGGCTTTTTAACTGGTAAAGAGTGAGGTCTTTCATGCCCATCAATC | 1367 |
| SEQ_ID_NO_234 | GACGGACCTGGAGGTGGCTTTTTAACTGGTAAAGAGTGAGGTCTTTCATGCCCATCAATC | 1332 |
| SEQ_ID_NO_218 | GACGGACCTGGAGGTGGCTTTTTAACTGGTAAAGAGTGAGGTCTTTCATGCCCATCAATC | 1770 |
| SEQ_ID_NO_219 | GACGGACCTGGAGGTGGCTTTTTAACTGGTAAAGAGTGAGGTCTTTCATGCCCATCAATC | 1770 |
| SEQ_ID_NO_217 | GACGGACCTGGAGGTGGCTTTTTAACTGGTAAAGAGTGAGGTCTTTCATGCCCATCAATC | 1770 |
| SEQ_ID_NO_221 | GACGGACCTGGAGGTGGCTTTTTAACTGGTAAAGAGTGAGGTCTTTCATGCCCATCAATC | 1362 |
| SEQ_ID_NO_224 | GACGGACCTGGAGGTGGCTTTTTAACTGGTAAAGAGTGAGGTCTTTCATGCCCATCAATC | 1367 |
| SEQ_ID_NO_213 | TGAGCACCGACTTGGGTGTTGCTCCTGTTCGCAGGAAGCACAAGAAATGGTCAGTACTCC | 1427 |
| SEQ_ID_NO_222 | NNNNNNNNNNNNNNNNNNNNNNNNNNNNNNNNNNNNNNNNNNNNNNNNNNNNNNNNNNNN | 1424 |
| SEQ_ID_NO_220 | TGAGCACCGACTTGGGTGTTGCTCCTGTTCGCAGGAAGCACAAGAAATGGTCAGTACTCC | 1419 |
| SEQ_ID_NO_235 | TGAGCACCGACTTGGGTGTTGCTCCTGTTCGCAGGAAGCACAAGAAATGGTCAGTACTCC | 1380 |
| SEQ_ID_NO_225 | TGAGCACCGACTTGGGTGTTGCTCCTGTTCGCAGGAAGCACAAGAAATGGTCAGTACTCC | 1427 |
| SEQ_ID_NO_226 | TGAGCACCGACTTGGGTGTTGCTCCTGTTCGCAGGAAGCACAAGAAATGGTCAGTACTCC | 1427 |
| SEQ_ID_NO_228 | TGAGCACCGACTTGGGTGTTGCTCCTGTTCGCAGGAAGCACAAGAAATGGTCAGTACTCC | 1428 |
| SEQ_ID_NO_227 | TGAGCACCGACTTGGGTGTTGCTCCTGTTCGCAGGAAGCACAAGAAATGGTCAGTACTCC | 1427 |
| SEQ_ID_NO_223 | TGAGCACCGACTTGGGTGTTGCTCCTGTTCGCAGGAAGCACAAGAAATGGTCAGTACTCC | 1416 |
| SEQ_ID_NO_215 | TGAGCACCGACTTGGGTGTTGCTCCTGTTCGCAGGAAGCACAAGAAATGGTCAGTACTCC | 1830 |
| SEQ_ID_NO_216 | TGAGCACCGACTTGGGTGTTGCTCCTGTTCGCAGGAAGCACAAGAAATGGTCAGTACTCC | 1830 |
| SEQ_ID_NO_214 | TGAGCACCGACTTGGGTGTTGCTCCTGTTCGCAGGAAGCACAAGAAATGGTCAGTACTCC | 1830 |
| SEQ_ID_NO_233 | TGAGCACCGACTTGGGTGTTGCTTCTGTTCGCAGGAAGCACAAGAAATGGTCAGTACTCC | 1427 |
| SEQ_ID_NO_236 | TGAGCACCGACTTGGGTGTTGCTTCTGTTCGCAGGAAGCACAAGAAATGGTCAGTACTCC | 1385 |
| SEQ_ID_NO_231 | TGAGCACCGACTTGGGTGTTGCTCCTGTTCGCAGGAAGCACAAGAAATGGTCAGTACTCC | 1427 |
| SEQ_ID_NO_229 | TGAGCACCGACTTGGGTGTTGCTCCTGTTCGCAGGAAGCACAAGAAATGGTCAGTACTCC | 1427 |
| SEQ_ID_NO_230 | TGAGCACCGACTTGGGTGTTGCTCCTGTTCGCAGGAAGCACAAGAAATGGTCAGTACTCC | 1427 |
| SEQ_ID_NO_232 | TGAGCACCGACTTGGGTGTTGCTCCTGTTCGCAGGAAGCACAAGAAATGGTCAGTACTCC | 1427 |
| SEQ_ID_NO_234 | TGAGCACCGACTTGGGTGTTGCTCCTGTTCGCAGGAAGCACAAGAAATGGTCAGTACTCC | 1392 |
| SEQ_ID_NO_218 | TGAGCACCGACTTGGGTGTTGCTCCTGTTCGCAGGAAGCACAAGAAATGGTCAGTACTCC | 1830 |

TABLE 27-continued

| SEQ_ID_NO_219 | TGAGCACCGACTTGGGTGTTGCTCCTGTTCGCAGGAAGCACAAGAAATGGTCAGTACTCC | 1830 |
| --- | --- | --- |
| SEQ_ID_NO_217 | TGAGCACCGACTTGGGTGTTGCTCCTGTTCGCAGGAAGCACAAGAAATGGTCAGTACTCC | 1830 |
| SEQ_ID_NO_221 | TGAGCACCGACTTGGGTGTTGCTCCTGTTCGCAGGAAGCACAAGAAATGGTCAGTACTCC | 1422 |
| SEQ_ID_NO_224 | TGAGCACCGACTTGGGTGTTGCTCCTGTTCGCAGGAAGCACAAGAAATGGTCAGTACTCC | 1427 |
| SEQ_ID_NO_213 | ACACCATAAGCATGTCGGTGGTGTGTTGGANNNNNNNNNNNNNNNNNNNNNNNNNNNNNN | 1487 |
| SEQ_ID_NO_222 | NNNNNNNNNNNNNNNNNNNNNNNNNNNNNNNNNNNNNNNNNNNNNNNNNNNNNNNNNNNN | 1484 |
| SEQ_ID_NO_220 | ACAGCGTAGGCATGTCGGTGGTGTGTTGGAGGAGGCAAGATTCAGATGATTATTATATGA | 1479 |
| SEQ_ID_NO_235 | ACAGCGTAGGCATGTCGGTGGTGTGTTGGAGGAGGCAAGATTCAGATGATTATTATATGA | 1440 |
| SEQ_ID_NO_225 | ACAGCGTAGGCATGTCGGTGGTGTGTTGGAGGAGGCAAGATTCAGATGATTATTATATGA | 1487 |
| SEQ_ID_NO_226 | ACAGCGTAGGCATGTCGGTGGTGTGTTGGAGGAGGCAAGATTCAGATGATTATTATATGA | 1487 |
| SEQ_ID_NO_228 | ACAGCGTAGGCATGTCGGTGGTGTGTTGGAGGAGGCAAGATTCAGATGATTATTATATGA | 1488 |
| SEQ_ID_NO_227 | ACAGCGTAGGCATGTCGGTGGTGTGTTGGAGGAGGCAAGATTCAGATGATTATTATATGA | 1487 |
| SEQ_ID_NO_223 | ACAGCGTAGGCATGTCGGTG---TGTTCGAGGAGGCAAGATTCAGATGATTATTATATGA | 1473 |
| SEQ_ID_NO_215 | ACAGCGTAGGCATGTCGGTGGTGTGTTGGAGGAGGCAAGATTCAGATGATTATTATATGA | 1890 |
| SEQ_ID_NO_216 | ACAGCGTAGGCATGTCGGTGGTGTGTTGGAGGAGGCAAGATTCAGATGATTATTATATGA | 1890 |
| SEQ_ID_NO_214 | ACAGCGTAGGCATGTCGGTGGTGTGTTGGAGGAGGCAAGATTCAGATGATTATTATATGA | 1890 |
| SEQ_ID_NO_233 | ACAGCGTAGGCATGTCGGTG---TGTTCGAGGAGGCAAGATTCAGATGATTATTATATGA | 1484 |
| SEQ_ID_NO_236 | ACAGCGTAGGCATGTCGGTG---TGTTCGAGGAGGCAAGATTCAGATGATTATTATATGA | 1442 |
| SEQ_ID_NO_231 | ACAGCGTAGGCATGTCGGTGGTGTGTTGGAGGAGGCAAGATTCAGATGATTATTATATGA | 1487 |
| SEQ_ID_NO_229 | ACAGCGTAGGCATGTCGGTGGTGTGTTGGAGGAGGCAAGATTCAGATGATTATTATATGA | 1487 |
| SEQ_ID_NO_230 | ACAGCGTAGGCATGTCGGTGGTGTGTTGGAGGAGGCAAGATTCAGATGATTATTATATGA | 1487 |
| SEQ_ID_NO_232 | ACAGCGTAGGCATGTCGGTGGTGTGTTGGAGGAGGCAAGATTCAGATGATTATTATATGA | 1487 |
| SEQ_ID_NO_234 | ACAGCGTAGGCATGTCGGTGGTGTGTTGGAGGAGGCAAGATTCAGATGATTATTATATGA | 1452 |
| SEQ_ID_NO_218 | ACAGCGTAGGCATGTCGGTGGTGTGTTGGAGGAGGCAAGATTCAGATGATTATTATATGA | 1890 |
| SEQ_ID_NO_219 | ACAGCGTAGGCATGTCGGTGGTGTGTTGGAGGAGGCAAGATTCAGATGATTATTATATGA | 1890 |
| SEQ_ID_NO_217 | ACAGCGTAGGCATGTCGGTGGTGTGTTGGAGGAGGNNNNNNNNNNNNNNNNNNNNNNNNN | 1890 |
| SEQ_ID_NO_221 | ACAGCGTAGGCATGTCGGTGGTGTGTTGGAGGAGGCAAGATNNNNNNNNNNNNNNNNNNN | 1482 |
| SEQ_ID_NO_224 | ACAGCGTAGGCATGTCGGTGGTGTGTTGGAGGAGGCAAGATTCAGATGATTATTATATGA | 1487 |
| SEQ_ID_NO_213 | NNNNNNNNNNNNNNNNNNNNNNNNNNNNNNNNNNNNNNNNNNNNNNNNNNNNNNNNNNNN | 1547 |
| SEQ_ID_NO_222 | NNNNNNNNNNNNNNNNNNNNNNNNNNNNNNNNNNNNNNNNNNNNNNNNNNNNNNNNNNNN | 1544 |
| SEQ_ID_NO_220 | GCTCGAAAAGCTAGAGAATGGATGTTCAGACTTGAGAGCTCTGATTTGAGAGAAATTGCA | 1539 |
| SEQ_ID_NO_235 | GCTCGAAAAGCTAGAGAATGGATGTTCAGACTTGAGAGCTCTGATTTGAGAGGAATTGCA | 1500 |
| SEQ_ID_NO_225 | GCTCGAAAAGCTAGAGAATGGATGTTCAGACTTGAGAGCTCTGATTTGAGAGRAATTGCA | 1547 |
| SEQ_ID_NO_226 | GCTCGAAAAGCTAGAGAATGGATGTTCAGACTTGAGAGCTCTGATTTGAGAGRAATTGCA | 1547 |
| SEQ_ID_NO_228 | GCTCGAAAAGCTAGAGAATGGATGTTCAGACTTGAGAGCTCTGATTTGAGAGGAATTGCA | 1548 |
| SEQ_ID_NO_227 | GCTCGAAAAGCTAGAGAATGGATGTTCAGACTTGAGAGCTCTGATTTGAGAGGAATTGCA | 1547 |
| SEQ_ID_NO_223 | GCTCGAAAAGCTAGAGAATGGATGTTCAGACTTGAGAGGTCTGATTTGAGAGGAATTGCA | 1533 |
| SEQ_ID_NO_215 | GCTCGAAAAGCTAGAGAATGGATGTTCAGACTTGAGAGCTCTGATTTGAGAGGAATTGCA | 1950 |
| SEQ_ID_NO_216 | GCTCGAAAAGCTAGAGAATGGATGTTCAGACTTGAGAGCTCTGATTTGAGAGGAATTGCA | 1950 |
| SEQ_ID_NO_214 | GCTCGAAAAGCTAGAGAATGGATGTTCAGACTTGAGAGCTCTGATTTGAGAGGAATTGCA | 1950 |

TABLE 27-continued

| SEQ_ID_NO_233 | GCTCGAAAAGCTAGAGAATGGATGTTCAGACTTGAGATCTCTGATTTGAGAGGAATTGCA | 1544 |
| --- | --- | --- |
| SEQ_ID_NO_236 | GCTCGAAAAGCTAGAGAATGGATGTTCAGACTTGAGATCTCTGATTTGAGAGGAATTGCA | 1502 |
| SEQ_ID_NO_231 | GCTCGAAAAGCTAGAGAATGGATGTTCAGACTTGAGAGCTCTGATTTGAGAGGAATTGCA | 1547 |
| SEQ_ID_NO_229 | GCTCGAAAAGCTAGAGAATGGATGTTCAGACTTGAGAGCTCTGATTTGATATGAATTGCA | 1547 |
| SEQ_ID_NO_230 | GCTCGAAAAGCTAGAGAATGGATGTTCAGACTTGAGAGCTCTGATTTGAGAGGAATTGCA | 1547 |
| SEQ_ID_NO_232 | GCTCGAAAAGCTAGAGAATGGATGTTCAGACTTGAGAGCTCTGATTTGAGAGGAATTGCA | 1547 |
| SEQ_ID_NO_234 | GCTCGAAAAGCTAGAGAATGGATGTTCAGACTTGAGAGCTCTGATTTGAGAGGAATTGCA | 1512 |
| SEQ_ID_NO_218 | GCTCGAAAAGCTAGAGAATGGATGTTCAGACTTGAGAGCTCTGATTTGAGAGGAATTGCA | 1950 |
| SEQ_ID_NO_219 | GCTCGAAAAGCTAGAGAATGGATGTTCAGACTTGAGAGCTCTGATTTGAGAGGAATTGCA | 1950 |
| SEQ_ID_NO_217 | NNNNNNNNNNNNNNNNNNNNNNNNNNNNNNNNNNNNNNNNNNNNNNNNNNNNNNNNNNNN | 1950 |
| SEQ_ID_NO_221 | NNNNNNNNNNNNNNNNNNNNNNNNNNNNNNNNNNNNNNNNNNNNNNNNNNNNNNNNNNNN | 1542 |
| SEQ_ID_NO_224 | GCTCGAAAAGCTAGAGAATGGATGTTCAGACTTGAGAGCTCTGATTTGAGAGRAATTGCA | 1547 |
| SEQ_ID_NO_213 | NNNNNNNNNNNNNNNNNNNNNNNNNNNNNNNNNNNNNNNNNNN-NNNNNNNNNNNNNNNN | 1606 |
| SEQ_ID_NO_222 | NNNNNNNNNNNNNNNNNNNNNNNNNNNNNNNNNNNNNNNNNNN-NNNNNNNNNNNNNNNN | 1603 |
| SEQ_ID_NO_220 | CTTGTCGTTTTCCCAAGGCGACGCGGCCTTTT-CCAGAGGTTTTTTTTTTTTNNNNNN | 1598 |
| SEQ_ID_NO_235 | CTTGTCGTTTTCCCAAGGCGACGCGGCCTTTT-CCAGAGGTTTTTTTTTTTTNNNNNN | 1559 |
| SEQ_ID_NO_225 | CTTGTCGTTTTCCCAAGGCGACGCGGCCTTTT-CCAGAGGTTTTTTTTTTTTNNNNNN | 1606 |
| SEQ_ID_NO_226 | CTTGTCGTTTTCCCAAGGCGACGCGGCCTTTTTCCAGAGGTTTTTTTTTTTTNNNNNN | 1607 |
| SEQ_ID_NO_228 | CTTGTCGTTTTCCCAAGGCGACGCGGCCTTTT-CCAGAGGTTTTTTTTTTTTTTTNNN | 1607 |
| SEQ_ID_NO_227 | CTTGTCGTTTTCCCAAGGCGACGCGGCCTTTT-CCAGAGGTTTTTTTTTTTTNNNNNN | 1606 |
| SEQ_ID_NO_223 | CTTGTCGTTTTCCCAGGGCGACGCGGCCTTTTTCCAGAGGCTTTTTTTTNNNNNNNNNN | 1593 |
| SEQ_ID_NO_215 | CTTGTCGTTTTCCCAAGGCGACGCGGCCTTTTTCCAGAGTT-TTTTTTTTNNNNNNNNNN | 2009 |
| SEQ_ID_NO_216 | CTTGTCGTTTTCCCAAGGCGACGCGGCCTTTTTCCAGAGTT-TTTTTTTTNNNNNNNNNN | 2009 |
| SEQ_ID_NO_214 | CTTGTCGTTTTCCCAAGGCGACGCGGCCTTTTTCCAGAGTT-TTTTTTTTNNNNNNNNNN | 2009 |
| SEQ_ID_NO_233 | CTTGTCGTTTTCCCAGGGCGACGCGGCCTTTTTCCAGAGGCATTTTTTTTCAACTGCCTT | 1604 |
| SEQ_ID_NO_236 | CTTGTCGTTTTCCCARGGCGACGCGGCCTTTTTCCAGAGGCATTTTTTTTCANNNNNNNN | 1562 |
| SEQ_ID_NO_231 | CTTGTCGTTTTCCCAAGGCGACGCGGCCTTTTTCCAGAGTTTTTTTTTTNNNNNNNNNN | 1607 |
| SEQ_ID_NO_229 | CTTGTCGTTTTCCCAAGGCGACACGGCCTTTTTCCAGAGTTTTTTTTTTNNNNNNNNNN | 1607 |
| SEQ_ID_NO_230 | CTTGTCGTTTTCCCAAGGCGACGCGGCCTTTTTCCAGAGGCTTTTTTTTTNNNNNNNNNN | 1607 |
| SEQ_ID_NO_232 | CTTGTCGTTTTCCCAAGGCGACGCGGCCTTTTTCCAGAGGCTTTTTTTTTNNNNNNNNNN | 1607 |
| SEQ_ID_NO_234 | CTTGTCGTTTTCCCAAGGCGACGCGGCCTTTTTCCAGAGTT-TTTTTTTTNNNNNNNNNN | 1571 |
| SEQ_ID_NO_218 | CTTGTCGTTTTCCCAAGGCGACGCGGCCTTTTTCCAGAGTT-TTTTTTTTTNNNNNNNN | 2009 |
| SEQ_ID_NO_219 | CTTGTCGTTTTCCCAAGGCGACGCGGCCTTTTTCCAGAGTT-TTTTTTTTTNNNNNNNN | 2009 |
| SEQ_ID_NO_217 | NNNNNNNNNNNNNNNNNNNNNNNNNNNNNNNNNNNNNNNNNNN-NNNNNNNNNNNNNNNN | 2009 |
| SEQ_ID_NO_221 | NNNNNNNNNNNNNNNNNNNNNNNNNNNNNNNNNNNNNNNNNNNNNNNNNNNNNNNNNNNN | 1602 |
| SEQ_ID_NO_224 | CTTGTCGTTTTCCCAAGGCGACGCGGCCTTTTTCCAGAGGTTTTTTTTTTNNNNNNNNNN | 1607 |
| SEQ_ID_NO_213 | NNNNNNNNNNNNNNNNNNNNNNNNNNNNNNNNNNNNNNNNNNNNNNNNNNNNNNNNNNNN | 1666 |
| SEQ_ID_NO_222 | NNNNNNNNNNNNNNNNNNNNNNNNNNNNNNNNNNNNNNNNNNNNNNNNNNNNNNNNNNNN | 1663 |
| SEQ_ID_NO_220 | NNNNNNNNNNNNNNNNNNNNNNNNNNNNNNNNNNNNNNNNNNNNNNNNNNNNNNNNNNNN | 1658 |
| SEQ_ID_NO_235 | NNNNNNNNNNNNNNNNNNNNNNNNNNNNNNNNNNNNNNNNNNNNNNNNNNNNNNNNNNNN | 1619 |

TABLE 27-continued

| | | |
|---|---|---|
| SEQ_ID_NO_225 | NNNNNNNNNNNNNNNNNNNNNNNNNNNNNNNNNNNNNNNNNNNNNNNNNNNNNNNNNN | 1666 |
| SEQ_ID_NO_226 | NNNNNNNNNNNNNNNNNNNNNNNNNNNNNNNNNNNNNNNNNNNNNNNNNNNNNNNNNN | 1667 |
| SEQ_ID_NO_228 | NNNNNNNNNNNNNNNNNNNNNNNNNNNNNNNNNNNNNNNNNNNNNNNNNNNNNNNNNN | 1667 |
| SEQ_ID_NO_227 | NNNNNNNNNNNNNNNNNNNNNNNNNNNNNNNNNNNNNNNNNNNNNNNNNNNNNNNNNN | 1666 |
| SEQ_ID_NO_223 | NNNNNNNNNNNNNNNNNNNNNNNNNNNNNNNNNNNNNNNNNNNNNNNNNNNNNNNNNN | 1653 |
| SEQ_ID_NO_215 | NNNNNNNNNNNNNNNNNNNNNNNNNNNNNNNNNNNNNNNNNNNNNNNNNNNNNNNNNN | 2069 |
| SEQ_ID_NO_216 | NNNNNNNNNNNNNNNNNNNNNNNNNNNNNNNNNNNNNNNNNNNNNNNNNNNNNNNNNN | 2069 |
| SEQ_ID_NO_214 | NNNNNNNNNNNNNNNNNNNNNNNNNNNNNNNNNNNNNNNNNNNNNNNNNNNNNNNNNN | 2069 |
| SEQ_ID_NO_233 | TTGGTCATGTCAACGGAACTGCCTTTTCCTCTGACTGCATGCTATAGACTTGGCAATGGC | 1664 |
| SEQ_ID_NO_236 | NNNNNNNNNNNNNNNNNNNNNNNNNNNNNNNNNNNNNNNNNNNNNNNNNNNNNNNNNN | 1622 |
| SEQ_ID_NO_231 | NNNNNNNNNNNNNNNNNNNNNNNNNNNNNNNNNNNNNNNNNNNNNNNNNNNNNNNNNN | 1667 |
| SEQ_ID_NO_229 | NNNNNNNNNNNNNNNNNNNNNNNNNNNNNNNNNNNNNNNNNNNNNNNNNNNNNNNNNN | 1667 |
| SEQ_ID_NO_230 | NNNNNNNNNNNNNNNNNNNNNNNNNNNNNNNNNNNNNNNNNNNNNNNNNNNNNNNNNN | 1667 |
| SEQ_ID_NO_232 | NNNNNNNNNNNNNNNNNNNNNNNNNNNNNNNNNNNNNNNNNNNNNNNNNNNNNNNNNN | 1667 |
| SEQ_ID_NO_234 | NNNNNNNNNNNNNNNNNNNNNNNNNNNNNNNNNNNNNNNNNNNNNNNNNNNNNNNNNN | 1631 |
| SEQ_ID_NO_218 | NNNNNNNNNNNNNNNNNNNNNNNNNNNNNNNNNNNNNNNNNNNNNNNNNNNNNNNNNN | 2069 |
| SEQ_ID_NO_219 | NNNNNNNNNNNNNNNNNNNNNNNNNNNNNNNNNNNNNNNNNNNNNNNNNNNNNNNNNN | 2069 |
| SEQ_ID_NO_217 | NNNNNNNNNNNNNNNNNNNNNNNNNNNNNNNNNNNNNNNNNNNNNNNNNNNNNNNNNN | 2069 |
| SEQ_ID_NO_221 | NNNNNNNNNNNNNNNNNNNNNNNNNNNNNNNNNNNNNNNNNNNNNNNNNNNNNNNNNN | 1662 |
| SEQ_ID_NO_224 | NNNNNNNNNNNNNNNNNNNNNNNNNNNNNNNNNNNNNNNNNNNNNNNNNNNNNNNNNN | 1667 |
| SEQ_ID_NO_213 | NNNNNNNNNNNNNNNNNNNNNNNNNNNNNNNNNNNNNNNNNNNNNNNNNNNNNNNNNN | 1726 |
| SEQ_ID_NO_222 | NNNNNNNNNNNNNNNNNNNNNNNNNNNNNNNNNNNNNNNNNNNNNNNNNNNNNNNNNN | 1723 |
| SEQ_ID_NO_220 | NNNNNNNNNNNNNNNNNNNNNNNNNNNNNNNNNNNNNNNNNNNNNNNNNNNNNNNNNN | 1718 |
| SEQ_ID_NO_235 | NNNNNNNNNNNNNNNNNNNNNNNNNNNNNNNNNNNNNNNNNNNNNNNNNNNNNNNNNN | 1679 |
| SEQ_ID_NO_225 | NNNNNNNNNNNNNNNNNNNNNNNNNNNNNNNNNNNNNNNNNNNNNNNNNNNNNNNNNN | 1726 |
| SEQ_ID_NO_226 | NNNNNNNNNNNNNNNNNNNNNNNNNNNNNNNNNNNNNNNNNNNNNNNNNNNNNNNNNN | 1727 |
| SEQ_ID_NO_228 | NNNNNNNNNNNNNNNNNNNNNNNNNNNNNNNNNNNNNNNNNNNNNNNNNNNNNNNNNN | 1727 |
| SEQ_ID_NO_227 | NNNNNNNNNNNNNNNNNNNNNNNNNNNNNNNNNNNNNNNNNNNNNNNNNNNNNNNNNN | 1726 |
| SEQ_ID_NO_223 | NNNNNNNNNNNNNNNNNNNNNNNNNNNNNNNNNNNNNNNNNNNNNNNNNNNNNNNNNN | 1713 |
| SEQ_ID_NO_215 | NNNNNNNNNNNNNNNNNNNNNNNNNNNNNNNNNNNNNNNNNNNNNNNNNNNNNNNNNN | 2129 |
| SEQ_ID_NO_216 | NNNNNNNNNNNNNNNNNNNNNNNNNNNNNNNNNNNNNNNNNNNNNNNNNNNNNNNNNN | 2129 |
| SEQ_ID_NO_214 | NNNNNNNNNNNNNNNNNNNNNNNNNNNNNNNNNNNNNNNNNNNNNNNNNNNNNNNNNN | 2129 |
| SEQ_ID_NO_233 | AGAAGCGCAAAGCCAGGCAGCGAAGGATTCGGACTGCAACTGGCCGTCGTTTTACAANNN | 1724 |
| SEQ_ID_NO_236 | NNNNNNNNNNNNNNNNNNNNNNNNNNNNNNNNNNNNNNNNNNNNNNNNNNNNNNNNNN | 1682 |
| SEQ_ID_NO_231 | NNNNNNNNNNNNNNNNNNNNNNNNNNNNNNNNNNNNNNNNNNNNNNNNNNNNNNNNNN | 1727 |
| SEQ_ID_NO_229 | NNNNNNNNNNNNNNNNNNNNNNNNNNNNNNNNNNNNNNNNNNNNNNNNNNNNNNNNNN | 1727 |
| SEQ_ID_NO_230 | NNNNNNNNNNNNNNNNNNNNNNNNNNNNNNNNNNNNNNNNNNNNNNNNNNNNNNNNNN | 1727 |
| SEQ_ID_NO_232 | NNNNNNNNNNNNNNNNNNNNNNNNNNNNNNNNNNNNNNNNNNNNNNNNNNNNNNNNNN | 1727 |
| SEQ_ID_NO_234 | NNNNNNNNNNNNNNNNNNNNNNNNNNNNNNNNNNNNNNNNNNNNNNNNNNNNNNNNNN | 1691 |
| SEQ_ID_NO_218 | NNNNNNNNNNNNNNNNNNNNNNNNNNNNNNNNNNNNNNNNNNNNNNNNNNNNNNNNNN | 2129 |

TABLE 27-continued

| | | |
|---|---|---|
| SEQ_ID_NO_219 | NNNNNNNNNNNNNNNNNNNNNNNNNNNNNNNNNNNNNNNNNNNNNNNNNNNN | 2129 |
| SEQ_ID_NO_217 | NNNNNNNNNNNNNNNNNNNNNNNNNNNNNNNNNNNNNNNNNNNNNNNNNNNN | 2129 |
| SEQ_ID_NO_221 | NNNNNNNNNNNNNNNNNNNNNNNNNNNNNNNNNNNNNNNNNNNNNNNNNNNN | 1722 |
| SEQ_ID_NO_224 | NNNNNNNNNNNNNNNNNNNNNNNNNNNNNNNNNNNNNNNNNNNNNNNNNNNN | 1727 |
| | *** | |
| SEQ_ID_NO_213 | NNNNNNNNNNNAAAAAAAAAAAAAAAAAAGAATGCACACCGACATGCTCTGTAGCACAA | 1786 |
| SEQ_ID_NO_222 | NNNNNNNNNNNAAAAAAAAAAAAAAAAAAGAATGCAGACCGACATGCTCTGTAGCACAA | 1783 |
| SEQ_ID_NO_220 | NNNNNNNNNNNNNNNNNNNNNCTGAAAAAAAAATGCACACCGACATGCTCTGTAGCACAA | 1778 |
| SEQ_ID_NO_235 | NNNNNNNNNNNNNNNNNNNNNNNTGAAAAAAAAATGCACACCGACATGCTCTGTAGCACAA | 1739 |
| SEQ_ID_NO_225 | NNNNNNNNNNNNNNNNNNNNNNNTGAAAAAAAAATGCACACCGACATGCTCTGTAGCACAA | 1786 |
| SEQ_ID_NO_226 | NNNNNNNNNNNNNNNNNNNNNNNNNNNNNNNNNNNNNNNNNNNNNNNNNNNN | 1787 |
| SEQ_ID_NO_228 | NNNNNNNNNNNNNNNNNNNNNNNNAAAAAAAAATGCACACCGACATGCTCTGTAGCACAA | 1787 |
| SEQ_ID_NO_227 | NNNNNNNNNNNNNNNNNNNNNNNTGAAAAAAAAATGCACACCGACATGCTCTGTAGCACAA | 1786 |
| SEQ_ID_NO_223 | NNNNNNNNNNNNNNNAAAAAAA-AAAAAAAGAATGCAGACCGACATGCTCTGTAGCACAA | 1772 |
| SEQ_ID_NO_215 | NNNNNNNNNNNAAAAAAAAAAAAAAAAAAGAATGCACACCGACATGCTCTGTAGCACAA | 2189 |
| SEQ_ID_NO_216 | NNNNNNNNNNNNNAAAAAAAAAAAAAAAAAAGAATGCACACCGACATGCTCTGTAGCACAA | 2189 |
| SEQ_ID_NO_214 | NNNNNNNNNNNNAAAAAAAAAAAAAAAAAAGAATGCACACCGACATGCTCTGTAGCACAA | 2189 |
| SEQ_ID_NO_233 | NNNNNNNNNNNNNNNNNNNAAAAAAAAAAGAATGCAGACCGACATGCTCTGTAGCACAA | 1784 |
| SEQ_ID_NO_236 | NNNNNNNNNNNNNNNNNNNNGAAAAAAAAAGAATGCAGACCGACATGCTCTGTAGCACAA | 1742 |
| SEQ_ID_NO_231 | NNNNNNNNNNNNNAAAAAAAAAAAAAAAGAATGCACACCGACATGCTCTGTAGCACAA | 1787 |
| SEQ_ID_NO_229 | NNNNNNNNNNNNNNAAAAAAAAAAAAAAGAATGCACACCGACATGCTCTGTAGCACAA | 1787 |
| SEQ_ID_NO_230 | NNNNNNNNNNNNNAAAAAAAAAAAAAAAGAATGCAGACCGACATGCTCTGTAGCACAA | 1787 |
| SEQ_ID_NO_232 | NNNNNNNNNNNNNAAAAAAAAAAAAAAAGAATGCAGACCGACATGCTCTGTAGCACAA | 1787 |
| SEQ_ID_NO_234 | NNNNNNNNNNNNNNAAAAAAAAAAAAAAGAATGCAGACCGACATGCTCTGTAGCACAA | 1751 |
| SEQ_ID_NO_218 | NNNNNNNNNNNNNAAAAAAAAAAAAAAAGAATGCAGACCGACATGCTCTGTAGCACAA | 2189 |
| SEQ_ID_NO_219 | NNNNNNNNNNNNNAAAAAAAAAAAAAAAGAATGCAGACCGACATGCTCTGTAGCACAA | 2189 |
| SEQ_ID_NO_217 | NNNNNNNNNNNNNAAAAAAAAAAAAAAAGAATGCAGACCGACATGCTCTGTAGCACAA | 2189 |
| SEQ_ID_NO_221 | NNNNNNNNNNNNNNNNNNNNNNNNNNNNNNNNNNNNNNNNNNNNNNNNNNNN | 1782 |
| SEQ_ID_NO_224 | NNNNNNNNNNNNNNNNNNNNNNNNNNNNNNNNNNNNNNNNNNNNNNNNNNNN | 1787 |
| | ********** | |
| SEQ_ID_NO_213 | GCACCATACTGGCGAACTGGAGAGGTCTCGGCTCATCAAGCAATCGCC-TTGGTGTCGGA | 1845 |
| SEQ_ID_NO_222 | GCACCATACTGGCGAACTGGAGAGGTCTCGGCTCATCAAGCAATCGCC-TTGGTGTCGGA | 1842 |
| SEQ_ID_NO_220 | GCACCATACCGGCGAACTGGAGAGGTCTCGGCTCATCAAGCAATCGCC-TTGGTGTCGGA | 1837 |
| SEQ_ID_NO_235 | GCACCATACCGGCGAACTGGAGAGGTCTCGGCTCATCAAGCAATCGCCCTTGGTGTCGGA | 1799 |
| SEQ_ID_NO_225 | GCACCATACCGGCGAACTGGAGAGGTCTCGGCTCATCAAGCAATCGCC-TTGGTGTCGGA | 1845 |
| SEQ_ID_NO_226 | NNNNNNNNNNNNNNNNNNNGGAGAGGTCTCGGCTCATCAAGCAATCGCC-TTGGTGTCGGA | 1846 |
| SEQ_ID_NO_228 | GCACCATACCGGCGAACTGGAGAGGTCTCGGCTCATCAAGCAATCGCC-TTGGTGTCGGA | 1846 |
| SEQ_ID_NO_227 | GCACCATACCGGCGAACTGGAGAGGTCTCGGCTCATCAAGCAATCGCC-TTGGTGTCGGA | 1845 |
| SEQ_ID_NO_223 | GCACCATACTGGCGAACTGGAGAGGTCTCGGCTCATCAAGCAATCGCC-TTGGTGTCGGA | 1831 |
| SEQ_ID_NO_215 | GCACCATACTGGCGAACTGGAGAGGTCTCGGCTCATCAAGCAATCGCC-TTGGTGTCGGA | 2248 |
| SEQ_ID_NO_216 | GCACCATACTGGCGAACTGGAGAGGTCTCGGCTCATCAAGCAATCGCC-TTGGTGTCGGA | 2248 |

TABLE 27-continued

| SEQ_ID_NO_214 | GCACCATACTGGCGAACTGGAGAGGTCTCGGCTCATCAAGCAATCGCC-TTGGTGTCGGA | 2248 |
|---|---|---|
| SEQ_ID_NO_233 | GCACCATACTTGCGAACTGCAGAGGTGTCGGGTCATCAAGCAATCGCC-TTGGTGTCGGA | 1843 |
| SEQ_ID_NO_236 | GCACCATACTTGCGAACTGCAGAGGTGTCGGGTCATCAAGCAATCGCC-TTGGTGTCGGA | 1801 |
| SEQ_ID_NO_231 | GCACCATACTGGCGAACTGGAGAGGTCTCGGCTCATCAAGCAATCGCC-TTGGTGTCGGA | 1846 |
| SEQ_ID_NO_229 | GCACCATACTGGCGAACTGGAGAGGTCTCGGCTCATCAAGCAATCGCC-TTGGTGTCGGA | 1846 |
| SEQ_ID_NO_230 | GCACCATACTGGCGAACTGGAGAGGTCTCGGCTCATCAAGCAATCGCC-TTGGTGTCGGA | 1846 |
| SEQ_ID_NO_232 | GCACCATACTGGCGAACTGGAGAGGTCTCGGCTCATCAAGCAATCGCC-TTGGTGTCGGA | 1846 |
| SEQ_ID_NO_234 | GCACCATACTGGCGAACTGGAGAGGTCTCGGCTCATCAAGCAATCGCC-TTGGTGTCGGA | 1810 |
| SEQ_ID_NO_218 | GCACCATACTGGCGAACTGGAGAGGTCTCGGCTCATCAAGCAATCGCC-TTGGTGTCGGA | 2248 |
| SEQ_ID_NO_219 | GCACCATACTGGCGAACTGGAGAGGTCTCGGCTCATCAAGCAATCGCC-TTGGTGTCGGA | 2248 |
| SEQ_ID_NO_217 | GCACCATACTGGCGAACTGGAGAGGTCTCGGCTCATCAAGCAATCGCC-TTGGTGTCGGA | 2248 |
| SEQ_ID_NO_221 | NNNNNNNNNNNNNNNNNNNNNNNNNNNNNNNNNNNNNNNNNNNNNNNNNNNNNNNNNNNN | 1842 |
| SEQ_ID_NO_224 | NNNNNNNNNNNNNNNNNNNNNNNNNNNNNNNNNNNNNNNNNNNNNNNNNNNNNNNNNNNN | 1847 |
| SEQ_ID_NO_213 | CGGGGT-----CATCAAGACAAGACGACTAGACGAGCACTACATATAGACGGG------- | 1893 |
| SEQ_ID_NO_222 | CGGGGT-----CATCAAGACAAGACGACTAGACGAGCACTACATATAGACGGG------- | 1890 |
| SEQ_ID_NO_220 | CGGGGT-----CATCAAGACAAGGCGACTAGAGGAGCACTACATCTACACGGGGTGAACG | 1892 |
| SEQ_ID_NO_235 | CGGGGT-----CATCAAGACAAGGCGACTAGAGGAGCACTACATCTACACGGGGTGAACG | 1854 |
| SEQ_ID_NO_225 | CGGGGT-----CATCAAGACAAGGCGACTAGAGGAGCACTACATCTACACGGGGTGAACG | 1900 |
| SEQ_ID_NO_226 | CGGGGT-----CATCAAGACAAGRCGACTAGAGGAGCACTACATCTACACGGGGTGAACG | 1901 |
| SEQ_ID_NO_228 | CGGGGT-----CATCAAGACAAGGCGACTAGAGGAGCACTACATCTACACGGGGTGAACG | 1901 |
| SEQ_ID_NO_227 | CGGGGT-----CATCAAGACAAGGCGACTAGAGGAGCACTACATCTACACGGGGTGAACG | 1900 |
| SEQ_ID_NO_223 | CGGGGT-----CATCAAGACAAGACGACTAGACGAGCACTACATATAGACGGGA------ | 1880 |
| SEQ_ID_NO_215 | CGGGGT-----CATCAAGACAAGACGACTAGACGAGCACTACATATAGACGGG------- | 2296 |
| SEQ_ID_NO_216 | CGGGGT-----CATCAAGACAAGACGACTAGACGAGCACTACATATAGACGGG------- | 2296 |
| SEQ_ID_NO_214 | CGGGGT-----CATCAAGACAAGACGACTAGACGAGCACTACATATAGACGGG------- | 2296 |
| SEQ_ID_NO_233 | CGGGGTGGGGTCATCAAGACAAGACGACTAGAGGAGCACTACATCTACACGGGG------ | 1897 |
| SEQ_ID_NO_236 | CGGGGTGGGGTCATCAAGACAAGACGACTAGAGGAGCACTACATCTACACGGGG------ | 1855 |
| SEQ_ID_NO_231 | CGGGGT-----CATCAAGACAAGACGACTAGACGAGCACTACATATAGACGGG------- | 1894 |
| SEQ_ID_NO_229 | CGGGGT-----CATCAAGACAAGACGACTAGACGAGCACTACATATAGACGGG------- | 1894 |
| SEQ_ID_NO_230 | CGGGGT-----CATCAAGACAAGACGACTAGACGAGCACTACATATAGACGGG------- | 1894 |
| SEQ_ID_NO_232 | CGGGGT-----CATCAAGACAAGACGACTAGACGAGCACTACATATAGACGGG------- | 1894 |
| SEQ_ID_NO_234 | CGGGGT-----CATCAAGACAAGACGACTAGACGAGCACTACATATAGACGGG------- | 1858 |
| SEQ_ID_NO_218 | CGGGGT-----CATCAAGACAAGACGACTAGACGAGCACTACATATAGACGGG------- | 2296 |
| SEQ_ID_NO_219 | CGGGGT-----CATCAAGACAAGACGACTAGACGAGCACTACATATAGACGGG------- | 2296 |
| SEQ_ID_NO_217 | CGGGGT-----CATCAAGACAAGACGACTAGACGAGCACTACATATAGACGGG------- | 2296 |
| SEQ_ID_NO_221 | NNNNNN-----NNNNNNNNNNNNNNNNNNNNNNNNNNNNNNNNNNNNNNNNNNN------ | 1891 |
| SEQ_ID_NO_224 | NNNNNN-----NNNNNNNNNNNNNNNNNNNNNNNNNNNNNNNNNNNNNNNNNNN------ | 1896 |
| SEQ_ID_NO_213 | -----------------------AAC---------------------------------- | 1896 |
| SEQ_ID_NO_222 | -----------------------AAC---------------------------------- | 1893 |
| SEQ_ID_NO_220 | GACGGGAGCAGTGGCGGACCCAGGAACTGATGACAGCCTTGGCGAGAATACGGTGTGATC | 1952 |

TABLE 27-continued

| | | |
|---|---|---|
| SEQ_ID_NO_235 | GACGGGAGCAGTGGCGGACCCAGGAACTGATGACAGCCTTGGCGAGAATACGGTGTGATC | 1914 |
| SEQ_ID_NO_225 | GACGGGAGCAGTGGCGGACCCAGGAACTGATGACAGCCTTGGCGAGAATACGGTGTGATC | 1960 |
| SEQ_ID_NO_226 | GACGGGAGCAGTGGCGGACCCAGGAACTGATGACAGCCTTGGCGAGAATACGGTGTGATC | 1961 |
| SEQ_ID_NO_228 | GACGGGAGCAGTGGCGGACCCAGGAACTGATGACAGCCTTGGCGAGAATACGGTGTGATC | 1961 |
| SEQ_ID_NO_227 | GACGGGAGCAGTGGCGGACCCAGGAACTGATGACAGCCTTGGCGAGAATACGGTGTGATC | 1960 |
| SEQ_ID_NO_223 | ------------------------------------------------------------ | |
| SEQ_ID_NO_215 | ----------------------AAC----------------------------------- | 2299 |
| SEQ_ID_NO_216 | ----------------------AAC----------------------------------- | 2299 |
| SEQ_ID_NO_214 | ----------------------AAC----------------------------------- | 2299 |
| SEQ_ID_NO_233 | --------------------GGGAAC---------------------------------- | 1903 |
| SEQ_ID_NO_236 | --------------------GGGAAC---------------------------------- | 1861 |
| SEQ_ID_NO_231 | ----------------------AAC----------------------------------- | 1897 |
| SEQ_ID_NO_229 | ----------------------AAC----------------------------------- | 1897 |
| SEQ_ID_NO_230 | ----------------------AAC----------------------------------- | 1897 |
| SEQ_ID_NO_232 | ----------------------AAC----------------------------------- | 1897 |
| SEQ_ID_NO_234 | ----------------------AAC----------------------------------- | 1861 |
| SEQ_ID_NO_218 | ----------------------AAC----------------------------------- | 2299 |
| SEQ_ID_NO_219 | ----------------------AAC----------------------------------- | 2299 |
| SEQ_ID_NO_217 | ----------------------AAC----------------------------------- | 2299 |
| SEQ_ID_NO_221 | ---------------------GGAC----------------------------------- | 1895 |
| SEQ_ID_NO_224 | --------------------- NNNN---------------------------------- | 1900 |
| SEQ_ID_NO_213 | ------------------------------------------------------------ | |
| SEQ_ID_NO_222 | ------------------------------------------------------------ | |
| SEQ_ID_NO_220 | CCCACGCCTGTGCTCGTGCCACGTGCTGCTTGCTTCCGTGCACTGTGCTCGCGCCTTGCC | 2012 |
| SEQ_ID_NO_235 | CCCACGCCTGTGCTCGTGCCACGTGCTGCTTGCTTCCGTGCACTGTGCTCGCGCCTTGCC | 1974 |
| SEQ_ID_NO_225 | CCCACGCCTGTGCTCGTGCCACGTGCTGCTTGCTTCCGTGCACTGTGCTCGTGCCTTGCC | 2020 |
| SEQ_ID_NO_226 | CCCACGCCTGTGCTCGTGCCACGTGCTGCTTGCTTCCGTGCACTGTGCTCGTGCCTTGCC | 2021 |
| SEQ_ID_NO_228 | CCCACGCCTGTGCTCGTGCCACGTGCTGCTTGCTTCCGTGCACTGTGCTCGCGCCTTGCC | 2021 |
| SEQ_ID_NO_227 | CCCACGCCTGTGCTCGTGCCACGTGCTGCTTGCTTCCGTGCACTGTGCTCGCGCCTTGCC | 2020 |
| SEQ_ID_NO_223 | --------------------ACGT------------------------------------ | 1884 |
| SEQ_ID_NO_215 | ------------------------------------------------------------ | |
| SEQ_ID_NO_216 | ------------------------------------------------------------ | |
| SEQ_ID_NO_214 | ------------------------------------------------------------ | |
| SEQ_ID_NO_233 | ------------------------------------------------------------ | |
| SEQ_ID_NO_236 | ------------------------------------------------------------ | |
| SEQ_ID_NO_231 | ------------------------------------------------------------ | |
| SEQ_ID_NO_229 | ------------------------------------------------------------ | |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |

TABLE 27-continued

| | | |
|---|---|---|
| SEQ_ID_NO_218 | ------------------------------------------------------------ | |
| SEQ_ID_NO_219 | ------------------------------------------------------------ | |
| SEQ_ID_NO_217 | ------------------------------------------------------------ | |
| SEQ_ID_NO_221 | ------------------------------------------------------------ | |
| SEQ_ID_NO_224 | ------------------------------------------------------------ | |
| SEQ_ID_NO_213 | -----------------------------------------------------------G | 1897 |
| SEQ_ID_NO_222 | -----------------------------------------------------------G | 1894 |
| SEQ_ID_NO_220 | CATTGCAGCCGGCGAGCCAGCTCAGGCCACCGCCTGCGGTGCCTGGTGAGTCCGCCCCTG | 2072 |
| SEQ_ID_NO_235 | CATTGCAGCCGGCGAGCCAGCTCAGGCCACCGCCTGCGGTGCCTGGTGAGTCCGCCCCTG | 2034 |
| SEQ_ID_NO_225 | CATTGCAGCCGGCGAGCCAGCTCAGGCCACCGCCTGCGGTGCCTGGTGAGTCCGCCCCTG | 2080 |
| SEQ_ID_NO_226 | CATTGCAGCCGGCGAGCCAGCTCAGGCCACCGCCTGCGGTGCCTGGTGAGTCCGCCCCTG | 2081 |
| SEQ_ID_NO_228 | CATTGCAGCCGGCGAGCCAGCTCAGGCCACCGCCTGCGGTGCCTGGTGAGTCCGCCCCTG | 2081 |
| SEQ_ID_NO_227 | CATTGCAGCCGGCGAGCCAGCTCAGGCCACCGCCTGCGGTGCCTGGTGAGTCCGCCCCTG | 2080 |
| SEQ_ID_NO_223 | -------------------------------------------------------- | |
| SEQ_ID_NO_215 | -----------------------------------------------------------G | 2300 |
| SEQ_ID_NO_216 | -----------------------------------------------------------G | 2300 |
| SEQ_ID_NO_214 | -----------------------------------------------------------G | 2300 |
| SEQ_ID_NO_233 | -----------------------------------------------------------G | 1904 |
| SEQ_ID_NO_236 | -----------------------------------------------------------G | 1862 |
| SEQ_ID_NO_231 | -----------------------------------------------------------G | 1898 |
| SEQ_ID_NO_229 | -----------------------------------------------------------G | 1898 |
| SEQ_ID_NO_230 | -----------------------------------------------------------G | 1898 |
| SEQ_ID_NO_232 | -----------------------------------------------------------G | 1898 |
| SEQ_ID_NO_234 | -----------------------------------------------------------G | 1862 |
| SEQ_ID_NO_218 | -----------------------------------------------------------G | 2300 |
| SEQ_ID_NO_219 | -----------------------------------------------------------G | 2300 |
| SEQ_ID_NO_217 | -----------------------------------------------------------G | 2300 |
| SEQ_ID_NO_221 | -----------------------------------------------------------G | 1896 |
| SEQ_ID_NO_224 | -----------------------------------------------------------N | 1901 |
| SEQ_ID_NO_213 | TACGGGAGGAAGGAAGGAAAACGAGAGCGAGGACTCACTGTCCGGTCCGCCCAGCTTGGT | 1957 |
| SEQ_ID_NO_222 | TACGGGAGGAAGGAAGGAAAACGAGAGCGAGGACTCACTGTCCGGTCCGCCCAGCTTGGT | 1954 |
| SEQ_ID_NO_220 | GACGGGAGGAAGGAAGGAAAACGAGAGCGAGGACTCACTGTCCGGTCCGCCCAGCTTGGT | 2132 |
| SEQ_ID_NO_235 | GACGGGAGGAAGGAAGGAAAACGAGAGCGAGGACTCACTGTCCGGTCCGCCCAGCTTGGT | 2094 |
| SEQ_ID_NO_225 | GACGGGAGGAAGGAAGGAAAACGAGAGCGAGGACTCACTGTCCGGTCCGCCCAGCTTGGT | 2140 |
| SEQ_ID_NO_226 | GACGGGAGGAAGGAAGGAAAACGAGAGCGAGGACTCACTGTCCGGTCCGCCCAGCTTGGT | 2141 |
| SEQ_ID_NO_228 | GACGGGAGGAAGGAAGGAAAACGAGAGCGAGGACTCACTGTCCGGTCCGCCCAGCTTGGT | 2141 |
| SEQ_ID_NO_227 | GACGGGAGGAAGGAAGGAAAACGAGAGCGAGGACTCACTGTCCGGTCCGCCCAGCTTGGT | 2140 |
| SEQ_ID_NO_223 | -ACGGGAGGAAGGAAGGAAAACGAGAGCGAGGACTCACTGTCCGGTCCGCCCAGCTTGGT | 1943 |
| SEQ_ID_NO_215 | TACGGGAGGAAGGAAGGAAAACGAGAGCGAGGACTCACTGTCCGGTCCGCCCAGCTTGGT | 2360 |
| SEQ_ID_NO_216 | TACGGGAGGAAGGAAGGAAAACGAGAGCGAGGACTCACTGTCCGGTCCGCCCAGCTTGGT | 2360 |

TABLE 27-continued

| SEQ_ID_NO_214 | TACGGGAGGAAGGAAGGAAAACGAGAGCGAGGACTCACTGTCCGGTCCGCCCAGCTTGGT | 2360 |
| SEQ_ID_NO_233 | GACGGGAGGAAGGAAGGAAAACGAGAGCGAGGACTCACTGTCCGGTCCGCCCAGCTTGGT | 1964 |
| SEQ_ID_NO_236 | GACGGGAGGAAGGAAGGAAAACGAGAGCGAGGACTCACTGTCCGGTCCGCCCAGCTTGGT | 1922 |
| SEQ_ID_NO_231 | TACGGGAGGAAGGAAGGAAAACGAGAGCGAGGACTCACTGTCCGGTCCGCCCAGCTTGGT | 1958 |
| SEQ_ID_NO_229 | TACGGGAGGAAGGAAGGAAAACGAGAGCGAGGACTCACTGTCCGGTCCGCCCAGCTTGGT | 1958 |
| SEQ_ID_NO_230 | TACGGGAGGAAGGAAGGAAAACGAGAGCGAGGACTCACTGTCCGGTCCGCCCAGCTTGGT | 1958 |
| SEQ_ID_NO_232 | TACGGGAGGAAGGAAGGAAAACGAGAGCGAGGACTCACTGTCCGGTCCGCCCAGCTTGGT | 1958 |
| SEQ_ID_NO_234 | TACGGGAGGAAGGAAGGAAAACGAGAGCGAGGACTCACTGTCCGGTCCGCCCAGCTTGGT | 1922 |
| SEQ_ID_NO_218 | TACGGGAGGAAGGAAGGAAAACGAGAGCGAGGACTCACTGTCCGGTCCGCCCAGCTTGGT | 2360 |
| SEQ_ID_NO_219 | TACGGGAGGAAGGAAGGAAAACGAGAGCGAGGACTCACTGTCCGGTCCGCCCAGCTTGGT | 2360 |
| SEQ_ID_NO_217 | TACGGGAGGAAGGAAGGAAAACGAGAGCGAGGACTCACTGTCCGGTCCGCCCAGCTTGGT | 2360 |
| SEQ_ID_NO_221 | G----GAGGAAGGAAGGAAAACGAGAGCGAGGACTCACTGTCCGGTCCGCCCAGCTTGGT | 1952 |
| SEQ_ID_NO_224 | NACGGGAGGAAGGAAGGAAAACGAGAGCGAGGACTCACTGTCCGGTCCGCCCAGCTTGGT | 1961 |
|  | ************************************************************ |  |
| SEQ_ID_NO_213 | GACGGCGTCGACGAAGCGCTGGTGGAGGTCCGGCGTCCAGCGCAGCCGCGGCTTGGGGTC | 2017 |
| SEQ_ID_NO_222 | GACGGCGTCGACGAAGCGCTGGTGGAGGTCCGGCGTCCAGCGCAGCCGCGGCTTGGGGTC | 2014 |
| SEQ_ID_NO_220 | GACGGCGTCGACGAAGCGCTGGTGGAGGTCCGGCGTCCAGCGCAGCCGCGGCTTGGGGTC | 2192 |
| SEQ_ID_NO_235 | GACGGCGTCGACGAAGCGCTGGTGGAGGTCCGGCGTCCAGCGCAGCCGCGGCTTGGGGTC | 2154 |
| SEQ_ID_NO_225 | GACGGCGTCGACGAAGCGCTGGTGGAGGTCCGGCGTCCAGCGCAGCCGCGGCTTGGGGTC | 2200 |
| SEQ_ID_NO_226 | GACGGCGTCGACGAAGCGCTGGTGGAGGTCCGGCGTCCAGCGCAGCCGCGGCTTGGGGTC | 2201 |
| SEQ_ID_NO_228 | GACGGCGTCGACGAAGCGCTGGTGGAGGTCCGGCGTCCAGCGCAGCCGCGGCTTGGGGTC | 2201 |
| SEQ_ID_NO_227 | GACGGCGTCGACGAAGCGCTGGTGGAGGTCCGGCGTCCAGCGCAGCCGCGGCTTGGGGTC | 2200 |
| SEQ_ID_NO_223 | GACGGCGTCGACGAAGCGCTGGTGGAGGTCCGGCGTCCAGCGCAGCCGCGGCTTGGGGTC | 2003 |
| SEQ_ID_NO_215 | GACGGCGTCGACGAAGCGCTGGTGGAGGTCCGGCGTCCAGCGCAGCCGCGGCTTGGGGTC | 2420 |
| SEQ_ID_NO_216 | GACGGCGTCGACGAAGCGCTGGTGGAGGTCCGGCGTCCAGCGCAGCCGCGGCTTGGGGTC | 2420 |
| SEQ_ID_NO_214 | GACGGCGTCGACGAAGCGCTGGTGGAGGTCCGGCGTCCAGCGCAGCCGCGGCTTGGGGTC | 2420 |
| SEQ_ID_NO_233 | GACGGCGTCGACGAAGCGCTGGTGGAGGACCGGCGTCCAGCGCAGCCGCGGCTTGGGGTC | 2024 |
| SEQ_ID_NO_236 | GACGGCGTCGACGAAGCGCTGGTGGAGGACCGGCGTCCAGCGCAGCCGCGGCTTGGGGTC | 1982 |
| SEQ_ID_NO_231 | GACGGCGTCGACGAAGCGCTGGTGGAGGTCCGGCGTCCAGCGCAGCCGCGGCTTGGGGTC | 2018 |
| SEQ_ID_NO_229 | GACGGCGTCGACGAAGCGCTGGTGGAGGTCCGGCGTCCAGCGCAGCCGCGGCTTGGGGTC | 2018 |
| SEQ_ID_NO_230 | GACGGCGTCGACGAAGCGCTGGTGGAGGTCCGGCGTCCAGCGCAGCCGCGGCTTGGGGTC | 2018 |
| SEQ_ID_NO_232 | GACGGCGTCGACGAAGCGCTGGTGGAGGTCCGGCGTCCAGCGCAGCCGCGGCTTGGGGTC | 2018 |
| SEQ_ID_NO_234 | GACGGCGTCGACGAAGCGCTGGTGGAGGTCCGGCGTCCAGCGCAGCCGCGGCTTGGGGTC | 1982 |
| SEQ_ID_NO_218 | GACGGCGTCGACGAAGCGCTGGTGGAGGTCCGGCGTCCAGCGCAGCCGCGGCTTGGGGTC | 2420 |
| SEQ_ID_NO_219 | GACGGCGTCGACGAAGCGCTGGTGGAGGTCCGGCGTCCAGCGCAGCCGCGGCTTGGGGTC | 2420 |
| SEQ_ID_NO_217 | GACGGCGTCGACGAAGCGCTGGTGGAGGTCCGGCGTCCAGCGCAGCCGCGGCTTGGGGTC | 2420 |
| SEQ_ID_NO_221 | GACGGCGTCGACGAAGCGCTGGTGGAGGTCCGGCGTCCAGCGCAGCCGCGGCTTGGGGTC | 2012 |
| SEQ_ID_NO_224 | GACGGCGTCGACGAAGCGCTGGTGGAGGTCCGGCGTCCAGCGCAGCCGCGGCTTGGGGTC | 2021 |
|  | ****************************** ***************************** |  |
| SEQ_ID_NO_213 | CCGTGACGCCGCCC--CGTCGTAGCCGTAGCTCCCCTGCATCGTCGTTCCTTCCTGGCGA | 2075 |
| SEQ_ID_NO_222 | CCGTGACGCCGCCC--CGTCGTAGCCGTAGCTCCCCTGCATCGCCGTTCCTTCCTGGCGA | 2072 |

TABLE 27-continued

| | | |
|---|---|---|
| SEQ_ID_NO_220 | CCGTGACGCCGCCC--CGTCGTAGCCGTAGCTCCCCTGCATCGCCGTTCCTTCCTGGCGA | 2250 |
| SEQ_ID_NO_235 | CCGTGACGCCGCCC--CGTCGTAGCCGTAGCTCCCCTGCATCGCCGTTCCTTCCTGGCGA | 2212 |
| SEQ_ID_NO_225 | CCGTGACGCCGCCC--CGTCGTAGCCGTAGCTCCCCTGCATCGCCGTTCCTTCCTGGCGA | 2258 |
| SEQ_ID_NO_226 | CCGTGACGCCGCCC--CGTCGTAGCCGTAGCTCCCCTGCATCGCCGTTCCTTCCTGGCGA | 2259 |
| SEQ_ID_NO_228 | CCGTGACGCCGCCC--CGTCGTAGCCGTAGCTCCCCTGCATCGCCGTTCCTTCCTGGCGA | 2259 |
| SEQ_ID_NO_227 | CCGTGACGCCGCCC--CGTCGTAGCCGTAGCTCCCCTGCATCGCCGTTCCTTCCTGGCGA | 2258 |
| SEQ_ID_NO_223 | CCGTGACGCAAACCAACGTCGTAGCCGTAGCTCCCCTGCATCGCCGTTCCTTCCTGGCGA | 2063 |
| SEQ_ID_NO_215 | CCGTGACGCCGCCC--CGTCGTAGCCGTAGCTCCCCTGCATCGTCGTTCCTTCCTGGCGA | 2478 |
| SEQ_ID_NO_216 | CCGTGACGCCGCCC--CGTCGTAGCCGTAGCTCCCCTGCATCGTCGTTCCTTCCTGGCGA | 2478 |
| SEQ_ID_NO_214 | CCGTGACGCCGCCC--CGTCGTAGCCGTAGCTCCCCTGCATCGTCGTTCCTTCCTGGCGA | 2478 |
| SEQ_ID_NO_233 | CCGTGACGCCGCCC--CGTCGTAGCCGTAGCTCCCCTGCATCGTCGTTCCTTCCTGGCGA | 2082 |
| SEQ_ID_NO_236 | CCGTGACGCCGCCC--CGTCGTAGCCGTAGCTCCCCTGCATCGTCGTTCCTTCCTGGCGA | 2040 |
| SEQ_ID_NO_231 | CCGTGACGCCGCCC--CGTCGTAGCCGTAGCTCCCCTGCATCGTCGTTCCTTCCTGGCGA | 2076 |
| SEQ_ID_NO_229 | CCGTGACGCCGCCC--CGTCGTAGCCGTAGCTCCCCTGCATCGTCGTTCCTTCCTGGCGA | 2076 |
| SEQ_ID_NO_230 | CCGTGACGCCGCCC--CGTCGTAGCCGTAGCTCCCCTGCATCGTCGTTCCTTCCTGGCGA | 2076 |
| SEQ_ID_NO_232 | CCGTGACGCCGCCC--CGTCGTAGCCGTAGCTCCCCTGCATCGTCGTTCCTTCCTGGCGA | 2076 |
| SEQ_ID_NO_234 | CCGTGACGCCGCCC--CGTCGTAGCCGTAGCTCCCCTGCATCGCCGTTCCTTCCTGGCGA | 2040 |
| SEQ_ID_NO_218 | CCGTGACGCCGCCC--CGTCGTAGCCGTAGCTCCCCTGCATCGCCGTTCCTTCCTGGCGA | 2478 |
| SEQ_ID_NO_219 | CCGTGACGCCGCCC--CGTCGTAGCCGTAGCTCCCCTGCATCGCCGTTCCTTCCTGGCGA | 2478 |
| SEQ_ID_NO_217 | CCGTGACGCCGCCC--CGTCGTAGCCGTAGCTCCCCTGCATCGCCGTTCCTTCCTGGCGA | 2478 |
| SEQ_ID_NO_221 | CCGTGACGCCGCCC--CGTCGTAGCCGTAGCTCCCCTGCATCGCCGTTCCTTCCTGGCGA | 2070 |
| SEQ_ID_NO_224 | CCGTGACGCCGCCC--CGTCGTAGCCGTAGCTCCCCTGCATCGCCGTTCCTTCCTGGCGA | 2079 |
| | ********   **  ******************************  *************** | |
| SEQ_ID_NO_213 | TCGCCGCTTCCTAGCTATCCGGTGGCCAAAGACACGGCTAGTGGTAGGCTCGAGTGAGAC | 2135 |
| SEQ_ID_NO_222 | TCGCCGCTCCCTAGCTATCCGGTGGCCAAAGACACGGCTAGTGGTAGGCTCGAGCGAGAC | 2132 |
| SEQ_ID_NO_220 | TCGCCGCTCCCTAGCTATCCGGTGGCCAAAGACACGGCTAGTGGTAGGCTCGAGCGAGAC | 2310 |
| SEQ_ID_NO_235 | TCGCCGCTCCCTAGCTATCCGGTGGCCAAAGACACGGCTAGTGGTAGGCTCGAGCGAGAC | 2272 |
| SEQ_ID_NO_225 | TCGCCGCTCCCTAGCTATCCGGTGGCCAAAGACACGGCTAGTGGTAGGCTCGAGCGAGAC | 2318 |
| SEQ_ID_NO_226 | TCGCCGCTCCCTAGCTATCCGGTGGCCAAAGACACGGCTAGTGGTAGGCTCGAGCGAGAC | 2319 |
| SEQ_ID_NO_228 | TCGCCGCTCCCTAGCTATCCGGTGGCCAAAGACACGGCTAGTGGTAGGCTCGAGCGAGAC | 2319 |
| SEQ_ID_NO_227 | TCGCCGCTCCCTAGCTATCCGGTGGCCAAAGACACGGCTAGTGGTAGGCTCGAGCGAGAC | 2318 |
| SEQ_ID_NO_223 | TCGCCGCTCCCTAGCTATCCGGTGGCCAAAGACACGGCTAGTGGTAGGCTCGAGCGAGAC | 2123 |
| SEQ_ID_NO_215 | TCGCCGCTTCCTAGCTATCCGGTGGCCAAAGACACGGCTAGTGGTAGGCTCGAGTGAGAC | 2538 |
| SEQ_ID_NO_216 | TCGCCGCTTCCTAGCTATCCGGTGGCCAAAGACACGGCTAGTGGTAGGCTCGAGTGAGAC | 2538 |
| SEQ_ID_NO_214 | TCGCCGCTTCCTAGCTATCCGGTGGCCAAAGACACGGCTAGTGGTAGGCTCGAGTGAGAC | 2538 |
| SEQ_ID_NO_233 | TCGCCGCTCCCTAGCTATCCGGTGGCCAAAGACACGGCTAGTG---------------- | 2125 |
| SEQ_ID_NO_236 | TCGCCGCTCCCTAGCTATCCGGTGGCCAAAGACACGGCTAGTG---------------- | 2083 |
| SEQ_ID_NO_231 | TCGCCGCTTCCTAGCTATCCGGTGGCCAAAGACACGGCTAGTGGTAGGCTCGAGTGAGAC | 2136 |
| SEQ_ID_NO_229 | TCGCCGCTTCCTAGCTATCCGGTGGCCAAAGACACGGCTAGTGGTAGGCTCGAGTGAGAC | 2136 |
| SEQ_ID_NO_230 | TCGCCGCTTCCTAGCTATCCGGTGGCCAAAGACACGGCTAGTGGTAGGCTCGAGTGAGAC | 2136 |
| SEQ_ID_NO_232 | TCGCCGCTTCCTAGCTATCCGGTGGCCAAAGACACGGCTAGTGGTAGGCTCGAGTGAGAC | 2136 |

TABLE 27-continued

| | | |
|---|---|---|
| SEQ_ID_NO_234 | TCGCCGCTCCCTAGCTATCCGGTGGCCAAAGACACGGCTAGTGGTAGGCTCGAGCGAGAC | 2100 |
| SEQ_ID_NO_218 | TCGCCGCTCCCTAGCTATCCGGTGGCCAAAGACACGGCTAGTGGTAGGCTCGAGCGAGAC | 2538 |
| SEQ_ID_NO_219 | TCGCCGCTCCCTAGCTATCCGGTGGCCAAAGACACGGCTAGTGGTAGGCTCGAGCGAGAC | 2538 |
| SEQ_ID_NO_217 | TCGCCGCTCCCTAGCTATCCGGTGGCCAAAGACACGGCTAGTGGTAGGCTCGAGCGAGAC | 2538 |
| SEQ_ID_NO_221 | TCGCCGCTCCCTAGCTATCCGGTGGCCAAAGACACGGCTAGTGGTAGGCTCGAGCGAGAC | 2130 |
| SEQ_ID_NO_224 | TCGCCGCTCCCTAGCTATCCGGTGGCCAAAGACACGGCTAGTGGTAGGCTCGAGCGAGAC | 2139 |
| | ******* ******************************* | |
| SEQ_ID_NO_213 | GAGCTCTTGCTGAAGAGAGAATGAATGTAACGTTACCGCCTCCTGGTCGTAGGTGTAATA | 2195 |
| SEQ_ID_NO_222 | GAGCTCTTGCTGAAGAGAGAATGAATGTAGCGTTACCGCCTCCTGGTCGTAGG------- | 2185 |
| SEQ_ID_NO_220 | GAGCTCTTGCTGAAGAGAGAATGAATGTAGCGTTACCGCCTCCTGGTCGTAGG------- | 2363 |
| SEQ_ID_NO_235 | GAGCTCTTGCTGAAGAGAGAATGAATGTAGCGTTACCGCCTCCTGGTCGTAGG------- | 2325 |
| SEQ_ID_NO_225 | GAGCTCTTGCTGAAGAGAGAATGAATGTAGCGTTACCGCCTCCTGGTCGTAGG------- | 2371 |
| SEQ_ID_NO_226 | GAGCTCTTGCTGAAGAGAGAATGAATGTAGCGTTACCGCCTCCTGGTCGTAGG------- | 2372 |
| SEQ_ID_NO_228 | GAGCTCTTGCTGAAGAGAGAATGAATGTAGCGTTACCGCCTCCTGGTCGTAGG------- | 2372 |
| SEQ_ID_NO_227 | GAGCTCTTGCTGAAGAGAGAATGAATGTAGCGTTACCGCCTCCTGGTCGTAGG------- | 2371 |
| SEQ_ID_NO_223 | GAGCTCTTGGTGAAGAGAGAATGAATGTAACGTTACCGCCTCCTGGTCGTAGG------- | 2176 |
| SEQ_ID_NO_215 | GAGCTCTTGCTGAAGAGAGAATGAATGTAACGTTACCGCCTCCTGGTCGTAGGTGTAATA | 2598 |
| SEQ_ID_NO_216 | GAGCTCTTGCTGAAGAGAGAATGAATGTAACGTTACCGCCTCCTGGTCGTAGGTGTAATA | 2598 |
| SEQ_ID_NO_214 | GAGCTCTTGCTGAAGAGAGAATGAATGTAACGTTACCGCCTCCTGGTCGTAGGTGTAATA | 2598 |
| SEQ_ID_NO_233 | ---------CTGAAGAGAGAATGAATGTAACGTTACCGCCTCCTGGTCGTAGGTGTAATA | 2176 |
| SEQ_ID_NO_236 | ---------CTGAAGAGAGAATGAATGTAACGTTACCGCCTCCTGGTCGTAGGTGTAATA | 2134 |
| SEQ_ID_NO_231 | GAGCTCTTGCTGAAGAGAGAATGAATGTAACGTTACCGCCTCCTGGTCGTAGGTGTAATA | 2196 |
| SEQ_ID_NO_229 | GAGCTCTTGCTGAAGAGAGAATGAATGTAACGTTACCGCCTCCTGGTCGTAGGTGTAATA | 2196 |
| SEQ_ID_NO_230 | GAGCTCTTGCTGAAGAGAGAATGAATGTAACGTTACCGCCTCCTGGTCGTAGGTGTAATA | 2196 |
| SEQ_ID_NO_232 | GAGCTCTTGCTGAAGAGAGAATGAATGTAACGTTACCGCCTCCTGGTCGTAGGTGTAATA | 2196 |
| SEQ_ID_NO_234 | GAGCTCTTGGTGAAGAGAGAATGAATGTAACGTTACCGCCTCCTGGTCGTAGG------- | 2153 |
| SEQ_ID_NO_218 | GAGCTCTTGGTGAAGAGAGAATGAATGTAACGTTACCGCCTCCTGGTCGTAGG------- | 2591 |
| SEQ_ID_NO_219 | GAGCTCTTGGTGAAGAGAGAATGAATGTAACGTTACCGCCTCCTGGTCGTAGG------- | 2591 |
| SEQ_ID_NO_217 | GAGCTCTTGGTGAAGAGAGAATGAATGTAACGTTACCGCCTCCTGGTCGTAGG------- | 2591 |
| SEQ_ID_NO_221 | GAGCTCTTGCTGAAGAGAGAATGAATGTAGCGTTACCGCCTCCTGGTCGTAGG------- | 2183 |
| SEQ_ID_NO_224 | GAGCTCTTGCTGAAGAGAGAATGAATGTAGCGTTACCGCCTCCTGGTCGTAGG------- | 2192 |
| | ****************** ********************* | |
| SEQ_ID_NO_213 | AGTTGTAACGCGAGCGTCGTTAGCAAGCACAGGGGTTTGTGTATGTGAGGACAAGAGGAG | 2255 |
| SEQ_ID_NO_222 | --------------------------------GGTGTGGGTATGTGAGGACAAGAGGAG | 2212 |
| SEQ_ID_NO_220 | --------------------------------GGTGTGGGTATGTGAGGACAAGAGGAG | 2390 |
| SEQ_ID_NO_235 | --------------------------------GGTGTGGGTATGTGAGGACAAGAGGAG | 2352 |
| SEQ_ID_NO_225 | --------------------------------GGTGTGGGTATGTGAGGACAAGAGGAG | 2398 |
| SEQ_ID_NO_226 | --------------------------------GGTGTGGGTATGTGAGGACAAGAGGAG | 2399 |
| SEQ_ID_NO_228 | --------------------------------GGTGTGGGTATGTGAGGACAAGAGGAG | 2399 |
| SEQ_ID_NO_237 | --------------------------------GGTGTGGGTATGTGAGGACAAGAGGAG | 2398 |
| SEQ_ID_NO_223 | --------------------------------GGTGTGTGTATGTGAGGACAAGAGGAG | 2203 |

TABLE 27-continued

| | | |
|---|---|---|
| SEQ_ID_NO_215 | AGTTGTAACGCGAGCGTCGTTAGCAAGCACAGGGGTTTGTGTATGTGAGGACAAGAGGAG | 2658 |
| SEQ_ID_NO_216 | AGTTGTAACGCGAGCGTCGTTAGCAAGCACAGGGGTTTGTGTATGTGAGGACAAGAGGAG | 2658 |
| SEQ_ID_NO_214 | AGTTGTAACGCGAGCGTCGTTAGCAAGCACAGGGGTTTGTGTATGTGAGGACAAGAGGAG | 2658 |
| SEQ_ID_NO_233 | AGTTGTAACGCGAGTGTCGTTAG-AAGCACAGGGGTGTGTGTATGTGAGGACAAGAGGAG | 2235 |
| SEQ_ID_NO_236 | AGTTGTAACGCGAGTGTCGTTAG-AAGCACAGGGGTGTGTGTATGTGAGGACAAGAGGAG | 2193 |
| SEQ_ID_NO_231 | AGTTGTAACGCGAGCGTCGTTAGCAAGCACAGGGGTTTGTGTATGTGAGGACAAGAGGAG | 2256 |
| SEQ_ID_NO_229 | AGTTGTAACGCGAGCGTCGTTAGCAAGCACAGGGGTTTGTGTATGTGAGGACAAGAGGAG | 2256 |
| SEQ_ID_NO_230 | AGTTGTAACGCGAGCGTCGTTAGCAAGCACAGGGGTTTGTGTATGTGAGGACAAGAGGAG | 2256 |
| SEQ_ID_NO_232 | AGTTGTAACGCGAGCGTCGTTAGCAAGCACAGGGGTTTGTGTATGTGAGGACAAGAGGAG | 2256 |
| SEQ_ID_NO_234 | -------------------------------GGTGTGTGTATGTGAGGACAAGAGGAG | 2180 |
| SEQ_ID_NO_218 | -------------------------------GGTGTGTGTATGTGAGGACAAGAGGAG | 2618 |
| SEQ_ID_NO_219 | -------------------------------GGTGTGTGTATGTGAGGACAAGAGGAG | 2618 |
| SEQ_ID_NO_217 | -------------------------------GGTGTGTGTATGTGAGGACAAGAGGAG | 2618 |
| SEQ_ID_NO_221 | -------------------------------GGTGTGGGTATGTGAGGACAAGAGGAG | 2210 |
| SEQ_ID_NO_224 | -------------------------------GGTGTGGGTATGTGAGGACAAGAGGAG | 2219 |
| |                                *** ** ******************* | |
| SEQ_ID_NO_213 | GAGCGAGAGGAGGAGCGCAGAGCGTGGCGGGGAAGGAGGGCGTCATGTGTGCGAGGAATC | 2315 |
| SEQ_ID_NO_222 | GAGCGAGAGGAGGAGCGCAGAGCGTGGCGGGGAAGGAGGGCGTCATGTGTGTGAGGAATC | 2272 |
| SEQ_ID_NO_220 | GAGCGAGAGGAGGAGCGCAGAGCGTGGCGGGGAAGGAGGGCGTCATGTGTGTGAGGAATC | 2450 |
| SEQ_ID_NO_235 | GAGCGAGAGGAGGAGCGCAGAGCGTGGCGGGGAAGGAGGGCGTCATGTGTGTGAGGAATC | 2412 |
| SEQ_ID_NO_225 | GAGCGAGAGGAGGAGCGCAGAGCGTGGCGGGGAAGGAGGGCGTCATGTGTGCGAGGAATC | 2458 |
| SEQ_ID_NO_226 | GAGCGAGAGGAGGAGCGCAGAGCGTGGCGGGGAAGGAGGGCGTCATGTGTGCGAGGAATC | 2459 |
| SEQ_ID_NO_228 | GAGCGAGAGGAGGAGCGCAGAGCGTGGCGGGGAAGGAGGGCGTCATGTGTGTGAGGAATC | 2459 |
| SEQ_ID_NO_227 | GAGCGAGAGGAGGAGCGCAGAGCGTGGCGGGGAAGGAGGGCGTCATGTGTGTGAGGAATC | 2458 |
| SEQ_ID_NO_223 | GAGCGAGAGGAGGAGCGCAGAGCGTGGCGGGGAAGGAGGGCGTCATGTGTGCGAGGAATC | 2263 |
| SEQ_ID_NO_215 | GAGCGAGAGGAGGAGCGCAGAGCGTGGCGGGGAAGGAGGGCGTCATGTGTGCGAGGAATC | 2718 |
| SEQ_ID_NO_216 | GAGCGAGAGGAGGAGCGCAGAGCGTGGCGGGGAAGGAGGGCGTCATGTGTGCGAGGAATC | 2718 |
| SEQ_ID_NO_214 | GAGCGAGAGGAGGAGCGCAGAGCGTGGCGGGGAAGGAGGGCGTCATGTGTGCGAGGAATC | 2718 |
| SEQ_ID_NO_233 | GAGCGAGAGGAGGAGCGCAGAGCGTGGCGGGGAAGGAGGGCGTCATGTGTGTGAGGAATC | 2295 |
| SEQ_ID_NO_236 | GAGCGAGAGGAGGAGCGCAGAGCGTGGCGGGGAAGGAGGGCGTCATGTGTGTGAGGAATC | 2253 |
| SEQ_ID_NO_231 | GAGCGAGAGGAGGAGCGCAGAGCGTGGCGGGGAAGGAGGGCGTCATGTGTGCGAGGAATC | 2316 |
| SEQ_ID_NO_229 | GAGCGAGAGGAGGAGCGCAGAGCGTGGCGGGGAAGGAGGGCGTCATGTGTGCGAGGAATC | 2316 |
| SEQ_ID_NO_230 | GAGCGAGAGGAGGAGCGCAGAGCGTGGCGGGGAAGGAGGGCGTCATGTGTGCGAGGAATC | 2316 |
| SEQ_ID_NO_232 | GAGCGAGAGGAGGAGCGCAGAGCGTGGCGGGGAAGGAGGGCGTCATGTGTGCGAGGAATC | 2316 |
| SEQ_ID_NO_234 | GAGCGAGAGGAGGAGCGCAGAGCGTGGCGGGGAAGGAGGGCGTCATGTGTGTGAGGAATC | 2240 |
| SEQ_ID_NO_218 | GAGCGAGAGGAGGAGCGCAGAGCGTGGCGGGGAAGGAGGGCGTCATGTGTGCGAGGAATC | 2678 |
| SEQ_ID_NO_219 | GAGCGAGAGGAGGAGCGCAGAGCGTGGCGGGGAAGGAGGGCGTCATGTGTGCGAGGAATC | 2678 |
| SEQ_ID_NO_217 | GAGCGAGAGGAGGAGCGCAGAGCGTGGCGGGGAAGGAGGGCGTCATGTGTGCGAGGAATC | 2678 |
| SEQ_ID_NO_221 | GAGCGAGAGGAGGAGCGCAGAGCGTGGCGGGGAAGGAGGGCGTCATGTGTGTGAGGAATC | 2270 |
| SEQ_ID_NO_224 | GAGCGAGAGGAGGAGCGCAGAGCGTGGCGGGGAAGGAGGGCGTCATGTGTGCGAGGAATC | 2279 |
| | ************************************************ ******* | |

TABLE 27-continued

```
SEQ_ID_NO_213    TAGGACGACTTGTTGGCACTTGGCAGCTGGGCCGGGGTGCGTGCGAGATGCAATGCAAGA    2375
SEQ_ID_NO_222    TAGGACGACTTGT-------TGGCAGCTGGGCCGGGGTGCGTGCGAGATGCAATGCAAGA    2325
SEQ_ID_NO_220    TAGGACGACTTGTT-------GGCAGCTGGGCCGGGGTGCGTGCGAGATGCAATGCAAGA    2503
SEQ_ID_NO_235    TAGGACGACTTGTT-------GGCAGCTGGGCCGGGGTGCGTGCGAGATGCAATGCAAGA    2465
SEQ_ID_NO_225    TAGGACGACTTGTT-------GGCAGCTGGGCCGGGGTGCGTGCGAGATGCAATGCAAGA    2511
SEQ_ID_NO_226    TAGGACGACTTGTT-------GGCAGCTGGGCCGGGGTGCGTGCGAGATGCAATGCAAGA    2512
SEQ_ID_NO_228    TAGGACGACTTGTT-------GGCAGCTGGGCCGGGGTGCGTGCGAGATGCAATGCAAGA    2512
SEQ_ID_NO_227    TAGGACGACTTGTT-------GGCAGCTGGGCCGGGGTGCGTGCGAGATGCAATGCAAGA    2511
SEQ_ID_NO_223    TCGGACGACTTGTT-------GGCAGCTGGGCCGGGGTGCGTGCGAGATGCAATGCAAGA    2316
SEQ_ID_NO_215    TAGGACGACTTGTTGGCACTTGGCAGCTGGGCCGGGGTGCGTGCGAGATGCAATGCAAGA    2778
SEQ_ID_NO_216    TAGGACGACTTGTTGGCACTTGGCAGCTGGGCCGGGGTGCGTGCGAGATGCAATGCAAGA    2778
SEQ_ID_NO_214    TAGGACGACTTGTTGGCACTTGGCAGCTGGGCCGGGGTGCGTGCGAGATGCAATGCAAGA    2778
SEQ_ID_NO_233    TAGGACGACTTGTT-------GGCAGCTGGGCCGGGGTGCGTGCGAGATGCAATGCAAGA    2348
SEQ_ID_NO_236    TAGGACGACTTGTT-------GGCAGCTGGGCCGGGGTGCGTGCGAGATGCAATGCAAGA    2306
SEQ_ID_NO_231    TAGGACGACTTGTTGGCACTTGGCAGCTGGGCCGGGGTGCGTGCGAGATGCAATGCAAGA    2376
SEQ_ID_NO_229    TAGGACGACTTGTTGGCACTTGGCAGCTGGGCCGGGGTGCGTGCGAGATGCAATGCAAGA    2376
SEQ_ID_NO_230    TAGGACGACTTGTTGGCACTTGGCAGCTGGGCCGGGGTGCGTGCGAGATGCAATGCAAGA    2376
SEQ_ID_NO_232    TAGGACGACTTGTTGGCACTTGGCAGCTGGGCCGGGGTGCGTGCGAGATGCAATGCAAGA    2376
SEQ_ID_NO_234    TAGGACGACTTGTT-------GGCAGCTGGGCCGGGGTGCGTGCGAGATGCAATGCAAGA    2293
SEQ_ID_NO_218    TAGGACGACTTGTT-------GGCAGCTGGGCCGGGGTGCGTGCGAGATGCAATGCAAGA    2731
SEQ_ID_NO_219    TAGGACGACTTGTT-------GGCAGCTGGGCCGGGGTGCGTGCGAGATGCAATGCAAGA    2731
SEQ_ID_NO_217    TAGGACGACTTGTT-------GGCAGCTGGGCCGGGGTGCGTGCGAGATGCAATGCAAGA    2731
SEQ_ID_NO_221    TAGGACGACTTGTT-------GGCAGCTGGGCCGGGGTGCGTGCGAGATGCAATGCAAGA    2323
SEQ_ID_NO_224    TAGGACGACTTGTT-------GGCAGCTGGGCCGGGGTGCGTGCGAGATGCAATGCAAGA    2332
                 * ***********        ****************************************

SEQ_ID_NO_213    ACAAAGCGGACGGGCATC----------ACGCCTCCAGGTCCAACCCGGGGCGCCACTC    2425
SEQ_ID_NO_222    ACAAAGCGGACGGGCATC----------ACGCCTCCAGGTCCAACCCGGGGCGCCACTC    2375
SEQ_ID_NO_220    ACAAAGCGGACGGGCATC----------ACGCCTCCAAGTCCAACCCGGGGCGCCACTC    2553
SEQ_ID_NO_235    ACAAAGCGGACGGGCATC----------ACGCCTCCAGGTCCAACCCGGGGCGCCACTC    2515
SEQ_ID_NO_225    ACAAAGCGGACGGGCATCTCGCTCGGCCACGCTTCCAAGTCCATCCGGGGGCGCCACTC    2571
SEQ_ID_NO_226    ACAAAGCGGACGGGCATCTCGCTCGGCCACGCTTCCAAGTCCATCCGGGGGCGCCACTC    2572
SEQ_ID_NO_228    ACAAAGCGGACGGGCATC----------ACGCCTCCAGGTCCAACCCGGGGCGCCACTC    2562
SEQ_ID_NO_227    ACAAAGCGGACGGGCATC----------ACGCCTCCAGGTCCAACCCGGGGCGCCACTC    2561
SEQ_ID_NO_223    ACAAAGCGGACGGGCATCTCGCTCGGCCACGCTTCCAAGTCCAACCGGGGGCGCCACTC    2376
SEQ_ID_NO_215    ACAAAGCGGACGGGCATC----------ACGCCTCCAGGTCCAACCCGGGGCGCCACTC    2828
SEQ_ID_NO_216    ACAAAGCGGACGGGCATC----------ACGCCTCCAGGTCCAACCCGGGGCGCCACTC    2828
SEQ_ID_NO_214    ACAAAGCGGACGGGCATC----------ACGCCTCCAGGTCCAACCCGGGGCGCCACTC    2828
SEQ_ID_NO_233    ACAAAGC--------ATC----------ACGCCTCCAAGTCCAACCGGGGGCGCCACTC    2390
SEQ_ID_NO_236    ACAAAGC--------ATC----------ACGCCTCCAAGTCCAACCGGGGGCGCCACTC    2348
SEQ_ID_NO_231    ACAAAGCGGACGGGCATC----------ACGCCTCCAGGTCCAACCCGGGGCGCCACTC    2426
```

TABLE 27-continued

| SEQ_ID_NO_229 | ACAAAGCGGACGGGCATC----------ACGCCTCCAGGTCCAACCCGGGGGCGCCACTC | 2426 |
| --- | --- | --- |
| SEQ_ID_NO_230 | ACAAAGCGGACGGGCATC----------ACGCCTCCAGGTCCAACCCGGGGGCGCCACTC | 2426 |
| SEQ_ID_NO_232 | ACAAAGCGGACGGGCATC----------ACGCCTCCAGGTCCAACCCGGGGGCGCCACTC | 2426 |
| SEQ_ID_NO_234 | ACAAAGCGGACGGGCATC----------ACGCCTCCAGGTCCAACCCGGGGGCGCCACTC | 2343 |
| SEQ_ID_NO_218 | ACAAAGCGGACGGGCATCTCGCTCGGCCACGCTTCCAAGTCCATCCGGGGGGCGCCACTC | 2791 |
| SEQ_ID_NO_219 | ACAAAGCGGACGGGCATCTCGCTCGGCCACGCTTCCAAGTCCATCCGGGGGGCGCCACTC | 2791 |
| SEQ_ID_NO_217 | ACAAAGCGGACGGGCATCTCGCTCGGCCACGCTTCCAAGTCCATCCGGGGGGCGCCACTC | 2791 |
| SEQ_ID_NO_221 | ACAAAGCGGACGGGCATC----------ACGCCTCCAGGTCCAACCCGGGGGCGCCACTC | 2373 |
| SEQ_ID_NO_224 | ACAAAGCGGACGGGCATCTCGCTCGGCCACGCTTCCAAGTCCATCCGGGGGGCGCCAC-- | 2390 |
|  | ******   ***         **** **** ***** ** ***********          |  |
| SEQ_ID_NO_213 | G----GCCGCCGCTCATTGAGGCCCAGGCGCCAAGACGGCGGCTCCACCCACATCACAAT | 2481 |
| SEQ_ID_NO_222 | GATCGGCCGCCGCTCATTGAGGCCCAGGCGCCAAGACGGCGGCTCCACCCACGTCACAAT | 2435 |
| SEQ_ID_NO_220 | G----GCCGCCGCTCATTGAGGCCCAGGCGCCAAGACGGCGGCTCCACCCACGTCACAAT | 2609 |
| SEQ_ID_NO_235 | GATCGGCCGCCGCTCATTGAGGCCCAGGCGCCAAGACGGCGGCTCCACCCACGTCACAAT | 2575 |
| SEQ_ID_NO_225 | G----GCCGCCGCTCATTGAGGCCCAGGCGCCAAGACGGCGGCTCCACCCACGTCACAAT | 2627 |
| SEQ_ID_NO_226 | G----GCCGCCGCTCATTGAGGCCCAGGCGCCAAGACGGCGGCTCCACCCACGTCACAAT | 2628 |
| SEQ_ID_NO_228 | G----GCCGCCGCTCATTGAGGCCCAGGCGCCAAGACGGCGGCTCCACCCACGTCACAAT | 2618 |
| SEQ_ID_NO_227 | G----GCCGCCGCTCATTGAGGCCCAGGCGCCAAGACGGCGGCTCCACCCACGTCACAAT | 2617 |
| SEQ_ID_NO_223 | G----GCCGCCGCTCATTGAGGCCCAGGCGCCAAGACGGCGGCTCCACCCACATCACAAT | 2432 |
| SEQ_ID_NO_215 | G----GCCGCCGCTCATTGAGGCCCAGGCGCCAAGACGGCGGCTCCACCCACATCACAAT | 2884 |
| SEQ_ID_NO_216 | G----GCCGCCGCTCATTGAGGCCCAGGCGCCAAGACGGCGGCTCCACCCACATCACAAT | 2884 |
| SEQ_ID_NO_214 | G----GCCGCCGCTCATTGAGGCCCAGGCGCCAAGACGGCGGCTCCACCCACATCACAAT | 2884 |
| SEQ_ID_NO_233 | G----GCCGCCGCTCATTGAGGCCCAGGCGCCAAGACGGCGGCTCCACCCACATCACAAT | 2446 |
| SEQ_ID_NO_236 | G----GCCGCCGCTCATTGAGGCCCAGGCGCCAAGACGGCGGCTCCACCCACATCACAAT | 2404 |
| SEQ_ID_NO_231 | G----GCCGCCGCTCATTGAGGCCCAGGCGCCAAGACGGCGGCTCCACCCACATCACAAT | 2482 |
| SEQ_ID_NO_229 | G----GCCGCCGCTCATTGAGGCCCAGGCGCCAAGACGGCGGCTCCACCCACATCACAAT | 2482 |
| SEQ_ID_NO_230 | G----GCCGCCGCTCATTGAGGCCCAGGCGCCAAGACGGCGGCTCCACCCACATCACAAT | 2482 |
| SEQ_ID_NO_232 | G----GCCGCCGCTCATTGAGGCCCAGGCGCCAAGACGGCGGCTCCACCCACATCACAAT | 2482 |
| SEQ_ID_NO_234 | G----GCCGCCGCTCATTGAGGCCCAGGCGCCAAGACGGCGGCTCCACCCACGTCACAAT | 2399 |
| SEQ_ID_NO_218 | G----GCCGCCGCTCATTGAGGCCCAGGCGCCAAGACGGCGGCTCCACCCACGTCACAAT | 2847 |
| SEQ_ID_NO_219 | G----GCCGCCGCTCATTGAGGCCCAGGCGCCAAGACGGCGGCTCCACCCACGTCACAAT | 2847 |
| SEQ_ID_NO_217 | G----GCCGCCGCTCATTGAGGCCCAGGCGCCAAGACGGCGGCTCCACCCACGTCACAAT | 2847 |
| SEQ_ID_NO_221 | GATCGGCCGCCGCTCATTGAGGCCCAGGCGCCAAGACGGCGGCTCCACCCACGTCACAAT | 2433 |
| SEQ_ID_NO_224 | --TCGGCCGCCGCTCATTGAGGCCCAGGCGCCAAGACGGCGGCTCCACCCACGTCACAAT | 2448 |
|  | ************************************************ *******  |  |
| SEQ_ID_NO_213 | TGGCAACAAGAAGCACACGGCTGGGGTTGGGACGCGTCGAATTTTTCACCAGAAAATACC | 2541 |
| SEQ_ID_NO_222 | TGGCAATAAGAAGCACACGGCTGGGGCTGGGACGCGTCGAATTTTTCACCAGAAAATACC | 2495 |
| SEQ_ID_NO_220 | TGGCAACAAGAAGCACACGGCTGGGGCTGGGACGCGTCGAATTTTTCACCAGAAAATACC | 2669 |
| SEQ_ID_NO_235 | TGGCAATAAGAAGCACACGGCTGGGGCTGGGACGCGTCGAATTTTTCACCAGAAAATACC | 2635 |
| SEQ_ID_NO_225 | TGGCAACAAGAAGCACACGGCTGGGGCTGGGACGCGTCGAATTTTTCACCAGAAAATACC | 2687 |
| SEQ_ID_NO_226 | TGGCAACAAGAAGCACACGGCTGGGGCTGGGACGCGTCGAATTTTTCACCAGAAAATACC | 2688 |

TABLE 27-continued

| SEQ_ID_NO_228 | TGGCAATAAGAAGCACACGGCTGGGGCTGGGACGCGTCGAATTTTTCACCAGAAAATACC | 2678 |
| SEQ_ID_NO_227 | TGGCAATAAGAAGCACACGGCTGGGGCTGGGACGCGTCGAATTTTTCACCAGAAAATACC | 2677 |
| SEQ_ID_NO_223 | TGGCAACAAGAAGCACACGGCTGGGGCTGGGACGCGTCGAATTTTTCACCAGAAAATACC | 2492 |
| SEQ_ID_NO_215 | TGGCAACAAGAAGCACACGGCTGGGGTTGGGACGCGTCGAATTTTTCACCAGAAAATACC | 2944 |
| SEQ_ID_NO_216 | TGGCAACAAGAAGCACACGGCTGGGGTTGGGACGCGTCGAATTTTTCACCAGAAAATACC | 2944 |
| SEQ_ID_NO_214 | TGGCAACAAGAAGCACACGGCTGGGGTTGGGACGCGTCGAATTTTTCACCAGAAAATACC | 2944 |
| SEQ_ID_NO_233 | TGGCAACAAGAAGCACACGGCTGGGGCTGGGACGCGTCGAATTTTTCACCAGAAAATACC | 2506 |
| SEQ_ID_NO_236 | TGGCAACAAGAAGCACACGGCTGGGGCTGGGACGCGTCGAATTTTTCACCAGAAAATACC | 2464 |
| SEQ_ID_NO_231 | TGGCAACAAGAAGCACACGGCTGGGGTTGGGACGCGTCGAATTTTTCACCAGAAAATACC | 2542 |
| SEQ_ID_NO_229 | TGGCAACAAGAAGCACACGGCTGGGGTTGGGACGCGTCGAATTTTTCACCAGAAAATACC | 2542 |
| SEQ_ID_NO_230 | TGGCAACAAGAAGCACACGGCTGGGGTTGGGACGCGTCGAATTTTTCACCAGAAAATACC | 2542 |
| SEQ_ID_NO_232 | TGGCAACAAGAAGCACACGGCTGGGGTTGGGACGCGTCGAATTTTTCACCAGAAAATACC | 2542 |
| SEQ_ID_NO_234 | TGGCAATAAGAAGCACACGGCTGGGGCTGGGACGCGTCGAATTTTTCACCAGAAAATACC | 2459 |
| SEQ_ID_NO_218 | TGGCAACAAGAAGCACACGGCTGGGGCTGGGACGCGTCGAATTTTTCACCAGAAAATACC | 2907 |
| SEQ_ID_NO_219 | TGGCAACAAGAAGCACACGGCTGGGGCTGGGACGCGTCGAATTTTTCACCAGAAAATACC | 2907 |
| SEQ_ID_NO_217 | TGGCAACAAGAAGCACACGGCTGGGGCTGGGACGCGTCGAATTTTTCACCAGAAAATACC | 2907 |
| SEQ_ID_NO_221 | TGGCAATAAGAAGCACACGGCTGGGGCTGGGACGCGTCGAATTTTTCACCAGAAAATACC | 2493 |
| SEQ_ID_NO_224 | TGGCAACAAGAAGCACACGGCTGGGGCTGGGACGCGTCGAATTTTTCACCAGAAAATACC | 2508 |
|  | ****** ****************** ********************************* |  |
| SEQ_ID_NO_213 | GTCTGATCCTGGCGTTTCGTCAGATGCTATGCTACGTGAACGGCAAAACCTAGCAGCAGC | 2601 |
| SEQ_ID_NO_222 | GTCTGATCCTGGCGTTTCGTCAGATGCTATGCTACGTGAACGGCAAAACCTAGCAGCAGC | 2555 |
| SEQ_ID_NO_220 | GTC-------GGCGTTTCGTCAGATGCTATGCTACGTGAACGGCAAAACCTAGCAGCAGC | 2722 |
| SEQ_ID_NO_235 | GTCTGATCCTGGCGTTTCGTCAGATGCTATGCTACGTGAACGGCAAAACCTAGCAGCAGC | 2695 |
| SEQ_ID_NO_225 | GTCTGATCCTGGCGTTTCGT----------------GAACGGCAAAACCTAGCAGCAGC | 2730 |
| SEQ_ID_NO_226 | GTCTGATCCTGGCGTTTCGT----------------GAACGGCAAAACCTAGCAGCAGC | 2731 |
| SEQ_ID_NO_228 | GTCTGATCCTGGCGTTTCGTCAGATGCTATGCTACGTGAACGGCAAAACCTAGCAGCAGC | 2738 |
| SEQ_ID_NO_227 | GTCTGATCCTGGCGTTTCGTCAGATGCTATGCTACGTGAACGGCAAAACCTAGCAGCAGC | 2737 |
| SEQ_ID_NO_223 | GTC-------GGCGTTTCGTCAGATGCTATGCTACGTGAACGGCAAAACCTAGCAGCAGC | 2545 |
| SEQ_ID_NO_215 | GTCTGATCCTGGCGTTTCGTCAGATGCTATGCTACGTGAACGGCAAAACCTAGCAGCAGC | 3004 |
| SEQ_ID_NO_216 | GTCTGATCCTGGCGTTTCGTCAGATGCTATGCTACGTGAACGGCAAAACCTAGCAGCAGC | 3004 |
| SEQ_ID_NO_214 | GTCTGATCCTGGCGTTTCGTCAGATGCTATGCTACGTGAACGGCAAAACCTAGCAGCAGC | 3004 |
| SEQ_ID_NO_233 | GTC-------GGCGTTTCGTCAGATGCTATGCTACGTGAACGGCAAAACCTAGCAGCAGC | 2559 |
| SEQ_ID_NO_236 | GTC-------GGCGTTTCGTCAGATGCTATGCTACGTGAACGGCAAAACCTAGCAGCAGC | 2517 |
| SEQ_ID_NO_231 | GTCTGATCCTGGCGTTTCGTCAGATGCTATGCTACGTGAACGGCAAAACCTAGCAGCAGC | 2602 |
| SEQ_ID_NO_229 | GTCTGATCCTGGCGTTTCGTCAGATGCTATGCTACGTGAACGGCAAAACCTAGCAGCAGC | 2602 |
| SEQ_ID_NO_230 | GTC-------GGCGTTTCGTCAGATGCTATGCTACGTGAACGGCAAAACCTAGCAGCAGC | 2595 |
| SEQ_ID_NO_232 | GTC-------GGCGTTTCGTCAGATGCTATGCTACGTGAACGGCAAAACCTAGCAGCAGC | 2595 |
| SEQ_ID_NO_234 | GTCTGATCCTGGCGTTTCGTCAGATGCTATGCTACGTGAACGGCAAAACCTAGCAGCAGC | 2519 |
| SEQ_ID_NO_218 | GTCTGATCCTGGCGTTTCGT----------------GAACGGCAAAACCTAGCAGCAGC | 2950 |
| SEQ_ID_NO_219 | GTCTGATCCTGGCGTTTCGT----------------GAACGGCAAAACCTAGCAGCAGC | 2950 |
| SEQ_ID_NO_217 | GTCTGATCCTGGCGTTTCGT----------------GAACGGCAAAACCTAGCAGCAGC | 2950 |

TABLE 27-continued

| SEQ_ID_NO_221 | GTCTGATCCTGGCGTTTCGTCAGATGCTATGCTACGTGAACGGCAAAACCTAGCAGCAGC | 2553 |
| --- | --- | --- |
| SEQ_ID_NO_224 | GTCTGATCCTGGCGTTTCGT----------------GAACGGCAAAACCTAGCAGCAGC | 2551 |
| | *** ********** ********************** | |
| SEQ_ID_NO_213 | AGCAGC---ACTCAGACTGGACAAGAGGAGGGAAATCTTTGCGTGGGAACCAAACTGAAC | 2658 |
| SEQ_ID_NO_222 | AGC------ACTCAGACTGGACAAGAGGAGGGAAATCTTTGCGTGGGAACCAAACTGAAC | 2609 |
| SEQ_ID_NO_220 | AGCAGC---ATTCAGACTGGACAAGAGGAGGGAAATCTTTGCGTGGGAACCAAACTGAAC | 2779 |
| SEQ_ID_NO_235 | AGC------ACTCAGACTGGACAAGAGGAGGGAAATCTTTGCGTGGGAACCAAACTGAAC | 2749 |
| SEQ_ID_NO_225 | AGC------A------------------------------------------------- | 2734 |
| SEQ_ID_NO_226 | AGC------A------------------------------------------------- | 2735 |
| SEQ_ID_NO_228 | AGC------ACTCAGACTGGACAAGAGGAGGGAAATCTTTGCGTGGGAACCAAACTGAAC | 2792 |
| SEQ_ID_NO_227 | AGCAGC---ACTCAGACTGGACAAGAGGAGGGAAATCTTTGCGTGGGAACCAAACTGAAC | 2794 |
| SEQ_ID_NO_223 | AGC------ACTCAGACTGGACAAGAGGAGGGAAATCTTTGCGTGGGAACCAAACTGAAC | 2599 |
| SEQ_ID_NO_215 | AGCAGC---ACTCAGACTGGACAAGAGGAGGGAAATCTTTGCGTGGGAACCAAACTGAAC | 3061 |
| SEQ_ID_NO_216 | AGCAGC---ACTCAGACTGGACAAGAGGAGGGAAATCTTTGCGTGGGAACCAAACTGAAC | 3061 |
| SEQ_ID_NO_214 | AGCAGC---ACTCAGACTGGACAAGAGGAGGGAAATCTTTGCGTGGGAACCAAACTGAAC | 3061 |
| SEQ_ID_NO_233 | AGCAGCAGCACTCAGACTGGACAAGAGGAGGGAAATCTTTGCGTGGGAACCAAACTGAAC | 2619 |
| SEQ_ID_NO_236 | AGCAGC---ACTCAGACTGGACAAGAGGAGGGAAATCTTTGCGTGGGAACCAAACTGAAC | 2574 |
| SEQ_ID_NO_231 | AGCAGC---ACTCAGACTGGACAAGAGGAGGGAAATCTTTGCGTGGGAACCAAACTGAAC | 2659 |
| SEQ_ID_NO_229 | AGCAGC---ACTCAGACTGGACAAGAGGAGGGAAATCTTTGCGTGGGAACCAAACTGAAC | 2659 |
| SEQ_ID_NO_230 | AGCA------CTCAGACTGGACGAGAGGAGGGAAATCTTTGCGTGGGAACCAAACTGAAC | 2649 |
| SEQ_ID_NO_232 | AGCA------CTCAGACTGGACGAGAGGAGGGAAATCTTTGCGTGGGAACCAAACTGAAC | 2649 |
| SEQ_ID_NO_234 | AGC------ACTCAGACTGGACAAGAGGAGGGAAATCTTTGCGTGGGAACCAAACTGAAC | 2573 |
| SEQ_ID_NO_218 | AGCA-------------------------------------------------------- | 2954 |
| SEQ_ID_NO_219 | AGCA-------------------------------------------------------- | 2954 |
| SEQ_ID_NO_217 | AGCA-------------------------------------------------------- | 2954 |
| SEQ_ID_NO_221 | AGCACT------CAGACTGGACAAGAGGAGGGAAATCTTTGCGTGGGAACCAAACTGAAC | 2607 |
| SEQ_ID_NO_224 | AGCA-------------------------------------------------------- | 2555 |
| | *** | |
| SEQ_ID_NO_213 | GCGAATCGCACGAGTCGGATGACATATC-----CTCGTCCGGAGCGGACTCGACCGCGAG | 2713 |
| SEQ_ID_NO_222 | GCGAATCGCACGGGTCGGATGACATATCATATCCTCGTGCGGAGCGGACTCAACGGCGAG | 2669 |
| SEQ_ID_NO_220 | GCGAATCGCACGAGTCGGATGACATATC-----CTCGTGCGGAGCGGACTCGACCGCGAG | 2834 |
| SEQ_ID_NO_235 | GCGAATCGCACGGGTCGGATGACATATCATATCCTCGTGCGGAGCGGACTCAACGGCGAG | 2809 |
| SEQ_ID_NO_225 | --GCATTCCACGGGTCGGATGACATATCATATCCTCGTGCGGAGCGGACTCAACGGCGAG | 2792 |
| SEQ_ID_NO_226 | --GCATTCCACGGGTCGGATGACATATCATATCCTCGTGCGGAGCGGACTCAACGGCGAG | 2793 |
| SEQ_ID_NO_228 | GCGAATCGCACGGGTCGGATGACATATCATATCCTCGTGCGGAGCGGACTCAACGGCGAG | 2852 |
| SEQ_ID_NO_227 | GCGAATCGCACGAGTCGGATGACATATC-----CTCGTCCGGAGCGGACTCGACCGCGAG | 2849 |
| SEQ_ID_NO_223 | GCGAATCGCACGAGTCGGATGACATATC-----CTCGTCCGGAGCGGACTCGGCCGCGAG | 2654 |
| SEQ_ID_NO_215 | GCGAATCGCACGAGTCGGATGACATATC-----CTCGTCCGGAGCGGACTCGACCGCGAG | 3116 |
| SEQ_ID_NO_215 | GCGAATCGCACGAGTCGGATGACATATC-----CTCGTCCGGAGCGGACTCGACCGCGAG | 3116 |
| SEQ_ID_NO_214 | GCGAATCGCACGAGTCGGATGACATATC-----CTCGTCCGGAGCGGACTCGACCGCGAG | 3116 |
| SEQ_ID_NO_233 | GCGAATCGCACGAGTCGGATGACATATC-----CTCGTCCGGAGCGGACTCGGCCGCGAG | 2674 |

TABLE 27-continued

| | | |
|---|---|---|
| SEQ_ID_NO_236 | GCGAATCGCACGAGTCGGATGACATATC-----CTCGTCCGGAGCGGACTCGGCCGCGAG | 2629 |
| SEQ_ID_NO_231 | GCGAATCGCACGAGTCGGATGACATATC-----CTCGTCCGGAGCGGACTCGACCGCGAG | 2714 |
| SEQ_ID_NO_229 | GCGAATCGCACGAGTCGGATGACATATC-----CTCGTCCGGAGCGGACTCGACCGCGAG | 2714 |
| SEQ_ID_NO_230 | GCGAATCGCACGAGTCGGATGACATATC-----CTCGTCCGGAGCGGACTCGACCGCGAG | 2704 |
| SEQ_ID_NO_232 | GCGAATCGCACGAGTCGGATGACATATC-----CTCGTCCGGAGCGGACTCGACCGCGAG | 2704 |
| SEQ_ID_NO_234 | GCGAATCGCACGGGTCGGATGACATATCATATCCTCGTGCGGAGCGGACTCAACGGCGAG | 2633 |
| SEQ_ID_NO_218 | --GCATTCCACGGGTCGGATGACATATCATATCCTCGTGCGGAGCGGACTCTACGGCGAG | 3012 |
| SEQ_ID_NO_219 | --GCATTCCACGGGTCGGATGACATATCATATCCTCGTGCGGAGCGGACTCTACGGCGAG | 3012 |
| SEQ_ID_NO_217 | --GCATTCCACGGGTCGGATGACATATCATATCCTCGTGCGGAGCGGACTCTACGGCGAG | 3012 |
| SEQ_ID_NO_221 | GCGAATCGCACGGGTCGGATGACATATCATATCCTCGTGCGGAGCGGACTCAACGGCGAG | 2667 |
| SEQ_ID_NO_224 | --GCATTCCACGGGTCGGATGACATATCATATCCTCGTGCGGAGCGGACTCAACGGCGAG | 2613 |
| | * ** **** **************     ***** ************ * ***** | |
| SEQ_ID_NO_213 | TCCAGCTGTGGCTGCGGAATATTCCGGCGGAAGCGCGGGGAGAACGACGGCGGCCTCCGG | 2773 |
| SEQ_ID_NO_222 | TCCAGCTGTGGCTGCGGAATATTCCGGCGGAAGCGCGGGGAGAGCGACGGCGGCCTCCGG | 2729 |
| SEQ_ID_NO_220 | TCCAGCTGTGGNTGCGGAATATTCCGGCGGAAGCGCGGGGAGAACGACGGCGGCCTCCGG | 2894 |
| SEQ_ID_NO_235 | TCCAGCTGTGGCTGCGGAATATTCCGGCGGAAGCGCGGGGAGAGCGACGGCGGCCTCCGG | 2869 |
| SEQ_ID_NO_225 | TCCAGCTGTGGNNCGGAATATTCCGGCGGAAGCGCGGGGAGAGCGACGGCGGCCTCCGG | 2852 |
| SEQ_ID_NO_226 | TCCAGCTGTGGCTGCGGAATATTCCGGCGGAAGCGCGGGGAGAGCGACGGCGGCCTCCGG | 2853 |
| SEQ_ID_NO_228 | TCCAGCTGTGGCTGCGGAATATTCCGGCGGAAGCGCGGGGAGAGCGACGGCGGCCTCCGG | 2912 |
| SEQ_ID_NO_227 | TCCAGCTGTGGCTGCGGAATATTCCGGCGGAAGCGCGGGGAGAACGACGGCGGCCTCCGG | 2909 |
| SEQ_ID_NO_223 | TCCAGCTGTGGCTGCGGAATATTCCGGCGGAATCGCGGGGAGAACGACGGCGGCCTCCGG | 2714 |
| SEQ_ID_NO_215 | TCCAGCTGTGGCTGCGGAATATTCCGGCGGAAGCGCGGGGAGAACGACGGCGGCCTCCGG | 3176 |
| SEQ_ID_NO_216 | TCCAGCTGTGGCTGCGGAATATTCCGGCGGAAGCGCGGGGAGAACGACGGCGGCCTCCGG | 3176 |
| SEQ_ID_NO_214 | TCCAGCTGTGGCTGCGGAATATTCCGGCGGAAGCGCGGGGAGAACGACGGCGGCCTCCGG | 3176 |
| SEQ_ID_NO_233 | TCCAGCTGTGGCTGCGGAATATTCCGGCGGAAGCGCGGGGAGAACGACGGCGGCCTCCGG | 2734 |
| SEQ_ID_NO_236 | TCCAGCTGTGGCTGCGGAATATTCCGGCGGAAGCGCGGGGAGAACGACGGCGGCCTCCGG | 2689 |
| SEQ_ID_NO_231 | TCCAGCTGTGGCTGCGGAATATTCCGGCGGAAGCGCGGGGAGAACGACGGCGGCCTCCGG | 2774 |
| SEQ_ID_NO_229 | TCCAGCTGTGGCTGCGGAATATTCCGGCGGAAGCGCGGGGAGAACGACGGCGGCCTCCGG | 2774 |
| SEQ_ID_NO_230 | TCCAGCTGTGGCTGCGGAATATTCCGGCGGAAGCGCGGGGAGAACGACGGCGGCCTCCGG | 2764 |
| SEQ_ID_NO_232 | TCCAGCTGTGGCTGCGGAATATTCCGGCGGAAGCGCGGGGAGAACGACGGCGGCCTCCGG | 2764 |
| SEQ_ID_NO_234 | TCCAGCTGTGGCTGCGGAATATTCCGGCGGAAGCGCGGGGAGAGCGACGGCGGCCTCCGG | 2693 |
| SEQ_ID_NO_218 | TCCAGCTGTGGCTGCGGAATATTCCGGCGGAAGCGCGGGGAGAGCGACGGCGGCCTCCGG | 3072 |
| SEQ_ID_NO_219 | TCCAGCTGTGGCTGCGGAATATTCCGGCGGAAGCGCGGGGAGAGCGACGGCGGCCTCCGG | 3072 |
| SEQ_ID_NO_217 | TCCAGCTGTGGCTGCGGAATATTCCGGCGGAAGCGCGGGGAGAGCGACGGCGGCCTCCGG | 3072 |
| SEQ_ID_NO_221 | TCCAGCTGTGGCTGCGGAATATTCCGGCGGAAGCGCGGGGAGAGCGACGGCGGCCTCCGG | 2727 |
| SEQ_ID_NO_224 | TCCAGCTGTGGCTGCGGAATATTCCGGCGGAAGCGCGGGGAGAGCGACGGCGGCCTCCGG | 2673 |
| | **********  ******************  **********  **************** | |
| SEQ_ID_NO_213 | TGGGACCCGGGGCGAGCGGGAGATGCGGCGAAGATGTTCGGCGCTGATGTCGCTGGAATA | 2833 |
| SEQ_ID_NO_222 | TGGGACCCGGGGCGAGCGGGAGATGCGGCGAAGATGTTCGGCGCTGATGTCGCTGGAATA | 2789 |
| SEQ_ID_NO_220 | TGGGACCCGGGGCGAGCGGGAGATGCGGCGAAGATGTTCGGCGCTGATGTCGCTGGAATA | 2954 |
| SEQ_ID_NO_235 | TGGGACCCGGGGCGAGCGGGAGATGCGGCGAAGATGTTCGGCGCTGATGTCGCTGGAATA | 2929 |

TABLE 27-continued

| SEQ_ID_NO_225 | TGG--------------------------------------------------------- | 2855 |
|---|---|---|
| SEQ_ID_NO_226 | TGGGACCCGGGGCGAGCGGGAGATGCGGCGAAGATGTTCGGCGCTGATGTCGCTGGAATA | 2913 |
| SEQ_ID_NO_228 | TGGGACCCGGGGCGAGCGGGAGATGCGGCGAAGATGTTCGGCGCTGATGTCGCTGGAATA | 2972 |
| SEQ_ID_NO_227 | TGGGACCCGGGGCGAGCGGGAGATGCGGCGAAGATGTTCGGCGCTGATGTCGCTGGAATA | 2969 |
| SEQ_ID_NO_223 | TGGGACCCGGGGCGAGCGGGAGATGCGGCGAAGATGTTCGGCGCTGATGTCGCTGGAATA | 2774 |
| SEQ_ID_NO_215 | TGGGACCCGGGGCGAGCGGGAGATGCGGCGAAGATGTTCGGCGCTGATGTCGCTGGAATA | 3236 |
| SEQ_ID_NO_216 | TGGGACCCGGGGCGAGCGGGAGATGCGGCGAAGATGTTCGGCGCTGATGTCGCTGGAATA | 3236 |
| SEQ_ID_NO_214 | TGGGACCCGGGGCGAGCGGGAGATGCGGCGAAGATGTTCGGCGCTGATGTCGCTGGAATA | 3236 |
| SEQ_ID_NO_233 | TGGGACCCGGGGCGAGCGGGAGATGCGGCGAAGATGTTCGGCGCTGATGTCGCTGGAATA | 2794 |
| SEQ_ID_NO_236 | TGGGACCCGGGGCGAGCGGGAGATGCGGCGAAGATGTTCGGCGCTGATGTCGCTGGAATA | 2749 |
| SEQ_ID_NO_231 | TGGGACCCGGGGCGAGCGGGAGATGCGGCGAAGATGTTCGGCGCTGATGTCGCTGGAATA | 2834 |
| SEQ_ID_NO_229 | TGGGACCCGGGGCGAGCGGGAGATGCGGCGAAGATGTTCGGCGCTGATGTCGCTGGAATA | 2834 |
| SEQ_ID_NO_230 | TGGGAACCGGGGCGAGCGGGAGATGCGGCGAAGATGTTCGGCGCTGATGTCGCTGGAATA | 2824 |
| SEQ_ID_NO_232 | TGGGAACCGGGGCGAGCGGGAGATGCGGCGAAGATGTTCGGCGCTGATGTCGCTGGAATA | 2824 |
| SEQ_ID_NO_234 | TGGGACCCGGGGCGAGCGGGAGATGCGGCGAAGATGTTCGGCGCTGATGTCGCTGGAATA | 2753 |
| SEQ_ID_NO_218 | TGGGACCCGGGGCGAGCGGGAGATGCGGCGAAGATGTTCGGCGCTGATGTCGCTGGAATA | 3132 |
| SEQ_ID_NO_219 | TGGGACCCGGGGCGAGCGGGAGATGCGGCGAAGATGTTCGGCGCTGATGTCGCTGGAATA | 3132 |
| SEQ_ID_NO_217 | TGGGACCCGGGGCGAGCGGGAGATGCGGCGAAGATGTTCGGCGCTGATGTCGCTGGAATA | 3132 |
| SEQ_ID_NO_221 | TGGGACCCGGGGCGAGCGGGAGATGCGGCGAAGATGTTCGGCGCTGATGTCGCTGGAATA | 2787 |
| SEQ_ID_NO_224 | TGGGACCCGGGGCGAGCGGGAGATGCGGCGAAGATGTTCGGCGCTGATGTCGCTGGAATA<br>*** | 2733 |
| SEQ_ID_NO_213 | TTCGCGCCAGCTGTGGCTGCCGGTGTGACCTGCTGACCAGACGACCAGTGGCAGTGGCCA | 2893 |
| SEQ_ID_NO_222 | TTCGCGCCAGCTGTGGCTGCCGGTGCGACCTGCTGACCAGACGACCAGTGGCAATGGCCA | 2849 |
| SEQ_ID_NO_220 | TTCGCGCCAGCTGTGGCTGCCGG------------------------------------- | 2977 |
| SEQ_ID_NO_235 | TTCGCGCCAGCTGTGGCTGCCGGTGCGACCTGCTGACCAG--------TGGCAATGGCCA | 2981 |
| SEQ_ID_NO_225 | ------------------------------------------------------------ | |
| SEQ_ID_NO_226 | TTCGCGCCAGCTGTGGCTGCCGGTGCGACCTGCTGACCAGACGACCAGTGGCAATGGCCA | 2973 |
| SEQ_ID_NO_228 | TTCGCGCCAGCTGTGGCTGCCGGTGCGACCTGCTGACCAGACGACCAGTGGCAATGGCCA | 3032 |
| SEQ_ID_NO_227 | TTCGCGCCAGCTGTGGCTGCCGGTGTGACCTGCTGACCAGACGACCAGTGGCAGTGGCCA | 3029 |
| SEQ_ID_NO_223 | TTCGCGCCAGCTGTGGCTGCCGGTGTGACCTGCTGACCAGACGACCAGTGGCAGTGGCCA | 2834 |
| SEQ_ID_NO_215 | TTCGCGCCAGCTGTGGCTGCCGGTGTGACCTGCTGACCAGACGACCAGTGGCAGTGGCCA | 3296 |
| SEQ_ID_NO_216 | TTCGCGCCAGCTGTGGCTGCCGGTGTGACCTGCTGACCAGACGACCAGTGGCAGTGGCCA | 3296 |
| SEQ_ID_NO_214 | TTCGCGCCAGCTGTGGCTGCCGGTGTGACCTGCTGACCAGACGACCAGTGGCAGTGGCCA | 3296 |
| SEQ_ID_NO_233 | TTCGCGCCAGCTGTGGCTGCCGGTGTGACCTGCTGACCAGACGACCAGTGGCAGTGGCCA | 2854 |
| SEQ_ID_NO_236 | TTCGCGCCAGCTGTGGCTGCCGGTGTGACCTGCTGACCAGACGACCAGTGGCAGTGGCCA | 2809 |
| SEQ_ID_NO_231 | TTCGCGCCAGCTGTGGCTGCCGGTGTGACCTGCTGACCAGACGACCAGTGGCAGTGGCCA | 2894 |
| SEQ_ID_NO_229 | TTCGCGCCAGCTGTGGCTGCCGGTGTGACCTGCTGACCAGACGACCAGTGGCAGTGGCCA | 2894 |
| SEQ_ID_NO_230 | TTCGCGCCAGCTGTGGCTGCCGGTGTGACCTGCT--------GACCAGTGGCAGTGGCCA | 2876 |
| SEQ_ID_NO_232 | TTCGCGCCAGCTGTGGCTGCCGGTGTGACCTGCT--------GACCAGTGGCAGTGGCCA | 2876 |
| SEQ_ID_NO_234 | TTCGCGCCAGCTGTGGCTGCCGGTGCGACCTGCTGACCAGACGACCAGTGGCAATGGCCA | 2813 |

TABLE 27-continued

| | | |
|---|---|---|
| SEQ_ID_NO_218 | TTCGCGCCAGCTGTGGCTGCCGGTGCGACCTGCTGACCAGACGACCAATGGCAGTGGCCA | 3192 |
| SEQ_ID_NO_219 | TTCGCGCCAGCTGTGGCTGCCGGTGCGACCTGCTGACCAGACGACCAATGGCAGTGGCCA | 3192 |
| SEQ_ID_NO_217 | TTCGCGCCAGCTGTGGCTGCCGGTGCGACCTGCTGACCAGACGACCAATGGCAGTGGCCA | 3192 |
| SEQ_ID_NO_221 | TTCGCGCCAGCTGTGGCTGCCGGTGCGACCTGCTGACCAGACGACCAGTGGCAATGGCCA | 2847 |
| SEQ_ID_NO_224 | TTCGCGCCAGCTGTGGCTGCCGGTGCGACCTGCTGACCAGACGACCAGTGGCAATGGCCA | 2793 |
| SEQ_ID_NO_213 | CCGCCTCTCC------------------------------------ATC---------- | 2906 |
| SEQ_ID_NO_222 | CCGCCTCTCC-------------------------------------ATCCAACCTCCAT | 2872 |
| SEQ_ID_NO_220 | ------------------------------------------------------------ | |
| SEQ_ID_NO_235 | CCGCCTCTCC-------------------------------------ATCCAACCTCCAT | 3004 |
| SEQ_ID_NO_225 | ------------------------------------------------------------ | |
| SEQ_ID_NO_226 | CCGCCTCTCC-------------------------------------ATCCAACCTCCAT | 2996 |
| SEQ_ID_NO_228 | CCGCCTCTCC-------------------------------------ATCCAACCTCCAT | 3055 |
| SEQ_ID_NO_227 | CCGCCTCTC---------------------------------------------CAT | 3041 |
| SEQ_ID_NO_223 | CCGCCTCTG---------------------------------------------CAT | 2846 |
| SEQ_ID_NO_215 | CCGCCTCTC---------------------------------------------CAT | 3308 |
| SEQ_ID_NO_216 | CCGCCTCTC---------------------------------------------CAT | 3308 |
| SEQ_ID_NO_214 | CCGCCTCTC---------------------------------------------CAT | 3308 |
| SEQ_ID_NO_233 | CCGCCTCTC---------------------------------------------CAT | 2866 |
| SEQ_ID_NO_236 | CCGCCTCTC---------------------------------------------CAT | 2821 |
| SEQ_ID_NO_231 | CCGCCTCTC---------------------------------------------CAT | 2906 |
| SEQ_ID_NO_229 | CCGCCTCTC---------------------------------------------CAT | 2906 |
| SEQ_ID_NO_230 | CCGCCTCTC---------------------------------------------CAT | 2888 |
| SEQ_ID_NO_232 | CCGCCTCTC---------------------------------------------CAT | 2888 |
| SEQ_ID_NO_234 | CCGCCTCTCC-------------------------------------ATCCAACCTCCAT | 2836 |
| SEQ_ID_NO_218 | CCGCCTCTCCCTCTTGCTGTTGGAGTTGGATCCACGGACCACTCTCCATCCAACATCCAT | 3252 |
| SEQ_ID_NO_219 | CCGCCTCTCCCTCTTGCTGTTGGAGTTGGATCCACGGACCACTCTCCATCCAACATCCAT | 3252 |
| SEQ_ID_NO_217 | CCGCCTCTCCCTCTTGCTGTTGGAGTTGGATCCACGGACCACTCTCCATCCAACATCCAT | 3252 |
| SEQ_ID_NO_221 | CCGCCTCTCC-------------------------------------ATCCAACCTCCAT | 2870 |
| SEQ_ID_NO_224 | CCGCCTCTCC-------------------------------------ATCCAACCTCCAT | 2816 |
| SEQ_ID_NO_213 | -ACAGATTCGCGGACGATTAGCCGAGACTAATCGCTATTCTCAACACTTTTAAAACCGTG | 2965 |
| SEQ_ID_NO_222 | CACAGATTGGCGGACGATTAGCCGAGACTAATCGCTATTCTCAACACTTTAAAAACCGTG | 2932 |
| SEQ_ID_NO_220 | ------------------------------------------------------------ | |
| SEQ_ID_NO_235 | CACAGATTGGCGGACGATTAGCCGAGACTAATCGCTATTCTCAACACTTTAAAAACCGTG | 3064 |
| SEQ_ID_NO_225 | ------------------------------------------------------------ | |
| SEQ_ID_NO_226 | CACAGATTGGCGGACGATTAGCCGAGACTAATCGCTATTCTCAACACTTTAAAAACCGTG | 3056 |
| SEQ_ID_NO_228 | CACAGATTGGCGGACGATTAGCCGAGACTAATCGCTATTCTCAACACTTTAAAAACCGTG | 3115 |
| SEQ_ID_NO_227 | CACAGATTCGCGGACGATTAGCCGAGACTAATCGCTATTCTCAACACTTTTAAAACCGTG | 3101 |
| SEQ_ID_NO_223 | CACAGATTGGCGGACGATTAGCCGAGACTAATTGCCATTCTCAACACTTTTAAAACCGTG | 2906 |
| SEQ_ID_NO_215 | CACAGATTCGCGGACGATTAGCCGAGACTAATCGCTATTCTCAACACTTTTAAAACCGTG | 3368 |
| SEQ_ID_NO_216 | CACAGATTCGCGGACGATTAGCCGAGACTAATCGCTATTCTCAACACTTTTAAAACCGTG | 3368 |

TABLE 27-continued

| | | |
|---|---|---|
| SEQ_ID_NO_214 | CACAGATTCGCGGACGATTAGCCGAGACTAATCGCTATTCTCAACACTTTTAAAACCGTG | 3368 |
| SEQ_ID_NO_233 | CACAGATTCGCGGACGATTAGCCGAGACTAATCGCTATTCTCAACACTTTTAAAACCGTG | 2926 |
| SEQ_ID_NO_236 | CACAGATTCGCGGACGATTAGCCGAGACTAATCGCTATTCTCAACACTTTTAAAACCGTG | 2881 |
| SEQ_ID_NO_231 | CACAGATTCGCGGACGATTAGCCGAGACTAATCGCTATTCTCAACACTTTTAAAACCGTG | 2966 |
| SEQ_ID_NO_229 | CACAGATTCGCGGACGATTAGCCGAGACTAATCGCTATTCTCAACACTTTTAAAACCGTG | 2966 |
| SEQ_ID_NO_230 | CACAGATTGGCGGACGATTAGCCGAGACTAATCGCTATTCTCAACACTTTTAAAACCGTG | 2948 |
| SEQ_ID_NO_232 | CACAGATTGGCGGACGATTAGCCGAGACTAATCGCTATTCTCAACACTTTTAAAACCGTG | 2948 |
| SEQ_ID_NO_234 | CACAGATTGGCGGACGATTAGCCGAGACTAATCGCTATTCTCAACACTTTAAAAACCGTG | 2896 |
| SEQ_ID_NO_218 | CACAGATTGGCGGACGATTAGCCGAGACTAATCGCTATTCTCAACACTTTTAAAACCGTA | 3312 |
| SEQ_ID_NO_219 | CACAGATTGGCGGACGATTAGCCGAGACTAATCGCTATTCTCAACACTTTTAAAACCGTA | 3312 |
| SEQ_ID_NO_217 | CACAGATTGGCGGACGATTAGCCGAGACTAATCGCTATTCTCAACACTTTTAAAACCGTA | 3312 |
| SEQ_ID_NO_221 | CACAGATTGGCGGACGATTAGCCGAGACTAATCGCTATTCTCAACACTTTAAAAACCGTG | 2930 |
| SEQ_ID_NO_224 | CACAGATTGGCGGACGATTAGCCGAGACTAATCGCTATTCTCAACACTTTAAAAACCGTG | 2876 |
| SEQ_ID_NO_213 | CGTGCAGAATGCTAAGGGCGCGTTCGTTTGCACAGCAATAGACATGGATTTATTTCAGCT | 3025 |
| SEQ_ID_NO_222 | CGTGCAGAATGCTAAG-------------------------------------------- | 2948 |
| SEQ_ID_NO_220 | ------------------------------------------------------------ | |
| SEQ_ID_NO_235 | CGTGCAGAATGCTAAGCCTGC-----TAGATTCGAGCATCTGCGTGACTCTACTTTGGCT | 3119 |
| SEQ_ID_NO_225 | ------------------------------------------------------------ | |
| SEQ_ID_NO_226 | CGTGCAGAATGCTAAGCCTGC-----TAGATTCGAGCATCTGCGTGACTCTACTTTGGCT | 3111 |
| SEQ_ID_NO_228 | CGTGCAGAATGCTAAGCCTGC-----TAGATTCGAGCATCTGCGTGACTCTACTTTGGCT | 3170 |
| SEQ_ID_NO_227 | CGTGCAGAATGCTAAGGGCGCGTTCGTTTGCACAGCAATAGACATGGATTTATTTCAGCT | 3161 |
| SEQ_ID_NO_223 | CGTGCAGAATGCTAAGCCTGC-----TAGATTCGAGCATCTGCGTGACTCTACTT----- | 2956 |
| SEQ_ID_NO_215 | CGTGCAGAATGCTAAGGGCGCGTTCGTTTGCACAGCAATAGACATGGATTTATTTCAGCT | 3428 |
| SEQ_ID_NO_216 | CGTGCAGAATGCTAAGGGCGCGTTCGTTTGCACAGCAATAGACATGGATTTATTTCAGCT | 3428 |
| SEQ_ID_NO_214 | CGTGCAGAATGCTAAGGGCGCGTTCGTTTGCACAGCAATAGACATGGATTTATTTCAGCT | 3428 |
| SEQ_ID_NO_233 | CGTGCAGAATGCTAAGGGCGCGTTCGTTTGCACAGCAATAGACATTGATTTATTTCAGCT | 2986 |
| SEQ_ID_NO_236 | CGTGCAGAATGCTAAGGGCGCGTTCGTTTGCACAGCAATAGACATGGATTTATTTCAGCT | 2941 |
| SEQ_ID_NO_231 | CGTGCAGAATGCTAAGGGCGCGTTCGTTTGCACAGCAATAGACATGGATTTATTTCAGCT | 3026 |
| SEQ_ID_NO_229 | CGTGCAGAATGCTAAGGGCGCGTTCGTTTGCACAGCAATAGACATGGATTTATTTCAGCT | 3026 |
| SEQ_ID_NO_230 | CGTGCAGAATGATAA--CCCTGCTAGATT---CGAGCATCTGCGTGACTCTACTCTGGCT | 3003 |
| SEQ_ID_NO_232 | CGTGCAGAATGATAA--CCCTGCTAGATT---CGAGCATCTGCGTGACTCTACTCTGGCT | 3003 |
| SEQ_ID_NO_234 | CGTGCAGAATGCTAAGCCTGC-----TAGATTCGAGCATCTGCGTGACTCTACTTTGGCT | 2951 |
| SEQ_ID_NO_218 | CGTGCAAAATGCTAAGGGGCCGTTCGTTT-------CTTAGCCGGAATGGCGGTTTGTTT | 3365 |
| SEQ_ID_NO_219 | CGTGCAAAATGCTAAGGGGCCGTTCGTTT-------CTTAGCCGGAATGGCGGTTTGTTT | 3365 |
| SEQ_ID_NO_217 | CGTGCAAAATGCTAAGGGGCCGTTCGTTT-------CTTAGCCGGAATGGCGGTTTGTTT | 3365 |
| SEQ_ID_NO_221 | CGTGCAGAATGCTAAGCCTGC-----TAGATTCGAGCATCTGCGTGACTCTACTTTGGCT | 2985 |
| SEQ_ID_NO_224 | CGTGCAGAATGCTAAGCCTGC-----TAGATTCGAGCATCTGCGTGACTCTACTTTGGCT | 2931 |
| SEQ_ID_NO_213 | CATCAAAATCTATATAAATTAAAGAAGTAATCCGGCTAGAAATTAATCCGGAGCTTCAAT | 3085 |
| SEQ_ID_NO_222 | ------------------------------------------------------------ | |
| SEQ_ID_NO_220 | ------------------------------------------------------------ | |

TABLE 27-continued

| SEQ_ID_NO_235 | CTTCTCGTACGATGCGACCTGACGATGCATTTGGGNNN------CCTNTAGCGTCACTTT | 3173 |
| --- | --- | --- |
| SEQ_ID_NO_225 | ------------------------------------------------------------ | |
| SEQ_ID_NO_226 | CTTCTCGTACGATGCGACCTGACGATGCATTTGGGCNNN-----CCTNTAGCGTCACTTT | 3166 |
| SEQ_ID_NO_228 | CTTCTCGTACGATGCGACCTGACGATGCATTTGGGCGTT-----CCTGTAGCGTCACTTT | 3225 |
| SEQ_ID_NO_227 | CATCAAAATTTATATAAATTAAAGAAGTAATCCGGCTAGAAATTAATCCGGAGCTTCAAT | 3221 |
| SEQ_ID_NO_223 | ------------------------------------------------------------ | |
| SEQ_ID_NO_215 | CATCAAAATCTATATAAATTAAAGAAGTAATCCGGCTAGAAATTAATCCGGAGCTTCAAT | 3488 |
| SEQ_ID_NO_216 | CATCAAAATCTATATAAATTAAAGAAGTAATCCGGCTAGAAATTAATCCGGAGCTTCAAT | 3488 |
| SEQ_ID_NO_214 | CATCAAAATCTATATAAATTAAAGAAGTAATCCGGCTAGAAATTAATCCGGAGCTTCAAT | 3488 |
| SEQ_ID_NO_233 | CATCAAAATCTATATAAATTAAAGAAGTAATCCGGCTAGAAATTAATCCGGAGCTTCAAT | 3046 |
| SEQ_ID_NO_236 | CATCAAAATCTATATAAATTAAAGAAGTAATCCGGCTAGAAATTAATCCGGAGCTTCAAT | 3001 |
| SEQ_ID_NO_231 | CATCAAAATCTATATAAATTAAAGAAGTAATCCGGCTAGAAATTAATCCGGAGCTTCAAT | 3086 |
| SEQ_ID_NO_229 | CATCAAAATCTATATAAATTAAAGAAGTAATCCGGCTAGAAATTAATCCGGAGCTTCAAT | 3086 |
| SEQ_ID_NO_230 | CTTCTCGTACGATGCGACTTGACGATGCATTTGCGCGCCTTTAGCGTCACTTTCCTGATT | 3063 |
| SEQ_ID_NO_232 | CTTCTCGTACGATGCGACTTGACGATGCATT----------------------------- | 3034 |
| SEQ_ID_NO_234 | CTTCTCGTACGATGCGACCTGACGATGCATTTGGGNNNN-----CCTNTAGCGTCACTTT | 3006 |
| SEQ_ID_NO_218 | CTCTAATTTATATAAGTTTTGATTAGCTGTATTGATTCC------------TGATCCAAT | 3413 |
| SEQ_ID_NO_219 | CTCTAATTTATATAAGTTTTGATTAGCTGTATTGATTCC------------TGATCCAAT | 3413 |
| SEQ_ID_NO_217 | CTCTAATTTATATAAGTTTTGATTAGCTGTATTGATTCC------------TGATCCAAT | 3413 |
| SEQ_ID_NO_221 | CTTCTCGTACGATGCGACCTGACGATGCATTTGGGCGNC-------CTNTAGCGTCACTT | 3038 |
| SEQ_ID_NO_224 | CTTCTCGTACGATGCGACCTGACGATGCATTTGG-------------------------- | 2965 |
| SEQ_ID_NO_213 | CCCTAACAACCGAACAGGGTCTAAGCCTGCTAGATTCGAGCATCTGCGTGACTCTACTTT | 3145 |
| SEQ_ID_NO_222 | -------------------------CCTGCTAGATTCGAGCATCTGCGTGACTCTACTTT | 2983 |
| SEQ_ID_NO_220 | ------------------------------------------------------------ | |
| SEQ_ID_NO_235 | CCTGATTAGTCCCCCGGAAACGCAACTCTACCACTATCAGCCGCCG-------------- | 3219 |
| SEQ_ID_NO_225 | ------------------------------------------------------------ | |
| SEQ_ID_NO_226 | CCTGATTAGTCCCCCGGAAACGCAACTCTACCACTATCAGCCGCCG-------------- | 3212 |
| SEQ_ID_NO_228 | CCTGATTAGTCCCCCGGAAACGCAACTCTACCACTATCAGCCGCCG-------------- | 3271 |
| SEQ_ID_NO_227 | CCCTAACAACCGAACAGGGTCTAAGCCTGCTAGATTCGAGCATCTGCGTGACTCTACTTT | 3281 |
| SEQ_ID_NO_223 | ------------------------------------------------------------ | |
| SEQ_ID_NO_215 | CCCTAACAACCGAACAGGGTCTAAGCCTGCTAGATTCGAGCATCTGCGTGACTCTACTTT | 3548 |
| SEQ_ID_NO_216 | CCCTAACAACCGAACAGGGTCTAAGCCTGCTAGATTCGAGCATCTGCGTGACTCTACTTT | 3548 |
| SEQ_ID_NO_214 | CCCTAACAACCGAACAGGGTCTAAGCCTGCTAGATTCGAGCATCTGCGTGACTCTACTTT | 3548 |
| SEQ_ID_NO_233 | CCCTAACAACCGAACAGGGTCTAAGCCTGCTAGATTCGAGCATCTGCGTGACTCTACTTT | 3106 |
| SEQ_ID_NO_236 | CCCTAACAACCGAACAGGGTCTAAGCCTGCTAGATTCGAGCATCTGCGTGACTCTACTTT | 3061 |
| SEQ_ID_NO_231 | CCCTAACAACCGAACAGGGTCTAAGCCTGCTAGATTCGAGCATCTGCGTGACTCTACTTT | 3146 |
| SEQ_ID_NO_229 | CCCTAACAACCGAACAGGGTCTAAGCCTGCTAGATTCGAGCATCTGCGTGACTCTACTTT | 3146 |
| SEQ_ID_NO_230 | AGTCCCACGGAAACGCAACTCTACCACTATCAGCCGCCA--------------------- | 3102 |
| SEQ_ID_NO_232 | ------------------------------------------------------------ | |
| SEQ_ID_NO_234 | CCTGATTAGTCCCCCGGAAACGCAACTCTACCACTATCAGCCGCCG-------------- | 3052 |

TABLE 27-continued

| | | |
|---|---|---|
| SEQ_ID_NO_218 | TCTGAACAAACGAACA------AAACCTGCTAGATTCGNGCATCTGCGTGACTCTACTTT | 3467 |
| SEQ_ID_NO_219 | TCTGAACAAACGAACA------AAACCTGCTAGATTCGAGCATCTGCGTGACTCTACTTT | 3467 |
| SEQ_ID_NO_217 | TCTGAACAAACGAACA------AAACCTGCTAGATTCGAGCATCTGCGTGACTCTACTTT | 3467 |
| SEQ_ID_NO_221 | CCTGATTAGTCCCCCGGAAACGCAAC---------------------------------- | 3064 |
| SEQ_ID_NO_224 | ------------------------------------------------------------ | |
| SEQ_ID_NO_213 | GGCTCTTCTCGTACGATGCGACTTGACGATGCATTTGGGNNNNCNTTAGCGACACTCTC | 3205 |
| SEQ_ID_NO_222 | GGCTCTTCTCGTACGATGCGACCTGACGATGCATT-GGGCGNNCCTNTAGCGTCACTTTC | 3042 |
| SEQ_ID_NO_220 | ------------------------------------------------------------ | |
| SEQ_ID_NO_235 | ------------------------------------------------------------ | |
| SEQ_ID_NO_225 | ------------------------------------------------------------ | |
| SEQ_ID_NO_226 | ------------------------------------------------------------ | |
| SEQ_ID_NO_228 | ------------------------------------------------------------ | |
| SEQ_ID_NO_227 | GGCTCTTCTCGTACGATGCGACTTGACGATGCAT-------------------------- | 3315 |
| SEQ_ID_NO_223 | ------------------------------------------------------------ | |
| SEQ_ID_NO_215 | GGCTCTTCTCGTACGATGCGACTTGACGATGCATTTGG---------------------- | 3586 |
| SEQ_ID_NO_216 | GGCTCTTCTCGTACGATGCGACTTGACGATGCATTTGGGC-------------------- | 3588 |
| SEQ_ID_NO_214 | GGCTCTTCTCGTACGATGCGACTTGACGATGCATTTGGGNNNNNNNNTAGCGACACTCTC | 3608 |
| SEQ_ID_NO_233 | GGCTCTTCTCGTACGATGCGACTTGACGATGCA--------------------------- | 3139 |
| SEQ_ID_NO_236 | GGCTCTTCTCGTACGATGCGACTTGACGATGCATTTGG---------------------- | 3099 |
| SEQ_ID_NO_231 | GGCTCTTCTCGTACGATGCGACTTGACGATGCATTTGGGNNNNNNGTAGCGACACTCTC | 3206 |
| SEQ_ID_NO_229 | GGCTCTTCTCGTACGATGCGACTTGACGATGCATTNGGGNCNNCCNNTAGCGACACTCTC | 3206 |
| SEQ_ID_NO_230 | ------------------------------------------------------------ | |
| SEQ_ID_NO_232 | ------------------------------------------------------------ | |
| SEQ_ID_NO_234 | ------------------------------------------------------------ | |
| SEQ_ID_NO_218 | GGCCCTTCTCGTACGAGCTTTTNGGCGTTCCTCTAGCGTCACTTTCCCCCGGAAACGCAA | 3527 |
| SEQ_ID_NO_219 | GGCCCTTCTCGTACG--------------------------------------------- | 3482 |
| SEQ_ID_NO_217 | GGCCCTTCTCGTACGNNNNNNNNTGGCGTTCCTCTAGCGTCACTTTCCCCCGGAAACGCAA | 3527 |
| SEQ_ID_NO_221 | ------------------------------------------------------------ | |
| SEQ_ID_NO_224 | ------------------------------------------------------------ | |
| SEQ_ID_NO_213 | CTGATTAGTCCCACGGAAACGCAACTCTACCACTATCAGCCGCCG | 3250 |
| SEQ_ID_NO_222 | CTGATTAGTCCCCGGAAACGCAACTCTACCACTATCAGCCGCCG | 3087 |
| SEQ_ID_NO_220 | --------------------------------------------- | |
| SEQ_ID_NO_235 | --------------------------------------------- | |
| SEQ_ID_NO_225 | --------------------------------------------- | |
| SEQ_ID_NO_226 | --------------------------------------------- | |
| SEQ_ID_NO_228 | --------------------------------------------- | |
| SEQ_ID_NO_227 | --------------------------------------------- | |
| SEQ_ID_NO_223 | --------------------------------------------- | |
| SEQ_ID_NO_215 | --------------------------------------------- | |
| SEQ_ID_NO_216 | --------------------------------------------- | |

TABLE 27-continued

| | | |
|---|---|---|
| SEQ_ID_NO_214 | CTGATTAGTCCCACGGAAACGCAACTCTACCACTATCAGCCGCCG | 3653 |
| SEQ_ID_NO_233 | ---------------------------------------- | |
| SEQ_ID_NO_236 | ---------------------------------------- | |
| SEQ_ID_NO_231 | CTGATTAGTCCCACGGAAACGCAACTCTACCACTATCAGCCGCCG | 3251 |
| SEQ_ID_NO_229 | CTGATTAGTCCCACGGAAACGCAACTCTACCACTATCAGCCGCCG | 3251 |
| SEQ_ID_NO_230 | ---------------------------------------- | |
| SEQ_ID_NO_232 | ---------------------------------------- | |
| SEQ_ID_NO_234 | ---------------------------------------- | |
| SEQ_ID_NO_218 | CTCTACCACTATCAGCCGCCG-------------------- | 3548 |
| SEQ_ID_NO_219 | ---------------------------------------- | |
| SEQ_ID_NO_217 | CTCTACCACTATCAGCCGCCG-------------------- | 3548 |
| SEQ_ID_NO_221 | ---------------------------------------- | |
| SEQ_ID_NO_224 | ---------------------------------------- | |

Sequence data was used to identify a putative homologue by descent segments between independent sources of resistance or susceptibility. The region from MRQV_00005-1 to MRQV_08351-1 was shared for most of the independent sources of susceptibility. The data for a key recombinant (from the high resolution mapping population; susceptible to the disease) showed that the recombinant point for this genetic material is located inside a putative Myb transcription factor (PCO644442) and that the sequence variation generating the resistance should be located from the position of this candidate gene towards MZA2038. There was also an expected IBD (identity-by-descent) relationship between independent sources of resistance at the region of or close to PCO644442 as:
  a) PHR33 and PH467.
  b) PHR33, PH9TJ, PHJ40 and PHDG9.
  c) PHK09 showed a specific haplotype.
  d) 630 showed a specific haplotype.
There was a group of target SNPs at MRQV_08351-1 very specific for most of resistant sources. However, recombinant data indicates that the target sequence should be located from MRQV_08351-1 (located at PCO644442) towards MZA2038.

Considering the specificity of target SNPs at MRQV_08351-1, this specific fragment was sequenced in a total of 625 inbreds from Pioneer germplasm. A genetic description was developed in relationship to MRCV resistance of part of Pioneer germplasm by using the combined information from: a) flanking markers of this interval (MZA15490 and MZA2038), b) the sequence data for the 625 inbreds and the tester's lines, c) the pedigree relationship between inbreds, and d) the phenotypic data for these inbreds.

A specific group of haplotypes at MRQV_08351-1 or combined with haplotypic information for MRQV_10673-1 and MZA2038 was used to increase the characterization and identity by descent information for the major resistance sources in Pioneer germplasm and to consider putative variants of the target region. Table 28 shows a description of specific haplotypes and the observed and expected response to the disease across materials by haplotype. The representative sources are included as reference.

TABLE 28

| MRQV_08351 | MRQV_10673 | MZA2038 link | Expected phenotype | MRCVSC | n | Source | Segregation data |
|---|---|---|---|---|---|---|---|
| 1 | 1, 2, 8, 9 | 4, 5, 9, 11 | Susceptible | 3.02 | 247 | PHFV5, 274, PHAN0, 165, OH7, other | |
| 1 | 3 | 5 | Resistant | 4.60 | 5 | PHJ40 | No |
| 2 | 1 | 12 | Resistant | 4.59 | 22 | PH7WT, 173, 630, PHB04, PH14J, PHAA4, PHG64 | Yes |
| 3 | 6 | 1, 14 | Susceptible | 3.21 | 19 | C103, 157, other | |
| 4 | | 4 | Susceptible | 3.31 | 13 | 216, other | |
| 5 | 4 | 4, 11 | Resistant | 5.00 | 3 | PHR33, PH467, 501 LACAUNEOP | No |
| 7 | 3 | 10, 15 | Resistant | 5.90 | 10 | PHP51, PHDG9, 546, LACAUNEOP | Yes |
| 9 | 7 | 6 | Resistant | 5.00 | 2 | PHK09, PH884, PHBD6, PHFCF | Yes |

Using the information for MRQV_08351-1 or combined with flanking sequences (MRQV_10673-1 and MZA2038), Applicants inferred the following:

a) Resistance source 1. The sources PHR33 and PH467 may share a common ancestor at MRQV_08351-1. Shared regions with European materials derived from LACAUNE open pollinated variety support a probable common origin from a single haplotype region.

b) Resistance source 2. The sources PHR33, PH9TJ, PHJ40 and PHDG9 may share a common ancestor at the flanking region of MRQV_08351-1. In addition, PHP51 may be inferred as part of this group. Shared regions with European materials derived from LACAUNE open pollinated variety support a probable common origin from a single haplotype region.

c) Resistance source 3. PHK09 showed a shared haplotype with PHBD6 at MRQV_08351-1, and they should share a common origin from Tuxpen germplasm.

d) Resistance source 4. 630 showed a specific haplotype, and there is not a confirmed IBD relationship with other sources.

From mapping population results, Applicants thus demonstrate a QTL at the region of preferred markers in these independent sources:

630.
PH9TJ. Allelic to 630.
PHP51. Allelic to 630.
PHBD6. Allelic to 630.

The integration of recombination, sequence, and pedigree analysis and the inference of an expected IBD relationship between independent sources permitted Applicants to consider that four major haplotypes at the region of two of the preferred markers (MZA15490 and MZA2038) can be used to characterize most of the sources of resistance in Pioneer germplasm. These four major haplotypes maybe grouped as these germplasm sources:

(a) Resistance source 1 and 2. Flint SWAN germplasm sharing homologue region with materials from the European flint LACAUNE open pollinated population.
(b) Resistance source 3. Materials from TUXPEN origin.
(c) Resistance source 4. Specific source, 630 is the representative inbred. The development of this inbred included a broad genetic base including TUXPEN and MEXICAN JUNE germplasm.

Figure 6:
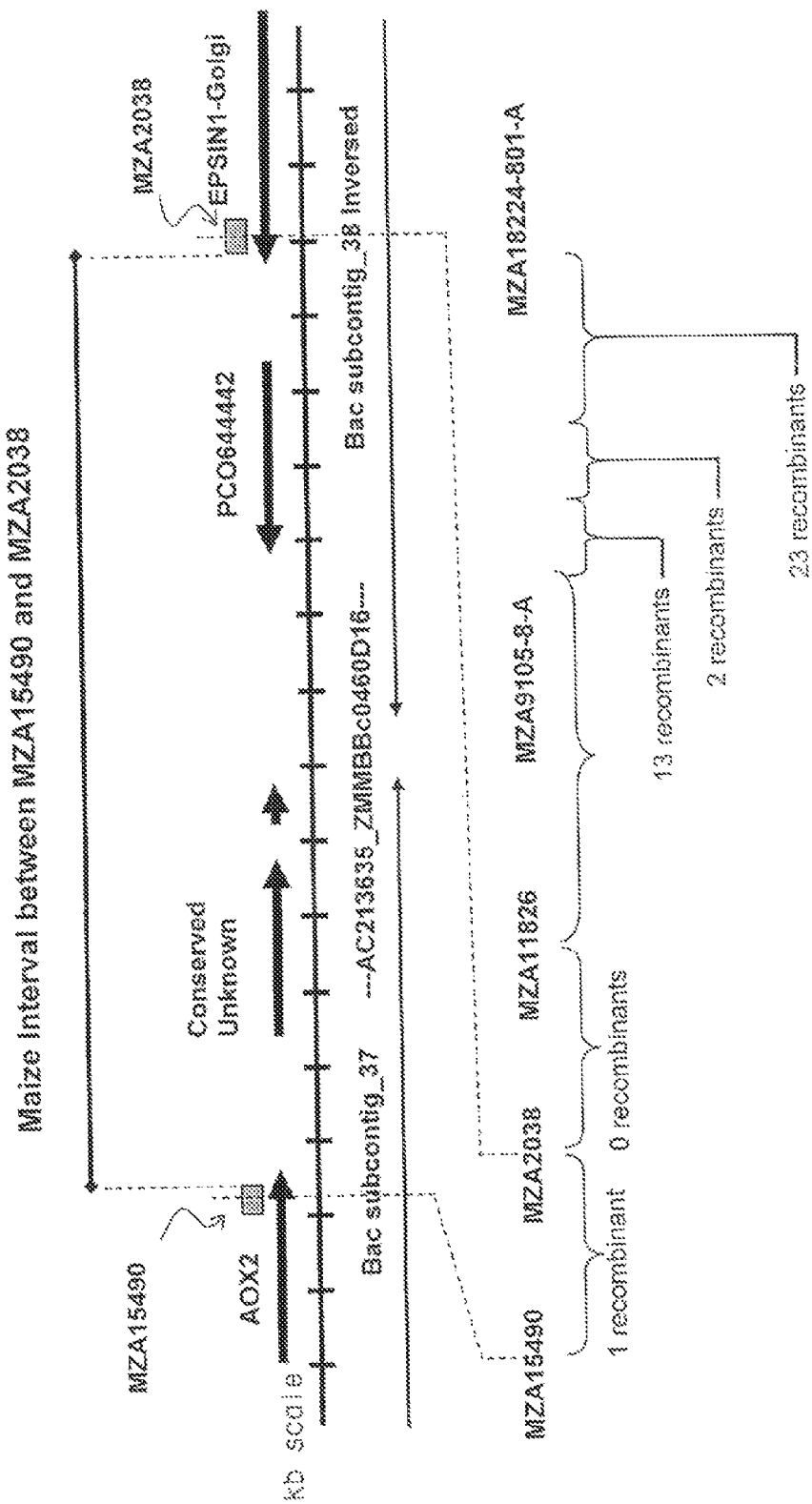
FIG. 6 shows the chromosome 2 QTL region between markers MZA15490 and MZA2038.

PCO644442 (FIG. 6, a putative Myb transcription factor) appears to be the likeliest candidate gene for the resistance to MRCV disease. Sequences closely linked to PCO644442 should be also considered as targets for gene cloning, including the putative EPSIN1 and flanking sequences of the interval MZA11826 to MZA9105.

A single recombinant at MZA15490 to MZA2038 from the cross PH3DT and PH7WT was characterized and the recombination point was located inside the PCO644442. The region from intron 3 of PCO644442 to the PCO644442's promoter sequences are considered key targets for the validation of effects on variations on resistance/susceptibility responses across genotypes. FIG. 8 shows the characterization of the recombinant at MZA15490 to MZA2038; a quimeric PCO644442 was originated from PH3DT and PH7WT genotypes. The sequences at promoter region of PCO644442 of PH3DT (SEQ ID NO:212) and PH7WT (SEQ ID NO:211) are included herein, showing polymorphic sites (see FIGS. 13A-C for sequence alignment).

Example 9

MRDV—Main Hybrids Characterization—Europe

A set of key European genetic materials was phenotypically and genetically characterized to confirm maize genetic marker loci associated with resistance to MRDV. By identifying such genetic markers, marker assisted selection (MAS) can be used to improve the efficiency of breeding for improved resistance of maize to MRDV.

Maize Hybrids and Resistance Scoring

The plant varieties used in the analysis were from diverse sources, including elite germplasm, commercially released cultivars and pre-commercial hybrids representing a broad range of germplasm related to a European breeding program.

The groups of maize hybrids were planted in a field experiment in Spain. The classifications of resistance and susceptible were based solely on observations of fortuitous, naturally occurring disease incidence in field tests. The degree of plant resistance to MRDV infection varied widely, as measured using a scale of incidence of MRDV symptoms.

Data collection was typically done in one scoring time. Scoring time is placed after flowering time.

In assessing association of markers to resistance, a comparison by using the IBD information of parent lines was used. Allele origin was checked by the identity by descent approach. Using this approach, those maize lines that were considered to be representative of either the genotypic classes were used for assessing association and predict performance at hybrid level.

Maize Genotyping

Each parent line of these hybrids has been genotyped and IBD calculations have been estimated for each line.

The underlying logic is that markers with significantly different allele distributions between the resistant and susceptible groups (i.e., non-random distributions) might be associated with the trait and can be used to separate them for purposes of marker assisted selection of maize lines with previously uncharacterized or characterized resistance or susceptibility to MRDV. The present analysis examined the IBD information at the genetic position of the region of preferred markers and determined if the allele distribution within the resistant group is significantly different from the allele distribution within the susceptible group. This analysis compares the plants' phenotypic score with the genotypes at the target loci; the genotypes were predicted by IBD.

Results

In order to evaluate the effect of the allelic variation at this QTL at the hybrid level, a set of 212 hybrids (heterogenous genetic backgrounds) was characterized according to the presence of one (heterozygous for the QTL) or two resistant alleles (homozygous for the QTL) from the parent lines. A positive and additive effect of the resistant allele at the major QTL was observed on the hybrid combinations. Table 29 shows the field performance of hybrids with different genotypes at the major QTL. The field performance was characterized as MRDV_score, similar protocol to MRCV score.

TABLE 29

| Hybrid genotype at major QTL | # hybrids | Average of MRDV_score | STD Dev |
|---|---|---|---|
| AA, homozygous susceptible allele | 163 | 4.25 | 0.92 |
| BA, heterozygous, female resistant allele | 37 | 5.45 | 1.01 |
| BB, homozygous resistant allele | 3 | 6.00 | 0.88 |

FIG. 9 shows the performance of maize hybrids under MRDV infection. The field performance expressed as MRDV_score.

Discussion/Conclusions

This example has identified chromosome intervals that correlate with MRDV resistance. Markers that lie within these intervals are useful for MAS, as well as other purposes. The prediction of MRDV increased resistance by using the preferred markers for MRCV resistance indicates that these markers may be used for MAS for different Fijivirus. A positive effect of the preferred markers for resistance to other Fijivirus, such as rice black-streaked dwarf fijivirus, is thus expected.

Example 10

MRCV Resistance Phenotypic Assay

What: A 1-9 score of Mal de Río Cuarto Virus with 1 meaning no resistance (stunted, internodes shortening, no ear), and 9 meaning that the genetic material is resistance to the disease (no symptoms).
When: From flowering through harvest
Check scores of known susceptible lines to see if their present ratings agree with historical ratings.

How:
1. Compare ratings that you would give a few known susceptible lines today with their historical ratings to see if they agree.
2. If the ratings are too high, then there is not enough disease pressure to score this location. However, note any plot that has more disease than the susceptible checks.
3. Score on a plot basis. Plants within a plot may vary in symptoms due to timing of infection or some plants may escape to the disease (natural infection depends on population of vectors).
4. Consider severity of symptoms and frequency of plants with symptoms. Scores of 1-3 are in susceptible category; 4-6 are in resistant category; 7-9 are in highly resistant category.

Description of Field Scores:
a) Scores 1-3. Susceptible category. Symptoms include severe dwarfism, severe internodes shortening, no ears or very poor ear development, premature dead of plants.
b) Scores 4-6. Resistant category. Plants with symptoms as enations and soft internodes shortening. Low frequency of plants with severe symptoms.
c) Scores 7-9. Highly resistant category. Healthy plant. Presence of enations or no symptoms.

What is claimed is:

1. A method of identifying a maize plant or germplasm that displays newly conferred resistance or enhanced resistance to a member of Serogroup 2 of Fijivirus, the method comprising:

a. Isolating nucleic acids from a maize plant or germplasm;

b. analyzing the isolated nucleic acids for the presence of a QTL allele associated with the newly conferred resistance or enhanced resistance to a member of Serogroup 2 of Fijivirus, wherein the presence of said QTL allele is determined by detecting in the maize plant or germplasm a haplotype within a chromosomal interval flanked by and including MZA8381 and MZA18180, wherein said haplotype comprises a "G" at MZA16656-19-A, a "G" at MZA15490-801-A, a "C" at MZA15490-137-A, an "A" at MZA2038-71-A, a "T" at MZA2038-76-A, an "A" at MZA11826-801-A, a "C" at MZA11826-803-A, and an "A" at MZA9105-8-A, and c. selecting said maize plant or germplasm if said QTL allele is detected.

2. The method of claim 1, wherein the haplotype lies within a chromosomal interval flanked by and including MZA4305 and MZA2803.

3. The method of claim 1, further comprising introgressing the haplotype in said maize plant or germplasm into a second maize plant or germplasm to produce an introgressed maize plant or germplasm.

4. The method of claim 1, wherein the member of Serogroup 2 of Fijivirus is Mal de Río Cuarto Virus (MRCV).

5. The method of claim 1, wherein the member of Serogroup 2 of Fijivirus is Maize Rough Dwarf Virus (MRDV).

* * * * *

```
                            SEQUENCE LISTING

<160> NUMBER OF SEQ ID NOS: 237

<210> SEQ ID NO 1
<211> LENGTH: 510
<212> TYPE: DNA
<213> ORGANISM: Zea mays

<400> SEQUENCE: 1
ggtttccccc aggtccagtt agttgttcat ggtggagtga taaatatatc agagcatctt      60
ttgcctcttc ccccagtttt tgtcgcacat ccctgacagt tctgtttgtg cagcccctga     120
tgacgcaacc tctaatgata aggaagacaa caagcccgag ccttgagatg tcagcaagat     180
tgatggttgc taacaatgac cttgtgctgt ttcttaccgg gttttgacgt gttggatttg     240
tgattaccac tgattgctat tgtacttcaa acaggaaggc tggaaatgca actcggcttc     300
tcttgagacc ttgtcatttg ctgtagttcg ttcgcaactg tatattgtag cttggaagac     360
tctgtgccgt ggtgcgtgta tttgagaaat ttctatgcaa agtgagctgg cgataacatt     420
ggatggcgca gcaaagcatc gcgcgcagtg tttcctaggc atcatccagt gcggctcgtg     480
gatcctttat ggtcatagct ggtccctccc                                      510

<210> SEQ ID NO 2
<211> LENGTH: 694
<212> TYPE: DNA
<213> ORGANISM: Zea mays

<400> SEQUENCE: 2
ttgggttaaa tctggggttt aaatttgtaa gcttaatcaa ggataagggg ttcaacatcc      60
agtcatccag tattgattat ggtgatagta tttgcttttg atgagtagaa gatgcacgtt     120
gatgcatgta tattcaatta gtttctgtta aaacattgct acaataggag agtctggagg     180
tagttactgc atctttgctt ggtgactcca gcttctcatg accttgctaa actgatatat     240
cttgtttagg tacccgaact tgaagagtgt cagggagttg atctacaaga ggggctacgg     300
```

```
aaaactgaac aagcagagga tccctctgtc taacaaccaa gtcatcgagg aggtttgcaa      360
tcttgaactc tgcacctgga tcctttgtga tctgtttgta tttgacaatt tacatgatga      420
tctccaccat ttggtgttct atcagggctt gggcaagcac aacatcatct gtattgagga      480
tcttgttcac gagatcatga ctgttggccc acacttcaag gaggcgaaca acttcctttg      540
gccatttaag ctgaaggcac cgctgggagg tctgaagaag aagaggaacc actatgtgga      600
gggtggtgat gccggtaacc gtgagaatta catcaacgag ctcatcaaaa ggatgaatta      660
gttcacgatc aagctctatg actttccgta aata                                 694

<210> SEQ ID NO 3
<211> LENGTH: 532
<212> TYPE: DNA
<213> ORGANISM: Zea mays

<400> SEQUENCE: 3
tatatttytt tttttctaag gttgattgga taaaaggggg atgcaggtct tgacagcaat       60
gggttgcact cactaaggag aacagtggca gggcatcacc aactaaacag caccagcagt      120
ataagaagaa gccttttgctg aagagattcg gtggtctgct aaaaaagaaa agcgaaaatt     180
agcataaaac cgtctgatga tattctttgt tctatcattt gacatttctt tgattagata     240
tctagttccc gagtcttccc ccatattatg gtaaactaag tgatggatgc ttcaaagaat     300
acaaaatgtc gactttattt acataattgc ctctcttgag ttagggagtg ttcgcagttc     360
agttcagctg tctggtgtga gctgtcggaa acagttgtg agctgcctgc tgtgaaaaac      420
tgttgtgagt aaactaaaag aaagtctttg gttggagctt cggtaaaaca ttagattttt     480
tatgatttat ctgtattgct tctgagattg ttatggtcaa cctgtccctt cc             532

<210> SEQ ID NO 4
<211> LENGTH: 522
<212> TYPE: DNA
<213> ORGANISM: Zea mays

<400> SEQUENCE: 4
aaagacccat agaacgttgt gctgtgggag ctcataactg gcatgctccc ttttgctaat       60
atgacagcag tgcaggctgc tttcgctgtg gtgaacaagg gtgtccgccc agctataccc      120
caggactgcc tgcccaccct tgctgagatc atgaccaggt gctgggatcc aaatcctgat      180
gtccgtccgc cattcactga agttgtgagg atgctggagc atgctgagat ggagatcctg      240
agcactgtcc gcaaggcccg atttcggtgt tgcatgtccc aaccgatgac taccgactga      300
atcaaacaag agagttgaaa tgaactccat ggaagcgtaa ttgagtgtat ttatcatgtg      360
tccaaacttc gctcagctga agtagaaagc cacctgagt ttatggctgt atgtgtgtat       420
actcaggtgt aagccttgtt gtctttgaaa tattcctgca cttagaatat acctagttcg      480
cgttttcaga ctcttgagat gttttaggct atctattcct ga                        522

<210> SEQ ID NO 5
<211> LENGTH: 652
<212> TYPE: DNA
<213> ORGANISM: Zea mays

<400> SEQUENCE: 5 ttttttttacc cctgccctttt ataccccgaa tcgagcagat agctgatctg attggggatg       60
ctggcaacac agtatgctcc ggaacttggt ccaccatagc tgagcttttc tttaatcgtt      120
gattattatg accgtaactt ccgttatctc aattttctat ctgaagtttg agctcctgaa      180
```

```
aaatttagg aacgacaaga tgtctataag ccggcaataa tttttcgtat cctgtaggga      240
tcatcaaggc tcacattctg tatcggtgga ccatacggtc tcgggttaca agtgcgagag      300
cgtgcagatg caacgattag gctgtcctca ctagttttga accatcaagt tgccttgata      360
gtcctcatgg agcagctcta caggtaagca attagcctat ctgatgctgt ttctgcactt      420
accacagttt ctgtggagca tacccctta tggctgtatg cctatggta tgagaaaggc      480 acaatgtaac actaccattt aaataccttc tttcaactat gaccggtcac tagtgacaat      540
tgcattaatt ttgcagggca tggactataa taaagggaca gaagtatcac cattaggcct      600
aagtgctatc atcattcgct gctgtttagg acttggaaaa tggaaaactg cc              652

<210> SEQ ID NO 6
<211> LENGTH: 171
<212> TYPE: DNA
<213> ORGANISM: Zea mays
<220> FEATURE:
<221> NAME/KEY: misc_feature
<222> LOCATION: (62)..(62)
<223> OTHER INFORMATION: n is unknown

<400> SEQUENCE: 6
gccggcaaga tcgagaaygt ccccgccccg gccatcgcca tcgactastg gcgcctcccc      60
gntaacgcca cgctcaagga cgtmgtcacc gtcgtscgcg ccgacgaggc tcaccaccgc     120
gacgtcaacc actttgcatc ggtacggrta cttccraatt ccaataccag c             171

<210> SEQ ID NO 7
<211> LENGTH: 280
<212> TYPE: DNA
<213> ORGANISM: Zea mays

<400> SEQUENCE: 7
ccgatgcaca acagaaagag gaaagctgat gacaagaaac agcaacatca aagaatgtct      60
gagaagtcaa gaacrggaat ttcgagcatc catgaactgc tgcaggattt cctggtgcag     120
caacagcaca ttgatgtccg gtggcgggag atgatcgaga acgygccca ggagcgggtg     180 gttttygaac aacaatggyg gctgacaatg cagaggctgg agcaggagcg gttgttgctg     240
gaacactcst ggatggaacg ggaggagcga agaaggatga                          280

<210> SEQ ID NO 8
<211> LENGTH: 480
<212> TYPE: DNA
<213> ORGANISM: Zea mays

<400> SEQUENCE: 8
ggaaaatccc agtcagaacg ctgaatctgg agtttctgtc aaaacgaaac tgaagcgacc      60
tggtggtgac tggtcatctc gggagtctga cgacaaggac gatgatggtg aagaaagtga     120
tgatgagaag ccgatgcaca acagaaagag gaaagctgat gacaagaaac agcaacatca     180
aagaatgtct gagaagtcaa gaacaggaat ttcgagcatc catgaactgc tgcaggattt     240
cctggtgcag caacagcaca ttgatgtccg gtggcgggag atgatcgaga acgtgcccca     300
ggagcgggtg gttttcgaac aacaatggcg gctgacaatg cagaggctgg agcaggagcg     360
gttgttgctg gaacactcgt ggatggaacg ggaggagcga agaaggatga gagaagaagc     420
acgagctgaa aaaaggatgc actcctgacc actctgtgaa caaactcctg cagaatatta     480

<210> SEQ ID NO 9
```

<211> LENGTH: 643
<212> TYPE: DNA
<213> ORGANISM: Zea mays

<400> SEQUENCE: 9

```
cacatactca catttcaggc acgtcttcgc tacatctaac cctgtaccaa caaaccaaag    60
gtattgccac ctaagacctt gtttgtttac accaatccag ctctggatta gaatggattg   120
gaattaaatc catgtcccaa ataaaccaag cctactcaat ttttttttatt tggctaaacc  180
catcatgaat tataacccaa gggtttatga ttttttttaaa ctatggaagg tatggattct  240
atccataact cattaggtat ggaacaaatc catgaagata ttgcacaagt ttatattaga   300
actgaaactg aaaggcaata taggcatata gcactatagc agaactgaaa ctgaaatatt   360
gaatacaagg ctacaatcag taatgcagta cctactacct agagcatatc atcatccaag   420
caaaaagcag cagcagcttc tccaacatat tcagattcat cagaattcag acaataggaa   480
agataggaaa gggggagaag gggggaacct tgagatgagg agctcatctc gtcgctagtg   540
ttctggagcc gccgccggtg ttctggagct actgctggtg ttctaaagcc gcagcctgtg   600
ttctggactc ggcaaagggg aaaaatttca agggttaaaa ggg                     643
```

<210> SEQ ID NO 10
<211> LENGTH: 694
<212> TYPE: DNA
<213> ORGANISM: Zea mays

<400> SEQUENCE: 10

```
gaccccctaat tttctcgtga ctttgaattt gtgggaccta tgaatttgtg caggaactgg    60
gggaggaggg tgacttcgtt tctatttggg gaacactgct cgcgtcctgc aaagcacagg   120
acaagcagga attggtgaat ttggtgacag agagattgat ctgcattgag aagaagtatg   180
gccatgctgg ttacagcgtt ttgttgtcac atattttgc tgctgagggc aactggagta    240
gtgctgatag cctgaggaag gagatgaggt tgagaggatt gagcaagatg gcaggttcta   300
gttggattaa agtccagcat gcagcattgc aaagctaccc taaaaatggc catgaacact   360
cattactgca tgtagttgat tacggtagag atgaaatcat ctgacatgaa tcagtactgc   420
agcagtggaa agcttgctga tctggtgttt gttcatgtcc catgacgtga tcagctcagg   480
ctatgacaga ttggccttttt ggttatctgc agcattgaca ccttgtcacc ttgacgaaat   540
tggggcattt cggaacattt acatatatat gaacaacaaa ctgaactccc gcactactcg   600
taagcggtga ataacccctg caggttaaaa ccctgatggc ctggacctgg atgcagtcat   660
gcaggaagga tatcgcatta gttgaatact taaa                               694
```

<210> SEQ ID NO 11
<211> LENGTH: 710
<212> TYPE: DNA
<213> ORGANISM: Zea mays

<400> SEQUENCE: 11

```
ttaagggccg gaaggcaagc caaggggttg ttgttcgaaa cggtggcggc cgtgccgggc    60
atggtgggcg gcatgttctt caacctgggt tcgttccgcc gtttcgagca cagcggcggc   120
tggatccgcg cgctgctcga ggaggccgag aacgagcgca tgcacctcat gacgttcctc   180
gaggtcacgc agccgcgctg gtgggagcgc gcgctcgtgc tcaccgcgca gggcgtcttc   240
ttcaacgcct acttcgtcgg ctacctcctc tcccccaagt tcgcgcaccg cgtcgtcggc   300
tacctcgagg aggaggcagt gcactcgtac accgagtacc tcaaggacct cgaggccggc   360
```

```
atcatcgaca acaccccggc gccggccatc gccatcgact actggcgcct cccgccgac     420 gccaagctca aggacgtcgt caccgtcgtg cgcgccgacg aggcgcacca ccgcgacgtc    480
aaccacttcg cgtcggtacg cactctgcac cttgcaacag gattcattgc tgtgagcaat    540
ctccagcagt tctagctaat tcattggttt atgtttgctt aatggagtac attattttgc    600
aggacatcca ttaccagggg atgaagctca aggacacgcc cgcaccgctc agttatcact    660
gacaagtagg cgttgcctgc ctgctgctca attcggaagt tggttaaaaa               710
```

<210> SEQ ID NO 12
<211> LENGTH: 423
<212> TYPE: DNA
<213> ORGANISM: Zea mays

<400> SEQUENCE: 12

```
tagggtacat ggaccctgrg tacttccaga caagccaact gactgagaag agtgatgtst    60
acagctttgg cgtcgtactc atcgagctac tgacaagraa gaagcctatc atggatgata   120
tcrcggaaga cattagaagc ctagcgctgc aatttagtat gctattccat ggaartaagc   180
tgttggaaat cgttgatcct gtagtagctg aagaagctgg agtcagacat gttgaaacgg   240
tttcgaagtt ggcgttacga tgcttaaggt tgaaagggga agaacgccca aggatgatag   300
atgttgcgat tgaacttgaa gcactgagaa ggctgatgaa acaacacttc atcttgaaga   360
acgagtcttt gcttcaggag tyatgttgca atgaagaaat gagcatcgac gcaccatcaa   420
gtt                                                                  423
```

<210> SEQ ID NO 13
<211> LENGTH: 423
<212> TYPE: DNA
<213> ORGANISM: Zea mays

<400> SEQUENCE: 13

```
tagggtacat ggaccctgrg tacttccaga caagccaact gactgagaag agtgatgtst    60
acagctttgg cgtcgtactc atcgagctac tgacaagraa gaagcctatc atggatgata   120
tcrcggaaga cattagaagc ctagcgctgc aatttagtat gctattccat ggaartaagc   180
tgttggaaat cgttgatcct gtagtagctg aagaagctgg agtcagacat gttgaaacgg   240
tttcgaagtt ggcgttacga tgcttaaggt tgaaagggga agaacgccca aggatgatag   300
atgttgcgat tgaacttgaa gcactgagaa ggctgatgaa acaacacttc atcttgaaga   360
acgagtcttt gcttcaggag tyatgttgca atgaagaaat gagcatcgac gcaccatcaa   420
gtt                                                                  423
```

<210> SEQ ID NO 14
<211> LENGTH: 503
<212> TYPE: DNA
<213> ORGANISM: Zea mays

<400> SEQUENCE: 14

```
aaagggaag gtcccagtca caacgtacat tagtgcaagg gacactaggg tacatggacc     60
ctgagtactt ccagacaagc caactgactg agaagagtga tgtgtacagc tttggcgtcg   120
tactcatcga gctactgaca aggaagaagc ctatcatgga tgatatcacg aagacatta    180 gaagcctagc gctgcaattt agtatgctat tccatggaaa taagctgttg gaaatcgttg   240
atcctgtagt agctgaagaa gctggagtca gacatgttga aacggtttcg aagttggcgt   300
```

```
tacgatgctt aaggttgaaa ggggaagaac gcccaaggat gatagatgtt gcgattgaac    360
ttgaagcact gagaaggctg atgaaacaac acttcatctt gaagaacgag tctttgcttc    420
aggagtcatg ttgcaatgaa gaaatgagca tcgacgcacc atcaagtttg ttccttgcgt    480
taatgcattt acttttcggt ata                                            503
```

```
<210> SEQ ID NO 15
<211> LENGTH: 613
<212> TYPE: DNA
<213> ORGANISM: Zea mays
<220> FEATURE:
<221> NAME/KEY: misc_feature
<222> LOCATION: (2)..(4)
<223> OTHER INFORMATION: n is unknown
<220> FEATURE:
<221> NAME/KEY: misc_feature
<222> LOCATION: (10)..(10)
<223> OTHER INFORMATION: n is unknown

<400> SEQUENCE: 15
```

```
annnggcttn acgacttacc catacctcgt tacaccgccg ccgccgtcac cgtaccaacc     60
tactcgtacc cgccgccgcc gcagccgcag ccgcggccac accagcaagc agaactagca   120
gccatgccgc ccaaattgga cccctctcag gtggtggagg tcttcgtccg cgtgacggga   180
ggcgaggtcg gcgcggcgtc gtcgctggcc cccaagatcg gcccgctcgg tctctccccg   240
aagaagatcg gcgaggacat cgccaaggag accgccaagg actggaaggg cctccgcgtc   300
accgtcaagc tcaccgtgca gaaccggcag gccaaggtct ccgtcgtccc ctccgccgcg   360
gcgctcgtca tcaaggcgct caaggaaccc gagagggaca ggaagaaggt caagaacatc   420
aagcacagcg gcaacatcag cctcgacgac gtcatcgaga tcgccaagac catgcggaac   480
aggtccatgg ccaaggagtt ggccgggact gtcaaggaga tcctggggac ctgcgtcagc   540
gtcgggtgca ctgtcgatgg gaaggacccc aaggacttgc agcaggagat cgatatggtc   600
atagcttgct ctt                                                      613
```

```
<210> SEQ ID NO 16
<211> LENGTH: 469
<212> TYPE: DNA
<213> ORGANISM: Zea mays
<220> FEATURE:
<221> NAME/KEY: misc_feature
<222> LOCATION: (306)..(306)
<223> OTHER INFORMATION: n is unknown
<220> FEATURE:
<221> NAME/KEY: misc_feature
<222> LOCATION: (311)..(311)
<223> OTHER INFORMATION: n is unknown
<220> FEATURE:
<221> NAME/KEY: misc_feature
<222> LOCATION: (316)..(316)
<223> OTHER INFORMATION: n is unknown
<220> FEATURE:
<221> NAME/KEY: misc_feature
<222> LOCATION: (322)..(323)
<223> OTHER INFORMATION: n is unknown
<220> FEATURE:
<221> NAME/KEY: misc_feature
<222> LOCATION: (326)..(327)
<223> OTHER INFORMATION: n is unknown
<220> FEATURE:
<221> NAME/KEY: misc_feature
<222> LOCATION: (404)..(404)
<223> OTHER INFORMATION: n is unknown
<220> FEATURE:
<221> NAME/KEY: misc_feature
<222> LOCATION: (421)..(424)
<223> OTHER INFORMATION: n is unknown
```

```
<220> FEATURE:
<221> NAME/KEY: misc_feature
<222> LOCATION: (437)..(438)
<223> OTHER INFORMATION: n is unknown

<400> SEQUENCE: 16
tgacaagctg cagcgaagaa ggtgaaccta gctgatattg gcatcgtcgg tggccttggc     60
gatgggtccg atgagaagrc mctgccctct tggaccatgg gcgccgkatc cggcctagga    120
atgtctggta ttccaccgtc aacacaacaa gctggtggca tcgagagctt ggccaactac    180
aacaagcatc atttcggctt caaataggcc tcgatctttc atactggaaa atacccgtca    240
tctgcggttt cctcctcwgt cggcctgctt cttacaygtg ctgccctatt gatttaatca    300
cttttntttg nttttntggt tnnttnnggt gatyacatta catggtrtcg accaatcttg    360
gccccgtctt gtcacrcgtg tatgttattt gtcgggtttg tggntaagca tgcaactaca    420
nnnncatcac accccnnkt gttccagytc gatrataggt ggyatgttg               469

<210> SEQ ID NO 17
<211> LENGTH: 469
<212> TYPE: DNA
<213> ORGANISM: Zea mays
<220> FEATURE:
<221> NAME/KEY: misc_feature
<222> LOCATION: (306)..(306)
<223> OTHER INFORMATION: n is unknown
<220> FEATURE:
<221> NAME/KEY: misc_feature
<222> LOCATION: (311)..(311)
<223> OTHER INFORMATION: n is unknown
<220> FEATURE:
<221> NAME/KEY: misc_feature
<222> LOCATION: (316)..(316)
<223> OTHER INFORMATION: n is unknown
<220> FEATURE:
<221> NAME/KEY: misc_feature
<222> LOCATION: (322)..(323)
<223> OTHER INFORMATION: n is unknown
<220> FEATURE:
<221> NAME/KEY: misc_feature
<222> LOCATION: (326)..(327)
<223> OTHER INFORMATION: n is unknown
<220> FEATURE:
<221> NAME/KEY: misc_feature
<222> LOCATION: (404)..(404)
<223> OTHER INFORMATION: n is unknown
<220> FEATURE:
<221> NAME/KEY: misc_feature
<222> LOCATION: (421)..(424)
<223> OTHER INFORMATION: n is unknown
<220> FEATURE:
<221> NAME/KEY: misc_feature
<222> LOCATION: (437)..(438)
<223> OTHER INFORMATION: n is unknown

<400> SEQUENCE: 17
tgacaagctg cagcgaagaa ggtgaaccta gctgatattg gcatcgtcgg tggccttggc     60
gatgggtccg atgagaagrc mctgccctct tggaccatgg gcgccgkatc cggcctagga    120
atgtctggta ttccaccgtc aacacaacaa gctggtggca tcgagagctt ggccaactac    180
aacaagcatc atttcggctt caaataggcc tcgatctttc atactggaaa atacccgtca    240
tctgcggttt cctcctcwgt cggcctgctt cttacaygtg ctgccctatt gatttaatca    300
cttttntttg nttttntggt tnnttnnggt gatyacatta catggtrtcg accaatcttg    360
gccccgtctt gtcacrcgtg tatgttattt gtcgggtttg tggntaagca tgcaactaca    420
nnnncatcac accccnnkt gttccagytc gatrataggt ggyatgttg               469
```

<210> SEQ ID NO 18
<211> LENGTH: 704
<212> TYPE: DNA
<213> ORGANISM: Zea mays

<400> SEQUENCE: 18

| ccaatcagag | agcctagggc | aaagaaagac | aattttcagg | tcaagtccgg | catatgggca | 60 |
| aactcgctga | gccggggatt | gattgatctg | aacataactg | cacgtatgtt | cctcgttcct | 120 |
| gtttcccctg | ttgccatggc | atctatcagc | ttggtgtaaa | tttgtttatg | gttcagacat | 180 |
| gttcatggtt | ctccttgttt | ctgacaagct | gcagcgaaga | aggtgaacct | agctgatatt | 240 |
| ggcatcgtcg | gtggccttgg | cgatgggtcc | gatgagaagg | ccctgccctc | ttggaccatg | 300 |
| ggcgccggat | ccggcctagg | aatgtctggt | attccaccgt | caacacaaca | agctggtggc | 360 |
| atcgagagct | tggccaacta | caacaagcat | catttcggct | tcaaataggc | ctcgatcttt | 420 |
| catactggaa | aatacccgtc | atctgcggtt | tcctcctctg | tcggcctgct | tcttacatgt | 480 |
| gctgccctat | tgatttaatc | acttttttg | ttttggttt | tggtgattac | attacatggt | 540 |
| gtcgaccaat | cttggccccg | tcttgtcacg | cgtgtatgtt | atttgtcggg | tttgtgggta | 600 |
| agcatgcaac | tacatacaca | tcacaccccc | tgtgttccag | ctcgatgata | ggtggtatgt | 660 |
| tggccatgca | gtttgtgaaa | ttccggccga | acttggttat | ttaa | | 704 |

<210> SEQ ID NO 19
<211> LENGTH: 406
<212> TYPE: DNA
<213> ORGANISM: Zea mays
<220> FEATURE:
<221> NAME/KEY: misc_feature
<222> LOCATION: (123)..(126)
<223> OTHER INFORMATION: n is unknown
<220> FEATURE:
<221> NAME/KEY: misc_feature
<222> LOCATION: (174)..(176)
<223> OTHER INFORMATION: n is unknown

<400> SEQUENCE: 19

| cagcaacgtt | agcgacctgg | aagccacgga | gtggatcgag | gargacgagc | cgggcgtgtg | 60 |
| cctcaccatc | cgcgagctcg | gcgayggcac | ycgcgarctc | cgccgcatcc | ggttcaggta | 120 |
| tgnnnngcac | tgaycagtca | tggacatgcg | gaagcataca | tcactggytc | agtnnnaacc | 180 |
| aaaatccttc | ttgatcactc | ggttcattca | tgtgatcatg | tctgttccat | gtttctgtgr | 240 |
| tgctgcagcc | gggagatatt | cggcgaggat | agggccaagg | tgtggtggga | gcagaacagg | 300 |
| gagagaatac | aggcggaata | tctgtagcaa | gcgatcagac | actgagctga | tgcaattttc | 360 |
| aggcctgatg | ggataatcaa | atatgtttgt | gagaggatag | attagg | | 406 |

<210> SEQ ID NO 20
<211> LENGTH: 372
<212> TYPE: DNA
<213> ORGANISM: Zea mays
<220> FEATURE:
<221> NAME/KEY: misc_feature
<222> LOCATION: (153)..(155)
<223> OTHER INFORMATION: n is unknown

<400> SEQUENCE: 20

| gccacggagt | ggatcgagga | rgacgagccg | ggcgtgtgcc | tcaccatccg | cgagctcggc | 60 |
| gayggcacyc | gcgarctccg | ccgcatccgg | ttcaggtatg | catggcactg | atcagtcatg | 120 |
| gacatgcgga | agcatacatc | actggctcag | tannnaccaa | aatccttctt | gatcactcgg | 180 |

```
ttcattcatg tgatcatgtc tgttccatgt ttctgtgrtg ctgcagccgg gagatattcg    240
gcgaggatag ggccaaggtg tggtgggagc agaacaggga gagaatacag gcggaatatc    300
tgtagcaagc gatcagacac tgagctgatg caattttcag gcctgatggg ataatcaaat    360
atgtttgtga ga                                                        372

<210> SEQ ID NO 21
<211> LENGTH: 582
<212> TYPE: DNA
<213> ORGANISM: Zea mays

<400> SEQUENCE: 21
ccaagtcaaa aagctcaact ccgctgctgc ggcggccggc acgtcagctg cgatgggcgg     60
cggggccccg tcgtcctacg acccgtcgcg cgccaccacg tcgtccaggg acgaggcctc    120
cgtgtccctc agcaacgtta gcgacctgga agccacggag tggatcgagg aggacgagcc    180
gggcgtgtgc ctcaccatcc gcgagctcgg cgacggcact cgcgagctcc gccgcatccg    240
gttcaggtat gcatggcact gatcagtcat ggacatgcgg aagcatacat cactggctca    300
gtagtaacca aaatccttct tgatcactcg gttcattcat gtgatcatgt ctgttccatg    360
tttctgtgat gctgcagccg ggagatattc ggcgaggata gggccaaggt gtggtgggag    420
cagaacaggg agagaataca gcggaatat ctgtagcaag cgatcagaca ctgagctgat     480
gcaattttca ggcctgatgg gataatcaaa tatgtttgtg agaggataga ttagggagat    540
gataccgcta tatacatgta aaaccactaa tttggtaaaa aa                       582

<210> SEQ ID NO 22
<211> LENGTH: 171
<212> TYPE: DNA
<213> ORGANISM: Zea mays
<220> FEATURE:
<221> NAME/KEY: misc_feature
<222> LOCATION: (62)..(62)
<223> OTHER INFORMATION: n is unknown

<400> SEQUENCE: 22
gccggcaaga tcgagaaygt ccccgccccg gccatcgcca tcgactastg gcgcctcccc     60
gntaacgcca cgctcaagga cgtmgtcacc gtcgtscgcg ccgacgaggc tcaccaccgc    120
gacgtcaacc actttgcatc ggtacggrta cttccraatt ccaataccag c             171

<210> SEQ ID NO 23
<211> LENGTH: 171
<212> TYPE: DNA
<213> ORGANISM: Zea mays
<220> FEATURE:
<221> NAME/KEY: misc_feature
<222> LOCATION: (62)..(62)
<223> OTHER INFORMATION: n is unknown

<400> SEQUENCE: 23
gccggcaaga tcgagaaygt ccccgccccg gccatcgcca tcgactastg gcgcctcccc     60
gntaacgcca cgctcaagga cgtmgtcacc gtcgtscgcg ccgacgaggc tcaccaccgc    120
gacgtcaacc actttgcatc ggtacggrta cttccraatt ccaataccag c             171

<210> SEQ ID NO 24
<211> LENGTH: 171
<212> TYPE: DNA
<213> ORGANISM: Zea mays
<220> FEATURE:
```

```
<221> NAME/KEY: misc_feature
<222> LOCATION: (62)..(62)
<223> OTHER INFORMATION: n is unknown

<400> SEQUENCE: 24
gccggcaaga tcgagaaygt ccccgccccg gccatcgcca tcgactastg gcgcctcccc    60
gntaacgcca cgctcaagga cgtmgtcacc gtcgtscgcg ccgacgaggc tcaccaccgc   120
gacgtcaacc actttgcatc ggtacggrta cttccraatt ccaataccag c            171

<210> SEQ ID NO 25
<211> LENGTH: 557
<212> TYPE: DNA
<213> ORGANISM: Zea mays

<400> SEQUENCE: 25
ggatwagggg agggtcccag tcacgacgat ccactcgtac accgagtacc tcaaggatct    60
ggaggccggc aagatcgaga acgtccccgc cccggccatc gccatcgact actggcgcct   120
ccccgctaac gccacgctca aggacgtagt caccgtcgtc cgcgccgacg aggctcacca   180
ccgcgacgtc aaccactttg catcggtacg gatacttccg aattccaata ccagcagcaa   240
ctctgcttga tctcgctcgc cgggcacgcg tatctcgtta tgggattggt tctgaaatct   300
gaattggtat gagcttgtgc cgtgcaggac atccattgcc agggaatgca gctgaagcag   360 tccccctgcgc cgatcggata ccactgagga agtgatgctg tttgtgctct cttaattt    420 gcatcgctaa taagcaaatg agtgtcttgt ctttaaggga aggaaaggat gcttattgag   480
ttacgagtac tgctacggcg attaggagga tattttccaa acccagtttt tggggaaatt   540
tgtaagtaat aaggtta                                                  557

<210> SEQ ID NO 26
<211> LENGTH: 823
<212> TYPE: DNA
<213> ORGANISM: Zea mays
<220> FEATURE:
<221> NAME/KEY: misc_feature
<222> LOCATION: (307)..(699)
<223> OTHER INFORMATION: n is unknown

<400> SEQUENCE: 26
attgaaaygc atttgagtga tgagagtatt accttttggg agaagtttga gtcgtttcaa    60
gtctttatgc atgaccaggt gagttagtrg ttttactttt twcctcaatg ccgtgtgaat   120
gtgaggttca tatwttttt tmtgctaatc tttgtagaag gactcaaggg ttattattct   180
attccttgaa agtcttcttt cttggcttga gcgtcgagac cytccagaaa atatggatgt   240
tcaattattc gtagagatca ggcacatatg cagtcaattt caagagaagt atcttaggta   300
tgtttcnnnn nnnnnnnnnn nnnnnnnnnn nnnnnnnnnn nnnnnnnnnn nnnnnnnnnn   360
nnnnnnnnnn nnnnnnnnnn nnnnnnnnnn nnnnnnnnnn nnnnnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn nnnnnnnnnn nnnnnnnnnn nnnnnnnnnn   660
nnnnnnnnnn nnnnnnnnnn nnnnnnnnnn nnnnnnnna gcatttatga wactgtactg   720
gtattataat gcacctactc tctaattagt agttgggtat tagagtgtga tgtttaacta   780
tcagcatcct tctgttgatg catgaagtat tcttgtaaaa gtt                     823
```

<210> SEQ ID NO 27
<211> LENGTH: 823
<212> TYPE: DNA
<213> ORGANISM: Zea mays
<220> FEATURE:
<221> NAME/KEY: misc_feature
<222> LOCATION: (294)..(686)
<223> OTHER INFORMATION: n is unknown
<220> FEATURE:
<221> NAME/KEY: misc_feature
<222> LOCATION: (687)..(699)
<223> OTHER INFORMATION: n is a, c, g, or t
<220> FEATURE:
<221> NAME/KEY: misc_feature
<222> LOCATION: (729)..(730)
<223> OTHER INFORMATION: n is unknown
<220> FEATURE:
<221> NAME/KEY: misc_feature
<222> LOCATION: (742)..(743)
<223> OTHER INFORMATION: n is a, c, g, or t

<400> SEQUENCE: 27

```
attgaaaygc atttgagtga tgagagtatt acctttgggg agaagtttga gtcgtttcaa     60
gtctttatgc atgaccaggt gagttagtrg ttttactttt twcctcaatg ccgtgtgaat    120
gtgaggttca tatawttttt tmtgctaatc tttgtagaag gactcaaggg ttattattct    180
attccttgaa agtcttcttt cttggcttga gcgtcgagac cytccagaaa atatggatgt    240
tcaattattc gtagagatca ggcacatatg cagtcaattt caagagaagt atcttaggta    300
tgtttcnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnna gcatttatga wacygtwctg    720
gtattatart gcacstactc tnnaattagt agttgggtat tagagtgtga tgtttaacta    780
tcagcatcct tctgttgatg catgaagtat tcttgtaaaa gtt                      823
```

<210> SEQ ID NO 28
<211> LENGTH: 823
<212> TYPE: DNA
<213> ORGANISM: Zea mays
<220> FEATURE:
<221> NAME/KEY: misc_feature
<222> LOCATION: (307)..(699)
<223> OTHER INFORMATION: n is uknown
<220> FEATURE:
<221> NAME/KEY: misc_feature
<222> LOCATION: (742)..(743)
<223> OTHER INFORMATION: n is uknown

<400> SEQUENCE: 28

```
attgaaaygc atttgagtga tgagagtatt acctttgggg agaagtttga gtcgtttcaa     60
gtctttatgc atgaccaggt gagttagtrg ttttactttt twcctcaatg ccgtgtgaat    120
gtgaggttca tatawttttt tmtgctaatc tttgtagaag gactcaaggg ttattattct    180
attccttgaa agtcttcttt cttggcttga gcgtcgagac cytccagaaa atatggatgt    240
tcaattattc gtagagatca ggcacatatg cagtcaattt caagagaagt atcttaggta    300
```

```
tgtttcnnnn nnnnnnnnnn nnnnnnnnnn nnnnnnnnnn nnnnnnnnnn nnnnnnnnnn    360
nnnnnnnnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn nnnnnnnnnn nnnnnnnnnn nnnnnnnnna gcatttatga wacygtwctg    720
gtattatart gcacstactc tnnaattagt agttgggtat tagagtgtga tgtttaacta    780
tcagcatcct tctgttgatg catgaagtat tcttgtaaaa gtt    823

<210> SEQ ID NO 29
<211> LENGTH: 583
<212> TYPE: DNA
<213> ORGANISM: Zea mays

<400> SEQUENCE: 29
gagatcaggc acatatgcag tcaatttcaa gagaagtatc ttaggtatgt ttctgtcaag     60
ggcgttaaac ccttggctgg ctggaccgcg gctacggagc tcgtagccgt cggccgtctt    120
ctccggtgag gttattcccc tctaccgtag gctttagaaa ataagagaga gagatgaggc    180
taataatctg cttgctttaa tggtcctggt tacaagaata tataggggcca tagcccaact    240 aactggagta acaaactcct gaaattatgg aactgataac tcctaaatcc atctgcctta    300
tctactcgat cagctcgagc cagctgtgcg cgcgtccccc ctggccgcac gttcctctgc    360
tcggcgtacg tccctggccc tgcgcctcct agtgtagact tgtccccaca tgacagtttc    420
agcatttatg aaaccgttct ggtattatag tgcacgtact ctctaattag tagttgggta    480
ttagagtgtg atgtttaact atcagcatcc ttctgttgat gcatgaagta ttcttgtaaa    540
agttttcctg caaaatcagt aattagtatc aatttagggt taa    583

<210> SEQ ID NO 30
<211> LENGTH: 669
<212> TYPE: DNA
<213> ORGANISM: Zea mays

<400> SEQUENCE: 30
gtggaacgtc tcaaaggtaa cagctactat gttcaaaatg gaactgagga ctagtggatg     60
aatccagctg tgtatcttca catgaagaga ctaacgcccc gtttggatcc ttggaattga    120
atttcattct aaaaatcata atttagtcac aaatcaattt aagttaatat ggttttatac    180
ggaatctatt tgtgtaccct attagccata tggggtacat atttatatgc tagaattcta    240
ttatagagta gcgagtcaaa gagtgtgtta taaattgtag agtagaaaca tagcctggag    300
atacataaaa tcaatttcca tccctccact ctatgaattt gagatagact tatatttgaa    360
ctttggaaag tggtaggatg ttaaattcca agctaaatag actactctat taagtaaatt    420
tcgattcctc caaaatgaag ggatccaaac tgcccctaat agaattttgt ttctggctat    480 ttacatttttt aaagttgtgg ttccgttcag gacttcgccc atatacgttt tggtttgtgc    540
tttgaccttt tagttgtgaa cttgtgatta tttcatttat gggattagaa ttattattat    600
taaataacga gattgaataa caagagccat gacttgattg aatttcataa gcgctagcaa    660
attatttgg    669
```

```
<210> SEQ ID NO 31
<211> LENGTH: 359
<212> TYPE: DNA
<213> ORGANISM: Zea mays
<220> FEATURE:
<221> NAME/KEY: misc_feature
<222> LOCATION: (30)..(30)
<223> OTHER INFORMATION: n is unknown
<220> FEATURE:
<221> NAME/KEY: misc_feature
<222> LOCATION: (48)..(48)
<223> OTHER INFORMATION: n is unknown
<220> FEATURE:
<221> NAME/KEY: misc_feature
<222> LOCATION: (50)..(50)
<223> OTHER INFORMATION: n is unknown

<400> SEQUENCE: 31 tagtttttycc ctcttcctaa cgtgtttaan ctcttataag agtgtgtntn catggtccga      60 caaactttg cttcycctca tgagatsatt tgtgcyctta tctctgcaga taaagggcat      120
cagtgagctc ctygagggcc ttattccgta ttcgcagagg catttcagca gagtggacag     180
actagtccga agcacgtttc tgttggacta tacgctgayg cgaatgtccg tggtagaycc     240
agatgtggat gcggggtcaa tcaaagacga aatgaatggt tcgtctgtgg agaacggtga     300
acttgcagag cctcggcctg cttcacctgt gccagagaag tcaagcaaga agagaaaat     359

<210> SEQ ID NO 32
<211> LENGTH: 591
<212> TYPE: DNA
<213> ORGANISM: Zea mays

<400> SEQUENCE: 32
tcatgtttca gttgtgcttt tcgggtattg aggagtttct ctcccactga tatcctggag      60
gtagtagttt ttccctcttc ctaacgtgtt taaactctta taagagtgtg ttcatggtcc     120
gacaaacttt tgcttctcct catgagatga tttgtgctct tatctctgca gataaagggc     180
atcagtgagc tccttgaggg ccttattccg tattcgcaga ggcatttcag cagagtggac     240
agactagtcc gaagcacgtt tctgttggac tatacgctga cgcgaatgtc cgtggtagac     300
ccagatgtgg atgcggggtc aatcaaagac gaaatgaatg gttcgtctgt ggagaacggt     360
gaacttgcag agcctcggcc tgcttcacct gtgccagaga agtcaagcaa gaagagaaaa     420
tctggcaaat caagtaaaaa gggaaggag aaggtgatga agcttgcctc gagtggactt     480
ggcaagggtg tttctgttga agcctgaaaa tctagctgag aatctggttt tgcttatgca     540
tgcatgcatc caattttgta gcagctgttg aaactgactt tctaacatgg t              591

<210> SEQ ID NO 33
<211> LENGTH: 312
<212> TYPE: DNA
<213> ORGANISM: Zea mays

<400> SEQUENCE: 33
tgttgccagg aactcctgga tcagaaactt tcagagagaa gttcatcaag gtcgatgacg      60
aaaactacat caaggagacg gtggtcactg aaggaggcct tctggatcac ggctttcgga     120
agtacatggt tcgaatcgag atcgtgggwa gagaagagaa grcatccatc gtaaggtcra     180
caattcarta cgaagtcgat crtgagcatg caggttcaca cgcaccccct gtgttcagta     240
ccgatgggyt rgctaccatt gccgaggcca tcaccaagya tatcaaggag magagaggct     300
ctgagtccgt aa                                                        312
```

<210> SEQ ID NO 34
<211> LENGTH: 669
<212> TYPE: DNA
<213> ORGANISM: Zea mays

<400> SEQUENCE: 34

```
tcaggaaaat tgccatgag ttggaaaccg ggctcccagc tgccgccgtg tgggaggtca      60
taatggaagc ctcctcttcg ggaaactgat gccccagctg ctccctgaag tggtctcgaa     120
ggttgagctt gtggagggag acggtggcgc tggaacggtc ctgcttgtta ccttccctcc     180
aggttagaag aacaacctga aaacacatac gagcttcttt tgaggtgtgg tacgatgatg     240
cggtctcggt ctcggctcca aacagttttt gctttcttgt ggttcatggc ttcatgcatg     300
ttgccaggaa ctcctggatc agaaactttc agagagaagt tcatcaaggt cgatgacgaa     360
aactacatca aggagacggt ggtcactgaa ggaggccttc tggatcacgg ctttcggaag     420
tacatggttc gaatcgagat cgtgggaaga gaagagaaga catccatcgt aaggtcaaca     480
attcagtacg aagtcgatcg tgagcatgca ggttcacacg caccccctgt gttcagtacc     540
gatgggttgg ctaccattgc cgaggccatc accaagtata tcaaggagaa gagaggctct     600
gagtccgtaa gctctcccaa gtaattaact caagtaattg aactctggaa ttaaaatttg     660
gggtaaaaa                                                             669
```

<210> SEQ ID NO 35
<211> LENGTH: 517
<212> TYPE: DNA
<213> ORGANISM: Zea mays

<400> SEQUENCE: 35

```
ccccaaaaac cccagtcaca acgtgtgccc tctcgtaatc ctcctcgcct gctccacgtc      60
caacgcttcc gtcctacaag acgcgtgcaa gtccttcgcc gctaagatcc cggacaccgg     120
ctacgcctac tgcatcaagt tcttccaggc cgacagggga agcgccggcg cggacaagcg     180
tggcctcgcc gccatcgccg tgaggatcat gggggcagcc gccaagagca ccgccagtca     240
catcgccgcc ctgcgggcct ccgagaagga caaggagcgg ctggcgtgcc tcagcgattg     300
ctccgaggtg tacgcgcagg ccgtggacca gaccggcgtg gcggcgaagg catcgcctc      360
gggcacgccc cggggccgcg cggacgcggt gatggcgctc agcacggtgg aggatgcccc     420
cggcacctgt gagcaggggt tccaggacct gggcgtgcgt tcgccgctgg cctcggagac     480
gccggttccg aagatctcag aatttttga aaaagaa                               517
```

<210> SEQ ID NO 36
<211> LENGTH: 647
<212> TYPE: DNA
<213> ORGANISM: Zea mays

<400> SEQUENCE: 36

```
ccagtcagaa cggaggtttt acttgagaac aagagtaatc tctttctctc tcgcacagtg      60
tgtgtatata tgaaccacct aattaccgct gtagtctctt aatcccatca atcaatcaat     120
ggcgcactgc atgttgacac acgctaatac atacaggtat ctacgaggcc aagacagatc     180
tcggcaagaa cacgtgcacc atcgagggtg tcattgagga ggacaagctc gtcaagtaca     240
tctacgagag gatgcgcaag aagggcgtcg tcgacaaggt cgagaagaag gtgatcatca     300
aggaggagaa ggtcttagtg aagaaggcgg ataaggagaa ggaagaagag gaaggagaa     360
aggagaaaga aaaggagaag gccaaggaga aggtgaagga ggctgtcgac aaggtcaagg     420
```

```
aggtcatcgc ccctacttc atccctgca cgcaccgaa cttcgtcgac tactcgcacc    480
cctggcaccg cggcggcggc ggctactgct cgtcgtacgg tgacggttac ggctacggct    540
acggcggggg ctgcggaggg tacccaccgt acggtttcag ctacacacac tctgagctca    600
aaggctacca tgacacgtcg ttctgcactc acacaacttg ggggtaa                  647
```

<210> SEQ ID NO 37
<211> LENGTH: 589
<212> TYPE: DNA
<213> ORGANISM: Zea mays

<400> SEQUENCE: 37

```
aggatcccag tcaggacgat ggcaggcgga ttctgttaac cactaaagct ggacgtgtcc     60
atgtgctaga ttcattccat ggcaatagcg taagcataca acctactgta ccttgtatct    120
tgcatatacc aacactagta agacatggtt cttatgattc cttttttctt tcagattgcg    180
tcgtgcaatg tgaagccagt ggtaaccaac tcaacactgg aggcgtcgtt cagccctgat    240
ggaaaccata tcatatctgg ttagagacca tccctatcgt gctttacaaa gagttgccat    300
cttctctcct gcttagcaat gcgttatggt cttctcttgc aggctccggt gacggtagtg    360
tttatgcttg gaatgttagg agtggaaagg tgcagaaaga tatatcatgt cgatattgaa    420
atcacttcgt atgttatatc tatttgactt gtatatggta aaacactttg acatgcaggt    480
cgcgcgctgg ggaagcacag acgacgaacc gccgctggta aggtgggctc caggatcctt    540
gatgttcgtg acagatcatc agaactgtca tgctgtactg ggcttatta               589
```

<210> SEQ ID NO 38
<211> LENGTH: 1180
<212> TYPE: DNA
<213> ORGANISM: Zea mays
<220> FEATURE:
<221> NAME/KEY: misc_feature
<222> LOCATION: (1164)..(1164)
<223> OTHER INFORMATION: n is unknown

<400> SEQUENCE: 38

```
tttgattctt gtcaatagca agttcactgc agcaacttt gcaaggacct tttctggttt      60
acatgctaga ggaatcgagc ctggtgttct ttatccagct gtctctgttg agcagtttca    120
cgaaccccat gcttataagt aacttcatgc ttgcatatct ccttacattt aggtctaact    180
tattcagttt atagactaaa cagatctttt taccattatc atattaatat ttagctaaag    240
tagacaacaa tcttttgtac aggttgaatt tcctatcaat caaccggttt gagaggaaaa    300
agaatcttga tcttgccatt tcagcatttg ctttgctccg ttctgctgct tggactctac    360
ctggtgatgc tctacaagaa gcaacattaa cagtggcagg tgtttatatt ttatttttcc    420
ttctagttgc atgttcaatg ttacaacacc accggtttta aaccatatga aatattgact    480
gctgatttcc taccatgcct attatttagg tggctctgat aagcgtctca aggaaaatgt    540
tgaataccct tgaggaactca aaagactcgc attgacggaa ggggtttctg gacaggttaa    600
wtttgttaca tcttgctcaa catctgaaag aaacgagctt ctctccaact gcctctgcgt    660
tttatacact ccaaaggtaa gtgcctaggg cttacatcca gctaagcagt ttgtttacct    720
ttaatttaac aagcctgcgt ctcttatcca ggatgaacat ttcggtattg tacctcttga    780
agccatggcc gcccataagc cggtaattgc ctgcaatagt ggtggcccag tggaaacagt    840
tgtgaatgaa gtaacagggt ttctgtgtga tccctctccc gcagaattct ccaaagccat    900
```

```
gctgaaacttt gtgaatgatc atgatcttgc tgtcagattg ggtgaacaag cacgtgacca    960
tgtggtgcaa aaattctcga ccaagacatt tggtgatctc ctcaacagct acgtcttgaa   1020
catctaccat gagaggatgg aatgatctat aatattgggt cagccatgcc atatgaaaac   1080
aatttgttca atacaaggtt ttttttgcac ctttacgtct aatctgattt tgatggacac   1140
acataatgac aatgacattc catngaatcc ctttggcata                         1180
```

<210> SEQ ID NO 39
<211> LENGTH: 601
<212> TYPE: DNA
<213> ORGANISM: Zea mays
<220> FEATURE:
<221> NAME/KEY: misc_feature
<222> LOCATION: (10)..(10)
<223> OTHER INFORMATION: n is unknown

<400> SEQUENCE: 39

```
cccccaaaan ccccaaaatt ctwraaaaat tccagaacac cttcttttaa gaagcaacat     60
taacagtggc aggtgtttat attttatttt tccttctagt tgcatgttca atgttacaac    120
accaccggtt ttaaaccata tgaaatattg actgctgatt tcctaccatg cccattattt    180
aggtggctat gataagcgtc tcaaggaaaa tgttgaatac cttgaggaac tcaaaagact    240
cgcattgacg gaagggggttt ctggacaggt taattttgtt acatcttgct caacatctga   300
aagaaacgag cttctctcca actgcctctg cgttttatac actccaaagg taagtgccta    360
gtggcttaca tccagctaag cagtttgttt accttaattt aacaagcctg cgtctcttac    420
ttatccagga tgaacatttc ggtattgtac ctcttgaagc catggccgcc ataagccgg     480 taattgcctg caatagtggt ggcccagtgg aaacagttgt gaatgaagta acagggtttc    540
tgtgtgatcc ctctcccgca gaattctcca aagccatgct gaaatggtca tagctgccct    600
t                                                                    601
```

<210> SEQ ID NO 40
<211> LENGTH: 369
<212> TYPE: DNA
<213> ORGANISM: Zea mays
<220> FEATURE:
<221> NAME/KEY: mmisc_feature
<222> LOCATION: (54)..(56)
<223> OTHER INFORMATION: n is unknown
<220> FEATURE:
<221> NAME/KEY: misc_feature
<222> LOCATION: (54)..(56)
<223> OTHER INFORMATION: n is a, c, g, or t
<220> FEATURE:
<221> NAME/KEY: mmisc_feature
<222> LOCATION: (119)..(121)
<223> OTHER INFORMATION: n is unknown
<220> FEATURE:
<221> NAME/KEY: misc_feature
<222> LOCATION: (119)..(121)
<223> OTHER INFORMATION: n is a, c, g, or t
<220> FEATURE:
<221> NAME/KEY: mmisc_feature
<222> LOCATION: (305)..(305)
<223> OTHER INFORMATION: n is unknown
<220> FEATURE:
<221> NAME/KEY: misc_feature
<222> LOCATION: (305)..(305)
<223> OTHER INFORMATION: n is a, c, g, or t

<400> SEQUENCE: 40

```
gcggcggaca tggaactgga ygatgcttca gccgagacac caaccagtgg aacnnntggg     60
aagctgtctt cccatgccgc agaagaagcr gagacatggt gcccgtggct ggtcggtann    120
```

```
ncacagcagt ttctgtacta tctccctcrg ggagaggtgt tctctatgca tcctggttgc    180
cagttcctaa actacggtaa cggaagcata tcctacwcag cgttggacgc acrgacagtt    240
acctcaaaca agcagcggag ccrrccatgg acggagtcga tcgaracctc cagcagcgtg    300
cctgnaacag ctcagaattc aratcctgya gaatctacga aagtaaacag aggtgaagac    360
aaagtggct                                                            369
```

```
<210> SEQ ID NO 41
<211> LENGTH: 462
<212> TYPE: DNA
<213> ORGANISM: Zea mays
<220> FEATURE:
<221> NAME/KEY: misc_feature
<222> LOCATION: (54)..(56)
<223> OTHER INFORMATION: n is unknown
<220> FEATURE:
<221> NAME/KEY: misc_feature
<222> LOCATION: (119)..(121)
<223> OTHER INFORMATION: n is unknown
<220> FEATURE:
<221> NAME/KEY: misc_feature
<222> LOCATION: (305)..(305)
<223> OTHER INFORMATION: n is unknown

<400> SEQUENCE: 41
gcggcggaca tggaactgga ygatgcttca gccgagacac caaccagtgg aacnnntggg     60
aagctgtctt cccatgccgc agaagaagcr gagacatggt gcccgtggct ggtcggtann    120
ncacagcagt ttctgtacta tctccctcrg ggagaggtgt tctctatgca tcctggttgc    180
cagttcctaa actacggtaa cggaagcata tcctacwcag cgttggacgc acrgacagtt    240
acctcaaaca agcagcggag ccrrccatgg acggagtcga tcgaracctc cagcagcgtg    300
cctgnaacag ctcagaattc aratcctgya gaatctacga aagtaaacag aggtgaagac    360
aaagtggctg tacccgttcc aggttcaagg aaatgcgcgr gcgcaattcc agcctgccgt    420
cgaggttttg taccgtacaa gaagtgcaca gctcggagca ag                       462
```

```
<210> SEQ ID NO 42
<211> LENGTH: 669
<212> TYPE: DNA
<213> ORGANISM: Zea mays

<400> SEQUENCE: 42
gagaaaaacc cctggtttga atttgacagc agcaagctca atactgggag cctacaacac     60
gcggcggaca tggaactgga tgatgcttca gccgagacac caaccagtgg aactgggaag    120
ctgtcttccc atgccgcaga agaagcagag acatggtgcc cgtggctggt cggtagtaca    180
cagcagtttc tgtactatct ccctcgggga gaggtgttct ctatgcatcc tggttgccag    240
ttcctaaact acggtaacgg aagcatatcc tacacagcgt ggacgcacg gacagttacc    300 tcaaacaagc agcggagcca accatggacg gagtcgatcg aaacctccag cagcgtgcct    360
gaaacagctc agaattcaga tcctgcagaa tctacgaaag taaacagagg tgaagacaaa    420
gtggctgtac ccgttccagg ttcaaggaaa tgcgcgagcg caattccagc ctgccgtcga    480
ggttttgtac cgtacaagaa gtgcacagct cggagcaagg tgctggcgct gcagcctgtg    540
gcacctggcg aggaggcaga tagagagctg acaaggctgt gcctgtagaa ttctgggccc    600
ttgccaccca cctctactct gtggataatt tttgctgcta ctcgaacact taatggtcat    660
agctgtttt                                                            669
```

<210> SEQ ID NO 43
<211> LENGTH: 498
<212> TYPE: DNA
<213> ORGANISM: Zea mays

<400> SEQUENCE: 43

| aagtcccagt cacaacgaaa gaacattacg aatgccattg tgatcgaggt ccgagtatta | 60 |
| gcgtaggatt gcgtacccgg tggacgtagg agtccggcat gagcgaacgg agcgcggcga | 120 |
| ggtactcgtt cacctggcgg cggcggttgc gctcgacggc gatgtgggtc atccgctggc | 180 |
| tctcggcgtt cttggtgctc ctctgccggc gccgccgccg ccgcttcatc cgcccctgct | 240 |
| gcacgctgtt cgcctgggac gccccccgcg gcggtgccac ctccgccgat ggtgcattgc | 300 |
| cggaaaagct cccccgtccc cccgcagaag cggcagacgc gtcggcggcg ttgaaggtgt | 360 |
| cgtagatgag atgagtacgt cgcggcacaa agcttccagc gtcatgtcga tcggcgattt | 420 |
| ggcggcctgt ggacttgtgg tatggcacgg aggccagcaa gaacctacgc gcggaccgcc | 480 |
| gcccgatttt ttgaattt | 498 |

<210> SEQ ID NO 44
<211> LENGTH: 608
<212> TYPE: DNA
<213> ORGANISM: Zea mays

<400> SEQUENCE: 44

| agtcagaacg caacagagaa aaattcatgt acaggtaaaa aaaaccacca ccgatttaga | 60 |
| gactagagta tccggggggg tcccttcccc tagaagaaga gatctccgtc cgtggcatgg | 120 |
| aggaacggac gaatggttcg ctgacggcgg tgtggctgtt tctttttttt gctatcgcag | 180 |
| aggtgacctg ccgttctgca gcgaggagtg ccggcaggag cagatcgaga tcgacgaggc | 240 |
| gcgagagcag cggctgaagc agacggggcg ggccgagcag cagcggcagc ggcagcagaa | 300 |
| gcagagcccc cagaggatcc ccatctgggc gtggtaggat gagaaaaatt ttgggcgccg | 360 |
| ggaaaacgaa cgaacgtagt aggatttagc tgcacctcaa gaagaacccc ccaagcaagg | 420 |
| gcgacttgct gcgtgtggaa acaaacggcc gtggatcacc gccggctcga cgcaggaaga | 480 |
| aggccacgcg ccacggcaca ggccgggcag ggcagggcat ccaaccggct gcgtcttttt | 540 |
| accttcgttg gttgacgaaa ccgaatgacc tctctcctcc tatctccgta gtaactttgg | 600 |
| taaaataa | 608 |

<210> SEQ ID NO 45
<211> LENGTH: 637
<212> TYPE: DNA
<213> ORGANISM: Zea mays

<400> SEQUENCE: 45

| aaggtctata ggggaggcaa acttgaaaaa gcgagaattc gctgttgatc catccacagc | 60 |
| tcgtttccac ctttcggaac cttccgccg gcctgttctg acgtcagaac catctatatc | 120 |
| ttcaagaatt cttggttcgc aagaccgttt tttgatcttt gcatcggatg gactatggga | 180 |
| gcacctctca aaccagcaag ctgttgaaat tgtccacaat agtccacgag aagtatggtt | 240 |
| ttcttctttc tcgctgcatt ttgtcttgaa ctggcaactc ttctcatatc gctcttgctg | 300 |
| atgatagcat tcctgttgcg gcaacgctga aatgggtttt ccttgttttt gtagggtgtt | 360 |
| gcaaggagat tggtacaaac agctctaaaa gaagctgcga ggaagaggga aatgaggtat | 420 |
| ggcgatatta agaagctcga aaaaggagtc cggcgctact tccacgacga cataacagtt | 480 |

```
gtcgtcgtct tcatagacca tgaactgcgg gcggagcatt cttcctcgac ctctgttcct    540
gaactctcgg tccgtgggtt cgttgatgcg ggggcacgct ccagcttttc agggatgaac    600
gacattactt atacagtaac cttgttaatt tttaaaa                             637
```

<210> SEQ ID NO 46
<211> LENGTH: 631
<212> TYPE: DNA
<213> ORGANISM: Zea mays

<400> SEQUENCE: 46

```
tccgcccccc ccagtcaggt ttttgaagct ctttgaaaac tcactttat tgtccgcccc    60 attacatcct ggaaaagatt attctcaatg ttactatcta atttggagaa atctttaggt    120
gtcaacattt taatgactag ctcaatgata atgatacaag actgataaac tggtcccatg    180
ttgtagaaaa ctgaatcatt aagtgatatt aggtcattct cagtgatcag ttttaatgta    240
ctgtttccaa aactgccaca tcagatttaa actagataac cgtgtatgca gagttctccc    300
ccatgaaact ctaccatctt ccatgaaatg gtgaaactct ccctatatct ctcttattaa    360
ttgcactgcc atgtcactaa gtgtgatgat gtgtcaccgc atttaatgag tatgaaaatc    420
ccattgagaa tggtcttaca agaaattcca tgtccactaa gttgtgaaag cctcattgga    480
ggagaacgca agtgacgtca atagatggac catggatgcg ctaggacgta atttagataa    540
catcttctac ttcacacccm ctcaatctat ctgatgctga atcgtgaaac tacaccatgg    600
tgcaaaccaa acgcatcaat gcaacyatgg t                                   631
```

<210> SEQ ID NO 47
<211> LENGTH: 672
<212> TYPE: DNA
<213> ORGANISM: Zea mays

<400> SEQUENCE: 47

```
gggcattcat ggaaaaggcc caaccgggtt tttcagggaa ggggattcct tacctccaga    60
tgttgatcca gatacagtta gatggattcc agcaaaccat cctttttgctg ctgcgtcaag    120 tgaagtagac gaggagaccg ccaaacaaaa tgtctatcaa aaggatggcg tcccatcccg    180
tgttaaggct gagcatgaag cttttgcaggc aaggctagag gcttcaaacg atgtgagtgc    240
cttgccgatg aacatgatct ccttgacatt aaaataaca acaatatatc tattattagt    300
tcctctcttc tgcaaaattg attatattga ttgataaaac tccaagctta gtttgacaaa    360
agagccaatc acattgtgta ttttttgttaa tcaccagcct tccagaataa cgattcctga    420
atcccaacac tgctttgcag gttaccagac tccctccgga tccaaggagt atgcagcgta    480
atgagagaca aatggaattg tcaggcaagc catctgaaaa tcttcagggc tccaagtttg    540
agaaccaaga tagacaactg gttatcgagt ctggtaaaca tagctccgat ggaagtttac    600
aatcaaatga gccggaaggg caataaaatt tggtactcaa gcgcttgata cattgtaatt    660
ggttgtatta tt                                                        672
```

<210> SEQ ID NO 48
<211> LENGTH: 450
<212> TYPE: DNA
<213> ORGANISM: Zea mays

<400> SEQUENCE: 48

```
taaaattaaa ggggaagtcc cagtcaaaac ggcatgtgct agattatctt ctttaagatg    60
```

```
gggtaagcaa cttcatgctc aggtgattcg gaacctaccg cacattgatc catatgttgc    120
aagtgctctt gttgaactgt atgcaaaatg tggctgtttc aaggaagcta aggggggtctt   180 caactctta catgaccgta acaatgtggc ttggacagtt ctcatctcag gattcttgca     240
gtatgggtgt ttcactgaat ctgttgaatt gttcaaccag atgagagctg agttgatgac    300
acttgatcag ttcgctttgg ctactcttat aagtggctgc tgcagcagga tggatttgtg    360
ccttgggagg caactacatt cactttgtct gaaaagtggg cagattcaag ctgtagtcgt    420
ctccaatttt tatttcactt tctggtaata                                     450
```

<210> SEQ ID NO 49
<211> LENGTH: 18
<212> TYPE: DNA
<213> ORGANISM: artificial
<220> FEATURE:
<223> OTHER INFORMATION: Primer

<400> SEQUENCE: 49

```
tctctctcgc gtgtgtgc                                                   18
```

<210> SEQ ID NO 50
<211> LENGTH: 20
<212> TYPE: DNA
<213> ORGANISM: artificial
<220> FEATURE:
<223> OTHER INFORMATION: Primer

<400> SEQUENCE: 50

```
tgggtctcct tctccgtcta                                                 20
```

<210> SEQ ID NO 51
<211> LENGTH: 20
<212> TYPE: DNA
<213> ORGANISM: artificial
<220> FEATURE:
<223> OTHER INFORMATION: Primer

<400> SEQUENCE: 51

```
gaaaggctcg ctagtcgcta                                                 20
```

<210> SEQ ID NO 52
<211> LENGTH: 20
<212> TYPE: DNA
<213> ORGANISM: artificial
<220> FEATURE:
<223> OTHER INFORMATION: Primer

<400> SEQUENCE: 52

```
aattcctatc gatcctggcc                                                 20
```

<210> SEQ ID NO 53
<211> LENGTH: 24
<212> TYPE: DNA
<213> ORGANISM: artificial
<220> FEATURE:
<223> OTHER INFORMATION: Primer

<400> SEQUENCE: 53

```
agaagtgcgt atgctacagt ggtg                                            24
```

<210> SEQ ID NO 54
<211> LENGTH: 24
<212> TYPE: DNA
<213> ORGANISM: artificial

<220> FEATURE:
<223> OTHER INFORMATION: Primer

<400> SEQUENCE: 54
cctagtggtg gagttctagg caaa                                              24

<210> SEQ ID NO 55
<211> LENGTH: 20
<212> TYPE: DNA
<213> ORGANISM: artificial
<220> FEATURE:
<223> OTHER INFORMATION: Primer

<400> SEQUENCE: 55
gtgaagctct gcaccacgct                                                   20

<210> SEQ ID NO 56
<211> LENGTH: 24
<212> TYPE: DNA
<213> ORGANISM: artificial
<220> FEATURE:
<223> OTHER INFORMATION: Primer

<400> SEQUENCE: 56
atcgtccaaa gaagaagagg gaga                                              24

<210> SEQ ID NO 57
<211> LENGTH: 20
<212> TYPE: DNA
<213> ORGANISM: artificial
<220> FEATURE:
<223> OTHER INFORMATION: Primer

<400> SEQUENCE: 57
aaggggagca aacaaggtag                                                   20

<210> SEQ ID NO 58
<211> LENGTH: 22
<212> TYPE: DNA
<213> ORGANISM: artificial
<220> FEATURE:
<223> OTHER INFORMATION: Primer

<400> SEQUENCE: 58
atttaagtag tgcatggtgg ag                                                22

<210> SEQ ID NO 59
<211> LENGTH: 19
<212> TYPE: DNA
<213> ORGANISM: Artificial
<220> FEATURE:
<223> OTHER INFORMATION: Primer

<400> SEQUENCE: 59
aaagcatcca cgagccgca                                                    19

<210> SEQ ID NO 60
<211> LENGTH: 19
<212> TYPE: DNA
<213> ORGANISM: Artificial
<220> FEATURE:
<223> OTHER INFORMATION: Primer

<400> SEQUENCE: 60
atgcatggca cgaacacag                                                    19

```
<210> SEQ ID NO 61
<211> LENGTH: 20
<212> TYPE: DNA
<213> ORGANISM: Artificial
<220> FEATURE:
<223> OTHER INFORMATION: Primer

<400> SEQUENCE: 61
tctatgtcag tcctgaggca                                                  20

<210> SEQ ID NO 62
<211> LENGTH: 21
<212> TYPE: DNA
<213> ORGANISM: Artificial
<220> FEATURE:
<223> OTHER INFORMATION: Primer

<400> SEQUENCE: 62
aggctaccat taacatgctt c                                                21

<210> SEQ ID NO 63
<211> LENGTH: 22
<212> TYPE: DNA
<213> ORGANISM: Artificial
<220> FEATURE:
<223> OTHER INFORMATION: Primer

<400> SEQUENCE: 63
acacaataga gcttgatcgt ga                                               22

<210> SEQ ID NO 64
<211> LENGTH: 22
<212> TYPE: DNA
<213> ORGANISM: Artificial
<220> FEATURE:
<223> OTHER INFORMATION: Primer

<400> SEQUENCE: 64
aaattgggag agcacagaaa gt                                               22

<210> SEQ ID NO 65
<211> LENGTH: 22
<212> TYPE: DNA
<213> ORGANISM: Artificial
<220> FEATURE:
<223> OTHER INFORMATION: Primer

<400> SEQUENCE: 65
aaatgtggga gaacagcaag tt                                               22

<210> SEQ ID NO 66
<211> LENGTH: 22
<212> TYPE: DNA
<213> ORGANISM: Artificial
<220> FEATURE:
<223> OTHER INFORMATION: Primer

<400> SEQUENCE: 66
acaggttgat ttggaatcaa ac                                               22

<210> SEQ ID NO 67
<211> LENGTH: 22
<212> TYPE: DNA
<213> ORGANISM: Artificial
<220> FEATURE:
<223> OTHER INFORMATION: Primer
```

```
<400> SEQUENCE: 67
aacaatctca gaagcaatac ag                                              22

<210> SEQ ID NO 68
<211> LENGTH: 21
<212> TYPE: DNA
<213> ORGANISM: Artificial
<220> FEATURE:
<223> OTHER INFORMATION: Primer

<400> SEQUENCE: 68
cgttctatta cggtcatttg c                                               21

<210> SEQ ID NO 69
<211> LENGTH: 18
<212> TYPE: DNA
<213> ORGANISM: Artificial
<220> FEATURE:
<223> OTHER INFORMATION: Primer

<400> SEQUENCE: 69
ctatcgttgg atggcacc                                                   18

<210> SEQ ID NO 70
<211> LENGTH: 20
<212> TYPE: DNA
<213> ORGANISM: Artificial
<220> FEATURE:
<223> OTHER INFORMATION: Primer

<400> SEQUENCE: 70
ttgtgctgtg ggagctcata                                                 20

<210> SEQ ID NO 71
<211> LENGTH: 21
<212> TYPE: DNA
<213> ORGANISM: Artificial
<220> FEATURE:
<223> OTHER INFORMATION: Primer

<400> SEQUENCE: 71
atgtttcgac aggacataga c                                               21

<210> SEQ ID NO 72
<211> LENGTH: 19
<212> TYPE: DNA
<213> ORGANISM: Artificial
<220> FEATURE:
<223> OTHER INFORMATION: Primer

<400> SEQUENCE: 72
aggcacattc cagtagcag                                                  19

<210> SEQ ID NO 73
<211> LENGTH: 21
<212> TYPE: DNA
<213> ORGANISM: Artificial
<220> FEATURE:
<223> OTHER INFORMATION: Primer

<400> SEQUENCE: 73
agcaactcaa gtctgacgat t                                               21

<210> SEQ ID NO 74
```

```
<211> LENGTH: 20
<212> TYPE: DNA
<213> ORGANISM: Artificial
<220> FEATURE:
<223> OTHER INFORMATION: Primer

<400> SEQUENCE: 74
gggaaggatg tcatatccga                                              20

<210> SEQ ID NO 75
<211> LENGTH: 19
<212> TYPE: DNA
<213> ORGANISM: Artificial
<220> FEATURE:
<223> OTHER INFORMATION: Primer

<400> SEQUENCE: 75
acaccaatcc agaagggga                                               19

<210> SEQ ID NO 76
<211> LENGTH: 22
<212> TYPE: DNA
<213> ORGANISM: Artificial
<220> FEATURE:
<223> OTHER INFORMATION: Primer

<400> SEQUENCE: 76
gaatggaaag tacaatgagt cc                                           22

<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77
ttcacagagc gtgctagaaa ta                                           22

<210> SEQ ID NO 78
<211> LENGTH: 21
<212> TYPE: DNA
<213> ORGANISM: Artificial
<220> FEATURE:
<223> OTHER INFORMATION: Primer

<400> SEQUENCE: 78
ctgaatctgg agtttctgtc a                                            21

<210> SEQ ID NO 79
<211> LENGTH: 22
<212> TYPE: DNA
<213> ORGANISM: Artificial
<220> FEATURE:
<223> OTHER INFORMATION: Primer

<400> SEQUENCE: 79
tatagatctt cctgcaggag tt                                           22

<210> SEQ ID NO 80
<211> LENGTH: 20
<212> TYPE: DNA
<213> ORGANISM: Artificial
<220> FEATURE:
<223> OTHER INFORMATION: Primer

<400> SEQUENCE: 80
```
ctgcagctaa accctgatga                                               20

<210> SEQ ID NO 81
<211> LENGTH: 21
<212> TYPE: DNA
<213> ORGANISM: Artificial
<220> FEATURE:
<223> OTHER INFORMATION: Primer

<400> SEQUENCE: 81
tcagggagtg gtatttcctt g                                             21

<210> SEQ ID NO 82
<211> LENGTH: 22
<212> TYPE: DNA
<213> ORGANISM: Artificial
<220> FEATURE:
<223> OTHER INFORMATION: Primer

<400> SEQUENCE: 82
tatcaggtca gcaaatttcc aa                                            22

<210> SEQ ID NO 83
<211> LENGTH: 20
<212> TYPE: DNA
<213> ORGANISM: Artificial
<220> FEATURE:
<223> OTHER INFORMATION: Primer

<400> SEQUENCE: 83
cattcctcct gtccacaaca                                               20

<210> SEQ ID NO 84
<211> LENGTH: 22
<212> TYPE: DNA
<213> ORGANISM: Artificial
<220> FEATURE:
<223> OTHER INFORMATION: Primer

<400> SEQUENCE: 84
tttacgactg caatgaatca ac                                            22

<210> SEQ ID NO 85
<211> LENGTH: 22
<212> TYPE: DNA
<213> ORGANISM: Artificial
<220> FEATURE:
<223> OTHER INFORMATION: Primer

<400> SEQUENCE: 85
tggcagcaat ttcagcatgt aa                                            22

<210> SEQ ID NO 86
<211> LENGTH: 22
<212> TYPE: DNA
<213> ORGANISM: Artificial
<220> FEATURE:
<223> OTHER INFORMATION: Primer

<400> SEQUENCE: 86
gaggaagctt atgaatttgt gc                                            22

<210> SEQ ID NO 87
<211> LENGTH: 21
<212> TYPE: DNA

```
<213> ORGANISM: Artificial
<220> FEATURE:
<223> OTHER INFORMATION: Primer

<400> SEQUENCE: 87
ctggtcttgt aaacactcac t                                              21

<210> SEQ ID NO 88
<211> LENGTH: 21
<212> TYPE: DNA
<213> ORGANISM: Artificial
<220> FEATURE:
<223> OTHER INFORMATION: Primer

<400> SEQUENCE: 88
tgcaccgagc aaatacctttt g                                             21

<210> SEQ ID NO 89
<211> LENGTH: 20
<212> TYPE: DNA
<213> ORGANISM: Artificial
<220> FEATURE:
<223> OTHER INFORMATION: Primer

<400> SEQUENCE: 89
tacctgatcg tcaagtcgct                                                20

<210> SEQ ID NO 90
<211> LENGTH: 19
<212> TYPE: DNA
<213> ORGANISM: Artificial
<220> FEATURE:
<223> OTHER INFORMATION: Primer

<400> SEQUENCE: 90
tgcccatgga cctcttctt                                                 19

<210> SEQ ID NO 91
<211> LENGTH: 20
<212> TYPE: DNA
<213> ORGANISM: Artificial
<220> FEATURE:
<223> OTHER INFORMATION: Primer

<400> SEQUENCE: 91
actctgaatt gagcagcagg                                                20

<210> SEQ ID NO 92
<211> LENGTH: 21
<212> TYPE: DNA
<213> ORGANISM: Artificial
<220> FEATURE:
<223> OTHER INFORMATION: Primer

<400> SEQUENCE: 92
actttggcta gcacaacaac a                                              21

<210> SEQ ID NO 93
<211> LENGTH: 18
<212> TYPE: DNA
<213> ORGANISM: Artificial
<220> FEATURE:
<223> OTHER INFORMATION: Primer

<400> SEQUENCE: 93
acttagctgc aaagatgc                                                  18
```

```
<210> SEQ ID NO 94
<211> LENGTH: 21
<212> TYPE: DNA
<213> ORGANISM: Artificial
<220> FEATURE:
<223> OTHER INFORMATION: Primer

<400> SEQUENCE: 94
aacattggtg caagggacac t                                           21

<210> SEQ ID NO 95
<211> LENGTH: 20
<212> TYPE: DNA
<213> ORGANISM: Artificial
<220> FEATURE:
<223> OTHER INFORMATION: Primer

<400> SEQUENCE: 95
cagaaatgcc atcaacgcca                                             20

<210> SEQ ID NO 96
<211> LENGTH: 22
<212> TYPE: DNA
<213> ORGANISM: Artificial
<220> FEATURE:
<223> OTHER INFORMATION: Primer

<400> SEQUENCE: 96
ggaatgatct ccatgctttc at                                          22

<210> SEQ ID NO 97
<211> LENGTH: 19
<212> TYPE: DNA
<213> ORGANISM: Artificial
<220> FEATURE:
<223> OTHER INFORMATION: Primer

<400> SEQUENCE: 97
ccagtccaaa ccctacggc                                              19

<210> SEQ ID NO 98
<211> LENGTH: 19
<212> TYPE: DNA
<213> ORGANISM: Artificial
<220> FEATURE:
<223> OTHER INFORMATION: Primer

<400> SEQUENCE: 98
cgaccaaacc ctactcgta                                              19

<210> SEQ ID NO 99
<211> LENGTH: 20
<212> TYPE: DNA
<213> ORGANISM: Artificial
<220> FEATURE:
<223> OTHER INFORMATION: Primer

<400> SEQUENCE: 99
atcgatctcc tgctgcaagt                                             20

<210> SEQ ID NO 100
<211> LENGTH: 21
<212> TYPE: DNA
<213> ORGANISM: Artificial
<220> FEATURE:
```

<223> OTHER INFORMATION: Primer

<400> SEQUENCE: 100
aataataggc gattgaggtg c                                                    21

<210> SEQ ID NO 101
<211> LENGTH: 21
<212> TYPE: DNA
<213> ORGANISM: Artificial
<220> FEATURE:
<223> OTHER INFORMATION: Primer

<400> SEQUENCE: 101
aataataggc gattgaggtg c                                                    21

<210> SEQ ID NO 102
<211> LENGTH: 20
<212> TYPE: DNA
<213> ORGANISM: Artificial
<220> FEATURE:
<223> OTHER INFORMATION: Primer

<400> SEQUENCE: 102
agcctagcgc aaagaaagac                                                      20

<210> SEQ ID NO 103
<211> LENGTH: 21
<212> TYPE: DNA
<213> ORGANISM: Artificial
<220> FEATURE:
<223> OTHER INFORMATION: Primer

<400> SEQUENCE: 103
caggccacgg aatttacaca a                                                    21

<210> SEQ ID NO 104
<211> LENGTH: 20
<212> TYPE: DNA
<213> ORGANISM: Artificial
<220> FEATURE:
<223> OTHER INFORMATION: Primer

<400> SEQUENCE: 104
tcgctgcgta gagtactgta                                                      20

<210> SEQ ID NO 105
<211> LENGTH: 18
<212> TYPE: DNA
<213> ORGANISM: Artificial
<220> FEATURE:
<223> OTHER INFORMATION: Primer

<400> SEQUENCE: 105
acccgtcgga ccacgtct                                                        18

<210> SEQ ID NO 106
<211> LENGTH: 18
<212> TYPE: DNA
<213> ORGANISM: Artificial
<220> FEATURE:
<223> OTHER INFORMATION: Primer

<400> SEQUENCE: 106
gctcaactcc gctgctgc                                                        18

```
<210> SEQ ID NO 107
<211> LENGTH: 22
<212> TYPE: DNA
<213> ORGANISM: Artificial
<220> FEATURE:
<223> OTHER INFORMATION: Primer

<400> SEQUENCE: 107
tcacgttgtt ttccaccatgt at                                            22

<210> SEQ ID NO 108
<211> LENGTH: 22
<212> TYPE: DNA
<213> ORGANISM: Artificial
<220> FEATURE:
<223> OTHER INFORMATION: Primer

<400> SEQUENCE: 108
tattagttta ggcaactaag ga                                             22

<210> SEQ ID NO 109
<211> LENGTH: 20
<212> TYPE: DNA
<213> ORGANISM: Artificial
<220> FEATURE:
<223> OTHER INFORMATION: Primer

<400> SEQUENCE: 109
aacgcatact tcctcggcta                                                20

<210> SEQ ID NO 110
<211> LENGTH: 20
<212> TYPE: DNA
<213> ORGANISM: Artificial
<220> FEATURE:
<223> OTHER INFORMATION: Primer

<400> SEQUENCE: 110
atccactcgt acaccgagta                                                20

<210> SEQ ID NO 111
<211> LENGTH: 21
<212> TYPE: DNA
<213> ORGANISM: Artificial
<220> FEATURE:
<223> OTHER INFORMATION: Primer

<400> SEQUENCE: 111
tcactctcaa acaactggtt g                                              21

<210> SEQ ID NO 112
<211> LENGTH: 21
<212> TYPE: DNA
<213> ORGANISM: Artificial
<220> FEATURE:
<223> OTHER INFORMATION: Primer

<400> SEQUENCE: 112
gaagaagtga taaacgccag a                                              21

<210> SEQ ID NO 113
<211> LENGTH: 22
<212> TYPE: DNA
<213> ORGANISM: Artificial
<220> FEATURE:
<223> OTHER INFORMATION: Primer
```

```
<400> SEQUENCE: 113
tactttgtcc agaagagcag aa                                              22

<210> SEQ ID NO 114
<211> LENGTH: 22
<212> TYPE: DNA
<213> ORGANISM: Artificial
<220> FEATURE:
<223> OTHER INFORMATION: Primer

<400> SEQUENCE: 114
tgtggaaatt tgtctattgc ta                                              22

<210> SEQ ID NO 115
<211> LENGTH: 21
<212> TYPE: DNA
<213> ORGANISM: Artificial
<220> FEATURE:
<223> OTHER INFORMATION: Primer

<400> SEQUENCE: 115
aggatgcttt cattactgat t                                               21

<210> SEQ ID NO 116
<211> LENGTH: 22
<212> TYPE: DNA
<213> ORGANISM: Artificial
<220> FEATURE:
<223> OTHER INFORMATION: Primer

<400> SEQUENCE: 116
aataggcaga taccaaggca at                                              22

<210> SEQ ID NO 117
<211> LENGTH: 20
<212> TYPE: DNA
<213> ORGANISM: Artificial
<220> FEATURE:
<223> OTHER INFORMATION: Primer

<400> SEQUENCE: 117
aaatgaatca aagggtcgga                                                 20

<210> SEQ ID NO 118
<211> LENGTH: 19
<212> TYPE: DNA
<213> ORGANISM: Artificial
<220> FEATURE:
<223> OTHER INFORMATION: Primer

<400> SEQUENCE: 118
ccctacatgt cggcaaccg                                                  19

<210> SEQ ID NO 119
<211> LENGTH: 21
<212> TYPE: DNA
<213> ORGANISM: Artificial
<220> FEATURE:
<223> OTHER INFORMATION: Primer

<400> SEQUENCE: 119
gttcctgttc atgttcccga a                                               21

<210> SEQ ID NO 120
<211> LENGTH: 22
```

```
<212> TYPE: DNA
<213> ORGANISM: Artificial
<220> FEATURE:
<223> OTHER INFORMATION: Primer

<400> SEQUENCE: 120
aatttacaag gttctatcgg tt                                              22

<210> SEQ ID NO 121
<211> LENGTH: 19
<212> TYPE: DNA
<213> ORGANISM: Artificial
<220> FEATURE:
<223> OTHER INFORMATION: Primer

<400> SEQUENCE: 121
gcttctagag tacgcccgt                                                  19

<210> SEQ ID NO 122
<211> LENGTH: 21
<212> TYPE: DNA
<213> ORGANISM: Artificial
<220> FEATURE:
<223> OTHER INFORMATION: Primer

<400> SEQUENCE: 122
catgttgcgc agtttgtgct t                                               21

<210> SEQ ID NO 123
<211> LENGTH: 20
<212> TYPE: DNA
<213> ORGANISM: Artificial
<220> FEATURE:
<223> OTHER INFORMATION: Primer

<400> SEQUENCE: 123
gttgggcaac gtcagtttca                                                 20

<210> SEQ ID NO 124
<211> LENGTH: 21
<212> TYPE: DNA
<213> ORGANISM: Artificial
<220> FEATURE:
<223> OTHER INFORMATION: Primer

<400> SEQUENCE: 124
gccttctaat aaacgcagca a                                               21

<210> SEQ ID NO 125
<211> LENGTH: 20
<212> TYPE: DNA
<213> ORGANISM: Artificial
<220> FEATURE:
<223> OTHER INFORMATION: Primer

<400> SEQUENCE: 125
ctacggagct caaagctatg                                                 20

<210> SEQ ID NO 126
<211> LENGTH: 20
<212> TYPE: DNA
<213> ORGANISM: Artificial
<220> FEATURE:
<223> OTHER INFORMATION: Primer

<400> SEQUENCE: 126
```

```
atctgccatg agttcgagac                                              20

<210> SEQ ID NO 127
<211> LENGTH: 22
<212> TYPE: DNA
<213> ORGANISM: Artificial
<220> FEATURE:
<223> OTHER INFORMATION: Primer

<400> SEQUENCE: 127
tcttcaattc ccagagttca at                                           22

<210> SEQ ID NO 128
<211> LENGTH: 20
<212> TYPE: DNA
<213> ORGANISM: Artificial
<220> FEATURE:
<223> OTHER INFORMATION: Primer

<400> SEQUENCE: 128
ttcacgctat ggccctttct                                              20

<210> SEQ ID NO 129
<211> LENGTH: 22
<212> TYPE: DNA
<213> ORGANISM: Artificial
<220> FEATURE:
<223> OTHER INFORMATION: Primer

<400> SEQUENCE: 129
atttggattt gcattgtcag tc                                           22

<210> SEQ ID NO 130
<211> LENGTH: 19
<212> TYPE: DNA
<213> ORGANISM: Artificial
<220> FEATURE:
<223> OTHER INFORMATION: Primer

<400> SEQUENCE: 130
tgtgccctct cgtcatcct                                               19

<210> SEQ ID NO 131
<211> LENGTH: 18
<212> TYPE: DNA
<213> ORGANISM: Artificial
<220> FEATURE:
<223> OTHER INFORMATION: Primer

<400> SEQUENCE: 131
cgatggacgc atccttcc                                                18

<210> SEQ ID NO 132
<211> LENGTH: 19
<212> TYPE: DNA
<213> ORGANISM: Artificial
<220> FEATURE:
<223> OTHER INFORMATION: Primer

<400> SEQUENCE: 132
ttacaacgcg gccgttaca                                               19

<210> SEQ ID NO 133
<211> LENGTH: 21
<212> TYPE: DNA
<213> ORGANISM: Artificial
```

<220> FEATURE:
<223> OTHER INFORMATION: Primer

<400> SEQUENCE: 133
cataactgta aagctgccgt t                                    21

<210> SEQ ID NO 134
<211> LENGTH: 22
<212> TYPE: DNA
<213> ORGANISM: Artificial
<220> FEATURE:
<223> OTHER INFORMATION: Primer

<400> SEQUENCE: 134
gaggttttac ttgagaacaa ga                                   22

<210> SEQ ID NO 135
<211> LENGTH: 20
<212> TYPE: DNA
<213> ORGANISM: Artificial
<220> FEATURE:
<223> OTHER INFORMATION: Primer

<400> SEQUENCE: 135
tgtgtgcagt gcaagaacga                                      20

<210> SEQ ID NO 136
<211> LENGTH: 20
<212> TYPE: DNA
<213> ORGANISM: Artificial
<220> FEATURE:
<223> OTHER INFORMATION: Primer

<400> SEQUENCE: 136
gttctcctcg ctgatgaact                                      20

<210> SEQ ID NO 137
<211> LENGTH: 22
<212> TYPE: DNA
<213> ORGANISM: Artificial
<220> FEATURE:
<223> OTHER INFORMATION: Primer

<400> SEQUENCE: 137
tctgttggta ataacgattc ag                                   22

<210> SEQ ID NO 138
<211> LENGTH: 20
<212> TYPE: DNA
<213> ORGANISM: Artificial
<220> FEATURE:
<223> OTHER INFORMATION: Primer

<400> SEQUENCE: 138
atggcaggcg gattctgtta                                      20

<210> SEQ ID NO 139
<211> LENGTH: 20
<212> TYPE: DNA
<213> ORGANISM: Artificial
<220> FEATURE:
<223> OTHER INFORMATION: Primer

<400> SEQUENCE: 139
gaacccagca tgacagttct                                      20

```
<210> SEQ ID NO 140
<211> LENGTH: 22
<212> TYPE: DNA
<213> ORGANISM: Artificial
<220> FEATURE:
<223> OTHER INFORMATION: Primer

<400> SEQUENCE: 140
ttcacctact tgctaatggt aa                                              22

<210> SEQ ID NO 141
<211> LENGTH: 21
<212> TYPE: DNA
<213> ORGANISM: Artificial
<220> FEATURE:
<223> OTHER INFORMATION: Primer

<400> SEQUENCE: 141
tttgctttgc tccgttctgc t                                               21

<210> SEQ ID NO 142
<211> LENGTH: 22
<212> TYPE: DNA
<213> ORGANISM: Artificial
<220> FEATURE:
<223> OTHER INFORMATION: Primer

<400> SEQUENCE: 142
gctctacaag aagcaacatt aa                                              22

<210> SEQ ID NO 143
<211> LENGTH: 21
<212> TYPE: DNA
<213> ORGANISM: Artificial
<220> FEATURE:
<223> OTHER INFORMATION: Primer

<400> SEQUENCE: 143
ttcagcatgg ctttggagaa t                                               21

<210> SEQ ID NO 144
<211> LENGTH: 21
<212> TYPE: DNA
<213> ORGANISM: Artificial
<220> FEATURE:
<223> OTHER INFORMATION: Primer

<400> SEQUENCE: 144
cacccaatct gacagcaaga t                                               21

<210> SEQ ID NO 145
<211> LENGTH: 21
<212> TYPE: DNA
<213> ORGANISM: Artificial
<220> FEATURE:
<223> OTHER INFORMATION: Primer

<400> SEQUENCE: 145
gctatttggc aagagggttg t                                               21

<210> SEQ ID NO 146
<211> LENGTH: 22
<212> TYPE: DNA
<213> ORGANISM: Artificial
<220> FEATURE:
<223> OTHER INFORMATION: Primer
```

<400> SEQUENCE: 146
gttagtaatt tagaccagca gc                                           22

<210> SEQ ID NO 147
<211> LENGTH: 21
<212> TYPE: DNA
<213> ORGANISM: Artificial
<220> FEATURE:
<223> OTHER INFORMATION: Primer

<400> SEQUENCE: 147
tatgtgttcg agtagcagca a                                            21

<210> SEQ ID NO 148
<211> LENGTH: 21
<212> TYPE: DNA
<213> ORGANISM: Artificial
<220> FEATURE:
<223> OTHER INFORMATION: Primer

<400> SEQUENCE: 148
aaatggaaac actagtcccg a                                            21

<210> SEQ ID NO 149
<211> LENGTH: 20
<212> TYPE: DNA
<213> ORGANISM: Artificial
<220> FEATURE:
<223> OTHER INFORMATION: Primer

<400> SEQUENCE: 149
ccagtgtgcc actatctgaa                                              20

<210> SEQ ID NO 150
<211> LENGTH: 22
<212> TYPE: DNA
<213> ORGANISM: Artificial
<220> FEATURE:
<223> OTHER INFORMATION: Primer

<400> SEQUENCE: 150
aaagaacact acgaatgcca tt                                           22

<210> SEQ ID NO 151
<211> LENGTH: 18
<212> TYPE: DNA
<213> ORGANISM: Artificial
<220> FEATURE:
<223> OTHER INFORMATION: Primer

<400> SEQUENCE: 151
accgggcggc ggtcgcgc                                                18

<210> SEQ ID NO 152
<211> LENGTH: 19
<212> TYPE: DNA
<213> ORGANISM: Artificial
<220> FEATURE:
<223> OTHER INFORMATION: Primer

<400> SEQUENCE: 152
tagcacccgt agtggcata                                               19

<210> SEQ ID NO 153

```
<211> LENGTH: 20
<212> TYPE: DNA
<213> ORGANISM: Artificial
<220> FEATURE:
<223> OTHER INFORMATION: Primer

<400> SEQUENCE: 153
cactacctcg acatctgctt                                              20

<210> SEQ ID NO 154
<211> LENGTH: 22
<212> TYPE: DNA
<213> ORGANISM: Artificial
<220> FEATURE:
<223> OTHER INFORMATION: Primer

<400> SEQUENCE: 154
caacagagac atcttcatgt ac                                           22

<210> SEQ ID NO 155
<211> LENGTH: 21
<212> TYPE: DNA
<213> ORGANISM: Artificial
<220> FEATURE:
<223> OTHER INFORMATION: Primer

<400> SEQUENCE: 155
tccatctttc ggagatcagg a                                            21

<210> SEQ ID NO 156
<211> LENGTH: 21
<212> TYPE: DNA
<213> ORGANISM: Artificial
<220> FEATURE:
<223> OTHER INFORMATION: Primer

<400> SEQUENCE: 156
aaactcacgc acaaaccaac c                                            21

<210> SEQ ID NO 157
<211> LENGTH: 21
<212> TYPE: DNA
<213> ORGANISM: Artificial
<220> FEATURE:
<223> OTHER INFORMATION: Primer

<400> SEQUENCE: 157
cgcatcaaag gcatcataca g                                            21

<210> SEQ ID NO 158
<211> LENGTH: 21
<212> TYPE: DNA
<213> ORGANISM: ARtificial
<220> FEATURE:
<223> OTHER INFORMATION: Primer

<400> SEQUENCE: 158
ttcaaggtct ataggtgatg c                                            21

<210> SEQ ID NO 159
<211> LENGTH: 21
<212> TYPE: DNA
<213> ORGANISM: Artificial
<220> FEATURE:
<223> OTHER INFORMATION: Primer

<400> SEQUENCE: 159
```

```
gcaacacaag gttactgtat c                                              21

<210> SEQ ID NO 160
<211> LENGTH: 21
<212> TYPE: DNA
<213> ORGANISM: Artificial
<220> FEATURE:
<223> OTHER INFORMATION: Primer

<400> SEQUENCE: 160
actacgcgct agtaacacca a                                              21

<210> SEQ ID NO 161
<211> LENGTH: 21
<212> TYPE: DNA
<213> ORGANISM: Artificial
<220> FEATURE:
<223> OTHER INFORMATION: Primer

<400> SEQUENCE: 161
gtgcctctct ataatagtgc c                                              21

<210> SEQ ID NO 162
<211> LENGTH: 21
<212> TYPE: DNA
<213> ORGANISM: Artificial
<220> FEATURE:
<223> OTHER INFORMATION: Primer

<400> SEQUENCE: 162
agctggtctt ctgaagctct t                                              21

<210> SEQ ID NO 163
<211> LENGTH: 21
<212> TYPE: DNA
<213> ORGANISM: Artificial
<220> FEATURE:
<223> OTHER INFORMATION: Primer

<400> SEQUENCE: 163
ggttgcattg atgcgtttgg t                                              21

<210> SEQ ID NO 164
<211> LENGTH: 19
<212> TYPE: DNA
<213> ORGANISM: Artificial
<220> FEATURE:
<223> OTHER INFORMATION: Primer

<400> SEQUENCE: 164
tcccatgtga gcgtgtcga                                                 19

<210> SEQ ID NO 165
<211> LENGTH: 22
<212> TYPE: DNA
<213> ORGANISM: Artificial
<220> FEATURE:
<223> OTHER INFORMATION: Primer

<400> SEQUENCE: 165
ggaacaagaa atgcatcaga ag                                             22

<210> SEQ ID NO 166
<211> LENGTH: 20
<212> TYPE: DNA
```

```
<213> ORGANISM: Artificial
<220> FEATURE:
<223> OTHER INFORMATION: Primer

<400> SEQUENCE: 166
ggagatcacg tgcatatcag                                              20

<210> SEQ ID NO 167
<211> LENGTH: 22
<212> TYPE: DNA
<213> ORGANISM: Artificial
<220> FEATURE:
<223> OTHER INFORMATION: Primer

<400> SEQUENCE: 167
caaagcaaat gtcatcaaag cg                                           22

<210> SEQ ID NO 168
<211> LENGTH: 21
<212> TYPE: DNA
<213> ORGANISM: Artificial
<220> FEATURE:
<223> OTHER INFORMATION: Primer

<400> SEQUENCE: 168
ctatgtaaac cggtaagccc a                                            21

<210> SEQ ID NO 169
<211> LENGTH: 21
<212> TYPE: DNA
<213> ORGANISM: Artificial
<220> FEATURE:
<223> OTHER INFORMATION: Primer

<400> SEQUENCE: 169
gggtgcgtct tgattcaaca a                                            21

<210> SEQ ID NO 170
<211> LENGTH: 22
<212> TYPE: DNA
<213> ORGANISM: Artificial
<220> FEATURE:
<223> OTHER INFORMATION: Primer

<400> SEQUENCE: 170
gcatgtgcta gattatcttc tt                                           22

<210> SEQ ID NO 171
<211> LENGTH: 21
<212> TYPE: DNA
<213> ORGANISM: Artificial
<220> FEATURE:
<223> OTHER INFORMATION: Primer

<400> SEQUENCE: 171
ggagatgaga gaattggaga c                                            21

<210> SEQ ID NO 172
<211> LENGTH: 22
<212> TYPE: DNA
<213> ORGANISM: Artificial
<220> FEATURE:
<223> OTHER INFORMATION: Primer

<400> SEQUENCE: 172
gattgtcgca ctttgcatac at                                           22
```

```
<210> SEQ ID NO 173
<211> LENGTH: 21
<212> TYPE: DNA
<213> ORGANISM: Artificial
<220> FEATURE:
<223> OTHER INFORMATION: Primer

<400> SEQUENCE: 173
gctgcaggat tcctggtgc a                                              21

<210> SEQ ID NO 174
<211> LENGTH: 18
<212> TYPE: DNA
<213> ORGANISM: Artificial
<220> FEATURE:
<223> OTHER INFORMATION: Primer

<400> SEQUENCE: 174
aaccgctcct gctccagc                                                 18

<210> SEQ ID NO 175
<211> LENGTH: 21
<212> TYPE: DNA
<213> ORGANISM: Artificial
<220> FEATURE:
<223> OTHER INFORMATION: Primer

<400> SEQUENCE: 175
gctgcaggat tcctggtgc a                                              21

<210> SEQ ID NO 176
<211> LENGTH: 18
<212> TYPE: DNA
<213> ORGANISM: Artificial
<220> FEATURE:
<223> OTHER INFORMATION: Primer

<400> SEQUENCE: 176
aaccgctcct gctccagc                                                 18

<210> SEQ ID NO 177
<211> LENGTH: 24
<212> TYPE: DNA
<213> ORGANISM: Artificial
<220> FEATURE:
<223> OTHER INFORMATION: Primer

<400> SEQUENCE: 177
cttccagaca agccaactga ctga                                          24

<210> SEQ ID NO 178
<211> LENGTH: 30
<212> TYPE: DNA
<213> ORGANISM: Artificial
<220> FEATURE:
<223> OTHER INFORMATION: Primer

<400> SEQUENCE: 178
caacgatttc caacagctta yttccatgga                                    30

<210> SEQ ID NO 179
<211> LENGTH: 24
<212> TYPE: DNA
<213> ORGANISM: Artificial
<220> FEATURE:
```

```
<223> OTHER INFORMATION: Primer

<400> SEQUENCE: 179
cttccagaca agccaactga ctga                                          24

<210> SEQ ID NO 180
<211> LENGTH: 30
<212> TYPE: DNA
<213> ORGANISM: Artificial
<220> FEATURE:
<223> OTHER INFORMATION: Primer

<400> SEQUENCE: 180
caacgatttc caacagctta yttccatgga                                    30

<210> SEQ ID NO 181
<211> LENGTH: 30
<212> TYPE: DNA
<213> ORGANISM: Artificial
<220> FEATURE:
<223> OTHER INFORMATION: Primer

<400> SEQUENCE: 181
aaataggcct cgatctttca tactggaaaa                                    30

<210> SEQ ID NO 182
<211> LENGTH: 26
<212> TYPE: DNA
<213> ORGANISM: Artificial
<220> FEATURE:
<223> OTHER INFORMATION: Primer

<400> SEQUENCE: 182
ggccaagatt ggtcgayacc atgtaa                                        26

<210> SEQ ID NO 183
<211> LENGTH: 30
<212> TYPE: DNA
<213> ORGANISM: Artificial
<220> FEATURE:
<223> OTHER INFORMATION: Primer

<400> SEQUENCE: 183
aaataggcct cgatctttca tactggaaaa                                    30

<210> SEQ ID NO 184
<211> LENGTH: 26
<212> TYPE: DNA
<213> ORGANISM: Artificial
<220> FEATURE:
<223> OTHER INFORMATION: Primer

<400> SEQUENCE: 184
ggccaagatt ggtcgayacc atgtaa                                        26

<210> SEQ ID NO 185
<211> LENGTH: 22
<212> TYPE: DNA
<213> ORGANISM: Artificial
<220> FEATURE:
<223> OTHER INFORMATION: Primer

<400> SEQUENCE: 185
agtggatcga ggargacgag cc                                            22
```

```
<210> SEQ ID NO 186
<211> LENGTH: 19
<212> TYPE: DNA
<213> ORGANISM: Artificial
<220> FEATURE:
<223> OTHER INFORMATION: Primer

<400> SEQUENCE: 186
ccttggccct atcctcgcc                                                   19

<210> SEQ ID NO 187
<211> LENGTH: 23
<212> TYPE: DNA
<213> ORGANISM: Artificial
<220> FEATURE:
<223> OTHER INFORMATION: Primer

<400> SEQUENCE: 187
cggaagcata catcactggc tca                                              23

<210> SEQ ID NO 188
<211> LENGTH: 19
<212> TYPE: DNA
<213> ORGANISM: Artificial
<220> FEATURE:
<223> OTHER INFORMATION: Primer

<400> SEQUENCE: 188
ccttggccct atcctcgcc                                                   19

<210> SEQ ID NO 189
<211> LENGTH: 17
<212> TYPE: DNA
<213> ORGANISM: Artificial
<220> FEATURE:
<223> OTHER INFORMATION: Primer

<400> SEQUENCE: 189
cggccatcgc catcgac                                                     17

<210> SEQ ID NO 190
<211> LENGTH: 23
<212> TYPE: DNA
<213> ORGANISM: Artificial
<220> FEATURE:
<223> OTHER INFORMATION: Primer

<400> SEQUENCE: 190
cgtaccgatg caaagtggtt gac                                              23

<210> SEQ ID NO 191
<211> LENGTH: 17
<212> TYPE: DNA
<213> ORGANISM: Artificial
<220> FEATURE:
<223> OTHER INFORMATION: Primer

<400> SEQUENCE: 191
cggccatcgc catcgac                                                     17

<210> SEQ ID NO 192
<211> LENGTH: 23
<212> TYPE: DNA
<213> ORGANISM: Artificial
<220> FEATURE:
<223> OTHER INFORMATION: Primer
```

<400> SEQUENCE: 192
cgtaccgatg caaagtggtt gac                                    23

<210> SEQ ID NO 193
<211> LENGTH: 17
<212> TYPE: DNA
<213> ORGANISM: Artificial
<220> FEATURE:
<223> OTHER INFORMATION: Primer

<400> SEQUENCE: 193
cggccatcgc catcgac                                           17

<210> SEQ ID NO 194
<211> LENGTH: 23
<212> TYPE: DNA
<213> ORGANISM: Artificial
<220> FEATURE:
<223> OTHER INFORMATION: Primer

<400> SEQUENCE: 194
cgtaccgatg caaagtggtt gac                                    23

<210> SEQ ID NO 195
<211> LENGTH: 33
<212> TYPE: DNA
<213> ORGANISM: Artificial
<220> FEATURE:
<223> OTHER INFORMATION: Primer

<400> SEQUENCE: 195
gcagtcaatt tcaagagaag tatcttaggt atg                         33

<210> SEQ ID NO 196
<211> LENGTH: 33
<212> TYPE: DNA
<213> ORGANISM: Artificial
<220> FEATURE:
<223> OTHER INFORMATION: Primer

<400> SEQUENCE: 196 aactttttaca agaatacttc atgcatcaac aga                        33

<210> SEQ ID NO 197
<211> LENGTH: 31
<212> TYPE: DNA
<213> ORGANISM: Artificial
<220> FEATURE:
<223> OTHER INFORMATION: Primer

<400> SEQUENCE: 197
gcatttgagt gatgagagta ttaccttttg g                           31

<210> SEQ ID NO 198
<211> LENGTH: 28
<212> TYPE: DNA
<213> ORGANISM: Artificial
<220> FEATURE:
<223> OTHER INFORMATION: Primer

<400> SEQUENCE: 198
cccttgagtc cttctacaaa gattagca                               28

<210> SEQ ID NO 199
<211> LENGTH: 27

```
<212> TYPE: DNA
<213> ORGANISM: Artificial
<220> FEATURE:
<223> OTHER INFORMATION: Primer

<400> SEQUENCE: 199
ttcaagtctt tatgcatgac caggtga                                    27

<210> SEQ ID NO 200
<211> LENGTH: 29
<212> TYPE: DNA
<213> ORGANISM: Artificial
<220> FEATURE:
<223> OTHER INFORMATION: Primer

<400> SEQUENCE: 200
aattgactgc atatgtgcct gatctctac                                  29

<210> SEQ ID NO 201
<211> LENGTH: 27
<212> TYPE: DNA
<213> ORGANISM: Artificial
<220> FEATURE:
<223> OTHER INFORMATION: Primer

<400> SEQUENCE: 201
ccgacaaact tttgcttcyc ctcatga                                    27

<210> SEQ ID NO 202
<211> LENGTH: 22
<212> TYPE: DNA
<213> ORGANISM: Artificial
<220> FEATURE:
<223> OTHER INFORMATION: Primer

<400> SEQUENCE: 202
tgcttcggac tagtctgtcc ac                                         22

<210> SEQ ID NO 203
<211> LENGTH: 26
<212> TYPE: DNA
<213> ORGANISM: Artificial
<220> FEATURE:
<223> OTHER INFORMATION: Primer

<400> SEQUENCE: 203
tttcggaagt acatggttcg aatcga                                     26

<210> SEQ ID NO 204
<211> LENGTH: 26
<212> TYPE: DNA
<213> ORGANISM: Artificial
<220> FEATURE:
<223> OTHER INFORMATION: Primer

<400> SEQUENCE: 204
ggtagcyarc ccatcggtac tgaaca                                     26

<210> SEQ ID NO 205
<211> LENGTH: 30
<212> TYPE: DNA
<213> ORGANISM: Artificial
<220> FEATURE:
<223> OTHER INFORMATION: Primer

<400> SEQUENCE: 205
```
aaaaagaatc ttgatcttgc catttcagca                                30

<210> SEQ ID NO 206
<211> LENGTH: 22
<212> TYPE: DNA
<213> ORGANISM: Artificial
<220> FEATURE:
<223> OTHER INFORMATION: Primer

<400> SEQUENCE: 206
gccctaggca cttacctttg ga                                        22

<210> SEQ ID NO 207
<211> LENGTH: 23
<212> TYPE: DNA
<213> ORGANISM: Artificial
<220> FEATURE:
<223> OTHER INFORMATION: Primer

<400> SEQUENCE: 207
gaactggayg atgcttcagc cga                                       23

<210> SEQ ID NO 208
<211> LENGTH: 23
<212> TYPE: DNA
<213> ORGANISM: Artificial
<220> FEATURE:
<223> OTHER INFORMATION: Primer

<400> SEQUENCE: 208
ggtacagcca ctttgtcttc acc                                       23

<210> SEQ ID NO 209
<211> LENGTH: 23
<212> TYPE: DNA
<213> ORGANISM: Artificial
<220> FEATURE:
<223> OTHER INFORMATION: Primer

<400> SEQUENCE: 209
gaactggayg atgcttcagc cga                                       23

<210> SEQ ID NO 210
<211> LENGTH: 23
<212> TYPE: DNA
<213> ORGANISM: Artificial
<220> FEATURE:
<223> OTHER INFORMATION: Primer

<400> SEQUENCE: 210
ggtacagcca ctttgtcttc acc                                       23

<210> SEQ ID NO 211
<211> LENGTH: 880
<212> TYPE: DNA
<213> ORGANISM: Zea mays

<400> SEQUENCE: 211
catcgccgtt ccttcctggc gatcgccgct ccctagctat ccggtggcca aagacacggc    60
tagtggtagg ctcgagcgag acgagctctt ggtgaagaga gaatgaatgt aacgttaccg   120
cctcctggtc gtaggggtgt gtgtatgtga ggacaagagg aggagcgaga ggaggagcgc   180
agagcgtggc ggggaaggag ggcgtcatgt gtgcgaggaa tctaggacga cttgttggca   240
gctgggccgg ggtgcgtgcg agatgcaatg caagaacaaa gcggacgggc atctcgctcg   300

```
gccacgcttc caagtccatc cgggggggcgc cactcggccg ccgctcattg aggcccaggc    360
gccaagacgg cggctccacc cacgtcacaa ttggcaacaa gaagcacacg gctgggctg      420 ggacgcgtcg aatttttcac cagaaaatac cgtctgatcc tggcgtttcg tgaacggcaa    480
aacctagcag cagcagcagc attccacggg tcggatgaca tatcatatcc tcgtgcggag    540
cggactctac ggcgagtcca gctgtggctg cggaatattc cggcggaagc gcggggagag    600
cgacggcggc ctccggtggg acccggggcg agcgggagat cgcgcgaaga tgttcggcgc    660
tgatgtcgct ggaatattcg cgccagctgt ggctgccggt gcgacctgct gaccagacga    720
ccaatggcag tggccaccgc ctctccctct tgctgttgga gttggatcca cggaccactc    780
tccatccaac atccatcaca gattggcgga cgattagccg agactaatcg ctattctcaa    840 cactttaaa  accgtacgtg caaaatgcta aggggccgtt                          880

<210> SEQ ID NO 212
<211> LENGTH: 936
<212> TYPE: DNA
<213> ORGANISM: Zea mays

<400> SEQUENCE: 212
catcgtcgtt ccttcctggc gatcgccgct tcctagctat ccggtggcca aagacacggc     60
tagtggtagg ctcgagtgag acgagctctt gctgaagaga gaatgaatgt aacgttaccg    120
cctcctggtc gtaggtgtaa taagttgtaa cgcgagcgtc gttagcaagc acagggttt     180 gtgtatgtga ggacaagagg aggagcgaga ggaggagcgc agagcgtggc gggggaaggag   240 ggcgtcatgt gtgcgaggaa tctaggacga cttgttggca cttggcagct gggccggggt    300
gcgtgcgaga tgcaatgcaa gaacaaagcg gacgggcatc acgcctccag gtccaacccg    360
ggggcgccac tcggccgccg ctcattgagg cccaggcgcc aagacggcgg ctccacccac    420
atcacaattg gcaacaagaa gcacacggct ggggttggga cgcgtcgaat ttttcaccag    480
aaaataccgt ctgatcctgg cgtttcgtca gatgctatgc tacgtgaacg gcaaaaccta    540
gcagcagcag cagcactcag actgacaaag aggagggaaa tctttgcgtg ggaaccaaac    600
tgaacgcgaa tcgcacgagt cggatgacat atcctcgtcc ggagcggact cgaccgcgag    660
tccagctgtg gctgcggaat attccggcgg aagcgcgggg agaacgacgg cggcctccgg    720
tgggacccgg ggcgagcggg agatgcgcg aagatgttcg gcgctgatgt cgctggaata    780
ttcgcgccag ctgtggctgc cggtgtgacc tgctgaccag acgaccagtg gcagtggcca    840
ccgcctctcc atcacagatt cgcggacgat tagccgagac taatcgctat tctcaacact    900
tttaaaaccg tgcgtgcaga atgctaaggg cgcgtt                             936

<210> SEQ ID NO 213
<211> LENGTH: 3250
<212> TYPE: DNA
<213> ORGANISM: Zea mays
<220> FEATURE:
<221> NAME/KEY: misc_feature
<222> LOCATION: (1458)..(1737)
<223> OTHER INFORMATION: n is unknown
<220> FEATURE:
<221> NAME/KEY: misc_feature
<222> LOCATION: (3185)..(3188)
<223> OTHER INFORMATION: n is unknown
<220> FEATURE:
<221> NAME/KEY: misc_feature
<222> LOCATION: (3191)..(3191)
<223> OTHER INFORMATION: n is unknown
```

```
<400> SEQUENCE: 213
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc aataggattc acattcctgg     300
gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gattttaat ttttcctgct tttggttaca cctctacagt cccatactcg     660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt ttttttcaag     840
gtaacatttt ctagcatctt cacctgtcta cttgactgaa tgcagtatat attagttgta     900
ataactactg gccttctgct gtgcacaaaa ggcgggtatt accacttgca gaaatttgtc     960
gggtaaaggt aattgccagt taccttgtgt tcttcccttg atcaggaaca cctggaggag    1020
gatgcgctgt ggttgaaccg aagccctgtg agcgaagtac tgatgacaga aagagcggaa    1080
gataagataa gaaaggaacc cttgcgcggc aaggcctggt gacatagagg tagtgcgagg    1140
ctcataccgc cgccgctggc aggttccagg cctgtgcttt tcttgccctg tatccccagt    1200
ctatacttct gcgcacatca gacgagcctc agtgtttcgg cacagtggtg caacagaaaa    1260
ggagagtgct ggtaggtaac gctgaggcgg tgaagaaaga gaggtcagac ggacctggag    1320
gtggcttttt aactggtaaa gagtgaggtc tttcatgccc atcaatctga gcaccgactt    1380
gggtgttgct cctgttcgca ggaagcacaa gaaatggtca gtactccaca ccataagcat    1440
gtcggtggtg tgttggannn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnaaa    1740
aaaaaaaaaa aaaaagaat gcacaccgac atgctctgta gcacaagcac catactggcg    1800
aactggagag gtctcggctc atcaagcaat cgccttggtg tcggacgggg tcatcaagac    1860
aagacgacta gacgagcact acatatagac gggaacgtac gggaggaagg aaggaaaacg    1920
agagcgagga ctcactgtcc ggtccgccca gcttggtgac ggcgtcgacg aagcgctggt    1980
ggaggtccgg cgtccagcgc agccgcggct tggggtcccg tgacgccgcc ccgtcgtagc    2040
cgtagctccc ctgcatcgtc gttccttcct ggcgatcgcc gcttcctagc tatccggtgg    2100
ccaaagacac ggctagtggt aggctcgagt gagacgagct cttgctgaag agagaatgaa    2160
tgtaacgtta ccgcctcctg gtcgtaggtg taataagttg taacgcgagc gtcgttagca    2220
agcacagggg tttgtgtatg tgaggacaag aggaggagcg agaggaggag cgcagagcgt    2280
ggcggggaag gagggcgtca tgtgtgcgag gaatctagga cgacttgttg gcacttggca    2340
```

```
gctgggccgg ggtgcgtgcg agatgcaatg caagaacaaa gcggacgggc atcacgcctc    2400
caggtccaac ccgggggcgc cactcggccg ccgctcattg aggcccaggc gccaagacgg    2460
cggctccacc cacatcacaa ttggcaacaa gaagcacacg gctggggttg gacgcgtcg    2520 aattttcac cagaaaatac cgtctgatcc tggcgtttcg tcagatgcta tgctacgtga    2580
acggcaaaac ctagcagcag cagcagcact cagactggac aagaggaggg aaatctttgc    2640
gtgggaacca aactgaacgc gaatcgcacg agtcggatga catatcctcg tccggagcgg    2700
actcgaccgc gagtccagct gtggctgcgg aatattccgg cggaagcgcg gggagaacga    2760
cggcggcctc cggtgggacc cggggcgagc gggagatgcg gcgaagatgt tcggcgctga    2820
tgtcgctgga atattcgcgc cagctgtggc tgccggtgtg acctgctgac cagacgacca    2880
gtggcagtgg ccaccgcctc tccatcacag attcgcggac gattagccga gactaatcgc    2940
tattctcaac acttttaaaa ccgtgcgtgc agaatgctaa gggcgcgttc gtttgcacag    3000
caatagacat ggatttattt cagctcatca aaatctatat aaattaaaga agtaatccgg    3060
ctagaaatta atccggagct tcaatcccta acaaccgaac agggtctaag cctgctagat    3120
tcgagcatct gcgtgactct actttggctc ttctcgtacg atgcgacttg acgatgcatt    3180
tgggnnnncc nttagcgaca ctctcctgat tagtcccacg gaaacgcaac tctaccacta    3240
tcagccgccg                                                          3250

<210> SEQ ID NO 214
<211> LENGTH: 3653
<212> TYPE: DNA
<213> ORGANISM: Zea mays
<220> FEATURE:
<221> NAME/KEY: misc_feature
<222> LOCATION: (2001)..(2142)
<223> OTHER INFORMATION: n is a, c, g, or t
<220> FEATURE:
<221> NAME/KEY: misc_feature
<222> LOCATION: (3588)..(3595)
<223> OTHER INFORMATION: n is a, c, g, or t

<400> SEQUENCE: 214
tcgcatctgc agcttctttt gcacctgatt acagacataa gcacttgtag cgtttatgga      60
agaaagtttt ggagtgcaaa tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaac     240 caaataaat gggcccactg cagtcaatta acaggcattc ataggattc acattcctgg      300 gcttctatat atggaagttt gcatacaaag ttttgaaat aaaatggaat agaaattgct      360
tgcatttagt gtaagttaat actagctccg ttctcgaata tttgtcgtcc gctagttcat     420
ttttgaacta aaacacgaca aataaaaaaa cggaaggagt acatgtttgt aacaggtgag     480
cccctgaata cttgcttgta acaggtggag cactaagtat gcttagaact ttaggcaact     540
tgtattcttt agcacttcga cgccgtttgt atggtaatat ctactgatag acagaatcct     600
ggttttggat tttttttta tttttcctgt ttttggttac acctctacag tcccatactc      660
gcagtccaat aatacatggt ctgataataa accaattaag aaggactcat gtctcagtca     720
ttaggctgtc tccaacaacg tcctctatat tcatcctcta tatctgtcct ttacagtctc     780
ctctaaaaaa tttcatccta tatatctcat ttctctccaa caacgtcctc taaatcacgt     840
cctctatact caaatactca tattaaagac atttttaat tttatttttt atacatacgt      900
```

```
aattatcata ctctcaaatg tattgtgcat attttagttt tgctaaaccg gttatttaaa    960
gtagtcaaat ggatagagga ccgtttagag aaactctata tatagagaat tcagcagcgt   1020
cctctaaatt taaaggaccg tttagaggac gttgctggag agcgtagagg accgtttggt   1080
cctctatatt tagggtagag aacccttttag ggggccttgt tggagccagc cttatgactt   1140
gagcatagga gttgagatca agaaatatgt gagttgcagc ttaaggttca gagaggaaat   1200
ccccatacac ttgcttgtaa cggtatgatc atatcttttc aaggtaacat tttctagcat   1260
cttcagctgt ctacttgact gaatgcagta tatattagtt gtaataaata ctgcccttct   1320
gctgtgcaca aaaggcgggt attaccactt gcagaaattt gtcgggtaaa ggtaattgcc   1380
agttaccttg tgttcttccc ttgatcagga acacctggag gaggatgcgc tgtggttgaa   1440
ccgaagccct gtgagcgaag tactgatgac agaaagagcg gaagataaga taagaaagga   1500
acccttgcgc ggcaaggcct ggtgacatag aggtagtgcg aggctcatac cgccgccgct   1560
ggcaggttcc aggcctgtgc ttttcttgcc ctgtatcccc agtctatact tctgcgcaca   1620
tcagacgagc ctcagtgttt cggcacagtg gtgcaacaga aaaggagagt gctggtaggt   1680
aacgctgagg cggtgaagaa agagaggtca gacggacctg gaggtggctt tttaactggt   1740
aaagagtgag gtctttcatg cccatcaatc tgagcaccga cttgggtgtt gctcctgttc   1800
gcaggaagca caagaaatgg tcagtactcc acagcgtagg catgtcggtg gtgtgttgga   1860
ggaggcaaga ttcagatgat tattatatga gctcgaaaag ctagagaatg gatgttcaga   1920
cttgagagct ctgatttgag aggaattgca cttgtcgttt tcccaaggcg acgcggcctt   1980
tttccagagt ttttttttt nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnaaaaaaaa aaaaaaaaag   2160
aatgcacacc gacatgctct gtagcacaag caccatactg gcgaactgga gaggtctcgg   2220
ctcatcaaga aatcgccttg gtgtcggacg gggtcatcaa gacaagacga ctagacgagc   2280
actacatata gacgggaacg tacgggagga aggaaggaaa acgagagcga ggactcactg   2340
tccggtccgc ccagcttggt gacggcgtcg acgaagcgct ggtggaggtc cggcgtccag   2400
cgcagccgcg gcttggggtc ccgtgacgcc gccccgtcgt agccgtagct cccctgcatc   2460
gtcgttcctt cctggcgatc gccgcttcct agctatccgg tggccaaaga cacggctagt   2520
ggtaggctcg agtgagacga gctcttgctg aagagagaat gaatgtaacg ttaccgcctc   2580
ctggtcgtag gtgtaataag ttgtaacgcg agcgtcgtta gcaagcacag gggtttgtgt   2640
atgtgaggac aagaggagga gcgagaggag gagcgcagag cgtggcgggg aaggagggcg   2700
tcatgtgtgc gaggaatcta ggacgacttg ttggcacttg gcagctgggc cggggtgcgt   2760
gcgagatgca atgcaagaac aaagcggacg ggcatcacgc ctccaggtcc aacccggggg   2820
cgccactcgg ccgccgctca ttgaggccca ggcgccaaga cggcggctcc acccacatca   2880
caattggcaa caagaagcac acggctgggg ttggacgcg tcgaattttt caccagaaaa   2940
taccgtctga tcctggcgtt tcgtcagatg ctatgctacg tgaacggcaa aacctagcag   3000
cagcagcagc actcagactg gacaagagga gggaaatctt tgcgtgggaa ccaaactgaa   3060
cgcgaatcgc acgagtcgga tgacatatcc tcgtccggag cggactcgac cgcgagtcca   3120
gctgtggctg cggaatattc cggcggaagc gcggggagaa cgacggcggc ctccggtggg   3180
acccggggcg agcgggagat gcggcgaaga tgttcggcgc tgatgtcgct ggaatattcg   3240
cgccagctgt ggctgccggt gtgacctgct gaccagacga ccagtggcag tggccaccgc   3300
```

```
ctctccatca cagattcgcg gacgattagc cgagactaat cgctattctc aacactttta    3360
aaaccgtgcg tgcagaatgc taagggcgcg ttcgtttgca cagcaataga catggattta    3420
tttcagctca tcaaaatcta tataaattaa agaagtaatc cggctagaaa ttaatccgga    3480
gcttcaatcc ctaacaaccg aacagggtct aagcctgcta gattcgagca tctgcgtgac    3540
tctactttgg ctcttctcgt acgatgcgac ttgacgatgc atttgggnnn nnnnntagcg    3600
acactctcct gattagtccc acggaaacgc aactctacca ctatcagccg ccg           3653
```

<210> SEQ ID NO 215
<211> LENGTH: 3586
<212> TYPE: DNA
<213> ORGANISM: Zea mays
<220> FEATURE:
<221> NAME/KEY: misc_feature
<222> LOCATION: (2001)..(2139)
<223> OTHER INFORMATION: n is a, c, g, or t

<400> SEQUENCE: 215

```
tcgcatctgc agcttctttt gcacctgatt acagacataa gcacttgtag cgtttatgga      60
agaaagtttt ggagtgcaaa tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaac     240
caaataaaat gggcccactg cagtcaatta acaggcattc aataggattc acattcctgg     300
gcttctatat atggaagttt gcatacaaag ttttttgaaat aaaatggaat agaaaattgct    360 tgcatttagt gtaagttaat actagctccg ttctcgaata tttgtcgtcc gctagttcat     420
ttttgaacta aaacacgaca aataaaaaaa cggaaggagt acatgtttgt aacaggtgag     480 ccccctgaata cttgcttgta acaggtggag cactaagtat gcttagaact ttaggcaact    540 tgtattctttt agcacttcga cgccgtttgt atggtaatat ctactgatag acagaatcct    600
ggttttggat tttttttta ttttttcctgt ttttggttac acctctacag tcccatactc     660
gcagtccaat aatacatggt ctgataataa accaattaag aaggactcat gtctcagtca     720
ttaggctgtc tccaacaacg tcctctatat tcatcctcta tatctgtcct ttacagtctc     780
ctctaaaaaa tttcatccta tatatctcat ttctctccaa caacgtcctc taaatcacgt    840
cctctatact caaatactca tattaaagac attttttaat tttatttttt atacatacgt    900
aattatcata ctctcaaatg tattgtgcat attttagttt tgctaaaccg gttatttaaa     960
gtagtcaaat ggatagagga ccgtttagag aaactctata tatagagaat tcagcagcgt    1020
cctctaaatt taaaggaccg tttagaggac gttgctggag agcgtagagg accgtttggt    1080
cctctatatt tagggtagag aacccttttag ggggccttgt tggagccagc cttatgactt    1140
gagcatagga gttgagatca agaaatatgt gagttgcagc ttaaggttca gagaggaaat    1200
ccccatacac ttgcttgtaa cggtatgatc atatctttc aaggtaacat ttctagcat     1260 cttcagctgt ctacttgact gaatgcagta tatattagtt gtaataaata ctgcccttct    1320
gctgtgcaca aaaggcgggt attaccactt gcagaaattt gtcgggtaaa ggtaattgcc    1380
agttaccttg tgttcttccc ttgatcagga acacctggag gaggatgcgc tgtggttgaa    1440
ccgaagccct gtgagcgaag tactgatgac agaaagagcg gaagataaga taagaaagga    1500
acccttgcgc ggcaaggcct ggtgacatag aggtagtgcg aggctcatac cgccgccgct    1560
ggcaggttcc aggcctgtgc ttttcttgcc ctgtatcccc agtctatact tctgcgcaca    1620
```

```
tcagacgagc ctcagtgttt cggcacagtg gtgcaacaga aaaggagagt gctggtaggt    1680
aacgctgagg cggtgaagaa agagaggtca gacggacctg gaggtggctt tttaactggt    1740
aaagagtgag gtctttcatg cccatcaatc tgagcaccga cttgggtgtt gctcctgttc    1800
gcaggaagca caagaaatgg tcagtactcc acagcgtagg catgtcggtg gtgtgttgga    1860
ggaggcaaga ttcagatgat tattatatga gctcgaaaag ctagagaatg gatgttcaga    1920
cttgagagct ctgatttgag aggaattgca cttgtcgttt tcccaaggcg acgcggcctt    1980
tttccagagt ttttttttt nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnna aaaaaaaaaa aaaaaaaag     2160
aatgcacacc gacatgctct gtagcacaag caccatactg gcgaactgga gaggtctcgg    2220
ctcatcaagc aatcgccttg gtgtcggacg gggtcatcaa gacaagacga ctagacgagc    2280
actacatata gacgggaacg tacgggagga aggaaggaaa acgagagcga ggactcactg    2340
tccggtccgc ccagcttggt gacggcgtcg acgaagcgct ggtggaggtc cggcgtccag    2400
cgcagccgcg gcttggggtc ccgtgacgcc gccccgtcgt agccgtagct cccctgcatc    2460
gtcgttcctt cctggcgatc gccgcttcct agctatccgg tggccaaaga cacggctagt    2520
ggtaggctcg agtgagacga gctcttgctg aagagagaat gaatgtaacg ttaccgcctc    2580
ctggtcgtag gtgtaataag ttgtaacgcg agcgtcgtta gcaagcacag gggtttgtgt    2640
atgtgaggac aagaggagga gcgagaggag gagcgcagag cgtggcgggg aaggagggcg    2700
tcatgtgtgc gaggaatcta ggacgacttg ttggcacttg gcagctgggc cggggtgcgt    2760
gcgagatgca atgcaagaac aaagcggacg ggcatcacgc ctccaggtcc aacccggggg    2820
cgccactcgg ccgccgctca ttgaggccca ggcgccaaga cggcggctcc acccacatca    2880
caattggcaa caagaagcac acggctgggg ttgggacgcg tcgaattttt caccagaaaa    2940
taccgtctga tcctggcgtt tcgtcagatg ctatgctacg tgaacggcaa aacctagcag    3000
cagcagcagc actcagactg gacaagagga gggaaatctt tgcgtgggaa ccaaactgaa    3060
cgcgaatcgc acgagtcgga tgacatatcc tcgtccggag cggactcgac cgcgagtcca    3120
gctgtggctg cggaatattc cggcggaagc gcggggagaa cgacggcggc ctccggtggg    3180
acccggggcg agcgggagat gcggcgaaga tgttcggcgc tgatgtcgct ggaatattcg    3240
cgccagctgt ggctgccggt gtgacctgct gaccagacga ccagtggcag tggccaccgc    3300
ctctccatca cagattcgcg gacgattagc cgagactaat cgctattctc aacactttta    3360
aaaccgtgcg tgcagaatgc taagggcgcg ttcgtttgca cagcaataga catggattta    3420
tttcagctca tcaaaatcta tataaattaa agaagtaatc cggctagaaa ttaatccgga    3480
gcttcaatcc ctaacaaccg aacagggtct aagcctgcta gattcgagca tctgcgtgac    3540
tctactttgg ctcttctcgt acgatgcgac ttgacgatgc atttgg                  3586
```

<210> SEQ ID NO 216
<211> LENGTH: 3588
<212> TYPE: DNA
<213> ORGANISM: Zea mays
<220> FEATURE:
<221> NAME/KEY: misc_feature
<222> LOCATION: (2000)..(2143)
<223> OTHER INFORMATION: n is a, c, g, or t

<400> SEQUENCE: 216

```
tcgcatctgc agcttctttt gcacctgatt acagacataa gcacttgtag cgtttatgga      60
```

```
agaaagtttt ggagtgcaaa tctcatgaca atgatgtaaa tctatcttgc ctcagtttgt    120
tcttgtagtt tcctttggac ttgaatttga taccttagtg catcgctaag tgctatttct    180
ctgattcaca taagaaatgt gatacaaatg gttagttcaa tcaatgcaga aaagttcaac    240
caaataaaat gggcccactg cagtcaatta acaggcattc aataggattc acattcctgg    300
gcttctatat atggaagttt gcatacaaag ttttgaaat aaaatggaat agaaattgct    360
tgcatttagt gtaagttaat actagctccg ttctcgaata tttgtcgtcc gctagttcat    420
ttttgaacta aaacacgaca aataaaaaaa cggaaggagt acatgtttgt aacaggtgag    480
cccctgaata cttgcttgta acaggtggag cactaagtat gcttagaact ttaggcaact    540
tgtattcttt agcacttcga cgccgtttgt atggtaatat ctactgatag acagaatcct    600
ggttttggat tttttttta tttttcctgt ttttggttac acctctacag tcccatactc    660
gcagtccaat aatacatggt ctgataataa accaattaag aaggactcat gtctcagtca    720
ttaggctgtc tccaacaacg tcctctatat tcatcctcta tatctgtcct ttacagtctc    780
ctctaaaaaa tttcatccta tatatctcat ttctctccaa caacgtcctc taaatcacgt    840
cctctatact caaatactca tattaaagac attttttaat tttatttttt atacatacgt    900
aattatcata ctctcaaatg tattgtgcat attttagttt tgctaaaccg gttatttaaa    960
gtagtcaaat ggatagagga ccgtttagag aaactctata tatagagaat tcagcagcgt   1020
cctctaaatt taaaggaccg tttagaggac gttgctggag agcgtagagg accgtttggt   1080
cctctatatt tagggtagag aacccttag ggggccttgt tggagccagc cttatgactt   1140
gagcatagga gttgagatca agaaatatgt gagttgcagc ttaaggttca gagaggaaat   1200
ccccatacac ttgcttgtaa cggtatgatc atatcttttc aaggtaacat tttctagcat   1260
cttcagctgt ctacttgact gaatgcagta tatattagtt gtaataaata ctgcccttct   1320
gctgtgcaca aaaggcgggt attaccactt gcagaaattt gtcgggtaaa ggtaattgcc   1380
agttaccttg tgttcttccc ttgatcagga acacctggag gaggatgcgc tgtggttgaa   1440
ccgaagccct gtgagcgaag tactgatgac agaaagagcg gaagataaga taagaaagga   1500
acccttgcgc ggcaaggcct ggtgacatag aggtagtgcg aggctcatac cgccgccgct   1560
ggcaggttcc aggcctgtgc ttttcttgcc ctgtatcccc agtctatact tctgcgcaca   1620
tcagacgagc ctcagtgttt cggcacagtg gtgcaacaga aaaggagagt gctggtaggt   1680
aacgctgagg cggtgaagaa agagaggtca gacggacctg gaggtggctt tttaactggt   1740
aaagagtgag gtctttcatg cccatcaatc tgagcaccga cttgggtgtt gctcctgttc   1800
gcaggaagca caagaaatgg tcagtactcc acagcgtagg catgtcggtg gtgtgttgga   1860
ggaggcaaga ttcagatgat tattatatga gctcgaaaag ctagagaatg gatgttcaga   1920
cttgagagct ctgatttgag aggaattgca cttgtcgttt tcccaaggcg acgcggcctt   1980
tttccagagt tttttttttn nnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnaaaaaaa aaaaaaaaag   2160
aatgcacacc gacatgctct gtagcacaag caccatactg gcgaactgga gaggtctcgg   2220
ctcatcaagc aatcgccttg gtgtcggacg gggtcatcaa gacaagacga ctagacgagc   2280
actacatata gacgggaacg tacggaggaa ggaaggaaa acgagagcga ggactcactg   2340
tccggtccgc ccagcttggt gacggcgtcg acgaagcgct ggtggaggtc cggcgtccag   2400
```

| | |
|---|---|
| cgcagccgcg gcttggggtc ccgtgacgcc gccccgtcgt agccgtagct cccctgcatc | 2460 |
| gtcgttcctt cctggcgatc gccgcttcct agctatccgg tggccaaaga cacggctagt | 2520 |
| ggtaggctcg agtgagacga gctcttgctg aagagagaat gaatgtaacg ttaccgcctc | 2580 |
| ctggtcgtag gtgtaataag ttgtaacgcg agcgtcgtta gcaagcacag gggtttgtgt | 2640 |
| atgtgaggac aagaggagga gcgagaggag gagcgcagag cgtggcgggg aaggagggcg | 2700 |
| tcatgtgtgc gaggaatcta ggacgacttg ttggcacttg gcagctgggc cggggtgcgt | 2760 |
| gcgagatgca atgcaagaac aaagcggacg ggcatcacgc ctccaggtcc aacccggggg | 2820 |
| cgccactcgg ccgccgctca ttgaggccca ggcgccaaga cggcggctcc acccacatca | 2880 |
| caattggcaa caagaagcac acggctgggg ttgggacgcg tcgaattttt caccagaaaa | 2940 |
| taccgtctga tcctggcgtt tcgtcagatg ctatgctacg tgaacggcaa aacctagcag | 3000 |
| cagcagcagc actcagactg acaagagga gggaaatctt tgcgtgggaa ccaaactgaa | 3060 |
| cgcgaatcgc acgagtcgga tgacatatcc tcgtccggag cggactcgac cgcgagtcca | 3120 |
| gctgtggctg cggaatattc cggcggaagc gcggggagaa cgacggcggc ctccggtggg | 3180 |
| acccggggcg agcggagat gcggcgaaga tgttcggcgc tgatgtcgct ggaatattcg | 3240 |
| cgccagctgt ggctgccggt gtgacctgct gaccagacga ccagtggcag tggccaccgc | 3300 |
| ctctccatca cagattcgcg gacgattagc cgagactaat cgctattctc aacacttta | 3360 |
| aaaccgtgcg tgcagaatgc taagggcgcg ttcgtttgca cagcaataga catggattta | 3420 |
| tttcagctca tcaaaatcta tataaattaa agaagtaatc cggctagaaa ttaatccgga | 3480 |
| gcttcaatcc ctaacaaccg aacagggtct aagcctgcta gattcgagca tctgcgtgac | 3540 |
| tctactttgg ctcttctcgt acgatgcgac ttgacgatgc atttgggc | 3588 |

<210> SEQ ID NO 217
<211> LENGTH: 3548
<212> TYPE: DNA
<213> ORGANISM: Zea mays
<220> FEATURE:
<221> NAME/KEY: misc_feature
<222> LOCATION: (1866)..(2143)
<223> OTHER INFORMATION: n is a, c, g, or t
<220> FEATURE:
<221> NAME/KEY: misc_feature
<222> LOCATION: (3483)..(3489)
<223> OTHER INFORMATION: n is a, c, g, or t

<400> SEQUENCE: 217

| | |
|---|---|
| tcgcatctgc agcttctttt gcacctgatt acagacataa gcacttgtag cgtttatgga | 60 |
| agaaagtttt ggagtgcaaa tctcatgaca atgatgtaaa tctatcttgc ctcagtttgt | 120 |
| tcttgtagtt tcctttggac ttgaatttga taccttagtg catcgctaag tgctatttct | 180 |
| ctgattcaca taagaaatgt gatacaaatg gttagttcaa tcaatgcaga aaagttcaac | 240 |
| caaataaaat gggcccactg cagtcaatta acaggcattc aataggattc acattcctgg | 300 |
| gcttctatat atggaagttt gcatacaaag ttttgaaat aaaatggaat agaaattgct | 360 |
| tgcatttagt gtaagttaat actagctccg ttctcgaata tttgtcgtcc gctagttcat | 420 |
| ttttgaacta aaacacgaca aataaaaaaa cggaaggagt acatgtttgt aacaggtgag | 480 |
| cccctgaata cttgcttgta acaggtggag cactaagtat gcttagaact ttaggcaact | 540 |
| tgtattcttt agcacttcga cgccgtttgt atggtaatat ctactgatag acagaatcct | 600 |
| ggttttggat tttttttta ttttttcctgt ttttggttac acctctacag tcccatactc | 660 |
| gcagtccaat aatacatggt ctgataataa accaattaag aaggactcat gtctcagtca | 720 |

```
ttaggctgtc tccaacaacg tcctctatat tcatcctcta tatctgtcct ttacagtctc    780
ctctaaaaaa tttcatccta tatatctcat ttctctccaa caacgtcctc taaatcacgt    840
cctctatact caaatactca tattaaagac atttttttaat tttattttttt atacatacgt   900
aattatcata ctctcaaatg tattgtgcat attttagttt tgctaaaccg gttatttaaa    960
gtagtcaaat ggatagagga ccgtttagag aaactctata tatagagaat tcagcagcgt   1020
cctctaaatt taaaggaccg tttagaggac gttgctggag agcgtagagg accgtttggt   1080
cctctatatt tagggtagag aaccctttag ggggccttgt tggagccagc cttatgactt   1140
gagcatagga gttgagatca agaaatatgt gagttgcagc ttaaggttca gagaggaaat   1200
ccccatacac ttgcttgtaa cggtatgatc atatcttttc aaggtaacat tttctagcat   1260
cttcagctgt ctacttgact gaatgcagta tatattagtt gtaataaata ctgcccttct   1320
gctgtgcaca aaaggcgggt attaccactt gcagaaattt gtcgggtaaa ggtaattgcc   1380
agttaccttg tgttcttccc ttgatcagga acacctggag gaggatgcgc tgtggttgaa   1440
ccgaagccct gtgagcgaag tactgatgac agaaagagcg gaagataaga taagaaagga   1500
acccttgcgc ggcaaggcct ggtgacatag aggtagtgcg aggctcatac cgccgccgct   1560
ggcaggttcc aggcctgtgc ttttcttgcc ctgtatcccc agtctatact tctgcgcaca   1620
tcagacgagc ctcagtgttt cggcacagtg gtgcaacaga aaaggagagt gctggtaggt   1680
aacgctgagg cggtgaagaa agagaggtca gacggacctg gaggtggctt tttaactggt   1740
aaagagtgag gtctttcatg cccatcaatc tgagcaccga cttgggtgtt gctcctgttc   1800
gcaggaagca caagaaatgg tcagtactcc acagcgtagg catgtcggtg gtgtgttgga   1860
ggaggnnnnn nnnnnnnnnn nnnnnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nnnnnnnnnn   1980
nnnnnnnnnn nnnnnnnnnn nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnaaaaaaa aaaaaaaaag   2160
aatgcagacc gacatgctct gtagcacaag caccatactg gcgaactgga gaggtctcgg   2220
ctcatcaagc aatcgccttg gtgtcggacg gggtcatcaa gacaagacga ctagacgagc   2280
actacatata gacgggaacg tacgggagga aggaaggaaa acgagagcga ggactcactg   2340
tccggtccgc ccagcttggt gacggcgtcg acgaagcgct ggtggaggtc cggcgtccag   2400
cgcagccgcg gcttggggtc ccgtgacgcc gccccgtcgt agccgtagct cccctgcatc   2460
gccgttcctt cctggcgatc gccgctccct agctatccgg tggccaaaga cacggctagt   2520
ggtaggctcg agcgagacga gctcttggtg aagagagaat gaatgtaacg ttaccgcctc   2580
ctggtcgtag gggtgtgtgt atgtgaggac aagaggagga gcgagaggag gagcgcagag   2640
cgtggcgggg aaggagggcg tcatgtgtgc gaggaatcta ggacgacttg ttggcagctg   2700
ggccggggtg cgtgcgagat gcaatgcaag aacaaagcgg acgggcatct cgctcggcca   2760
cgcttccaag tccatccggg gggcgccact cggccgccgc tcattgaggc ccaggcgcca   2820
agacggcggc tccaccccacg tcacaattgg caacaagaag cacacggctg gggctgggac   2880
gcgtcgaatt tttcaccaga aaataccgtc tgatcctggc gtttcgtgaa cggcaaaacc   2940
tagcagcagc agcagcattc cacgggtcgg atgacatatc atatcctcgt gcggagcgga   3000
ctctacggcg agtccagctg tggctgcgga atattccggc ggaagcgcgg ggagagcgac   3060
```

```
ggcggcctcc ggtgggaccc ggggcgagcg ggagatgcgg cgaagatgtt cggcgctgat   3120
gtcgctggaa tattcgcgcc agctgtggct gccggtgcga cctgctgacc agacgaccaa   3180
tggcagtggc caccgcctct ccctcttgct gttggagttg gatccacgga ccactctcca   3240
tccaacatcc atcacagatt ggcggacgat tagccgagac taatcgctat tctcaacact   3300
tttaaaaccg tacgtgcaaa atgctaaggg gccgttcgtt tcttagccgg aatggcggtt   3360
tgtttctcta atttatataa gttttgatta gctgtattga ttcctgatcc aattctgaac   3420
aaacgaacaa aacctgctag attcgagcat ctgcgtgact ctactttggc ccttctcgta   3480
cgnnnnnnnt ggcgttcctc tagcgtcact ttcccccgga aacgcaactc taccactatc   3540
agccgccg                                                             3548
```

<210> SEQ ID NO 218
<211> LENGTH: 3548
<212> TYPE: DNA
<213> ORGANISM: Zea mays
<220> FEATURE:
<221> NAME/KEY: misc_feature
<222> LOCATION: (2003)..(2144)
<223> OTHER INFORMATION: n is a, c, g, or t
<220> FEATURE:
<221> NAME/KEY: misc_feature
<222> LOCATION: (3446)..(3446)
<223> OTHER INFORMATION: n is a, c, g, or t
<220> FEATURE:
<221> NAME/KEY: misc_feature
<222> LOCATION: (3490)..(3490)
<223> OTHER INFORMATION: n is a, c, g, or t

<400> SEQUENCE: 218

```
tcgcatctgc agcttctttt gcacctgatt acagacataa gcacttgtag cgtttatgga     60
agaaagtttt ggagtgcaaa tctcatgaca atgatgtaaa tctatcttgc ctcagtttgt    120
tcttgtagtt tcctttggac ttgaatttga taccttagtg catcgctaag tgctatttct    180
ctgattcaca taagaaatgt gatacaaatg gttagttcaa tcaatgcaga aaagttcaac    240
caaataaaat gggcccactg cagtcaatta acaggcattc aataggattc acattcctgg    300
gcttctatat atggaagttt gcatacaaag ttttttgaaat aaaatggaat agaaattgct    360
tgcatttagt gtaagttaat actagctccg ttctcgaata tttgtcgtcc gctagttcat    420
ttttgaacta aaacacgaca aataaaaaaa cggaaggagt acatgtttgt aacaggtgag    480
cccctgaata cttgcttgta acaggtggag cactaagtat gcttagaact ttaggcaact    540
tgtattcttt agcacttcga cgccgttgt atggtaatat ctactgatag acagaatcct    600
ggttttggat ttttttttta ttttttcctgt ttttggttac acctctacag tcccatactc    660
gcagtccaat aatacatggt ctgataataa accaattaag aaggactcat gtctcagtca    720
ttaggctgtc tccaacaacg tcctctatat tcatcctcta tatctgtcct ttacagtctc    780
ctctaaaaaa tttcatccta tatatctcat ttctctccaa caacgtcctc taaatcacgt    840
cctctatact caaatactca tattaaagac atttttttaat tttatttttt atacatacgt    900
aattatcata ctctcaaatg tattgtgcat attttagttt tgctaaaccg gttatttaaa    960
gtagtcaaat ggatagagga ccgtttagag aaactctata tatagagaat tcagcagcgt   1020
cctctaaatt taaggaccg tttagaggac gttgctggag agcgtagagg accgtttggt    1080
cctctatatt tagggtagag aacccttag ggggccttgt tggagccagc cttatgactt    1140
gagcatagga gttgagatca agaaatatgt gagttgcagc ttaaggttca gagaggaaat   1200
ccccatacac ttgcttgtaa cggtatgatc atatcttttc aaggtaacat tttctagcat   1260
```

```
cttcagctgt ctacttgact gaatgcagta tatattagtt gtaataaata ctgcccttct    1320
gctgtgcaca aaaggcgggt attaccactt gcagaaattt gtcgggtaaa ggtaattgcc    1380
agttaccttg tgttcttccc ttgatcagga cacctggag gaggatgcgc tgtggttgaa     1440
ccgaagccct gtgagcgaag tactgatgac agaaagagcg gaagataaga taagaaagga    1500
acccttgcgc ggcaaggcct ggtgacatag aggtagtgcg aggctcatac cgccgccgct    1560
ggcaggttcc aggcctgtgc ttttcttgcc ctgtatcccc agtctatact tctgcgcaca    1620
tcagacgagc ctcagtgttt cggcacagtg gtgcaacaga aaaggagagt gctggtaggt    1680
aacgctgagg cggtgaagaa agagaggtca gacggacctg gaggtggctt tttaactggt    1740
aaagagtgag gtctttcatg cccatcaatc tgagcaccga cttgggtgtt gctcctgttc    1800
gcaggaagca caagaaatgg tcagtactcc acagcgtagg catgtcggtg gtgtgttgga    1860
ggaggcaaga ttcagatgat tattatatga gctcgaaaag ctagagaatg gatgttcaga    1920
cttgagagct ctgatttgag aggaattgca cttgtcgttt cccaaggcg acgcggcctt     1980 tttccagagt ttttttttt ttnnnnnnnn nnnnnnnnnn nnnnnnnnnn nnnnnnnnnn     2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnaaaaaa aaaaaaaaag    2160
aatgcagacc gacatgctct gtagcacaag caccatactg gcgaactgga gaggtctcgg    2220
ctcatcaagc aatcgccttg gtgtcggacg gggtcatcaa gacaagacga ctagacgagc    2280
actacatata gacgggaacg tacgggagga aggaaggaaa acgagagcga ggactcactg    2340
tccggtccgc ccagcttggt gacggcgtcg acgaagcgct ggtggaggtc cggcgtccag    2400
cgcagccgcg gcttggggtc ccgtgacgcc gccccgtcgt agccgtagct cccctgcatc    2460
gccgttcctt cctggcgatc gccgctccct agctatccgg tggccaaaga cacggctagt    2520
ggtaggctcg agcgagacga gctcttggtg aagagagaat gaatgtaacg ttaccgcctc    2580
ctggtcgtag gggtgtgtgt atgtgaggac aagaggagga gcgagaggag gagcgcagag    2640
cgtggcgggg aaggagggcg tcatgtgtgc gaggaatcta ggacgacttg ttggcagctg    2700
ggccggggtg cgtgcgagat gcaatgcaag aacaaagcgg acgggcatct cgctcggcca    2760
cgcttccaag tccatccggg gggcgccact cggccgccgc tcattgaggc ccaggcgcca    2820
agacggcggc tccacccacg tcacaattgg caacaagaag cacacggctg gggctgggac    2880
gcgtcgaatt tttcaccaga aaataccgtc tgatcctggc gtttcgtgaa cggcaaaacc    2940
tagcagcagc agcagcattc cacgggtcgg atgacatatc atatcctcgt gcggagcgga    3000
ctctacggcg agtccagctg tggctgcgga atattccggc ggaagcgcgg ggagagcgac    3060
ggcggcctcc ggtgggaccc ggggcgagcg ggagatgcgg cgaagatgtt cggcgctgat    3120
gtcgctggaa tattcgcgcc agctgtggct gccggtgcga cctgctgacc agacgaccaa    3180
tggcagtggc caccgcctct ccctcttgct gttggagttg gatccacgga ccactctcca    3240
tccaacatcc atcacagatt ggcggacgat tagccgagac taatcgctat tctcaacact    3300
tttaaaaccg tacgtgcaaa atgctaaggg gccgttcgtt tcttagccgg aatggcggtt    3360
tgtttctcta atttatataa gttttgatta gctgtattga ttcctgatcc aattctgaac    3420
aaacgaacaa aacctgctag attcgngcat ctgcgtgact ctactttggc ccttctcgta    3480
cgagcttttn ggcgttcctc tagcgtcact ttccccccgga aacgcaactc taccactatc    3540
agccgccg                                                             3548
```

<210> SEQ ID NO 219
<211> LENGTH: 3482
<212> TYPE: DNA
<213> ORGANISM: Zea mays
<220> FEATURE:
<221> NAME/KEY: misc_feature
<222> LOCATION: (2003)..(2143)
<223> OTHER INFORMATION: n is a, c, g, or t

<400> SEQUENCE: 219

```
tcgcatctgc agcttctttt gcacctgatt acagacataa gcacttgtag cgtttatgga      60
agaaagtttt ggagtgcaaa tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaac     240
caaataaaat gggcccactg cagtcaatta acaggcattc aataggattc acattcctgg     300
gcttctatat atggaagttt gcatacaaag ttttttgaaat aaaatggaat agaaattgct     360
tgcatttagt gtaagttaat actagctccg ttctcgaata tttgtcgtcc gctagttcat     420
ttttgaacta aaacacgaca aataaaaaaa cggaaggagt acatgtttgt aacaggtgag     480
cccctgaata cttgcttgta acaggtggag cactaagtat gcttagaact ttaggcaact     540
tgtattctttt agcacttcga cgccgtttgt atggtaatat ctactgatag acagaatcct     600
ggttttggat ttttttttta ttttttcctgt ttttggttac acctctacag tcccatactc     660
gcagtccaat aatacatggt ctgataataa accaattaag aaggactcat gtctcagtca     720
ttaggctgtc tccaacaacg tcctctatat tcatcctcta tatctgtcct ttacagtctc     780
ctctaaaaaa tttcatccta tatatctcat ttctctccaa caacgtcctc taaatcacgt     840
cctctatact caaatactca tattaaagac attttttaat tttatttttt atacatacgt     900
aattatcata ctctcaaatg tattgtgcat attttagttt tgctaaaccg gttatttaaa     960
gtagtcaaat ggatagagga ccgtttagag aaactctata tatagagaat tcagcagcgt    1020
cctctaaatt taaaggaccg tttagaggac gttgctggag agcgtagagg accgtttggt    1080
cctctatatt tagggtagag aacccttttag ggggccttgt tggagccagc cttatgactt    1140
gagcatagga gttgagatca agaaatatgt gagttgcagc ttaaggttca gagaggaaat    1200
ccccatacac ttgcttgtaa cggtatgatc atatcttttc aaggtaacat tttctagcat    1260
cttcagctgt ctacttgact gaatgcagta tatattagtt gtaataaata ctgcccttct    1320
gctgtgcaca aaaggcgggt attaccactt gcagaaattt gtcgggtaaa ggtaattgcc    1380
agttaccttg tgttcttccc ttgatcagga acacctggag gaggatgcgc tgtggttgaa    1440
ccgaagccct gtgagcgaag tactgatgac agaaagagcg gaagataaga taagaaagga    1500
acccttgcgc ggcaaggcct ggtgacatag aggtagtgcg aggctcatac cgccgccgct    1560
ggcaggttcc aggcctgtgc ttttcttgcc ctgtatcccc agtctatact tctgcgcaca    1620
tcagacgagc ctcagtgttt cggcacagtg gtgcaacaga aaaggagagt gctggtaggt    1680
aacgctgagg cggtgaagaa agagaggtca gacggacctg gaggtggctt tttaactggt    1740
aaagagtgag gtctttcatg cccatcaatc tgagcaccga cttgggtgtt gctcctgttc    1800
gcaggaagca caagaaatgg tcagtactcc acagcgtagg catgtcggtg gtgtgttgga    1860
ggaggcaaga ttcagatgat tattatatga gctcgaaaag ctagagaatg gatgttcaga    1920
cttgagagct ctgatttgag aggaattgca cttgtcgttt tcccaaggcg acgcggcctt    1980
tttccagagt tttttttttt ttnnnnnnnn nnnnnnnnnn nnnnnnnnnn nnnnnnnnnn    2040
```

| | |
|---|---|
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnaaaaaaa aaaaaaaaag | 2160 |
| aatgcagacc gacatgctct gtagcacaag caccatactg gcgaactgga gaggtctcgg | 2220 |
| ctcatcaagc aatcgccttg gtgtcggacg gggtcatcaa gacaagacga ctagacgagc | 2280 |
| actacatata gacgggaacg tacgggagga aggaaggaaa acgagagcga ggactcactg | 2340 |
| tccggtccgc ccagcttggt gacggcgtcg acgaagcgct ggtggaggtc cggcgtccag | 2400 |
| cgcagccgcg gcttggggtc ccgtgacgcc gccccgtcgt agccgtagct cccctgcatc | 2460 |
| gccgttcctt cctggcgatc gccgctccct agctatccgg tggccaaaga cacggctagt | 2520 |
| ggtaggctcg agcgagacga gctcttggtg aagagagaat gaatgtaacg ttaccgcctc | 2580 |
| ctggtcgtag gggtgtgtgt atgtgaggac aagaggagga gcgagaggag gagcgcagag | 2640 |
| cgtggcgggg aaggagggcg tcatgtgtgc gaggaatcta ggacgacttg ttggcagctg | 2700 |
| ggccggggtg cgtgcgagat gcaatgcaag aacaaagcgg acgggcatct cgctcggcca | 2760 |
| cgcttccaag tccatccggg gggcgccact cggccgccgc tcattgaggc ccaggcgcca | 2820 |
| agacggcggc tccacccacg tcacaattgg caacaagaag cacacggctg gggctgggac | 2880 |
| gcgtcgaatt tttcaccaga aaataccgtc tgatcctggc gtttcgtgaa cggcaaaacc | 2940 |
| tagcagcagc agcagcattc cacgggtcgg atgacatatc atatcctcgt gcggagcgga | 3000 |
| ctctacggcg agtccagctg tggctgcgga atattccggc ggaagcgcgg ggagagcgac | 3060 |
| ggcggcctcc ggtgggaccc ggggcgagcg ggagatgcgg cgaagatgtt cggcgctgat | 3120 |
| gtcgctggaa tattcgcgcc agctgtggct gccggtgcga cctgctgacc agacgaccaa | 3180 |
| tggcagtggc caccgcctct ccctcttgct gttggagttg gatccacgga ccactctcca | 3240 |
| tccaacatcc atcacagatt ggcggacgat tagccgagac taatcgctat tctcaacact | 3300 |
| tttaaaaccg tacgtgcaaa atgctaaggg gccgttcgtt tcttagccgg aatggcggtt | 3360 |
| tgtttctcta atttatataa gttttgatta gctgtattga ttcctgatcc aattctgaac | 3420 |
| aaacgaacaa aacctgctag attcgagcat ctgcgtgact ctactttggc ccttctcgta | 3480 |
| cg | 3482 |

<210> SEQ ID NO 220
<211> LENGTH: 2977
<212> TYPE: DNA
<213> ORGANISM: Zea mays
<220> FEATURE:
<221> NAME/KEY: misc_feature
<222> LOCATION: (1593)..(1739)
<223> OTHER INFORMATION: n is a, c, g, or t
<220> FEATURE:
<221> NAME/KEY: misc_feature
<222> LOCATION: (2846)..(2846)
<223> OTHER INFORMATION: n is a, c, g, or t

<400> SEQUENCE: 220

| | |
|---|---|
| tcgcatctgc agcttctttt gcacctgatt acagacataa gcacttgtag cgtttatgga | 60 |
| agaaagtttt ggagtgcaga tctcatgaca atgatgtaaa tctatcttgc ctcagtttgt | 120 |
| tcttgtagtt tcctttggac ttgaatttga taccttagtg catcgctaag tgctatttct | 180 |
| ctgattcaca taagaaatgc gatacaaatg gttagttcag tcaatgcaga aaagttcaac | 240 |
| aaaataaaat gggcccactg cagtcaatta acaggcattc aacagcattc acattcctgg | 300 |
| gcctctatat atggaagttt gcatacaaag ttttggaaat aaaatggaat agaaattgct | 360 |

```
tgcatttagt gtaagttaat acccgctccg ttctcgaata tttgtcgcct gctagttcat    420
ttttgaacta aaacacgaca aataaaaaaa acggaaggag tacatgtttg taacaggaga    480 gccctgaat acttgcttgt aacaggtgga gcgctaagta tgcttaggag aactttaggc    540
aacttgtatt ctttagcact tcgacgccgt ttgtatggta atatctactg atagacagaa    600
tcctggtttt ggaattttt tattttcct gcttttggtt acacctctac agtcccatac    660
tcgcagtcga ataatacatg gtctgataat aaaccaatta aggactcatg tctcagtcat    720
tatgacttga gcataggagt tcagatcgag aaatatttga gttgcagctt aaggttcaga    780
gaggaaaccc ccatacactt gcttgtaacg gtatgatcat ttttttgaa ggtaacattt    840 tctagcatct tcagctgtct acttgactga atgcagtata tattagttgt aataaatact    900
gcccttctgc tgtgcacaaa aggcgggtat taccacttgc agaaatttgt cgggtaaagg    960
taattgccag ttaccttgtg ttcttccctt catcaggaac acctggagga ggatgcgctg   1020
tggttgaact gaagccctgc gagagaagta ctgatgacag aaagagcgga agataagata   1080
agaaaggaaa cccttgcgcg gcagggcctg gtgacataga ggtagtgcga ggctcatacc   1140
gccgccgctg gcaggttcca ggcctgtgct tttcttgccc tgtatcccca gtctatactt   1200
ctgcgcacat cagacgagcg tcagtgtttc ggcacagtgg tgcaacagaa aaggagagtg   1260
ctggtaggta acgctgaggc ggtgaagaaa gagaggtcag acggacctgg aggtggcttt   1320
ttaactggta aagagtgagg tctttcatgc ccatcaatct gagcaccgac ttgggtgttg   1380
ctcctgttcg caggaagcac aagaaatggt cagtactcca cagcgtaggc atgtcggtgg   1440
tgtgttggag gaggcaagat tcagatgatt attatatgag ctcgaaaagc tagagaatgg   1500
atgttcagac ttgagagctc tgatttgaga gaaattgcac ttgtcgtttt cccaaggcga   1560
cgcggccttt tccagaggtt ttttttttt ttnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnc   1740
tgaaaaaaaa atgcacaccg acatgctctg tagcacaagc accataccgg cgaactggag   1800
aggtctcggc tcatcaagca atcgccttgg tgtcggacgg ggtcatcaag acaaggcgac   1860
tagaggagca ctacatctac acggggtgaa cggacgggag cagtggcgga cccaggaact   1920
gatgacagcc ttggcgagaa tacggtgtga tccccacgcc tgtgctcgtg ccacgtgctg   1980
cttgcttccg tgcactgtgc tcgcgccttg cccattgcag ccggcgagcc agctcaggcc   2040
accgcctgcg gtgcctggtg agtccgcccc tggacgggga gaaggaagga aaacgagagc   2100
gaggactcac tgtccggtcc gcccagcttg gtgacggcgt cgacgaagcg ctggtggagg   2160
tccggcgtcc agcgcagccg cggcttgggg tcccgtgacg ccgccccgtc gtagccgtag   2220
ctcccctgca tcgccgttcc ttcctggcga tcgccgctcc ctagctatcc ggtggccaaa   2280
gacacggcta gtggtaggct cgagcgagac gagctcttgc tgaagagaga atgaatgtag   2340
cgttaccgcc tcctggtcgt aggggtgtgg gtatgtgagg acaagaggag gagcgagagg   2400
aggagcgcag agcgtggcgg ggaaggaggg cgtcatgtgt gtgaggaatc taggacgact   2460
tgttggcagc tgggccgggg tgcgtgcgag atgcaatgca agaacaaagc ggacgggcat   2520
cacgcctcca agtccaaccc gggggcgcca ctcggccgcc gctcattgag gcccaggcgc   2580
caagacggcg gctccaccca cgtcacaatt ggcaacaaga agcacacggc tggggctggg   2640
acgcgtcgaa ttttttcacca gaaaataccg tcggcgtttc gtcagatgct atgctacgtg   2700
aacggcaaaa cctagcagca gcagcagcat tcagactgga caagaggagg gaaatctttg   2760
```

```
cgtgggaacc aaactgaacg cgaatcgcac gagtcggatg acatatcctc gtgcggagcg    2820
gactcgaccg cgagtccagc tgtggntgcg gaatattccg gcggaagcgc ggggagaacg    2880
acggcggcct ccggtgggac ccggggcgag cgggagatgc ggcgaagatg ttcggcgctg    2940
atgtcgctgg aatattcgcg ccagctgtgg ctgccgg                             2977
```

<210> SEQ ID NO 221
<211> LENGTH: 3064
<212> TYPE: DNA
<213> ORGANISM: Zea mays
<220> FEATURE:
<221> NAME/KEY: misc_feature
<222> LOCATION: (1464)..(1891)
<223> OTHER INFORMATION: n is a, c, g, or t
<220> FEATURE:
<221> NAME/KEY: misc_feature
<222> LOCATION: (3023)..(3023)
<223> OTHER INFORMATION: n is a, c, g, or t
<220> FEATURE:
<221> NAME/KEY: misc_feature
<222> LOCATION: (3027)..(3027)
<223> OTHER INFORMATION: n is a, c, g, or t

<400> SEQUENCE: 221

```
tcgcatctgc agcttctttt gcacctgatt acagacataa gcacttgtag cgtttatgga     60
agaaaggttt ggagtgcaga tctcatgaca atgatgtaaa tctatcttgc ctcagtttgt    120
tcttgtagtt tcctttggac ttgaatttga taccttagtg catcgctaag tgctatttct    180
ctgattcaca taagaaatgt gatacaaatg gttagctcaa tcaatgcaga aaagttcaac    240
caaataaaat gggcccactg cagtcaatta acaggcattc aataggattc acattcctgg    300
gcttctatat atggaagttt gcatacaaag ttttggaaat aaaatggaat ataaattgct    360
tgcatttagt gtaagttaat acccgctctg ttctcgaata tttgtcaccc gctagttcat    420
ttttgaacta aaacacgaca aataaaaaaa cggaaggagt acatgtttgt aacaggagag    480
cccctgaata cttgcttgta acaggtggag cgctaagtat gcttaggaga actttaggca    540
acttgtattc tttagcactt cgacgccgtt tgtatggtaa tatctactga tagacagaat    600
cctggttttg gaatttttttt tatttttcct gcttttggtt acacctctac agtcccatac    660
tcgcagtcga ataatacatg gtctgataat aaaccaatta aggactcatg tctcagtcat    720
tatgacttga gcataggagt tgagatcaag aaatatttga gttgcagctt aaggttcaga    780
gaggaaatcc ccatacacgt gcttgtaacg gtatggtcat tttttttttca aggtaacatt    840 ttctagcatc ttcagctgtc tacttgactg aatgcagtat atattagttg taataaaatac    900 tggccttctg ctgtgcacaa aaggcgggta ttaccacttg cagaaatttg tcgggtcaag    960
gtaattgcca gttaccttgt gttcttccct tgatcaggaa cacctggagg aggatgcgct   1020
gtggttgaac tgaagccgcc ctgtgagcga agtactgatg acagaaagag cggaagataa   1080
gataagaaag gaacgcttgc gcggcaaggc ctggtgacat agaggtagtg cgaggctcat   1140
accgccgccg ctggcaggtt cgaggcctgt gcttttcttg ccctgtatcc ccagtctata   1200
cttctgcgca catcagacga gcctcagtgt ttcggcacag tggtgcaaca gaaaaggaga   1260
gtgctggtag gtaacgctga ggcggtgaag aaagagaggt cagacggacc tggaggtggc   1320
tttttaactg gtaaagagtg aggtctttca tgcccatcaa tctgagcacc gacttgggtg   1380 ttgctccctgt tcgcaggaag cacaagaaat ggtcagtact ccacagcgta ggcatgtcgg   1440
tggtgtgttg gaggaggcaa gatnnnnnnn nnnnnnnnn nnnnnnnnnn nnnnnnnnnn   1500
```

```
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nggacgggag gaaggaagga aaacgagagc   1920
gaggactcac tgtccggtcc gcccagcttg gtgacggcgt cgacgaagcg ctggtggagg   1980
tccggcgtcc agcgcagccg cggcttgggg tcccgtgacg ccgccccgtc gtagccgtag   2040
ctcccctgca tcgccgttcc ttcctggcga tcgccgctcc ctagctatcc ggtggccaaa   2100
gacacggcta gtggtaggct cgagcgagac gagctcttgc tgaagagaga atgaatgtag   2160
cgttaccgcc tcctggtcgt aggggtgtgg gtatgtgagg acaagaggag gagcgagagg   2220
aggagcgcag agcgtggcgg ggaaggaggg cgtcatgtgt gtgaggaatc taggacgact   2280
tgttggcagc tgggccgggg tgcgtgcgag atgcaatgca agaacaaagc ggacgggcat   2340
cacgcctcca ggtccaaccc gggggcgcca ctcgatcggc cgccgctcat tgaggcccag   2400
gcgccaagac ggcggctcca cccacgtcac aattggcaat aagaagcaca cggctggggc   2460
tgggacgcgt cgaattttc accagaaaat accgtctgat cctggcgttt cgtcagatgc   2520
tatgctacgt gaacggcaaa acctagcagc agcagcactc agactggaca agaggaggga   2580
aatctttgcg tgggaaccaa actgaacgcg aatcgcacgg gtcggatgac atatcatatc   2640
ctcgtgcgga gcggactcaa cggcgagtcc agctgtggct gcggaatatt ccggcggaag   2700
cgcggggaga gcgacggcgg cctccggtgg gacccggggc gagcgggaga tgcggcgaag   2760
atgttcggcg ctgatgtcgc tggaatattc gcgccagctg tggctgccgg tgcgacctgc   2820
tgaccagacg accagtggca atggccaccg cctctccatc caacctccat cacagattgg   2880
cggacgatta gccgagacta atcgctattc tcaacacttt aaaaaccgtg cgtgcagaat   2940
gctaagcctg ctagattcga gcatctgcgt gactctactt tggctcttct cgtacgatgc   3000
gacctgacga tgcatttggg cgncctntag cgtcacttcc tgattagtcc cccggaaacg   3060
caac                                                                3064

<210> SEQ ID NO 222
<211> LENGTH: 3087
<212> TYPE: DNA
<213> ORGANISM: Zea mays
<220> FEATURE:
<221> NAME/KEY: misc_feature
<222> LOCATION: (1281)..(1735)
<223> OTHER INFORMATION: n is a, c, g, or t
<220> FEATURE:
<221> NAME/KEY: misc_feature
<222> LOCATION: (3024)..(3025)
<223> OTHER INFORMATION: n is a, c, g, or t
<220> FEATURE:
<221> NAME/KEY: misc_feature
<222> LOCATION: (3029)..(3029)
<223> OTHER INFORMATION: n is a, c, g, or t

<400> SEQUENCE: 222
tcgcatctgc agcttctttt gcacctgatt acagacataa gcacttgtag cgtttatgga     60
agaaaggttt ggagtgcaga tctcatgaca atgatgtaaa tctatcttgc ctcagtttgt    120
tcttgtagtt tcctttggac ttgaatttga taccttagtg catcgctaag tgctatttct    180
```

```
ctgattcaca taagaaatgt gatacaaatg gttagctcaa tcaatgcaga aaagttcaac    240
caaataaaat gggcccactg cagtcaatta acaggcattc aataggattc acattcctgg    300
gcttctatat atggaagttt gcatacaaag ttttggaaat aaaatggaat ataaattgct    360
tgcatttagt gtaagttaat acccgctctg ttctcgaata tttgtcaccc gctagttcat    420
ttttgaacta aaacacgaca aataaaaaaa cggaaggagt acatgtttgt aacaggagag    480
cccctgaata cttgcttgta acaggtggag cgctaagtat gcttaggaga actttaggca    540
acttgtattc tttagcactt cgacgccgtt tgtatggtaa tatctactga tagacagaat    600
cctggttttg gaatttttt ttattttttcc tgcttttggt tacacctcta cagtcccata    660
ctcgcagtcg aataatacat ggtctgataa taaaccaatt aaggactcat gtctcagtca    720
ttatgacttg agcataggag ttgagatcaa gaaatatttg agttgcagct taaggttcag    780
agaggaaatc cccatacacg tgcttgtaac ggtatggtca tttttttttt caaggtaaca    840
ttttctagca tcttcagctg tctacttgac tgaatgcagt atatattagt tgtaataaat    900
actggccttc tgctgtgcac aaaaggcggg tattaccact tgcagaaatt tgtcgggtca    960
aggtaattgc cagttacctt tgttcttcc cttcatcagg aacacctgga ggaggatgcg   1020
ctgtggttga actgaagccg ccctgtgagc gaagtactga tgacagaaag agcggaagat   1080
aagataagaa aggaacgctt gcgcggcaag gcctggtgac atagaggtag tgcgaggctc   1140
ataccgccgc cgctggcagg ttcgaggcct gtgcttttct tgccctgttt ccccattcta   1200
tacttctgcg cacatcagac gagcctcagt gtttcggcac agtggtgcaa caaaaaaga    1260
gagtgctggt aggtaaccct nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnaaaaa   1740
aaaaaaaaaa aaagaatgca gaccgacatg ctctgtagca caagcaccat actggcgaac   1800
tggagaggtc tcggctcatc aagcaatcgc cttggtgtcg gacggggtca tcaagacaag   1860
acgactagac gagcactaca tatagacggg aacgtacggg aggaaggaag gaaaacgaga   1920
gcgaggactc actgtccggt ccgcccagct tggtgacggc gtcgacgaag cgctggtgga   1980
ggtccggcgt ccagcgcagc gcggcttgg ggtcccgtga cgccgcccg tcgtagccgt   2040
agctcccctg catcgccgtt ccttcctggc gatcgccgct ccctagctat ccggtggcca   2100
aagacacggc tagtggtagg ctcgagcgag acgagctctt gctgaagaga gaatgaatgt   2160
agcgttaccg cctcctggtc gtagggggtgt gggtatgtga ggacaagagg aggagcgaga   2220
ggaggagcgc agagcgtggc ggggaaggag ggcgtcatgt gtgtgaggaa tctaggacga   2280
cttgttggca gctgggccgg ggtgcgtgcg agatgcaatg caagaacaaa gcggacgggc   2340
atcacgcctc caggtccaac ccggggggcgc cactcgatcg gccgccgctc attgaggccc   2400
aggcgccaag acgcggctc cacccacgtc acaattggca ataagaagca cacggctggg   2460
gctgggacgc gtcgaatttt tcaccagaaa ataccgtctg atcctggcgt ttcgtcagat   2520
```

```
gctatgctac gtgaacggca aaacctagca gcagcagcac tcagactgga caagaggagg      2580
gaaatctttg cgtgggaacc aaactgaacg cgaatcgcac gggtcggatg acatatcata      2640
tcctcgtgcg gagcggactc aacggcgagt ccagctgtgg ctgcggaata ttccggcgga      2700
agcgcgggga gagcgacggc ggcctccggt gggacccggg gcgagcggga gatgcggcga      2760
agatgttcgg cgctgatgtc gctggaatat tcgcgccagc tgtggctgcc ggtgcgacct      2820
gctgaccaga cgaccagtgg caatggccac cgcctctcca tccaacctcc atcacagatt      2880
ggcggacgat tagccgagac taatcgctat tctcaacact ttaaaaaccg tgcgtgcaga      2940
atgctaagcc tgctagattc gagcatctgc gtgactctac tttggctctt ctcgtacgat      3000
gcgacctgac gatgcattgg gcgnncctnt agcgtcactt tcctgattag tcccccggaa      3060
acgcaactct accactatca gccgccg                                           3087

<210> SEQ ID NO 223
<211> LENGTH: 2956
<212> TYPE: DNA
<213> ORGANISM: Zea mays
<220> FEATURE:
<221> NAME/KEY: misc_feature
<222> LOCATION: (1584)..(1728)
<223> OTHER INFORMATION: n is a, c, g, or t

<400> SEQUENCE: 223
tcgcatctgc agcttctttt gcacctgatt acagacataa gcacttgtag cgtttatgga       60 agaaagttttt ggagtgcaaa tctcatgaca atgatgtaaa tctgtcttgc ctcagtttgt      120
tcttgtagtt tcctttggac ttgaatttga taccttagtg catcgctaag tgctatttct      180
ctgattcgca taagaaatgc gatacaaatg gttagttcaa tcaatgcaga aaagttcaac      240
aaaataaaat gggcccactg cagtcaatta acaggcattc aacagcattc acattcctgg      300
gcctctatat atggaagttt gcatacaaag ttttggaaat aaaatggaat agaaattgct      360
tgcatttagt gtaagttaat actccatccg ttcttaaata tttgtcggcc gctagtttat      420
ttttgaacta aaacacgaca aataaaaaaa acggagggag tacatgttta taacaggtga      480
gccgaatact tggttgtaac aggtggggcg ctaagtatgc ttaggagaac tttaggcaac      540
ttgtattctg tagcacttcg acgccgtttg tatggtaata tctactgata gacagaatcc      600 tggttttttgg aaaaaaaaaa ttcctgcttt tggttacacc tctacagtcc catactcgca      660
gtcgaataat acatggtctg ataataaacc aattaaggac tcatgtctca gtcattatga      720
cttgagcata ggagttgaga tcgagaaata tttgagttac agcttaaggt tcagacttca      780
gagaggaaat ccccatacac ttgcttgtaa cggtatgatc atttttttc aaggtaacat      840 tttctagcat cttcacctgt ctacttgact gaatgcagta tatattagtt gtaataaata      900
ctgctcttct gctgtgcaga aaaggcgggt attaccactt gcagaaattt gtcgggtaaa      960
ggtaattgcc agttaccttg tgttcttccc ttcatcagga acacctggag gaggatgcgc     1020
tgtggttgaa ccgaagccct gtgagcgaag tactgatgac agaaagagcg gaagataaga     1080
taagaaagga acccttgcgc ggcaaggcct ggtgacatag aggtagtgcg aggctcatac     1140
cgccgccgct ggcaggttcc aggcctgtgc ttttcttgcc ctgtatcccc agtctatact     1200
tctgcgcaca tcagacgagc ctcagtgttt cggcacagtg gtgcaacaga aaaggagagt     1260
gctgctaacg ctgaggcggt gaagaaagag aggtcggacg gacctggagg tggcttttta     1320
actggtaaag agtgaggtct ttcatgccca tcaatctgag caccgacttg ggtgttgctc     1380
ctgttcgcag gaagcacaag aaatggtcag tactccacag cgtaggcatg tcggtgtgtt     1440
```

```
cgaggaggca agattcagat gattattata tgagctcgaa aagctagaga atggatgttc    1500
agacttgaga ggtctgattt gagaggaatt gcacttgtcg ttttcccagg gcgacgcggc    1560 cttttccag aggcttttt tttnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnaa aaaaaaaaaa    1740
aagaatgcag accgacatgc tctgtagcac aagcaccata ctggcgaact ggagaggtct    1800
cggctcatca agcaatcgcc ttggtgtcgg acggggtcat caagacaaga cgactagacg    1860
agcactacat atagacggga acgtacggga ggaaggaagg aaaacgagag cgaggactca    1920
ctgtccggtc cgcccagctt ggtgacggcg tcgacgaagc gctggtggag gtccggcgtc    1980
cagcgcagcc gcggcttggg gtcccgtgac gcaaaccaac gtcgtagccg tagctcccct    2040
gcatcgccgt tccttcctgg cgatcgccgc tccctagcta tccggtggcc aaagacacgg    2100
ctagtggtag gctcgagcga gacgagctct tggtgaagag agaatgaatg taacgttacc    2160
gcctcctggt cgtaggggtg tgtgtatgtg aggacaagag gaggagcgag aggaggagcg    2220
cagagcgtgg cggggaagga gggcgtcatg tgtgcgagga atctcggacg acttgttggc    2280
agctgggccg gggtgcgtgc gagatgcaat gcaagaacaa agcggacggg catctcgctc    2340
ggccacgctt ccaagtccaa ccggggggcg ccactcggcc gccgctcatt gaggcccagg    2400
cgccaagacg gcggctccac ccacatcaca attggcaaca agaagcacac ggctggggct    2460
gggacgcgtc gaattttca ccagaaaata ccgtcggcgt ttcgtcagat gctatgctac    2520
gtgaacggca aaacctagca gcagcagcac tcagactgga caagaggagg gaaatctttg    2580
cgtgggaacc aaactgaacg cgaatcgcac gagtcggatg acatatcctc gtccggagcg    2640
gactcggccg cgagtccagc tgtggctgcg gaatattccg gcggaatcgc ggggagaacg    2700
acggcggcct ccggtgggac ccggggcgag cgggagatgc ggcgaagatg ttcggcgctg    2760
atgtcgctgg aatattcgcg ccagctgtgg ctgccggtgt gacctgctga ccagacgacc    2820
agtggcagtg gccaccgcct ctgcatcaca gattggcgga cgattagccg agactaattg    2880
ccattctcaa cacttttaaa accgtgcgtg cagaatgcta agcctgctag attcgagcat    2940
ctgcgtgact ctactt                                                    2956
```

<210> SEQ ID NO 224
<211> LENGTH: 2965
<212> TYPE: DNA
<213> ORGANISM: Zea mays
<220> FEATURE:
<221> NAME/KEY: misc_feature
<222> LOCATION: (1600)..(1902)
<223> OTHER INFORMATION: n is a, c, g, or t

<400> SEQUENCE: 224

```
tcgcatctgc agcttctttt gcacctgatt acagacataa gcacttgtag cgtttatgga     60
agaaagtttt ggagtgcaga tctcatgaca atgatgtaaa tctatcttgc ctcagtttgt    120
tcttgtagtt tcctttggac ttgaatttga taccttagtg catcgctaag tgctggttct    180
ctgattcaca taagaaatgt gatacaaatg gttagttcaa tcaatgcaga aaagttcaat    240
caaataaaat gggcccactg cagtcaatta acaggcattc aataggattc acattcctgg    300
gcttctatat atggaagttt gcatacaatg ttttggaaat aaaatgaaat ataaattgct    360
tgcatttagt gtaagttaat actcgctccc ttctcgaata tttgtcgtcc gctagttcat    420
```

```
ttttgaacta aaacatgata aataaaaaaa cggaaggagt acatgtttgt aacaggagag    480
cccatgaata cttgcttgta acaggtggag cgctaagtat gcttaggaga actttaggca    540
acttgtattc tttagcactt cgacgcagtt tgtatggtaa tatctactga tagacagaat    600
cctggttttg gattttttaat ttttcctgct tttggttaca cctctacagt cccatactcg    660
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt ttttttcaag    840
gtaacatttt ctagcatctt cacctgtcta cttgactgaa tgcagtatat attagttgta    900
ataactactg gccttctgct gtgcacaaaa ggcgggtatt accacttgca gaaatttgtc    960
gggtaaaggt aattgccagt taccttgtgt tcttcccttg atcaggaaca cctggaggag   1020
gatgcgctgt ggttgaaccg aagccctgtg agcgaagtac tgatgacaga aagagcggaa   1080
gataagataa gaaaggaacc cttgcgcggc aaggcctggt gacatagagg tagtgcgagg   1140
ctcataccgc cgccgctggc aggttccagg cctgtgcttt tcttgccctg tatccccagt   1200
ctatacttct gcgcacatca gacgagcctc agtgtttcgg cacagtggtg caacagaaaa   1260
ggagagtgct ggtaggtaac gctgaggcgg tgaagaaaga gaggtcagac ggacctggag   1320
gtggcttttt aactggtaaa gagtgaggtc tttcatgccc atcaatctga gcaccgactt   1380
gggtgttgct cctgttcgca ggaagcacaa gaaatggtca gtactccaca gcgtaggcat   1440
gtcggtggtg tgttggagga ggcaagattc agatgattat tatatgagct cgaaaagcta   1500
gagaatggat gttcagactt gagagctctg atttgagagr aattgcactt gtcgttttcc   1560
caaggcgacg cggccttttt ccagaggttt tttttttttn nnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nnnnnnnnnn nnacgggagg aaggaaggaa   1920
aacgagagcg aggactcact gtccggtccg cccagcttgg tgacggcgtc gacgaagcgc   1980
tggtggaggt ccggcgtcca gcgcagccgc ggcttgggt cccgtgacgc cgccccgtcg   2040
tagccgtagc tcccctgcat cgccgttcct tcctggcgat cgccgctccc tagctatccg   2100
gtggccaaag acacggctag tggtaggctc gagcgagacg agctcttgct gaagagagaa   2160
tgaatgtagc gttaccgcct cctggtcgta ggggtgtggg tatgtgagga caagaggagg   2220
agcgagagga ggagcgcaga gcgtggcggg gaaggagggc gtcatgtgtg cgaggaatct   2280
aggacgactt gttggcagct gggccggggt gcgtgcgaga tgcaatgcaa gaacaaagcg   2340
gacgggcatc tcgctcggcc acgcttccaa gtccatccgg ggggcgccac tcggccgccg   2400
ctcattgagg cccaggcgcc aagacggcgg ctccacccac gtcacaattg caacaagaa   2460
gcacacggct ggggctggga cgcgtcgaat ttttcaccag aaaataccgt ctgatcctgg   2520
cgtttcgtga acggcaaaac ctagcagcag cagcagcatt ccacgggtcg gatgacatat   2580
catatcctcg tgcggagcgg actcaacggc gagtccagct gtggctgcgg aatattccgg   2640
cggaagcgcg gggagagcga cggcggcctc cggtgggacc cggggcgagc gggagatgcg   2700
gcgaagatgt tcggcgctga tgtcgctgga atattcgcgc cagctgtggc tgccggtgcg   2760
acctgctgac cagacgacca gtggcaatgg ccaccgcctc tccatccaac ctccatcaca   2820
```

```
gattggcgga cgattagccg agactaatcg ctattctcaa cactttaaaa accgtgcgtg      2880
cagaatgcta agcctgctag attcgagcat ctgcgtgact ctactttggc tcttctcgta      2940
cgatgcgacc tgacgatgca tttgg                                            2965
```

<210> SEQ ID NO 225
<211> LENGTH: 2855
<212> TYPE: DNA
<213> ORGANISM: Zea mays
<220> FEATURE:
<221> NAME/KEY: misc_feature
<222> LOCATION: (1601)..(1748)
<223> OTHER INFORMATION: n is a, c, g, or t
<220> FEATURE:
<221> NAME/KEY: misc_feature
<222> LOCATION: (2804)..(2806)
<223> OTHER INFORMATION: n is a, c, g, or t

<400> SEQUENCE: 225

```
tcgcatctgc agcttctttt gcacctgatt acagacataa gcacttgtag cgtttatgga        60
agaaagtttt ggagtgcaga tctcatgaca atgatgtaaa tctatcttgc ctcagtttgt       120
tcttgtagtt tcctttggac ttgaatttga taccttagtg catcgctaag tgctatttct       180
ctgattcaca taagaaatgt gatacaaatg gttagttcaa tcaatgcaga aaagttcaat       240
caaataaaat gggcccactg cagtcaatta acaggcattc aataggattc acattcctgg       300
gcttctatat atggaagttt gcatacaatg ttttggaaat aaaatgaaat ataaattgct       360
tgcatttagt gtaagttaat actcgctccc ttctcgaata tttgtcgtcc gctagttcat       420
ttttgaacta aaacatgata aataaaaaaa cggaaggagt acatgtttgt aacaggagag       480
cccatgaata cttgcttgta acaggtggag cgctaagtat gcttaggaga actttaggca       540
acttgtattc tttagcactt cgacgcagtt tgtatggtaa tatctactga tagacagaat       600
cctggttttg gattttaat ttttcctgct tttggttaca cctctacagt cccatactcg       660
cagtccaata gtacatggtc tgataataaa ccaattaaga aggactcatg tctcagtcat       720
tatgacttga gcataggagt tgagatcaag aaatatttga gttgcagctt aaggtccaga       780
gaggaaatcc ccatacactt gcttgtaacg gtatgaatgt atgatcattt tttttttcaag      840 gtaacatttt ctagcatctt cacctgtcta cttgactgaa tgcagtatat attagttgta       900
ataactactg gccttctgct gtgcacaaaa ggcgggtatt accacttgca gaaatttgtc       960
gggtaaaggt aattgccagt taccttgtgt tcttcccttg atcaggaaca cctggaggag      1020
gatgcgctgt ggttgaaccg aagccctgtg agcgaagtac tgatgacaga aagagcggaa      1080
gataagataa gaaaggaacc cttgcgcggc aaggcctggt gacatagagg tagtgcgagg      1140
ctcataccgc cgccgctggc aggttccagg cctgtgcttt tcttgccctg tatcccagt       1200 ctatacttct gcgcacatca gacgagcctc agtgtttcgg cacagtggtg caacagaaaa      1260
ggagagtgct ggtaggtaac gctgaggcgg tgaagaaaga gaggtcagac ggacctggag      1320
gtggcttttt aactggtaaa gagtgaggtc tttcatgccc atcaatctga gcaccgactt      1380
gggtgttgct cctgttcgca ggaagcacaa gaaatggtca gtactccaca gcgtaggcat      1440
gtcggtggtg tgttggagga ggcaagattc agatgattat tatatgagct cgaaaagcta      1500
gagaatggat gttcagactt gagagctctg atttgagagr aattgcactt gtcgttttcc      1560
caaggcgacg cggcctttc cagaggtttt ttttttttttt nnnnnnnnnn nnnnnnnnnn      1620
nnnnnnnnnn nnnnnnnnnn nnnnnnnnnn nnnnnnnnnn nnnnnnnnnn nnnnnnnnnn      1680
```

```
nnnnnnnnnn nnnnnnnnnn nnnnnnnnnn nnnnnnnnnn nnnnnnnnnn nnnnnnnnnn      1740
nnnnnnnntg aaaaaaaaat gcacaccgac atgctctgta gcacaagcac ataccggcg        1800 aactggagag gtctcggctc atcaagcaat cgccttggtg tcggacgggg tcatcaagac       1860
aaggcgacta gaggagcact acatctacac ggggtgaacg gacgggagca gtggcggacc       1920
caggaactga tgacagcctt ggcgagaata cggtgtgatc cccacgcctg tgctcgtgcc       1980
acgtgctgct tgcttccgtg cactgtgctc gtgccttgcc cattgcagcc ggcgagccag       2040
ctcaggccac cgcctgcggt gcctggtgag tccgccctg gacgggagga aggaaggaaa        2100
acgagagcga ggactcactg tccggtccgc ccagcttggt gacggcgtcg acgaagcgct       2160
ggtggaggtc cggcgtccag cgcagccgcg gcttgggtc ccgtgacgcc gccccgtcgt        2220
agccgtagct cccctgcatc gccgttcctt cctggcgatc gccgctccct agctatccgg       2280
tggccaaaga cacggctagt ggtaggctcg agcgagacga gctcttgctg aagagagaat       2340
gaatgtagcg ttaccgcctc ctggtcgtag gggtgtgggt atgtgaggac aagaggagga      2400
gcgagaggag gagcgcagag cgtggcgggg aaggagggcg tcatgtgtgc gaggaatcta      2460
ggacgacttg ttggcagctg ggccggggtg cgtgcgagat gcaatgcaag aacaaagcgg      2520
acgggcatct cgctcggcca cgcttccaag tccatccggg gggcgccact cggccgccgc      2580
tcattgaggc ccaggcgcca agacggcggc tccacccacg tcacaattgg caacaagaag      2640 cacacgctg gggctgggac gcgtcgaatt tttcaccaga aaataccgtc tgatcctggc       2700
gtttcgtgaa cggcaaaacc tagcagcagc agcagcattc cacgggtcgg atgacatatc      2760
atatcctcgt gcggagcgga ctcaacgcg agtccagctg tggnnncgga atattccggc       2820
ggaagcgcgg ggagagcgac ggcggcctcc ggtgg                                  2855

<210> SEQ ID NO 226
<211> LENGTH: 3212
<212> TYPE: DNA
<213> ORGANISM: Zea mays
<220> FEATURE:
<221> NAME/KEY: misc_feature
<222> LOCATION: (1601)..(1805)
<223> OTHER INFORMATION: n is a, c, g, or t
<220> FEATURE:
<221> NAME/KEY: misc_feature
<222> LOCATION: (3148)..(3150)
<223> OTHER INFORMATION: n is a, c, g, or t
<220> FEATURE:
<221> NAME/KEY: misc_feature
<222> LOCATION: (3154)..(3154)
<223> OTHER INFORMATION: n is a, c, g, or t

<400> SEQUENCE: 226
tcgcatctgc agcttctttt gcacctgatt acagacataa gcacttgtag cgtttatgga        60
agaaagtttt ggagtgcaga tctcatgaca atgatgtaaa tctatcttgc ctcagtttgt       120
tcttgtagtt tcctttggac ttgaatttga taccttagtg catcgctaag tgctatttct       180
ctgattcaca taagaaatgt gatacaaatg gttagttcaa tcaatgcaga aaagttcaat       240
caaataaaat gggcccactg cagtcaatta acaggcattc aataggattc acattcctgg       300
gcttctatat atggaagttt gcatacaatg ttttggaaat aaaatgaaat ataaattgct       360
tgcatttagt gtaagttaat actcgctccc ttctcgaata tttgtcgtcc gctagttcat       420
ttttgaacta aaacatgata aataaaaaaa cggaaggagt acatgtttgt aacaggagag       480
cccatgaata cttgcttgta acaggtggag cgctaagtat gcttaggaga acttaggca        540 acttgtattc tttagcactt cgacgcagtt tgtatggtaa tatctactga tagacagaat       600
```

```
cctggttttg gattttaat ttttcctgct tttggttaca cctctacagt cccatactcg    660
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt tttttcaag    840
gtaacatttt ctagcatctt cacctgtcta cttgactgaa tgcagtatat attagttgta    900
ataactactg gccttctgct gtgcacaaaa ggcgggtatt accacttgca gaaatttgtc    960
gggtaaaggt aattgccagt taccttgtgt tcttcccttg atcaggaaca cctggaggag   1020
gatgcgctgt ggttgaaccg aagccctgtg agcgaagtac tgatgacaga aagagcggaa   1080
gataagataa gaaaggaacc cttgcgcggc aaggcctggt gacatagagg tagtgcgagg   1140
ctcataccgc cgccgctggc aggttccagg cctgtgcttt tcttgccctg tatccccagt   1200
ctatacttct gcgcacatca gacgagcctc agtgtttcgg cacagtggtg caacagaaaa   1260
ggagagtgct ggtaggtaac gctgaggcgg tgaagaaaga gaggtcagac ggacctggag   1320
gtggcttttt aactggtaaa gagtgaggtc tttcatgccc atcaatctga gcaccgactt   1380
gggtgttgct cctgttcgca ggaagcacaa gaaatggtca gtactccaca gcgtaggcat   1440
gtcggtggtg tgttggagga ggcaagattc agatgattat tatatgagct cgaaaagcta   1500
gagaatggat gttcagactt gagagctctg atttgagagr aattgcactt gtcgttttcc   1560
caaggcgacg cggcctttt ccagaggttt ttttttttt nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnggaga ggtctcggct catcaagcaa tcgccttggt gtcggacggg gtcatcaaga   1860
caagrcgact agaggagcac tacatctaca cggggtgaac ggacgggagc agtggcggac   1920
ccaggaactg atgacagcct tggcgagaat acggtgtgat ccccacgcct gtgctcgtgc   1980
cacgtgctgc ttgcttccgt gcactgtgct cgtgccttgc ccattgcagc cggcgagcca   2040
gctcaggcca ccgcctgcgg tgcctggtga gtccgcccct ggacgggagg aaggaaggaa   2100
aacgagagcg aggactcact gtccggtccg cccagcttgg tgacggcgtc gacgaagcgc   2160
tggtggaggt ccggcgtcca gcgcagccgc ggcttgggt cccgtgacgc cgccccgtcg   2220
tagccgtagc tcccctgcat cgccgttcct tcctggcgat cgccgctccc tagctatccg   2280
gtggccaaag acacggctag tggtaggctc gagcgagacg agctcttgct gaagagagaa   2340
tgaatgtagc gttaccgcct cctggtcgta ggggtgtggg tatgtgagga caagaggagg   2400
agcgagagga ggagcgcaga gcgtggcggg gaaggagggc gtcatgtgtg cgaggaatct   2460
aggacgactt gttggcagct gggccggggt gcgtgcgaga tgcaatgcaa gaacaaagcg   2520
gacgggcatc tcgctcggcc acgcttccaa gtccatccgg ggggcgccac tcggccgccg   2580
ctcattgagg cccaggcgcc aagacggcgg ctccacccac gtcacaattg caacaagaa   2640
gcacacggct ggggctggga cgcgtcgaat ttttcaccag aaaataccgt ctgatcctgg   2700
cgtttcgtga acgcaaaac ctagcagcag cagcagcatt ccacgggtcg gatgacatat   2760
catatcctcg tgcggagcgg actcaacggc gagtccagct gtggctgcgg aatattccgg   2820
cggaagcgcg gggagagcga cggcggcctc cggtgggacc cggggcgagc gggagatgcg   2880
gcgaagatgt tcggcgctga tgtcgctgga atattcgcgc cagctgtggc tgccggtgcg   2940
```

| | |
|---|---|
| acctgctgac cagacgacca gtggcaatgg ccaccgcctc tccatccaac ctccatcaca | 3000 |
| gattggcgga cgattagccg agactaatcg ctattctcaa cactttaaaa accgtgcgtg | 3060 |
| cagaatgcta agcctgctag attcgagcat ctgcgtgact ctactttggc tcttctcgta | 3120 |
| cgatgcgacc tgacgatgca tttgggcnnn cctntagcgt cactttcctg attagtcccc | 3180 |
| cggaaacgca actctaccac tatcagccgc cg | 3212 |

```
<210> SEQ ID NO 227
<211> LENGTH: 3315
<212> TYPE: DNA
<213> ORGANISM: Zea mays
<220> FEATURE:
<221> NAME/KEY: misc_feature
<222> LOCATION: (1601)..(1748)
<223> OTHER INFORMATION: n is a, c, g, or t

<400> SEQUENCE: 227
```

| | |
|---|---|
| tcgcatctgc agcttctttt gcacctgatt acagacataa gcacttgtag cgtttatgga | 60 |
| agaaagtttt ggagtgcaga tctcatgaca atgatgtaaa tctatcttgc ctcagtttgt | 120 |
| tcttgtagtt tcctttggac ttgaatttga taccttagtg catcgctaag tgctatttct | 180 |
| ctgattcaca taagaaatgt gatacaaatg gttagttcaa tcaatgcaga aaagttcaat | 240 |
| caaataaaat gggcccactg cagtcaatta acaggcattc aataggattc acattcctgg | 300 |
| gcttctatat atggaagttt gcatacaatg ttttggaaat aaaatgaaat ataaattgct | 360 |
| tgcatttagt gtaagttaat actcgctccc ttctcgaata tttgtcgtcc gctagttcat | 420 |
| ttttgaacta aaacatgata aataaaaaaa cggaaggagt acatgtttgt aacaggagag | 480 |
| cccatgaata cttgcttgta acaggtggag cgctaagtat gcttaggaga actttaggca | 540 |
| acttgtattc tttagcactt cgacgcagtt tgtatggtaa tatctactga tagacagaat | 600 |
| cctggttttg gattttttaat ttttcctgct tttggttaca cctctacagt cccatactcg | 660 |
| cagtccaata gtacatggtc tgataataaa ccaattaaga aggactcatg tctcagtcat | 720 |
| tatgacttga gcataggagt tgagatcaag aaatatttga gttgcagctt aaggtccaga | 780 |
| gaggaaatcc ccatacactt gcttgtaacg gtatgaatgt atgatcattt tttttttcaag | 840 |
| gtaacatttt ctagcatctt cacctgtcta cttgactgaa tgcagtatat attagttgta | 900 |
| ataactactg gccttctgct gtgcacaaaa ggcgggtatt accacttgca gaaatttgtc | 960 |
| gggtaaaggt aattgccagt taccttgtgt tcttcccttg atcaggaaca cctggaggag | 1020 |
| gatgcgctgt ggttgaaccg aagccctgtg agcgaagtac tgatgacaga aagagcggaa | 1080 |
| gataagataa gaaaggaacc cttgcgcggc aaggcctggt gacatagagg tagtgcgagg | 1140 |
| ctcataccgc cgccgctggc aggttccagg cctgtgcttt tcttgccctg tatccccagt | 1200 |
| ctatacttct gcgcacatca gacgagcctc agtgtttcgg cacagtggtg caacagaaaa | 1260 |
| ggagagtgct ggtaggtaac gctgaggcgg tgaagaaaga gaggtcagac ggacctggag | 1320 |
| gtggctttt aactggtaaa gagtgaggtc tttcatgccc atcaatctga gcaccgactt | 1380 |
| gggtgttgct cctgttcgca ggaagcacaa gaaatggtca gtactccaca gcgtaggcat | 1440 |
| gtcggtggtg tgttggagga ggcaagattc agatgattat tatatgagct cgaaaagcta | 1500 |
| gagaatggat gttcagactt gagagctctg atttgagagg aattgcactt gtcgttttcc | 1560 |
| caaggcgacg cggccttttc cagaggtttt tttttttttt nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |

```
nnnnnnnntg aaaaaaaaat gcacaccgac atgctctgta gcacaagcac cataccggcg    1800
aactggagag gtctcggctc atcaagcaat cgccttggtg tcggacgggg tcatcaagac    1860
aaggcgacta gaggagcact acatctacac ggggtgaacg gacgggagca gtggcggacc    1920
caggaactga tgacagcctt ggcgagaata cggtgtgatc cccacgcctg tgctcgtgcc    1980
acgtgctgct tgcttccgtg cactgtgctc gcgccttgcc cattgcagcc ggcgagccag    2040
ctcaggccac cgcctgcggt gcctggtgag tccgccctg gacgggagga aggaaggaaa    2100
acgagagcga ggactcactg tccggtccgc ccagcttggt gacggcgtcg acgaagcgct    2160
ggtggaggtc cggcgtccag cgcagccgcg gcttggggtc ccgtgacgcc gccccgtcgt    2220
agccgtagct cccctgcatc gccgttcctt cctggcgatc gccgctccct agctatccgg    2280
tggccaaaga cacggctagt ggtaggctcg agcgagacga gctcttgctg aagagagaat    2340
gaatgtagcg ttaccgcctc ctggtcgtag gggtgtgggt atgtgaggac aagaggagga    2400
gcgagaggag gagcgcagag cgtggcgggg aaggagggcg tcatgtgtgt gaggaatcta    2460
ggacgacttg ttggcagctg ggccggggtg cgtgcgagat gcaatgcaag aacaaagcgg    2520
acgggcatca cgcctccagg tccaacccgg gggcgccact cggccgccgc tcattgaggc    2580
ccaggcgcca agacggcggc tccacccacg tcacaattgg caataagaag cacacggctg    2640
gggctgggac gcgtcgaatt tttcaccaga aaataccgtc tgatcctggc gtttcgtcag    2700
atgctatgct acgtgaacgg caaaacctag cagcagcagc agcactcaga ctggacaaga    2760
ggagggaaat ctttgcgtgg gaaccaaact gaacgcgaat cgcacgagtc ggatgacata    2820
tcctcgtccg gagcggactc gaccgcgagt ccagctgtgg ctgcggaata ttccggcgga    2880
agcgcgggga gaacgacggc ggcctccggt gggacccggg gcgagcggga gatgcggcga    2940
agatgttcgg cgctgatgtc gctggaatat tcgcgccagc tgtggctgcc ggtgtgacct    3000
gctgaccaga cgaccagtgg cagtggccac cgcctctcca tcacagattc gcggacgatt    3060
agccgagact aatcgctatt ctcaacactt ttaaaaccgt gcgtgcagaa tgctaagggc    3120
gcgttcgttt gcacagcaat agacatggat ttatttcagc tcatcaaaat ttatataaat    3180
taaagaagta atccggctag aaattaatcc ggagcttcaa tccctaacaa ccgaacaggg    3240
tctaagcctg ctagattcga gcatctgcgt gactctactt tggctcttct cgtacgatgc    3300
gacttgacga tgcat                                                    3315
```

<210> SEQ ID NO 228
<211> LENGTH: 3271
<212> TYPE: DNA
<213> ORGANISM: Zea mays
<220> FEATURE:
<221> NAME/KEY: misc_feature
<222> LOCATION: (1605)..(1751)
<223> OTHER INFORMATION: n is a, c, g, or t

<400> SEQUENCE: 228

```
tcgcatctgc agcttctttt gcacctgatt acagacataa gcacttgtag cgtttatgga     60
agaaagtttt ggagtgcaga tctcatgaca atgatgtaaa tctatcttgc ctcagtttgt    120
tcttgtagtt tcctttggac ttgaatttga taccttagtg catcgctaag tgctatttct    180
ctgattcaca taagaaatgt gatacaaatg gttagttcaa tcaatgcaga aaagttcaat    240
caaataaaat gggcccactg cagtcaatta acaggcattc ataggattc acattcctgg    300 gcttctatat atggaagttt gcatacaatg ttttggaaat aaaatgaaat ataaattgct    360
```

```
tgcatttagt gtaagttaat actcgctccc ttctcgaata tttgtcgtcc gctagttcat    420
ttttgaacta aaacatgata aataaaaaaa cggaaggagt acatgtttgt aacaggagag    480
cccatgaata cttgcttgta acaggtggag cgctaagtat gcttaggaga actttaggca    540
acttgtattc tttagcactt cgacgcagtt tgtatggtaa tatctactga tagacagaat    600
cctggttttg gatttttaat ttttcctgct tttggttaca cctctacagt cccatactcg    660
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt tttttttcaag   840
gtaacatttt ctagcatctt cacctgtcta cttgactgaa tgcagtatat attagttgta    900
ataactactg gccttctgct gtgcacaaaa ggcgggtatt accacttgca gaaatttgtc    960
gggtaaaggt aattgccagt taccttgtgt tcttcccttg atcaggaaca cctggaggag   1020
gatgcgctgt ggttgaaccg aagccctgtg agcgaagtac tgatgacaga aagagcggaa   1080
gataagataa gaaaggaacc cttgcgcggc aaggcctggt gacatagagg tagtggcgag   1140
gctcataccg ccgccgctgg caggttccag gcctgtgctt tcttgccct gtatccccag    1200
tctatacttc tgcgcacatc agacgagcct cagtgtttcg gcacagtggt gcaacagaaa   1260
aggagagtgc tggtaggtaa cgctgaggcg gtgaagaaag agaggtcaga cggacctgga   1320
ggtggctttt taactggtaa agagtgaggt ctttcatgcc catcaatctg agcaccgact   1380
tgggtgttgc tcctgttcgc aggaagcaca agaaatggtc agtactccac agcgtaggca   1440
tgtcggtggt gtgttggagg aggcaagatt cagatgatta ttatatgagc tcgaaaagct   1500
agagaatgga tgttcagact tgagagctct gatttgagag gaattgcact tgtcgttttc   1560
ccaaggcgac gcggcctttt ccagaggttt tttttttttt ttttnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn naaaaaaaaa tgcacaccga catgctctgt agcacaagca ccataccggc   1800
gaactggaga ggtctcggct catcaagcaa tcgccttggt gtcggacggg gtcatcaaga   1860
caaggcgact agaggagcac tacatctaca cggggtgaac ggacgggagc agtggcggac   1920
ccaggaactg atgacagcct tggcgagaat acggtgtgat ccccacgcct gtgctcgtgc   1980
cacgtgctgc ttgcttccgt gcactgtgct cgcgccttgc ccattgcagc cggcgagcca   2040
gctcaggcca ccgcctgcgg tgcctggtga gtccgcccct ggacgggagg aaggaaggaa   2100
aacgagagcg aggactcact gtccggtccg cccagcttgg tgacggcgtc gacgaagcgc   2160
tggtggaggt ccggcgtcca gcgcagccgc ggcttgggt cccgtgacgc cgccccgtcg    2220
tagccgtagc tcccctgcat cgccgttcct tcctggcgat cgccgctccc tagctatccg   2280
gtggccaaag acacggctag tggtaggctc gagcgagacg agctcttgct gaagagagaa   2340
tgaatgtagc gttaccgcct cctggtcgta ggggtgtggg tatgtgagga caagaggagg   2400
agcgagagga ggagcgcaga gcgtggcggg gaaggagggc gtcatgtgtg tgaggaatct   2460
aggacgactt gttggcagct gggccggggt gcgtgcgaga tgcaatgcaa gaacaaagcg   2520
gacgggcatc acgcctccag gtccaacccg ggggcgccac tcggccgccg ctcattgagg   2580
cccaggcgcc aagacggcgg ctccacccac gtcacaattg gcaataagaa gcacacggct   2640
ggggctggga cgcgtcgaat ttttcaccag aaaataccgt ctgatcctgg cgtttcgtca   2700
gatgctatgc tacgtgaacg gcaaaaccta gcagcagcag cactcagact ggacaagagg   2760
```

```
agggaaatct tgcgtggga accaaactga acgcgaatcg cacgggtcgg atgacatatc    2820
atatcctcgt gcggagcgga ctcaacggcg agtccagctg tggctgcgga atattccggc    2880
ggaagcgcgg ggagagcgac ggcggcctcc ggtgggaccc ggggcgagcg ggagatgcgg    2940
cgaagatgtt cggcgctgat gtcgctggaa tattcgcgcc agctgtggct gccggtgcga    3000
cctgctgacc agacgaccag tggcaatggc caccgcctct ccatccaacc tccatcacag    3060
attggcggac gattagccga gactaatcgc tattctcaac actttaaaaa ccgtgcgtgc    3120
agaatgctaa gcctgctaga ttcgagcatc tgcgtgactc tactttggct cttctcgtac    3180
gatgcgacct gacgatgcat ttgggcgttc ctgtagcgtc actttcctga ttagtccccc    3240
ggaaacgcaa ctctaccact atcagccgcc g                                   3271
```

<210> SEQ ID NO 229
<211> LENGTH: 3251
<212> TYPE: DNA
<213> ORGANISM: Zea mays
<220> FEATURE:
<221> NAME/KEY: misc_feature
<222> LOCATION: (1599)..(1745)
<223> OTHER INFORMATION: n is a, c, g, or t
<220> FEATURE:
<221> NAME/KEY: misc_feature
<222> LOCATION: (3182)..(3182)
<223> OTHER INFORMATION: n is a, c, g, or t
<220> FEATURE:
<221> NAME/KEY: misc_feature
<222> LOCATION: (3186)..(3186)
<223> OTHER INFORMATION: n is a, c, g, or t
<220> FEATURE:
<221> NAME/KEY: misc_feature
<222> LOCATION: (3188)..(3189)
<223> OTHER INFORMATION: n is a, c, g, or t
<220> FEATURE:
<221> NAME/KEY: misc_feature
<222> LOCATION: (3192)..(3193)
<223> OTHER INFORMATION: n is a, c, g, or t

<400> SEQUENCE: 229

```
tcgcatctgc agcttctttt gcacctgatt acagacataa gcacttgtag cgtttatgga     60
agaaagtttt ggagtgcaga tctcatgaca atgatgtaaa tctatcttgc ctcagtttgt    120
tcttgtagtt tcctttggac ttgaatttga taccttagtg catcgctaag tgctatttct    180
ctgattcaca taagaaatgt gatacaaatg gttagttcaa tcaatgcaga aaagttcaat    240
caaataaaat gggcccactg cagtcaatta acaggcattc aataggattc acattcctgg    300
gcttctatat atggaagttt gcatacaatg ttttggaaat aaaatgaaat ataaattgct    360
tgcatttagt gtaagttaat actcgctccc ttctcgaata tttgtcgtcc gctagttcat    420
ttttgaacta aaacatgata aataaaaaaa cggaaggagt acatgtttgt aacaggagag    480
cccatgaata cttgcttgta acaggtggag cgctaagtat gcttaggaga actttaggca    540
acttgtattc tttagcactt cgacgcagtt tgtatggtaa tatctactga tagacagaat    600
cctggttttg gattttttaat ttttcctgct tttggttaca cctctacagt cccatactcg    660
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt ttttttcaag    840
gtaacatttt ctagcatctt cacctgtcta cttgactgaa tgcagtatat attagttgta    900
ataactactg gccttctgct gtgcacaaaa ggcgggtatt accacttgca gaaatttgtc    960
```

```
gggtaaaggt aattgccagt taccttgtgt tcttcccttg atcaggaaca cctggaggag    1020
gatgcgctgt ggttgaaccg aagccctgtg agcgaagtac tgatgacaga aagagcggaa    1080
gataagataa gaaaggaacc cttgcgcggc aaggcctggt gacatagagg tagtgcgagg    1140
ctcataccgc cgccgctggc aggttccagg cctgtgcttt tcttgccctg tatccccagt    1200
ctatacttct gcgcacatca gacgagcctc agtgtttcgg cacagtggtg caacagaaaa    1260
ggagagtgct ggtaggtaac gctgaggcgg tgaagaaaga gaggtcagac ggacctggag    1320
gtggcttttt aactggtaaa gagtgaggtc tttcatgccc atcaatctga gcaccgactt    1380
gggtgttgct cctgttcgca ggaagcacaa gaaatggtca gtactccaca gcgtaggcat    1440
gtcggtggtg tgttggagga ggcaagattc agatgattat tatatgagct cgaaaagcta    1500
gagaatggat gttcagactt gagagctctg atttgatatg aattgcactt gtcgttttcc    1560
caaggcgaca cggccttttt ccagagtttt tttttttnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnaaaaa aaaaaaagaa tgcacaccga catgctctgt agcacaagca ccatactggc    1800
gaactggaga ggtctcggct catcaagcaa tcgccttggt gtcggacggg gtcatcaaga    1860
caagacgact agacgagcac tacatataga cgggaacgta cgggaggaag gaaggaaaac    1920
gagagcgagg actcactgtc cggtccgccc agcttggtga cggcgtcgac gaagcgctgg    1980
tggaggtccg gcgtccagcg cagccgcggc ttggggtccc gtgacgccgc ccgtcgtag    2040 ccgtagctcc cctgcatcgt cgttccttcc tggcgatcgc cgcttcctag ctatccggtg    2100
gccaaagaca cggctagtgg taggctcgag tgagacgagc tcttgctgaa gagagaatga    2160
atgtaacgtt accgcctcct ggtcgtaggt gtaataagtt gtaacgcgag cgtcgttagc    2220
aagcacaggg gtttgtgtat gtgaggacaa gaggaggagc gagaggagga gcgcagagcg    2280
tggcggggaa ggagggcgtc atgtgtgcga ggaatctagg acgacttgtt ggcacttggc    2340
agctgggccg gggtgcgtgc gagatgcaat gcaagaacaa agcggacggg catcacgcct    2400
ccaggtccaa cccgggggcg ccactcggcc gccgctcatt gaggcccagg cgccaagacg    2460
gcggctccac ccacatcaca attggcaaca agaagcacac ggctggggtt gggacgcgtc    2520 gaattttttca ccagaaaata ccgtctgatc ctggcgtttc gtcagatgct atgctacgtg    2580
aacggcaaaa cctagcagca gcagcagcac tcagactgga caagaggagg gaaatctttg    2640
cgtgggaacc aaactgaacg cgaatcgcac gagtcggatg acatatcctc gtccggagcg    2700
gactcgaccg cgagtccagc tgtggctgcg gaatattccg gcggaagcgc ggggagaacg    2760
acggcggcct ccggtgggac ccggggcgag cgggagatgc ggcgaagatg ttcggcgctg    2820
atgtcgctgg aatattcgcg ccagctgtgg ctgccggtgt gacctgctga ccagacgacc    2880
agtggcagtg gccaccgcct ctccatcaca gattcgcgga cgattagccg agactaatcg    2940
ctattctcaa cacttttaaa accgtgcgtg cagaatgcta agggcgcgtt cgtttgcaca    3000
gcaatagaca tggatttatt tcagctcatc aaaatctata taaattaaag aagtaatccg    3060
gctagaaatt aatccggagc ttcaatccct aacaaccgaa cagggtctaa gcctgctaga    3120
ttcgagcatc tgcgtgactc tactttggct cttctcgtac gatgcgactt gacgatgcat    3180
tngggncnnc cnntagcgac actctcctga ttagtcccac ggaaacgcaa ctctaccact    3240
atcagccgcc g                                                         3251
```

```
<210> SEQ ID NO 230
<211> LENGTH: 3102
<212> TYPE: DNA
<213> ORGANISM: Zea mays
<220> FEATURE:
<221> NAME/KEY: misc_feature
<222> LOCATION: (1599)..(1743)
<223> OTHER INFORMATION: n is a, c, g, or t

<400> SEQUENCE: 230
```

| | | | | | |
|---|---|---|---|---|---|
| tcgcatctgc | agcttctttt | gcacctgatt | acagacataa | gcacttgtag | cgtttatgga | 60 |
| agaaagtttt | ggagtgcaga | tctcatgaca | atgatgtaaa | tctatcttgc | ctcagtttgt | 120 |
| tcttgtagtt | tcctttggac | ttgaatttga | taccttagtg | catcgctaag | tgctatttct | 180 |
| ctgattcaca | taagaaatgt | gatacaaatg | gttagttcaa | tcaatgcaga | aaagttcaat | 240 |
| caaataaaat | gggcccactg | cagtcaatta | acaggcattc | aataggattc | acattcctgg | 300 |
| gcttctatat | atggaagttt | gcatacaatg | ttttggaaat | aaaatgaaat | ataaattgct | 360 |
| tgcatttagt | gtaagttaat | actcgctccc | ttctcgaata | tttgtcgtcc | gctagttcat | 420 |
| ttttgaacta | aaacatgata | aataaaaaaa | cggaaggagt | acatgtttgt | aacaggagag | 480 |
| cccatgaata | cttgcttgta | acaggtggag | cgctaagtat | gcttaggaga | actttaggca | 540 |
| acttgtattc | tttagcactt | cgacgcagtt | tgtatggtaa | tatctactga | tagacagaat | 600 |
| cctggttttg | gattttaat | ttttcctgct | tttggttaca | cctctacagt | cccatactcg | 660 |
| cagtccaata | gtacatggtc | tgataataaa | ccaattaaga | aggactcatg | tctcagtcat | 720 |
| tatgacttga | gcataggagt | tgagatcaag | aaatatttga | gttgcagctt | aaggtccaga | 780 |
| gaggaaatcc | ccatacactt | gcttgtaacg | gtatgaatgt | atgatcattt | tttttttcaag | 840 |
| gtaacatttt | ctagcatctt | cacctgtcta | cttgactgaa | tgcagtatat | attagttgta | 900 |
| ataactactg | gccttctgct | gtgcacaaaa | ggcgggtatt | accacttgca | gaaatttgtc | 960 |
| gggtaaaggt | aattgccagt | taccttgtgt | tcttcccttg | atcaggaaca | cctggaggag | 1020 |
| gatgcgctgt | ggttgaaccg | aagccctgtg | agcgaagtac | tgatgacaga | aagagcggaa | 1080 |
| gataagataa | gaaaggaacc | cttgcgcggc | aaggcctggt | gacatagagg | tagtgcgagg | 1140 |
| ctcataccgc | cgccgctggc | aggttccagg | cctgtgcttt | tcttgccctg | tatccccagt | 1200 |
| ctatacttct | gcgcacatca | gacgagcctc | agtgtttcgg | cacagtggtg | caacagaaaa | 1260 |
| ggagagtgct | ggtaggtaac | gctgaggcgg | tgaagaaaga | gaggtcagac | ggacctggag | 1320 |
| gtggcttttt | aactggtaaa | gagtgaggtc | tttcatgccc | atcaatctga | gcaccgactt | 1380 |
| gggtgttgct | cctgttcgca | ggaagcacaa | gaaatggtca | gtactccaca | gcgtaggcat | 1440 |
| gtcggtggtg | tgttggagga | ggcaagattc | agatgattat | tatatgagct | cgaaaagcta | 1500 |
| gagaatggat | gttcagactt | gagagctctg | atttgagagg | aattgcactt | gtcgttttcc | 1560 |
| caaggcgacg | cggcctttt | ccagaggctt | tttttttnn | nnnnnnnnn | nnnnnnnnn | 1620 |
| nnnnnnnnn | nnnnnnnnn | nnnnnnnnn | nnnnnnnnn | nnnnnnnnn | nnnnnnnnn | 1680 |
| nnnnnnnnn | nnnnnnnnn | nnnnnnnnn | nnnnnnnnn | nnnnnnnnn | nnnnnnnnn | 1740 |
| nnnaaaaaaa | aaaaaaagaa | tgcagaccga | catgctctgt | agcacaagca | ccatactggc | 1800 |
| gaactggaga | ggtctcggct | catcaagcaa | tcgccttggt | gtcggacggg | gtcatcaaga | 1860 |
| caagacgact | agacgagcac | tacatataga | cgggaacgta | cgggaggaag | gaaggaaaac | 1920 |
| gagagcgagg | actcactgtc | cggtccgccc | agcttggtga | cggcgtcgac | gaagcgctgg | 1980 |
| tggaggtccg | gcgtccagcg | cagccgcggc | ttggggtccc | gtgacgccgc | cccgtcgtag | 2040 |

```
ccgtagctcc cctgcatcgt cgttccttcc tggcgatcgc cgcttcctag ctatccggtg    2100
gccaaagaca cggctagtgg taggctcgag tgagacgagc tcttgctgaa gagagaatga    2160
atgtaacgtt accgcctcct ggtcgtaggt gtaataagtt gtaacgcgag cgtcgttagc    2220
aagcacaggg gtttgtgtat gtgaggacaa gaggaggagc gagaggagga gcgcagagcg    2280
tggcggggaa ggagggcgtc atgtgtgcga ggaatctagg acgacttgtt ggcacttggc    2340
agctgggccg gggtgcgtgc gagatgcaat gcaagaacaa gcggacggg catcacgcct     2400 ccaggtccaa cccgggggcg ccactcggcc gccgctcatt gaggcccagg cgccaagacg    2460
gcggctccac ccacatcaca attggcaaca agaagcacac ggctgggtt gggacgcgtc     2520 gaattttca ccagaaaata ccgtcggcgt ttcgtcagat gctatgctac gtgaacggca     2580
aaacctagca gcagcagcac tcagactgga cgagaggagg gaaatctttg cgtgggaacc    2640
aaactgaacg cgaatcgcac gagtcggatg acatatcctc gtccggagcg gactcgaccg    2700
cgagtccagc tgtggctgcg gaatattccg gcggaagcgc ggggagaacg acggcggcct    2760
ccggtgggaa ccggggcgag cgggagatgc ggcgaagatg ttcggcgctg atgtcgctgg    2820
aatattcgcg ccagctgtgg ctgccggtgt gacctgctga ccagtggcag tggccaccgc    2880
ctctccatca cagattggcg gacgattagc cgagactaat cgctattctc aacacttta    2940 aaaccgtgcg tgcagaatga taaccctgct agattcgagc atctgcgtga ctctactctg    3000
gctcttctcg tacgatgcga cttgacgatg catttgcgcg cctttagcgt cacttcctg    3060 attagtccca cggaaacgca actctaccac tatcagccgc ca                      3102
```

<210> SEQ ID NO 231
<211> LENGTH: 3251
<212> TYPE: DNA
<213> ORGANISM: Zea mays
<220> FEATURE:
<221> NAME/KEY: misc_feature
<222> LOCATION: (1598)..(1740)
<223> OTHER INFORMATION: n is a, c, g, or t
<220> FEATURE:
<221> NAME/KEY: misc_feature
<222> LOCATION: (3186)..(3192)
<223> OTHER INFORMATION: n is a, c, g, or t

<400> SEQUENCE: 231

```
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc ataggattc acattcctgg      300 gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gattttttaat ttttcctgct tttggttaca cctctacagt cccatactcg    660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt ttttttcaag    840
```

```
gtaacatttt ctagcatctt cacctgtcta cttgactgaa tgcagtatat attagttgta    900
ataactactg gccttctgct gtgcacaaaa ggcgggtatt accacttgca gaaatttgtc    960
gggtaaaggt aattgccagt taccttgtgt tcttcccttg atcaggaaca cctggaggag   1020
gatgcgctgt ggttgaaccg aagccctgtg agcgaagtac tgatgacaga aagagcggaa   1080
gataagataa gaaaggaacc cttgcgcggc aaggcctggt gacatagagg tagtgcgagg   1140
ctcataccgc cgccgctggc aggttccagg cctgtgcttt tcttgccctg tatccccagt   1200
ctatacttct gcgcacatca gacgagcctc agtgtttcgg cacagtggtg caacagaaaa   1260
ggagagtgct ggtaggtaac gctgaggcgg tgaagaaaga gaggtcagac ggacctggag   1320
gtggcttttt aactggtaaa gagtgaggtc tttcatgccc atcaatctga gcaccgactt   1380
gggtgttgct cctgttcgca ggaagcacaa gaaatggtca gtactccaca gcgtaggcat   1440
gtcggtggtg tgttggagga ggcaagattc agatgattat tatatgagct cgaaaagcta   1500
gagaatggat gttcagactt gagagctctg atttgagagg aattgcactt gtcgttttcc   1560
caaggcgacg cggccttttt ccagagtttt ttttttttnnn nnnnnnnnn nnnnnnnnnn   1620 nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
aaaaaaaaaa aaaaaagaa tgcacaccga catgctctgt agcacaagca ccatactggc   1800
gaactggaga ggtctcggct catcaagcaa tcgccttggt gtcggacggg gtcatcaaga   1860
caagacgact agacgagcac tacatataga cgggaacgta cgggaggaag gaaggaaaac   1920
gagagcgagg actcactgtc cggtccgccc agcttggtga cggcgtcgac gaagcgctgg   1980
tggaggtccg gcgtccagcg cagccgcggc ttggggtccc gtgacgccgc ccgtcgtag    2040 ccgtagctcc cctgcatcgt cgttccttcc tggcgatcgc cgcttcctag ctatccggtg   2100
gccaaagaca cggctagtgg taggctcgag tgagacgagc tcttgctgaa gagagaatga   2160
atgtaacgtt accgcctcct ggtcgtaggt gtaataagtt gtaacgcgag cgtcgttagc   2220
aagcacaggg gtttgtgtat gtgaggacaa gaggaggagc gagaggagga gcgcagagcg   2280
tggcggggaa ggagggcgtc atgtgtgcga ggaatctagg acgacttgtt ggcacttggc   2340
agctgggccg gggtgcgtgc gagatgcaat gcaagaacaa agcggacggg catcacgcct   2400
ccaggtccaa cccgggggcg ccactcggcc gccgctcatt gaggcccagg cgccaagacg   2460
gcggctccac ccacatcaca attggcaaca agaagcacac ggctggggtt gggacgcgtc   2520 gaattttttca ccagaaaata ccgtctgatc ctggcgtttc gtcagatgct atgctacgtg   2580
aacggcaaaa cctagcagca gcagcagcac tcagactgga caagaggagg gaaatctttg   2640
cgtgggaacc aaactgaacg cgaatcgcac gagtcggatg acatatcctc gtccggagcg   2700
gactcgaccg cgagtccagc tgtggctgcg gaatattccg gcggaagcgc ggggagaacg   2760
acggcggcct ccggtgggac ccggggcgag cgggagatgc ggcgaagatg ttcggcgctg   2820
atgtcgctgg aatattcgcg ccagctgtgg ctgccggtgt gacctgctga ccagacgacc   2880
agtggcagtg gccaccgcct ctccatcaca gattcgcgga cgattagccg agactaatcg   2940
ctattctcaa cacttttaaa accgtgcgtg cagaatgcta agggcgcgtt cgtttgcaca   3000
gcaatagaca tggatttatt tcagctcatc aaaatctata taaattaaag aagtaatccg   3060
gctagaaatt aatccggagc ttcaatccct aacaaccgaa cagggtctaa gcctgctaga   3120
ttcgagcatc tgcgtgactc tactttggct cttctcgtac gatgcgactt gacgatgcat   3180
```

-continued

```
ttgggnnnnn nngtagcgac actctcctga ttagtcccac ggaaacgcaa ctctaccact    3240
atcagccgcc g                                                        3251

<210> SEQ ID NO 232
<211> LENGTH: 3034
<212> TYPE: DNA
<213> ORGANISM: Zea mays
<220> FEATURE:
<221> NAME/KEY: misc_feature
<222> LOCATION: (1599)..(1742)
<223> OTHER INFORMATION: n is a, c, g, or t

<400> SEQUENCE: 232
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttagtg catcgctaag tgctatttct     180
ctgattcaca taagaaatgt gatacaaatg gttagttcaa tcaatgcaga aaagttcaat     240
caaataaaat gggcccactg cagtcaatta acaggcattc aataggattc acattcctgg     300
gcttctatat atggaagttt gcatacaatg ttttggaaat aaaatgaaat ataaattgct     360
tgcatttagt gtaagttaat actcgctccc ttctcgaata tttgtcgtcc gctagttcat     420
ttttgaacta aaacatgata aataaaaaaa cggaaggagt acatgtttgt aacaggagag     480
cccatgaata cttgcttgta acaggtggag cgctaagtat gcttaggaga actttaggca     540
acttgtattc tttagcactt cgacgcagtt tgtatggtaa tatctactga tagacagaat     600
cctggttttg gatttttaat ttttcctgct tttggttaca cctctacagt cccatactcg     660
cagtccaata gtacatggtc tgataataaa ccaattaaga aggactcatg tctcagtcat     720
tatgacttga gcataggagt tgagatcaag aaatatttga gttgcagctt aaggtccaga     780
gaggaaatcc ccatacactt gcttgtaacg gtatgaatgt atgatcattt ttttttcaag     840
gtaacatttt ctagcatctt cacctgtcta cttgactgaa tgcagtatat attagttgta     900
ataactactg gccttctgct gtgcacaaaa ggcgggtatt accacttgca gaaatttgtc     960
gggtaaaggt aattgccagt taccttgtgt tcttcccttg atcaggaaca cctggaggag    1020
gatgcgctgt ggttgaaccg aagccctgtg agcgaagtac tgatgacaga aagagcggaa    1080
gataagataa gaaaggaacc cttgcgcggc aaggcctggt gacatagagg tagtgcgagg    1140
ctcataccgc cgccgctggc aggttccagg cctgtgcttt tcttgccctg tatccccagt    1200
ctatacttct gcgcacatca gacgagcctc agtgtttcgg cacagtggtg caacagaaaa    1260
ggagagtgct ggtaggtaac gctgaggcgg tgaagaaaga gaggtcagac ggacctggag    1320
gtggcttttt aactggtaaa gagtgaggtc tttcatgccc atcaatctga gcaccgactt    1380
gggtgttgct cctgttcgca ggaagcacaa gaaatggtca gtactccaca gcgtaggcat    1440
gtcggtggtg tgttggagga ggcaagattc agatgattat tatatgagct cgaaaagcta    1500
gagaatggat gttcagactt gagagctctg atttgagagg aattgcactt gtcgttttcc    1560
caaggcgacg cggccttttt ccagaggctt tttttttnn nnnnnnnnn nnnnnnnnn    1620 nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnaaaaaaaa aaaaaaagaa tgcagaccga catgctctgt agcacaagca ccatactggc    1800
gaactggaga ggtctcggct catcaagcaa tcgccttggt gtcggacggg gtcatcaaga    1860
caagacgact agacgagcac tacatataga cgggaacgta cgggaggaag gaaggaaaac    1920
```

```
gagagcgagg actcactgtc cggtccgccc agcttggtga cggcgtcgac gaagcgctgg    1980
tggaggtccg gcgtccagcg cagccgcggc ttggggtccc gtgacgccgc cccgtcgtag    2040
ccgtagctcc cctgcatcgt cgttccttcc tggcgatcgc cgcttcctag ctatccggtg    2100
gccaaagaca cggctagtgg taggctcgag tgagacgagc tcttgctgaa gagagaatga    2160
atgtaacgtt accgcctcct ggtcgtaggt gtaataagtt gtaacgcgag cgtcgttagc    2220
aagcacaggg gtttgtgtat gtgaggacaa gaggaggagc gagaggagga gcgcagagcg    2280
tggcggggaa ggagggcgtc atgtgtgcga ggaatctagg acgacttgtt ggcacttggc    2340
agctgggccg gggtgcgtgc gagatgcaat gcaagaacaa agcggacggg catcacgcct    2400
ccaggtccaa cccgggggcg ccactcggcc gccgctcatt gaggcccagg cgccaagacg    2460
gcggctccac ccacatcaca attggcaaca agaagcacac ggctgggggtt gggacgcgtc    2520 gaattttcta ccagaaaata ccgtcggcgt ttcgtcagat gctatgctac gtgaacggca    2580
aaacctagca gcagcagcac tcagactgga cgagaggagg gaaatctttg cgtgggaacc    2640
aaactgaacg cgaatcgcac gagtcggatg acatatcctc gtccggagcg gactcgaccg    2700
cgagtccagc tgtggctgcg gaatattccg gcggaagcgc ggggagaacg acggcggcct    2760
ccggtgggaa ccggggcgag cgggagatgc ggcgaagatg ttcggcgctg atgtcgctgg    2820
aatattcgcg ccagctgtgg ctgccggtgt gacctgctga ccagtggcag tggccaccgc    2880
ctctccatca cagattggcg gacgattagc cgagactaat cgctattctc aacacttta    2940 aaaccgtgcg tgcagaatga taaccctgct agattcgagc atctgcgtga ctctactctg    3000
gctcttctcg tacgatgcga cttgacgatg catt                                3034
```

<210> SEQ ID NO 233
<211> LENGTH: 3139
<212> TYPE: DNA
<213> ORGANISM: Zea mays
<220> FEATURE:
<221> NAME/KEY: misc_feature
<222> LOCATION: (1722)..(1744)
<223> OTHER INFORMATION: n is a, c, g, or t

<400> SEQUENCE: 233

```
tcgcatctgc agcttctttt gcacctgatt acagacataa gcacttgtag cgtttatgga     60
agaaagtttt ggagtgcaga tctcatgaca atgatgtaaa tctatcttgc ctcagtttgt    120
tcttgtagtt tcctttggac ttgaatttga taccttagtg catcgctaag tgctatttct    180
ctgattcaca taagaaatgt gatacaaatg gttagttcaa tcaatgcaga aaagttcaat    240
caaataaaat gggcccactg cagtcaatta acaggcattc aataggattc acattcctgg    300
gcttctatat atggaagttt gcatacaatg ttttggaaat aaaatgaaat ataaattgct    360
tgcatttagt gtaagttaat actcgctccc ttctcgaata tttgtcgtcc gctagttcat    420
ttttgaacta aacatgata aataaaaaaa cggaaggagt acatgtttgt aacaggagag    480
cccatgaata cttgcttgta acaggtggag cgctaagtat gcttaggaga actttaggca    540
acttgtattc tttagcactt cgacgcagtt tgtatggtaa tatctactga tagacagaat    600
cctggttttg gattttaat ttttcctgct tttggttaca cctctacagt cccatactcg    660
cagtccaata gtacatggtc tgataataaa ccaattaaga aggactcatg tctcagtcat    720
tatgacttga gcataggagt tgagatcaag aaatatttga gttgcagctt aaggtccaga    780
gaggaaatcc ccatacactt gcttgtaacg gtatgaatgt atgatcattt ttttttcaag    840
```

```
gtaacattt     ctagcatctt    cacctgtcta    cttgactgaa    tgcagtatat    attagttgta    900
ataactactg    gccttctgct    gtgcacaaaa    ggcgggtatt    accacttgca    gaaatttgtc    960
gggtaaaggt    aattgccagt    taccttgtgt    tcttcccttg    atcaggaaca    cctggaggag    1020
gatgcgctgt    ggttgaaccg    aagccctgtg    agcgaagtac    tgatgacaga    aagagcggaa    1080
gataagataa    gaaaggaacc    cttgcgcggc    aaggcctggt    gacatagagg    tagtgcgagg    1140
ctcataccgc    cgccgctggc    aggttcsagg    cctgtgcttt    tcttgccctg    tatccccagt    1200
ctatacttct    gcgcacatca    gacgagcgtc    agtgtttcgg    cacagtggtg    caacagaaaa    1260
ggagagtgct    ggtaggtaac    gctgaggcgg    tgaagaaaga    gaggtcagac    ggacctggag    1320
gtggctttt     aactggtaaa    gagtgaggtc    tttcatgccc    atcaatctga    gcaccgactt    1380
gggtgttgct    tctgttcgca    ggaagcacaa    gaaatggtca    gtactccaca    gcgtaggcat    1440
gtcggtgtgt    tcgaggaggc    aagattcaga    tgattattat    atgagctcga    aaagctagag    1500
aatggatgtt    cagacttgag    atctctgatt    tgagaggaat    tgcacttgtc    gttttcccag    1560
ggcgacgcgg    cctttttcca    gaggcatttt    ttttcaactg    cctttttggtc    atgtcaacgg    1620
aactgccttt    tcctctgact    gcatgctata    gacttggcaa    tggcagaagc    gcaaagccag    1680
gcagcgaagg    attcggactg    caactggccg    tcgtttttaca   annnnnnnnn    nnnnnnnnnn    1740
nnnnaaaaaa    aaaagaatgc    agaccgacat    gctctgtagc    acaagcacca    tacttgcgaa    1800
ctgcagaggt    gtcgggtcat    caagcaatcg    ccttggtgtc    ggacggggtg    gggtcatcaa    1860
gacaagacga    ctagaggagc    actacatcta    cacgggggg     aacggacggg    aggaaggaag    1920
gaaaacgaga    gcgaggactc    actgtccggt    ccgcccagct    tggtgacggc    gtcgacgaag    1980
cgctggtgga    ggaccggcgt    ccagcgcagc    cgcggcttgg    ggtcccgtga    cgccgccccg    2040
tcgtagccgt    agctccctg     catcgtcgtt    ccttcctggc    gatcgccgct    ccctagctat    2100
ccggtggcca    aagacacggc    tagtgctgaa    gagagaatga    atgtaacgtt    accgcctcct    2160
ggtcgtaggt    gtaataagtt    gtaacgcgag    tgtcgttaga    agcacagggg    tgtgtgtatg    2220
tgaggacaag    aggaggagcg    agaggaggag    cgcagagcgt    ggcggggaag    gagggcgtca    2280
tgtgtgtgag    gaatctagga    cgacttgttg    gcagctgggc    cggggtgcgt    gcgagatgca    2340
atgcaagaac    aaagcatcac    gcctccaagt    ccaaccgggg    ggcgccactc    ggccgccgct    2400
cattgaggcc    caggcgccaa    gacggcggct    ccacccacat    cacaattggc    aacaagaagc    2460
acacggctgg    ggctgggacg    cgtcgaattt    ttcaccagaa    aataccgtcg    gcgtttcgtc    2520
agatgctatg    ctacgtgaac    ggcaaaacct    agcagcagca    gcagcagcac    tcagactgga    2580
caagaggagg    gaaatctttg    cgtgggaacc    aaactgaacg    cgaatcgcac    gagtcggatg    2640
acatatcctc    gtccggagcg    gactcggccg    cgagtccagc    tgtggctgcg    gaatattccg    2700
gcggaagcgc    ggggagaacg    acggcggcct    ccggtggac     ccggggcgag    cgggagatgc    2760
ggcgaagatg    ttcggcgctg    atgtcgctgg    aatattcgcg    ccagctgtgg    ctgccggtgt    2820
gacctgctga    ccagacgacc    agtggcagtg    gccaccgcct    ctccatcaca    gattcgcgga    2880
cgattagccg    agactaatcg    ctattctcaa    cacttttaaa    accgtgcgtg    cagaatgcta    2940
agggcgcgtt    cgtttgcaca    gcaatagaca    ttgatttatt    tcagctcatc    aaaatctata    3000
taaattaaag    aagtaatccg    gctagaaatt    aatccggagc    ttcaatccct    aacaaccgaa    3060
cagggtctaa    gcctgctaga    ttcgagcatc    tgcgtgactc    tactttggct    cttctcgtac    3120
gatgcgactt    gacgatgca                                                             3139
```

```
<210> SEQ ID NO 234
<211> LENGTH: 3052
<212> TYPE: DNA
<213> ORGANISM: Zea mays
<220> FEATURE:
<221> NAME/KEY: misc_feature
<222> LOCATION: (1563)..(1708)
<223> OTHER INFORMATION: n is a, c, g, or t
<220> FEATURE:
<221> NAME/KEY: misc_feature
<222> LOCATION: (2987)..(2990)
<223> OTHER INFORMATION: n is a, c, g, or t
<220> FEATURE:
<221> NAME/KEY: misc_feature
<222> LOCATION: (2994)..(2994)
<223> OTHER INFORMATION: n is a, c, g, or t

<400> SEQUENCE: 234
tcgcatctgc agcttctttt gcacctgatt acagacataa gcacttgtag cgtttatgga      60
agaaagtttt ggagtgcaga tctcatgaca atgatgtaaa tctatcttgc ctcagtttgt     120
tcttgtagtt tcctttggac ttgaatttga taccttaatg catcgctaag tgctatttct     180
ctgattcaca taagaaatgc gatacaaatg gttagttcaa tcaatgcaga aaagttcaac     240
caaataaaat gggcccactg cagtcaatta acaggcattc ataggattc acattcctgg      300 gcttctatat atggaagttt gcatacaaag ttttggaaat aaaatggaat agaaattgct     360
tgcatttagt gtaagttaat acccgctagt tcattttta actaaaacac dacaaataaa      420
aaaatggagg agtacatctt tgtaacaggt gagcctgaat acttgtttgt agcaggtggg     480
gcgctaagta tgcttaggag aagtttaggc aacttgtatt ctgtagcatt tcgacgccgt     540
ttgtatggta atatctactg ataggcagaa tcctggttgg atttttttc ctgcttttgt      600 ttacacctat acagtcccat actcgcagtc gaataataca tggtctgatg ataaaccaat     660
taagaaggac tcatgtctca gtcattatga cttgagcata ggagttgaga tcaagaaata     720
tttgagttgc agcttaaggt ccagagagga aatccccata cacttgcttg taacggtatg     780
aatgtatgat catttttttt tcaaggtaac attttctagc atcttcacct gtctacttga     840
ctgaatgcag tatatattag ttgtaataac tactggcctt ctgctgtgca caaaaggcgg     900
gtattaccac ttgcagaaat ttgtcgggta aggtaattg ccagttacct tgtgttcttc      960
ccttgatcag gaacacctgg aggaggatgc gctgtggttg aaccgaagcc ctgtgagcga    1020
agtactgatg acagaaagag cggaagataa gataagaaag gaacccttgc gcggcaaggc    1080
ctggtgacat agaggtagtg cgaggctcat accgccgccg ctggcaggtt ccaggcctgt    1140
gcttttcttg ccctgtatcc ccagtctata cttctgcgca catcgagcga gcctcagtgt    1200
ttcggcacag tggtgcaaca gaaaaggaga gtgctggtag gtaacgctga ggcggtgaag    1260
aaagagaggt cagacggacc tggaggtggc ttttaactg gtaaagagtg aggtcttca     1320 tgcccatcaa tctgagcacc gacttgggtg ttgctcctgt tcgcaggaag cacaagaaat    1380
ggtcagtact ccacagcgta ggcatgtcgg tggtgtgttg gaggaggcaa gattcagatg    1440
attattatat gagctcgaaa agctagagaa tggatgttca gacttgagag ctctgatttg    1500
agaggaattg cacttgtcgt tttcccaagg cgacgcggcc ttttttccaga gttttttttt    1560 ttnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnaa aaaaaaaaa agaatgcaga ccgacatgct     1740
ctgtagcaca agcaccatac tggcgaactg gagaggtctc ggctcatcaa gcaatcgcct    1800
```

| | |
|---|---|
| tggtgtcgga cggggtcatc aagacaagac gactagacga gcactacata tagacgggaa | 1860 |
| cgtacgggag gaaggaagga aaacgagagc gaggactcac tgtccggtcc gcccagcttg | 1920 |
| gtgacggcgt cgacgaagcg ctggtggagg tccggcgtcc agcgcagccg cggcttgggg | 1980 |
| tcccgtgacg ccgccccgtc gtagccgtag ctcccctgca tcgccgttcc ttcctggcga | 2040 |
| tcgccgctcc ctagctatcc ggtggccaaa gacacggcta gtggtaggct cgagcgagac | 2100 |
| gagctcttgg tgaagagaga atgaatgtaa cgttaccgcc tcctggtcgt aggggtgtgt | 2160 |
| gtatgtgagg acaagaggag gagcgagagg aggagcgcag agcgtggcgg ggaaggaggg | 2220 |
| cgtcatgtgt gtgaggaatc taggacgact tgttggcagc tgggccgggg tgcgtgcgag | 2280 |
| atgcaatgca agaacaaagc ggacgggcat cacgcctcca ggtccaaccc ggggcgcca | 2340 |
| ctcggccgcc gctcattgag gcccaggcgc aagacggcg ctccaccca cgtcacaatt | 2400 |
| ggcaataaga agcacacggc tggggctggg acgcgtcgaa ttttcacca gaaaataccg | 2460 |
| tctgatcctg gcgtttcgtc agatgctatg ctacgtgaac ggcaaaacct agcagcagca | 2520 |
| gcactcagac tggacaagag gagggaaatc tttgcgtggg aaccaaactg aacgcgaatc | 2580 |
| gcacgggtcg gatgacatat catatcctcg tgcggagcgg actcaacggc gagtccagct | 2640 |
| gtggctgcgg aatattccgg cggaagcgcg gggagagcga cggcggcctc cggtgggacc | 2700 |
| cggggcgagc gggagatgcg gcgaagatgt tcggcgctga tgtcgctgga atattcgcgc | 2760 |
| cagctgtggc tgccggtgcg acctgctgac cagacgacca gtggcaatgg ccaccgcctc | 2820 |
| tccatccaac ctccatcaca gattggcgga cgattagccg agactaatcg ctattctcaa | 2880 |
| cactttaaaa accgtgcgtg cagaatgcta agcctgctag attcgagcat ctgcgtgact | 2940 |
| ctactttggc tcttctcgta cgatgcgacc tgacgatgca tttgggnnnn cctntagcgt | 3000 |
| cactttcctg attagtcccc cggaaacgca actctaccac tatcagccgc cg | 3052 |

<210> SEQ ID NO 235
<211> LENGTH: 3219
<212> TYPE: DNA
<213> ORGANISM: Zea mays
<220> FEATURE:
<221> NAME/KEY: misc_feature
<222> LOCATION: (1554)..(1701)
<223> OTHER INFORMATION: n is a, c, g, or t
<220> FEATURE:
<221> NAME/KEY: misc_feature
<222> LOCATION: (3155)..(3157)
<223> OTHER INFORMATION: n is a, c, g, or t
<220> FEATURE:
<221> NAME/KEY: misc_feature
<222> LOCATION: (3161)..(3161)
<223> OTHER INFORMATION: n is a, c, g, or t

<400> SEQUENCE: 235

| | |
|---|---|
| tcgcatctgc agcttctttt gcacctgatt acagacataa gcacttgtag cgtttatgga | 60 |
| agaaagtttt ggagtgcaga tctcatgaca atgatgtaaa tctatcttgc ctcagtttgt | 120 |
| tcttgtagtt tcctttggac ttgaatttga taccttagtg catcgctaag tgctatttct | 180 |
| ctgattcaca taagaaatgt gatacaaatg gttagctcaa tcaatgcaga aaagttcaac | 240 |
| caaataaaat gggcccactg cagtcaatta acaggcattc aataggattc acattcctgg | 300 |
| gcttctatat atggaagttt gcatacaaag ttttggaaat aaaatggaat agaaattgct | 360 |
| tgcatttagt gtaagttaat acccgctagt tcatttttta actaaaacac gacaaataaa | 420 |
| aaatggagg agtacatctt tgtaacaggt gagcctgaat acttgtttgt agcaggtggg | 480 |
| gcgctaagta tgcttaggag aagtttaggc aacttgtatt ctgtagcatt tcgacgccgt | 540 |

```
ttgtatggta atatctactg ataggcagaa tcctggttgg attttttttc ctgcttttgt     600
ttacacctat acagtcccat actcgcagtc gaataataca tggtctgatg ataaaccaat     660
taagaaggac tcatgtctca gtcattatga cttgagcata ggagttcaga tcgagaaata     720
tttgagttgc agcttaaggt tcagagagga atcccatac acttgcttgt aacgatatga      780
tcattttttt tcaaggtaac attttctagc atcttcagct gtctacttga ctgaatgcag     840
tatatattag ttgtaataaa tactgccctt ctgctgtgca caaaaggcgg gtattaccac    900
ttgcagaaat ttgtcgggta aaggtaattg ccagttacct tgtgttcttc ccttcatcag    960
gaacacctgg aggaggatgc gctgtggttg aactgaagcc ctgcgagaga agtactgatg   1020
acagaaagag cggaagataa gataagaaag gaaaccttg cgcggcaagg cctggtgaca    1080
tagaggtagt gcgaggctca taccgccgct ggcaggttcc aggcctgtgc ttttcttgcc   1140
ctgtatcccc agtctatact tctgcgcaca tcagacgagc ctcagtgttt cggcacagtg   1200
gtgcaacaga aaaggagagt gctggtaggt aacgctgagg cggtgaagaa agagaggtca   1260
gacggacctg gaggtggctt tttaactggt aaagagtgag gtctttcatg cccatcaatc   1320
tgagcaccga cttgggtgtt gctcctgttc gcaggaagca caagaaatgg tcagtactcc   1380
acagcgtagg catgtcggtg gtgtgttgga ggaggcaaga ttcagatgat tattatatga   1440
gctcgaaaag ctagagaatg gatgttcaga cttgagagct ctgatttgag aggaattgca   1500
cttgtcgttt tcccaaggcg acgcggcctt ttccagaggt tttttttttt tttnnnnnn    1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn ntgaaaaaaa aatgcacacc gacatgctct gtagcacaag   1740
caccataccg gcgaactgga gaggtctcgg ctcatcaagc aatcgccctt ggtgtcggac   1800
ggggtcatca agacaaggcg actagaggag cactacatct acacggggtg aacgacggg    1860
agcagtggcg gacccaggaa ctgatgacag ccttggcgag aatacggtgt gatccccacg   1920
cctgtgctcg tgccacgtgc tgcttgcttc cgtgcactgt gctcgcgcct tgcccattgc   1980
agccggcgag ccagctcagg ccaccgcctg cggtgcctgg tgagtccgcc cctggacggg   2040
aggaaggaag gaaaacgaga gcgaggactc actgtccggt ccgcccagct tggtgacggc   2100
gtcgacgaag cgctggtgga ggtccggcgt ccagcgcagc cgcggcttgg ggtcccgtga   2160
cgccgccccg tcgtagccgt agctcccctg catcgccgtt ccttcctggc gatcgccgct   2220
ccctagctat ccggtggcca aagacacggc tagtggtagg ctcgagcgag acgagctctt   2280
gctgaagaga gaatgaatgt agcgttaccg cctcctggtc gtaggggtgt gggtatgtga   2340
ggacaagagg aggagcgaga ggaggagcgc agagcgtggc ggggaaggag ggcgtcatgt   2400
gtgtgaggaa tctaggacga cttgttggca gctgggccgg ggtgcgtgcg agatgcaatg   2460
caagaacaaa gcgacgggc atcacgcctc caggtccaac ccgggggcgc cactcgatcg    2520
gccgccgctc attgaggccc aggcgccaag acggcggctc cacccacgtc acaattggca   2580
ataagaagca cacggctggg gctgggacgc gtcgaatttt tcaccagaaa ataccgtctg   2640
atcctggcgt ttcgtcagat gctatgctac gtgaacggca aaacctagca gcagcagcac   2700
tcagactgga caagaggagg gaaatctttg cgtgggaacc aaactgaacg cgaatcgcac   2760
gggtcggatg acatatcata tcctcgtgcg gagcggactc aacggcgagt ccagctgtgg   2820
ctgcggaata ttccggcgga agcgcgggga gagcgacggc ggcctccggt gggacccggg   2880
```

| | |
|---|---|
| gcgagcggga gatgcggcga agatgttcgg cgctgatgtc gctggaatat tcgcgccagc | 2940 |
| tgtggctgcc ggtgcgacct gctgaccagt ggcaatggcc accgcctctc catccaacct | 3000 |
| ccatcacaga ttggcggacg attagccgag actaatcgct attctcaaca ctttaaaaac | 3060 |
| cgtgcgtgca gaatgctaag cctgctagat tcgagcatct gcgtgactct actttggctc | 3120 |
| ttctcgtacg atgcgacctg acgatgcatt tgggnnncct ntagcgtcac tttcctgatt | 3180 |
| agtcccccgg aaacgcaact ctaccactat cagccgccg | 3219 |

<210> SEQ ID NO 236
<211> LENGTH: 3099
<212> TYPE: DNA
<213> ORGANISM: Zea mays
<220> FEATURE:
<221> NAME/KEY: misc_feature
<222> LOCATION: (1555)..(1693)
<223> OTHER INFORMATION: n is a, c, g, or t
<220> FEATURE:
<221> NAME/KEY: misc_feature
<222> LOCATION: (1695)..(1701)
<223> OTHER INFORMATION: n is a, c, g, or t

<400> SEQUENCE: 236

| | |
|---|---|
| tcgcatctgc agcttctttt gcacctgatt acagacataa gcacttgtag cgtttatgga | 60 |
| agaaagtttt ggagtgcaga tctcatgaca atgatgtaaa tctatcttgc ctcagtttgt | 120 |
| tcttgtagtt tcctttggac ttgaatttga taccttaatg catcgctaag tgctatttct | 180 |
| ctgattcaca taagaaatgc gatacaaatg gttagttcaa tcaatgcaga aaagttcaac | 240 |
| caaataaaat gggcccactg cagtcaatta acaggcattc aataggattc acattcctgg | 300 |
| gcttctatat atggaagttt gcatacaaag ttttggaaat aaaatggaat agaaattgct | 360 |
| tgcatttagt gtaagttaat acccgctagt tcattttta actaaaacac gacaaataaa | 420 |
| aaaatggagg agtacatctt tgtaacaggt gagcctgaat acttgtttgt agcaggtggg | 480 |
| gcgctaagta tgcttaggag aagtttaggc aacttgtatt ctgtagcatt tcgacgccgt | 540 |
| ttgtatggta atatctactg ataggcagaa tcctggttgg atttttttc ctgcttttgt | 600 |
| ttacacctat acagtcccat actcgcagtc gaataataca tggtctgatg ataaaccaat | 660 |
| taagaaggac tcatgtctca gtcattatga cttgagcata ggagttcaga tcgagaaata | 720 |
| tttgagttgc agcttaaggt tcagagagga aatcccatac acttgcttgt aacgatatga | 780 |
| tcattttttt tcaaggtaac attttctagc atcttcagct gtctacttga ctgaatgcag | 840 |
| tatatattag ttgtaataaa tactgcccctt ctgctgtgca caaaaggcgg gtattaccac | 900 |
| ttgcagaaat ttgtcgggta aaggtaattg ccagttacct tgtgttcttc ccttcatcag | 960 |
| gaacacctgg aggaggatgc gctgtggttg aactgaagcc ctgcgagaga agtactgatg | 1020 |
| acagaaagag cggaagataa gataagaaag gaaacccttg cgcggcaagg cctggtgaca | 1080 |
| tagaggtagt gcgaggctca taccgccgct ggcaggttcc aggcctgtgc ttttcttgcc | 1140 |
| ctgtatcccc agtctatact tctgcgcaca tcagacgagc ctcagtgttt cggcacagtg | 1200 |
| gtgcaacaga aaaggagag tgctggactg ctggtaacgc tgaggcggtg aagaaagaga | 1260 |
| ggtcagacgg acctggaggt ggcttttaa ctggtaaaga gtgaggtctt tcatgcccat | 1320 |
| caatctgagc accgacttgg gtgttgcttc tgttcgcagg aagcacaaga aatggtcagt | 1380 |
| actccacagc gtaggcatgt cggtgtgttc gaggaggcaa gattcagatg attattatat | 1440 |
| gagctcgaaa agctagagaa tggatgttca gacttgagat ctctgatttg agaggaattg | 1500 |
| cacttgtcgt tttcccargg cgacgcggcc tttttccaga ggcatttttt ttcannnnnn | 1560 |

```
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnntnnnnnn ngaaaaaaaa aagaatgcag accgacatgc tctgtagcac    1740
aagcaccata cttgcgaact gcagaggtgt cgggtcatca agcaatcgcc ttggtgtcgg    1800
acggggtggg gtcatcaaga caagacgact agaggagcac tacatctaca cggggggaa     1860 cggacgggag gaaggaagga aaacgagagc gaggactcac tgtccggtcc gcccagcttg    1920
gtgacggcgt cgacgaagcg ctggtggagg accggcgtcc agcgcagccg cggcttgggg    1980
tcccgtgacg ccgccccgtc gtagccgtag ctcccctgca tcgtcgttcc ttcctggcga    2040
tcgccgctcc ctagctatcc ggtggccaaa gacacggcta gtgctgaaga gagaatgaat    2100
gtaacgttac cgcctcctgg tcgtaggtgt aataagttgt aacgcgagtg tcgttagaag    2160
cacaggggtg tgtgtatgtg aggacaagag gaggagcgag aggaggagcg cagagcgtgg    2220
cggggaagga gggcgtcatg tgtgtgagga atctaggacg acttgttggc agctgggccg    2280
gggtgcgtgc gagatgcaat gcaagaacaa agcatcacgc ctccaagtcc aaccgggggg    2340
cgccactcgg ccgccgctca ttgaggccca ggcgccaaga cggcggctcc acccacatca    2400
caattggcaa caagaagcac acggctgggg ctgggacgcg tcgaattttt caccagaaaa    2460
taccgtcggc gtttcgtcag atgctatgct acgtgaacgg caaaacctag cagcagcagc    2520
agcactcaga ctggacaaga ggagggaaat ctttgcgtgg gaaccaaact gaacgcgaat    2580
cgcacgagtc ggatgacata tcctcgtccg gagcggactc ggccgcgagt ccagctgtgg    2640
ctgcggaata ttccggcgga agcgcgggga gaacgacggc ggcctccggt gggacccggg    2700
gcgagcggga gatgcggcga agatgttcgg cgctgatgtc gctggaatat tcgcgccagc    2760
tgtggctgcc ggtgtgacct gctgaccaga cgaccagtgg cagtggccac cgcctctcca    2820
tcacagattc gcggacgatt agccgagact aatcgctatt ctcaacactt ttaaaaccgt    2880
gcgtgcagaa tgctaagggc gcgttcgttt gcacagcaat agacatggat ttatttcagc    2940
tcatcaaaat ctatataaat taaagaagta atccggctag aaattaatcc ggagcttcaa    3000
tccctaacaa ccgaacaggg tctaagcctg ctagattcga gcatctgcgt gactctactt    3060
tggctcttct cgtacgatgc gacttgacga tgcatttgg                          3099
```

<210> SEQ ID NO 237
<211> LENGTH: 821
<212> TYPE: DNA
<213> ORGANISM: Zea mays
<220> FEATURE:
<221> NAME/KEY: misc_feature
<222> LOCATION: (307)..(699)
<223> OTHER INFORMATION: n is a, c, g, or t

<400> SEQUENCE: 237

```
attgaaaygc atttgagtga tgagagtatt accttttggg agaagtttga gtcgtttcaa      60
gtctttatgc atgaccaggt gagttagtrg ttttactttt twcctcaatg ccgtgtgaat     120
gtgaggttca tatawttttt tmtgctaatc tttgtagaag gactcaaggg ttattattct     180
attccttgaa agtcttcttt cttggcttga gcgtcgagcc cytccagaaa atatggatgt     240
tcaattattc gtagagatca ggcacatatg cagtcaattt caagagaagt atcttaggta     300
tgtttcnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
```

-continued

```
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnna gcatttatga waccgttctg     720
gtattatagt gcacgtactc taattagtag ttgggtatta gagtgtgatg tttaactatc     780
agcatccttc tgttgatgca tgaagtattc ttgtaaaagt t                         821
```